US011505591B2

(12) United States Patent
Seidel, III et al.

(10) Patent No.: US 11,505,591 B2
(45) Date of Patent: *Nov. 22, 2022

(54) T-CELL MODULATORY MULTIMERIC POLYPEPTIDES AND METHODS OF USE THEREOF

(71) Applicant: Cue Biopharma, Inc., Cambridge, MA (US)

(72) Inventors: Ronald D. Seidel, III, Cambridge, MA (US); Rodolfo Chaparro, Cambridge, MA (US)

(73) Assignee: Cue Biopharma, Inc., Boston, MA (US)

( * ) Notice: Subject to any disclaimer, the term of this patent is extended or adjusted under 35 U.S.C. 154(b) by 695 days.

This patent is subject to a terminal disclaimer.

(21) Appl. No.: 16/089,335

(22) PCT Filed: May 17, 2017

(86) PCT No.: PCT/US2017/033187
§ 371 (c)(1),
(2) Date: Sep. 27, 2018

(87) PCT Pub. No.: WO2017/201210
PCT Pub. Date: Nov. 23, 2017

(65) Prior Publication Data
US 2019/0106476 A1 Apr. 11, 2019

Related U.S. Application Data

(60) Provisional application No. 62/338,410, filed on May 18, 2016.

(51) Int. Cl.
| *C07K 14/705* | (2006.01) |
|---|---|
| *C07K 14/74* | (2006.01) |
| *C07K 14/715* | (2006.01) |
| *A61K 39/395* | (2006.01) |
| *C07K 16/28* | (2006.01) |
| *A61K 48/00* | (2006.01) |
| *A61P 35/00* | (2006.01) |
| *C07K 14/77* | (2006.01) |
| *A61K 38/00* | (2006.01) |

(52) U.S. Cl.
CPC .... *C07K 14/70532* (2013.01); *A61K 39/3955* (2013.01); *A61K 48/00* (2013.01); *A61P 35/00* (2018.01); *C07K 14/70521* (2013.01); *C07K 14/70539* (2013.01); *C07K 14/70578* (2013.01); *C07K 14/7151* (2013.01); *C07K 14/77* (2013.01); *C07K 16/2818* (2013.01); *A61K 38/00* (2013.01); *C07K 2319/30* (2013.01); *C07K 2319/31* (2013.01); *C07K 2319/40* (2013.01)

(58) Field of Classification Search
None
See application file for complete search history.

(56) References Cited

U.S. PATENT DOCUMENTS

| 5,635,363 A | 6/1997 | Altman et al. |
|---|---|---|
| 6,197,302 B1 | 3/2001 | Hirsch et al. |
| 6,211,342 B1 | 4/2001 | Hirsch et al. |
| 6,268,411 B1 | 7/2001 | Schneck et al. |
| 6,696,304 B1 | 2/2004 | Parker |
| 7,098,306 B2 | 8/2006 | Economou et al. |
| 7,186,804 B2 | 3/2007 | Gillies et al. |
| 7,432,351 B1 | 10/2008 | Chen |
| 7,670,595 B2 | 3/2010 | Gillies et al. |
| 8,992,937 B2 | 3/2015 | Hansen et al. |
| 9,284,349 B2 | 3/2016 | Tsunoda et al. |
| 9,359,424 B2 | 6/2016 | Maoult et al. |
| 9,494,588 B2 | 11/2016 | Springer et al. |
| 10,272,042 B2 | 4/2019 | Daftarian et al. |
| 10,501,521 B2 | 12/2019 | Georges et al. |
| 10,927,158 B2 | 2/2021 | Seidel et al. |
| 10,927,161 B2 | 2/2021 | Seidel et al. |
| 11,104,712 B2 * | 8/2021 | Seidel, III .......... C07K 16/2827 |
| 11,117,945 B2 * | 9/2021 | Seidel, III .......... G01N 33/5008 |
| 11,380,821 B2 | 7/2022 | Jia et al. |
| 2002/0006664 A1 | 1/2002 | Sabatini |
| 2002/0031520 A1 | 3/2002 | Economou et al. |
| 2004/0038349 A1 | 2/2004 | Hilbert et al. |
| 2004/0132977 A1 | 7/2004 | Gantier et al. |
| 2004/0161817 A1 | 8/2004 | Benton et al. |
| 2004/0209363 A1 | 10/2004 | Watts et al. |
| 2005/0003431 A1 | 1/2005 | Wucherpfennig et al. |
| 2005/0009012 A1 | 1/2005 | Holzberg et al. |
| 2005/0100926 A1 | 5/2005 | Hedley et al. |
| 2005/0142142 A1 | 6/2005 | Burrows et al. |

(Continued)

FOREIGN PATENT DOCUMENTS

| CN | 1791675 | 6/2006 |
|---|---|---|
| CN | 101384621 | 3/2009 |
| CN | 101418309 | 4/2009 |
| CN | 101448951 | 6/2009 |
| CN | 101688213 | 3/2010 |

(Continued)

OTHER PUBLICATIONS

Brzostek et al. (2016) Front. Immunol. 7: 24, p. 1-15.*
U.S. Appl. No. 17/410,453, filed Aug. 2021, Seidel, III; Ronald D.*
U.S. Appl. No. 17/381,858, filed Jul. 2021, Seidel, III; Ronald D.*
U.S. Appl. No. 17/342,501, filed Jun. 2021, Seidel, III; Ronald D.*
U.S. Appl. No. 17/342,513, filed Jun. 2021, Seidel, III; Ronald D.*

(Continued)

*Primary Examiner* — Ilia I Ouspenski
(74) *Attorney, Agent, or Firm* — Bozicevic Field & Francis, LLP; Paula A. Borden

(57) ABSTRACT

The present disclosure provides T-cell modulatory multimeric polypeptides comprising two different immunomodulatory polypeptides, at least one of which is a variant immunomodulatory polypeptide. The present disclosure provides nucleic acids comprising nucleotide sequences encoding the T-cell modulatory multimeric polypeptides, and host cells comprising the nucleic acids. The present disclosure provides methods of modulating the activity of a T cell; the methods comprise contacting the T cell with a T-cell modulatory multimeric polypeptide of the present disclosure.

17 Claims, 35 Drawing Sheets

Specification includes a Sequence Listing.

(56) References Cited

U.S. PATENT DOCUMENTS

| | | |
|---|---|---|
| 2006/0034865 A1 | 2/2006 | Hildebrand et al. |
| 2006/0269515 A1 | 11/2006 | Deniz-Mize et al. |
| 2007/0036752 A1 | 2/2007 | Gillies et al. |
| 2007/0148162 A1 | 6/2007 | Bhardwaj et al. |
| 2007/0286843 A1 | 12/2007 | Pfizenmaier et al. |
| 2008/0199485 A1 | 8/2008 | Kundig et al. |
| 2008/0219947 A1 | 9/2008 | Linette et al. |
| 2008/0269070 A1 | 10/2008 | Ramseier et al. |
| 2010/0159594 A1 | 6/2010 | Hansen et al. |
| 2011/0002956 A1 | 1/2011 | Weiner et al. |
| 2011/0268737 A1 | 11/2011 | Favier et al. |
| 2011/0318380 A1 | 12/2011 | Brix et al. |
| 2012/0003220 A1 | 1/2012 | Chen |
| 2012/0121577 A1 | 5/2012 | Weidanz et al. |
| 2012/0177595 A1 | 7/2012 | Wong et al. |
| 2012/0264161 A1 | 10/2012 | Scholler et al. |
| 2013/0017199 A1 | 1/2013 | Langermann |
| 2013/0149305 A1 | 6/2013 | Ostrand-Rosenberg |
| 2014/0046026 A1 | 2/2014 | Garcia et al. |
| 2014/0162293 A1 | 6/2014 | Springer et al. |
| 2014/0242077 A1 | 8/2014 | Choi et al. |
| 2015/0071987 A1 | 3/2015 | Selvaraj |
| 2015/0224186 A1 | 8/2015 | Nakagawa |
| 2015/0232532 A1 | 8/2015 | Ostrand-Rosenberg |
| 2015/0374788 A1 | 12/2015 | Paulsen et al. |
| 2016/0011204 A1 | 1/2016 | Almo et al. |
| 2016/0083477 A1 | 3/2016 | Klein et al. |
| 2016/0090407 A1 | 3/2016 | Hosse et al. |
| 2016/0114019 A1 | 4/2016 | Li et al. |
| 2016/0152725 A1 | 6/2016 | Cheung et al. |
| 2016/0175397 A1 | 6/2016 | Umana et al. |
| 2016/0304580 A1 | 10/2016 | Ellmark et al. |
| 2016/0362465 A1 | 12/2016 | Nishimura et al. |
| 2017/0044229 A1 | 2/2017 | Garcia et al. |
| 2017/0058015 A1* | 3/2017 | Seidel, III ............... A61P 35/00 |
| 2017/0334951 A1 | 11/2017 | O'Reilly et al. |
| 2018/0064795 A1 | 3/2018 | Sugiyama |
| 2018/0208626 A1 | 7/2018 | Scheinberg et al. |
| 2019/0046648 A1* | 2/2019 | Seidel, III ........... A61K 38/1774 |
| 2019/0062400 A1* | 2/2019 | Seidel, III ........ C07K 14/70532 |
| 2020/0010528 A1* | 1/2020 | Seidel, III ............. C07K 14/79 |
| 2020/0140519 A1* | 5/2020 | Seidel, III ............ C12N 5/0636 |
| 2020/0148744 A1* | 5/2020 | Seidel, III ............... C40B 40/10 |
| 2020/0172595 A1* | 6/2020 | Seidel, III ........ C07K 14/70539 |
| 2020/0317747 A1* | 10/2020 | Seidel, III ........ C07K 14/70539 |
| 2020/0325205 A1* | 10/2020 | Seidel, III ........ A61K 39/3955 |
| 2020/0369745 A1* | 11/2020 | Seidel, III ........ C07K 14/70539 |
| 2020/0377569 A1* | 12/2020 | Seidel, III ............... A61P 43/00 |
| 2020/0407416 A1* | 12/2020 | Seidel, III ........ C07K 14/70575 |
| 2021/0047384 A1* | 2/2021 | Seidel, III ............... A61P 33/02 |
| 2021/0107962 A1* | 4/2021 | Seidel, III ............... A61K 35/17 |
| 2021/0238254 A1* | 8/2021 | Seidel, III ............... A61P 37/04 |
| 2021/0284712 A1* | 9/2021 | Seidel, III ........ C07K 14/70539 |

FOREIGN PATENT DOCUMENTS

| | | |
|---|---|---|
| CN | 105121715 | 12/2015 |
| CN | 108431022 | 11/2016 |
| EP | 3596118 | 1/2020 |
| JP | 2000515363 | 11/2000 |
| JP | 2004501364 | 1/2004 |
| JP | 2005506058 | 3/2005 |
| JP | 2007530021 | 11/2007 |
| JP | 2009537175 | 10/2009 |
| JP | 2010524506 | 7/2010 |
| JP | 2012516854 | 7/2012 |
| JP | 2015537043 | 12/2015 |
| WO | WO 1997/028191 | 8/1997 |
| WO | WO 2001/090747 | 11/2001 |
| WO | WO 2002/072631 | 9/2002 |
| WO | WO 2002/087613 | 11/2002 |
| WO | WO 2002/093129 | 11/2002 |
| WO | WO 2002/102299 | 12/2002 |
| WO | WO 2003/048334 | 6/2003 |
| WO | WO 2004/029197 | 4/2004 |
| WO | WO 2004/111190 | 12/2004 |
| WO | WO 2007/136778 | 11/2007 |
| WO | WO 2008/019888 | 2/2008 |
| WO | WO 2008/113970 | 9/2008 |
| WO | WO 2008/116468 | 10/2008 |
| WO | WO 2008/134461 | 11/2008 |
| WO | WO 2010/037395 | 4/2010 |
| WO | WO 2010/085495 | 7/2010 |
| WO | WO 2010/091122 | 8/2010 |
| WO | WO 2011/066342 | 6/2011 |
| WO | WO 2011/066389 | 6/2011 |
| WO | WO 2012/127464 | 9/2012 |
| WO | WO 2012/175508 | 12/2012 |
| WO | WO 2013/003761 | 1/2013 |
| WO | WO 2013/079174 | 6/2013 |
| WO | WO 2014/083004 | 6/2014 |
| WO | WO 2014/093118 | 6/2014 |
| WO | WO 2015/007903 | 1/2015 |
| WO | WO 2015/112541 | 7/2015 |
| WO | WO 2015/164815 | 10/2015 |
| WO | 2015-195531 | 12/2015 |
| WO | WO 2015/195531 | 12/2015 |
| WO | WO 2016/000619 | 1/2016 |
| WO | WO 2016/014428 | 1/2016 |
| WO | WO 2016/025642 | 2/2016 |
| WO | WO 2016/029043 | 2/2016 |
| WO | WO 2016/030350 | 3/2016 |
| WO | WO 2016/141357 | 9/2016 |
| WO | WO 2016/164937 | 10/2016 |
| WO | WO 2016/168771 | 10/2016 |
| WO | WO 2017/008844 | 1/2017 |
| WO | WO 2017/023779 | 2/2017 |
| WO | WO 2017/059819 | 4/2017 |
| WO | WO 2017/120222 | 7/2017 |
| WO | WO 2017/151818 | 9/2017 |
| WO | WO 2017/151940 | 9/2017 |
| WO | WO 2017/201131 | 11/2017 |
| WO | WO 2017/201210 | 11/2017 |
| WO | WO 2019/051126 | 3/2019 |

OTHER PUBLICATIONS

U.S. Appl. No. 17/326,837, filed May 2021, Seidel, III; Ronald D.*
U.S. Appl. No. 17/327,171, filed May 2021, Seidel, III; Ronald D.*
U.S. Appl. No. 17/245,999, filed Apr. 2021, Seidel, III; Ronald D.*
Solinas et al. (2020) ESMO Open; 5:e000544; 1-7.*
Huang, et al.; "Bone regeneration in a rat cranial defect with delivery of PEI-condensed plasmid DNA encoding for bone morphogenetic protein-4 (BMP-4)"; Gene Therapy; vol. 12, No. 5, p. 418 (2005).
Stamper, et al.; "Crystal structure of the B7-1/CTLA-4 complex that inhibits human immune responses"; Nature; vol. 410, pp. 608-611 (Mar. 29, 2001).
Tham, et al.; "Activation of antigen-specific T cells by artificial cell constructs having immobilized multimeric peptide-class I complexes and recombinant B7-Fc proteins"; Journal of Immunological Methods; vol. 249, pp. 111-119 (2001).
Zheng, et al.; "B7-CTLA4 interaction enhances both production of antitumor cytotoxic T lymphocytes and resistance to tumor challenge"; PNAS; vol. 95, pp. 6284-6289 (May 1998).
Chames, et al.; "Bispecific antibodies for cancer therapy; The light at the end of the tunnel?" mAbs; vol. 1, No. 6, pp. 539-547 (Nov.-Dec. 2009).
Dimasi, et al.; "The design and characterization of oligospecific antibodies for simultaneous targeting of multiple disease mediators"; Journal of Molecular Biology; 393(3): p. 672-692 (2009).
Doussal, et al.; "Phage display of peptide /major histocompatibility complex"; Journal of Immunological Methods; vol. 241, pp. 147-158 (2000).
Greten, et al.; "Peptide-β2-microglobulin-MHC fusion molecules bind antigen-specific T cells and can be used for multivalent MHC-lg complexes"; Journal of Immunological Methods; vol. 271, pp. 125-135 (2002).
Grupp, et al.; "Adoptive Cellular Therapy"; Curr Top Microbiol Immunol.; 344: p. 149-172 (2011).

(56) References Cited

OTHER PUBLICATIONS

Mott, et al.; "The Solution Structure of the F42A Mutant of Human Interleukin 2"; J. Mol. Biol.; vol. 247, pp. 979-994 (1995).
Oates, et al.; "ImmTACs: Novel bi-specific agents for targeted cancer therapy"; OncoImmunology; vol. 2, No. 2, 3 pages (Feb. 2013).
Obermann, et al.; "Peptide-β2-microglobulin-major histocompatibility complex expressing cells are potent antigen-presenting cells that can generate specific T cells"; Immunology; vol. 122, pp. 90-97 (2007).
Peach, et al.; "Both Extracellular Immunoglobin-like Domains of CD80 Contain Residues Critical for Binding T Cell Surface Receptors CTLA-4 and CD28*"; The Journal of Biological Chemistry; vol. 270, No. 36, pp. 21181-21187 (1995).
Ponstingl, et al.; "The Rule of Antibody Structure: The Primary Structure of a Monoclonal IgG1 Immunoglobulin (Myeloma Protein Nie)"; Hoppe Seylers Z Physiol Chem.; vol. 357, No. 11, pp. 1571-1604 (Nov. 1976). [English translation of Abstract ONLY].
Rabu, et al.; "Production of recombinant human trimeric CD137L (4-1BBL). Cross-linking is essential to its T cell co-stimulation activity"; The Journal of Biological Chemistry; vol. 280, No. 50, pp. 41472-41481 (Dec. 16, 2005).
Sharma, et al.; "A synthetic chimeric peptide harboring human papillomavirus 16 cytotoxic T lymphocyte epitopes shows therapeutic potential in a murine model of cervical cancer"; Immunologic Research; 58(1): p. 132-138 (2014).
Won, et al.; "The structure of the trimer of human 4-1BB ligand is unique among members of the tumor necrosis factor superfamily"; J Biol Chem; vol. 285, No. 12, pp. 9202-9210 (Mar. 19, 2010).
Wu, et al.; "Simultaneous targeting of multiple disease mediators by a dual-variable-domain immunoglobulin"; Nature Biotechnology; 25: p. 1290-1297 (2007).
Xu, et al.; "Cytokine release syndrome in cancer immunotherapy with chimeric antigen receptor engineered T cells"; Cancer Letters; 343(2): p. 172-178 (2014).
Buonaguro, et al.; "Translating Tumor Antigens into Cancer Vaccines"; Clinical and Vaccine Immunology; vol. 18, No. 1, pp. 23-24 (Jan. 2011).
Celis, et al.; "Identification of Potential CTL Epitopes of Tumor-Associated Antigen Mage-1 for Five Common HLA-A Alleles"; Molecular Immunology; vol. 31, No. 18, pp. 1423-1430 (1994).
De Charette, et al.; "Turning tumour cells into antigen presenting cells: The next step to improve cancer immunotherapy?"; European Journal of Cancer; vol. 68, pp. 134-147 (2016).
HLA Nomenclature; "HLA Alleles Numbers"; 2 pages (Mar. 17, 2015).
Karin, et al.; "Reversal of Experimental Autoimmune Encephalomyelitis by a Soluble Peptide Variant of a Myelin Basic Protein Epitope: T Cell Receptor Antagonism and Reduction of Interferon γ and Tumor Necrosis Factor α Production"; J. Exp. Med.; vol. 180, pp. 2227-2237 (Dec. 1994).
Martin-Orozco, et al.; "Melanoma Cells Express ICOS Ligand to Promote the Activation and Expansion of T-Regulatory Cells"; Cancer Research; vol. 70, No. 23, pp. 9581-9590 (2010).
Motz, et al.; "Tumor Endothelium FasL Establishes a Selective Immune Barrier Promoting Tolerance in Tumors"; Nat. Med.; vol. 20, No. 6, pp. 607-615 (Jun. 2014).
Ochoa-Garay, et al.; "The Ability of Peptides to Induce Cytotoxic T Cells In Vitro Does Not Strongly Correlate with Their Affinity for the $H-2L^d$ Molecule: Implications for Vaccine Design and Immunotherapy"; Molecular Immunology; vol. 34, No. 3, pp. 273-281 (1997).
Repana, et al.; "The Network of Cancer Genes (NCG): a comprehensive catalogue of known and candidate cancer genes from cancer sequencing screens"; Genome Biology; vol. 20, No. 1, 12 pages (2019).
Schumacher, et al.; "Neoantigens in cancer immunotherapy"; Science; vol. 348, No. 6230, pp. 69-74 (Apr. 2, 2015).

White, et al.; "Soluble Class I MHC with $β_2$-MicroglobulinCovalently Linked Peptides: Specific Binding to a T Cell Hybridoma"; J Immunol; vol. 162, pp. 2671-2676 (1999).
Lin, et al.; "The PD-1/PD-L1 complex resembles the antigen-binding Fv domains of antibodies and T cell receptors"; PNAS; vol. 105, No. 8, pp. 3011-3016 (Feb. 26, 2008).
McNally, et al.; "CD4+CD25+ regulatory T cells control CD8+ T-cell effector differentiation by modulating IL-2 homeostasis"; PNAS; vol. 108, No. 18, pp. 7529-7534 (May 3, 2011).
Tafuro, et al.; "Reconstitution of antigen presentation in HLA class I-negative cancer cells with peptide-β2m fusion molecules"; Eur. J. Immunol.; vol. 31, pp. 440-449 (2001).
Lazar-Molnar, et al.; "The PD-1/PD-L costimulatory pathway critically affects host resistance to the pathogenic fungus *Histoplasma capsulatum*"; PNAS; vol. 105, No. 7, pp. 2658-2663 (Feb. 19, 2008).
Azuma, et al.; "B7-H1 is a ubiquitous antiapoptotic receptor on cancer cells"; Immunobiology; vol. 111, No. 7, pp. 3635-3643 (Apr. 1, 2008).
Crawford, et al.; "Use of baculovirus MHC/ peptide display libraries to characterize T-cell receptor ligands"; Immunological Reviews; vol. 210, pp. 156-170 (2006).
Wang, et al.; "Using a baculovirus display library to identify MHC class I mimotopes"; PNAS; vol. 102, No. 7, pp. 2476-2481 (Feb. 15, 2005).
GENBANK:AEV43323.1; "Fc IgG1 heavy chain constant region, partial [*Homo sapiens*]"; 2 pages (Jul. 25, 2016).
Kreiter, et al.; "Increased Antigen Presentation Efficiency by Coupling Antigens to MHC Class I Trafficking Signals"; The Journal of Immunology; vol. 180, No. 1, pp. 309-318 (Jan. 1, 2008).
Strohl; "Optimization of Fc-mediated effector functions of monoclonal antibodies"; Current Opinion in Biotechnology; vol. 20, pp. 685-691 (2009).
Carey, et al.; "A soluble divalent class I MHC/IgG1 fusion protein activates CD8+ T cells in vivo"; Clinical Immunology; vol. 116, pp. 65-76 (2005).
GENEBANK:NP_001009066.1; 2 pages (2003).
Lazar-Molnar, et al.; "Crystal structure of the complex between programmed death-1 (PD-1) and its ligand PD-L2"; PNAS; vol. 105, No. 30, pp. 10483-10488 (Jul. 29, 2008).
Medina, et al.; "PD-1 Pathway Inhibitors: Immuno-Onology Agents for Restoring Anititumor Immune Responses"; Pharmacotherapy; vol. 36, No. 3, pp. 317-334 (2016).
Oliveira, et al.; "Design, Immune Responses and Anti-Tumor Potential of an HPV16 E6E7 Multi-Epitope Vaccine"; PLoS One; vol. 10, No. 9, 13 pages (Sep. 21, 2015).
Quayle, et al.; "CUE-101, a Novel HPV16 E7-pHLA-IL-2-Fc Fusion Protein, Enhances Tumor Antigen Specific T Cell Activation for the Treatment of HPV16-Driven Malignancies"; Clinical Cancer Research; vol. 26, No. 8, pp. 1953-1964 (Jan. 21, 2020).
Rocha-Zavaleta, et al.; "Interleukin-2 (IL-2) receptor-βγ signalling is activated by c-Kit in the absence of IL-2, or by exogenous IL-2 via JAK3/STAT5 in human papillomavirus-associated cervical cancer"; Cellular Signalling; vol. 16, pp. 1239-1247 (2004).
Schmittnaegel, et al.; "A New Class of Bifunctional Major Histocompatibility Class I Antibody Fusion Molecules to Redirect CD8 T Cells"; Molecular Cancer Therapeutics; vol. 15, No. 9, pp. 2130-2142 (Sep. 2016).
Trolle, et al.; "The length distribution of class I restricted T cell epitopes is determined by both peptide supply and MHC allele specific binding preference"; J Immunol; vol. 196, No. 4, pp. 1480-1487 (Feb. 15, 2016).
Wang, et al.; "Molcular Modeling and Functional Mapping of B7-H1 and B7-DC Uncouple Costimulatory Function from PD-1 Interaction"; J. Exp. Med.; vol. 197, No. 9, pp. 1083-1091 (May 5, 2003).
Büttner; "Cell-based assays for high-throughput screening"; Expert Opin. Drug Discov..; vol. 1, No. 4, pp. 301-306 (Sep. 2006).
GENBANK:NP_068693.1; "programmed cell death 1 ligand 1 precursor [Mus musculus]"; 3 pages (Jun. 9, 2021).
GENBANK:NP_001300958.1; "programmed cell death 1 ligand 1 isoform c precursor [*Homo sapiens*]"; 3 pages (Jun. 9, 2021).

(56) References Cited

OTHER PUBLICATIONS

Liao, et al.; "Interleukin-2 at the Crossroads of Effector Responses, Tolerance, and Immunotherapy"; Immunity; vol. 38, No. 1, pp. 13-25 (Jan. 1, 2013).
Ackerman, et al.; "Highly Avid Magnetic Bead Capture: An Efficient Selection Method for de novo Protein Engineering Utilizing yeast Surface Display"; Biotechnol. Prog.; vol. 25, No. 3, pp. 774-783 (2009).
Aina, et al.; "Identification of novel targeting peptides for human ovarian cancer cells using 'one-bead one-compount' combinatorial libraries"; Mol. Cancer Ther.; vol. 4, No. 5, 8 pages (May 2005).
Arduin, et al.; "Highly reduced binding to high and low affinity mouse Fc gamma receptors by L234A/L235A and N297A Fc mutations engineered into mouse IgG2a"; Molecular Immunology; vol. 63, pp. 456-463 (2015).
Baldi, et al.; "Recombinant protein production by large-scale transient gene expression in mammalian cells: state of the art and future perspectives"; Biotechnol. Lett.; vol. 29, pp. 677-684 (2007).
Bowers, et al.; "Coupling mammalian cell surface display with somatic hypermutation for the discovery and maturation of human antibodies"; PNAS; vol. 108, No. 51, pp. 20455-20460 (Dec. 20, 2011).
Cafri, et al.; "Development of novel genetic cancer vaccines based on membrane-attached β2 microglobulin"; Ann. N.Y. Acad. Sci.; vol. 1283, pp. 87-90 (2013).
Cebecauer, et al.; "Soluble MHC-Peptide Complexes Induce Rapid Death of CD8+ CTL"; The Journal of Immunology; vol. 174, pp. 6809-6819 (2005).
Center for Disease Control and Prevention; "How Many Cancers Are Linked with HPV Each Year?"; 4 pages (2016).
Cheever, et al.; "The Prioritization of Cancer Antigens: A National Cancer Institute Pilot Project for the Acceleration of Translational Research"; Clinical Cancer Research; vol. 15, No. 17, pp. 5324-5337 (Sep. 1, 2009).
Crisci, et al.; "Virus-like particles: The new frontier of vaccines for animal viral infections"; Veterinary Immunology and Immunopathology; vol. 148, pp. 211-225 (2012).
Czajkowsky, et al.; "Fc-fusion proteins: new developments and future perspectives"; EMBO Mol. Med.; vol. 4, pp. 1015-1028 (2012).
Das, et al.; "Generation of murine tumor cell lines deficient in MHC molecule surface expression using the CRISPR/Cas9 system"; PLoS One; vol. 12, No. 3, 19 pages (Mar. 16, 2017).
Desmond, et al.; "A systematic review of T-cell epitopes in hepatitis B virus: identification, genotypic variation and relevance to antiviral therapeutics"; Antiviral Therapy; vol. 13, pp. 161-175 (2008).
Dulberger, et al.; "Human leukocyte antigen F (HLA-F) presents peptides and regulates immunity through interactions with NK-cell receptors"; Immunity; vol. 46, No. 6, pp. 1018-1027 (Jun. 20, 2017).
Edwards, et al.; "The Remarkable Flexibility of the Human Antibody Repertoire; Isolation of Over One Thousand Different Antibodies to a Single Protein, BLyS"; J. Mol. Biol.; vol. 334, pp. 103-118 (2003).
Engelhard; "Structure of peptides associated with MHC class I molecules"; Current Opinion in Immunology; vol. 6, pp. 13-23 (1994).
Goel, et al.; "Plasticity within the Antigen-Combining Site May Manifest as Molecufar Mimicry in the Humoral Immune Response"; The Journal of Immunology; vol. 173, pp. 7358-7367 (2004).
Gough, et al.; "The HLA Region and Autoimmune Disease: Associations and Mechanisms of Action"; Current Genomics; vol. 8, pp. 453-465 (2007).
Guo, et al.; "Different length peptides bind to HLA-Aw68 similarly at their ends but bulge out in the middle"; Nature; vol. 360, pp. 364-366 (Nov. 26, 1992).
Hansen, et al.; "Phage display of peptide/major histocompatibility class I complexes"; Eur. J. Immunol.; vol. 31, pp. 32-38 (2001).
Huang, et al.; "Cancer immunotherapy using a DNA vaccine encoding a single-chain trimer of MHC class I linked to an HPV-16 E6 immunodominant CTL epitope"; Gene Ther.; vol. 12, No. 15, pp. 1180-1186 (Aug. 2005).
Hug, et al.; "T-cadherin is a receptor for hexameric and high-molecular-weight forms of Acrp30/adiponectin"; PNAS; vol. 101, No. 28, pp. 10308-10313 (Jul. 13, 2004).
Hugues, et al.; "Generation and use of alternative multimers of peptide/MHC complexes"; Journal of Immunological Methods; vol. 268, pp. 83-92 (2002).
Judkowski, et al.; "Identification of MHC Class II-Restricted Peptide Ligands, Including a Glutamic Acid Decarboxylase 65 Sequence, that Stimulate Diabetogenic T Cells from Transgenic BDC2.5 Nonobese Diabetic Mice"; The Journal of Immunology; vol. 166, pp. 908-917 (2001).
Karaki, et al.; "Is There Still Room for Cancer Vaccines at the Era of Checkpoint Inhibitors"; Vaccines; vol. 4, No. 37, 24 pages (2016).
Khan, et al.; "Adjustable Locks and Flexible Keys: Plasticity of Epitope-Paratope Interactions in Germline Antibodies"; The Journal of Immunology; vol. 192, pp. 5398-5405 (2014).
Kim, et al.; "Single chain MHC I trimer-based DNA vaccines for protection against Listeria monocytogenes infection"; Vaccine; vol. 30, pp. 2178-2186 (2012).
Krautwurst, et al.; "Identification of Ligands for Olfactory Receptors by Functional Expression of a Receptor Library"; Cell; vol. 95, pp. 917-926 (Dec. 23, 1998).
Kushnir, et al.; "Virus-like particles as a highly efficient vaccine platform: Diversity of targets and production systems and advances in clinical development"; Vaccine; vol. 31, pp. 58-83 (2012).
Lenormand, et al.; "HLA-DQA2 and HLA-DQB2 Genes Are Specifically Expressed in Human Langerhans Cells and Encode a New HLA Class II Molecule"; The Journal of Immunology; vol. 199, No. 8, pp. 3903-3911 (Apr. 15, 2012).
Liu, et al.; "Attaining High Transient Titers in CHO Cells"; Genetic Engineering & Biotechnology News; vol. 35, No. 17, 3 pages (Oct. 1, 2015).
Lloyd, et al.; "Modelling the human immune response: performance of a 1011 human antibody repertoire against a broad panel of therapeutically relevant antigens"; Protein Engineering, Design & Selection; vol. 22, No. 3, pp. 159-168 (2009).
Mallone, et al.; "T Cell Recognition of Autoantigens in Human Type 1 Diabetes: Clinical Perspectives"; Clinical and Developmental Immunology; vol. 2011, 16 pages (2011).
Margalit, et al.; "Induction of Antitumor Immunity by CTL Epitopes Genetically Linked to Membrane-Anchored β2-Microglobulin"; The Journal of Immunology; vol. 176, pp. 217-224 (2006).
McAllister, et al.; "Adaptation of Recombinant HEK-293 Cells to Growth in Serum Free Suspension"; Animal Cell Technology: Products from Cells, Cells as Products; 3 pages (1999).
Miao, et al.; "Transient expression of fluorescent fusion proteins in protoplasts of suspension cultured cells"; Nature Protocols; vol. 2, No. 10, pp. 2348-2353 (2007).
Mizukoshi, et al.; "Identification of α-fetoprotein-derived peptides recognized by cytotoxic T lymphocytes in HLA-A24+ patients with hepatocellular carcinoma"; Int. J. Cancer; vol. 118, pp. 1194-1204 (2006).
Muller, et al.; "Random peptide libraries displayed on adeno-associated virus to select for targeted gene therapy vectors"; Nature Biotechnology; vol. 21, No. 9, pp. 1040-1046 (Sep. 2003).
Naidoo, et al.; "Toxicities of the anti-PD-1 and anti-PD-L1 immune checkpoint antibodies"; Annals of Oncology; vol. 26, pp. 2375-2391 (2015).
Nielsen, et al.; "MHC Class II epitope predictive algorithms"; Immunology; vol. 130, pp. 319-328 (2010).
Oka, et al.; "Induction of WT1 (Wilms' tumor gene)-specific cytotoxic T lymphocytes by WT1 peptide vaccine and the resultant cancer regression"; PNAS; vol. 101, No. 38, pp. 13885-13890 (Sep. 21, 2004).
Poosarla, et al.; "Computational De Novo Design of Antibodies Binding to a Peptide With High Affinity"; Biotechnology & Bioengineering; vol. 114, No. 6, pp. 1331-1342 (Jun. 2017).

(56) References Cited

OTHER PUBLICATIONS

Ramani, et al.; "A secreted protein microarray platform for extracellular protein interaction discovery"; Analytical Biochemistry; vol. 420, pp. 127-138 (2012).
Reche, et al.; "Sequence Variability Analysis of Human Class I and Class Ii Mhc Molecules: Functional and Structural Correlates of Amino Acid Polymorphisms"; Journal of Molecular Biology; vol. 331, No. 3, pp. 623-641 (Aug. 15, 2003).
Ressing, et al.; "Human CTL epitopes encoded by human papillomavirus type 16 E6 and E7 identified through in vivo and in vitro immunogenicity studies of HLA-A*0201-binding peptides"; The Journal of Immunology; vol. 154, pp. 5934-5943 (1995).
Shah, et al.; "Bio-layer Interferometry for Measuring Kinetics of Protein-protein Interactions and Allosteric Ligand Effects"; Journal of Visualized Experiments; vol. 84, 11 pages (2014).
Spang, et al.; "Heterodimeric Barnase-Barstar Vaccine Molecules: Influence of One versus Two Targeting Units Specific for Antigen Presenting Cells"; PLoS One; vol. 7, No. 9, 11 pages (Sep. 2012).
Stadinski, et al.; "Diabetogenic T cells recognize insulin bound to IAg7 in an unexpected, weakly binding register"; PNAS; vol. 107, No. 24, pp. 10978-10983 (Jun. 15, 2010).
Taube, et al.; "Lentivirus Display: Stable Expression of Human Antibodies on the Surface of Human Cells and Virus Particles"; PLoS One; vol. 3, No. 9, 12 pages (Sep. 2008).
Torres, et al.; "The immunoglobulin constant region contributes to affinity and specificity"; Trends in Immunology; vol. 29, No. 2, pp. 91-97 (Jan. 10, 2008).
Toukam, et al.; "Targeting Antibody Responses to the Membrane Proximal External Region of the Envelope Glycoprotein of Human Immunodeficiency Virus"; PLoS One; vol. 7, No. 5, 10 pages (May 2012).
Van Der Burg, et al.; "An HLA Class I Peptide-Binding Assay Based on Competition for Binding to Class I Molecules on Intact Human B Cells Identification of Conserved HIV-1 Polymerase Peptides Binding to HLA-A*0301"; Hum. Immunol.; vol. 44, No. 4, pp. 189-198 (Dec. 1995).
Venkatakrishnan, et al.; "The Structural Biology of Hepatitis B Virus: Form and Function"; Annu. Rev. Virol.; vol. 3, No. 1, pp. 429-451 (Sep. 29, 2016).
Wen, et al.; "Construction and screening of an antigen-derived peptide library displayed on yeast cell surface for CD4+ T cell epitope identification"; Methods Mol. Biol.; vol. 1061, pp. 245-264 (2013).
Whitehead, et al.; "Optimization of affinity, specificity and function of designed influenza inhibitors using deep sequencing"; Nat. Biotechnol.; vol. 30, No. 6, pp. 543-548 (Apr. 29, 2013).
Ziauddin, et al.; "Microarrays of cells expressing defined cDNAs"; Nature; vol. 411, pp. 107-110 (May 3, 2011).
Brophy, et al.; "A yeast display system for engineering functional peptide-MHC complexes"; Journal of Immunological Methods; vol. 272, pp. 235-246 (2003).
Emboss Needle; 2 pages (Feb. 10, 2022).
GenCore AEE04235; 4 pages (2005).
Liu, et al.; "Major Histocompatibility Complex: Interaction with Peptides"; eLS; 12 pages (Aug. 15, 2011).
Mottez, et al.; "Cells Expressing a Major Histocompatibility Complex Class I Molecule with a Single Covalently Bound Peptide Are Highly Immunogenic"; J. Exp. Med.; vol. 181, pp. 493-502 (Feb. 1995).
Vitello, et al.; "Neoantigen prediction and the need for validation"; Nature Biotechnology; vol. 35, No. 9, pp. 815-817 (Sep. 2017).
Wieczorek, et al.; "Major Histocompatibility Complex (MHC) Class I and MHC Class II Proteins: Conformational Plasticity in Antigen Presentation"; Frontiers in Immunology; vol. 8, No. 292, pp. 1-16 (Mar. 2017).
Card, et al.; "A soluble single-chain T-cell receptor IL-2 fusion protein retains MHC-restricted peptide specificity and IL-2 bioactivity"; Cancer Immunol Immunother; vol. 53, pp. 345-357 (Nov. 11, 2003).
Engler, et al.; "Peptide vaccines against hepatitis B virus: from animal model to human studies"; Molecular Immunology; vol. 38, pp. 457-465 (Dec. 2001).
PDB:1I8L_A; "Chain A, T Lymphocyte Activation Antigen Cd80" 2 pages (Dec. 27, 2012).
Quayle, et al.; "Immuno-STAT(TM) (Selective Targeting and Alteration of T cells) Platform: Targeting Tumor Heterogeneity and Tumor Escape Mechanisms"; DOI:10.1158/1078-0432.CCR-19-3354; URL:https://www.cuebiopharma.com/our-appro ch/scien ific-presentatjons-publications/; 1 page (Jan. 21, 2020).
Seidel, et al.; "Peptide-HLA-based immunotherapeutics platforms for direct modulation of antigen-specific T cells"; Scientific Reports; vol. 11, No. 19220, 8 pages (Sep. 2021).
Accession No. 1 IRL_A chain A Interleukin-2; 1 page (Aug. 25, 1995).

* cited by examiner

FIG. 2

*Homo sapiens*
CD80 (B7-1)

```
                                           vihvtk evkevatlsc ghnvsveela qtriywqkek kmvltmmsgd mniwpeyknr tifditnnls ivilalrpsd egtyecvvlk yekdafkreh laevtlsvka dftpsisdf eiptsnirri icstsggfpe phlswlenge elnainttvs qdpetelyav sskldfnmtt nhsfmcliky ghlrvnqtfn wnttkqehfp dnllpswait lisvngifvi ccltycfapr crerrrnerl rresvrpv (SEQ ID NO:1)
```

FIG. 3
4-1-BBL
*Homo sapiens*
GenBank NP_003802
Cytoplasmic domain = 1-25
Transmembrane domain = 26-48
Ectodomain = 49-254
TNF homology domain = 80-254, 81-254, or 80-246

```
  1 MEYASDASLD PEAPWPPAPR ARACRVLPWA LVAGLLLLL LAAACAVFLA CPWAVSGARA
 61 SPGSAASPRL REGPELSPDD PAGLLDLRQG MFAQLVAQNV LLIDGPLSWY SDPGLAGVSL
121 TGGLSYKEDT KELVVAKAGV YYVFFQLELR RVVAGEGSGS VSLALHLQPL RSAAGAAALA
181 LTVDLPPASS EARNSAFGFQ GRLLHLSAGQ RLGVHLHTEA RARHAWQLTQ GATVLGLFRV
241 TPEIPAGLPS PRSE (SEQ ID NO:47)
```

FIG. 4A
CD28 isoform 1
*Homo sapiens*
Mature protein amino acids 19-220

```
  1 mlrlllalnl fpsiqvtgnk ilvkqspmlv aydnavnlsc kysynlfsre fraslhkgld
 61 savevcvvyg nysqqlqvys ktgfncdgkl gnesvtfylq nlyvnqtdiy fckievmypp
121 pyldneksng tiihvkgkhl cpsplfpgps kpfwvlvvvg gvlacysllv tvafiifwvr
181 skrsrllhsd ymmmtprrpg ptrkhyqpya pprdfaayrs (SEQ ID NO:48)
```

FIG. 4B
CD28 isoform 2
*Homo sapiens*
Mature protein amino acids 19-123

```
  1 mlrlllalnl fpsiqvtgnk ilvkqspmlv aydnavnlsw khlcpsplfp gpskpfwvlv
 61 vvggvlacys llvtvafiif wvrskrsrll hsdymmmtpr rpgpptrkhyq pyapprdfaa
121 yrs (SEQ ID NO:49)
```

FIG. 4C
CD28 isoform 2
*Homo sapiens*
Mature protein amino acids 19-101

```
  1 mlrlllalnl fpsiqvtgkh lcpsplfpgp skpfwvlvvv ggvlacysll vtvafiifwv
 61 rskrsrllhs dymmmtprrp gptrkhyqpy apprdfaayr s (SEQ ID NO:50)
```

FIG. 5

*Homo sapiens*

4-1BB

```
  1 mgnscyniva tlllvlnfer trslqdpcsn cpagtfcdnn rnqicspcpp nsfssaggqr
 61 tcdicrqckg vfrtrkecss tsnaecdctp gfhclgagcs mceqdckqgq eltkkgckdc
121 cfgtfndqkr gicrpwtncs ldgksvlvng tkerdvvcgp spadlspgas svtppapare
181 pghspqiisf flaltstall fllfltlrf svvkrgrkkl lyifkqpfmr pvqttqeedg
241 cscrfpeee ggcel (SEQ ID NO:51)
```

Figure 6A
GenBank 3S7G_A
*Homo sapiens* IgG1 Fc (SEQ ID NO:52)
227 aa

```
  1 dkthtcppcp apellggpsv flfppkpkdt lmisrtpevt cvvvdvshed pevkfnwyvd
 61 gvevhnaktk preeqynsty rvvsvltvlh qdwlngkeyk ckvsnkalpa piektiskak
121 gqprepqvyt lppsrdeltk nqvsltclvk gfypsdiave wesngqpenn ykttppvlds
181 dgsfflyskl tvdksrwqqg nvfscsvmhe alhnhytqks lslspgk
```

GenBank AAN76044
*Homo sapiens* IgG2 Fc (amino acids 99-325) (SEQ ID NO:53)
227 aa

```
  1 stkgpsvfpl apcsrstses taalgclvkd yfpepvtvsw nsgaltsgvh tfpavlqssg
 61 lyslssvvtv pssnfgtqty tcnvdhkpsn tkvdktverk ccvecppcpa ppvagpsvfl
121 fppkpkdtlm isrtpevtcv vvdvshedpe vqfnwyvdgv evhnaktkpr eeqfnstfrv
181 vsvltvvhqd wlngkeykck vsnkglpapi ektisktkgq prepqvytlp psreemtknq
241 vsltclvkgf ypsdiavewe sngqpennyk ttppmldsdg sfflyskltv dksrwqqgnv
301 fscsvmheal hnhytqksls lspgk
```

GenBank AAW65947
*Homo sapiens* IgG3 Fc (amino acids 19-246) (SEQ ID NO:54)
238 aa

```
  1 hkpsntkvdk rvelktplgd tthtcppcpa pellggpsvf lfppkpkdtl misrtpevtc
 61 vvvdvshedp evkfnwyvdg vevhnaktkp reeqynstyr vvsvltvlhq dwlngkeykc
121 kvsnkalpap iektiskakg qprepqvytl ppsrdeltkn qvsltclvkg fypsdiavew
181 esngqpenny kttppvldsd gsfflysklt vdksrwqqgn vfscsvmhea lhnhytqksl
241 slspgk
```

Figure 6B

GenBank AAA52770
*Homo sapiens* IgD Fc (amino acids 162-383) (SEQ ID NO:55)
222 aa

```
  1 ptkapdvfpi isgcrhpkdn spvvlaclit gyhptsvtvt wymgtqsqpq rtfpeiqrrd
 61 syymtssqls tplqqwrqge ykcvvqhtas kskkeifrwp espkaqassv ptaqpqaegs
121 lakattapat trntgrggee kkkekekeeq eeretktpec pshtqplgvy lltpavqdlw
181 lrdkatftcf vvgsdlkdah ltwevagkvp tggveeglle rhsngsqsqh srtlprslw
241 nagtsvtctl nhpslppqrl malrepaaqa pvklslnlla ssdppeaasw llcevsgfsp
301 pnillmwled qrevntsgfa parpppqprs ttfwawsvlr vpappspqpa tytcvvshed
361 srtllnasrs levsyvtdhg pmk
```

GenBank O3082221A
*Homo sapiens* IgM Fc (SEQ ID NO:56)
276 aa

```
  1 vtstltikzs dwlgesmftc rvdhrgltfq qnassmcvpd qdtairvfai ppsfasiflt
 61 kstkltclvt dlttybsvti swtreengav kthtnisesh pnatfsavge asicedbdws
121 gerftctvth tdlpsplkqt isrpkgvalh rpbvyllppa rzzlnlresa titclvtgfs
181 padvfvewmq rgeplspqky vtsapmpepq apgryfahsi ltvseeewnt ggtytcvvah
241 ealpnrvter tvdkstgkpt lynvslvmsd tagtcy
```

Figure 6C

GenBank P01876
*Homo sapiens* IgA Fc (amino acids 120-353) (SEQ ID NO:57)
234 aa

```
  1 asptspkvfp lslcstqpdg nvviaclvqg ffpqeplsvt wsesgqgvta rnfppsqdas
 61 gdlyttssql tlpatqclag ksvtchvkhy tnpsqdvtvp cpvpstpptp spstpptpsp
121 scchprlslh rpaledlllg seanltctlt glrdasgvtf twtpssgksa vqgpperdlc
181 gcysvssvlp gcaepwnhgk tftctaaype sktpltatls ksgntfrpev hlpppseel
241 alnelvtltc largfspkdv lvrwlqgsqe lprekyltwa srqepsqgtt tfavtsilrv
301 aaedwkkgdt fscmvgheal plaftqktid rlagkpthvn vsvvmaevdg tcy
```

GenBank 1F6A_B
*Homo sapiens* IgE Fc (amino acids 6-222) (SEQ ID NO:58)
212 aa

```
  1 adpcdsnprg vsaylsrpsp fdlfirkspt itclvvdlap skgtvnltws rasgkpvnhs
 61 trkeekqrng tltvtstlpv gtrdwieget yqcrvthphl pralmrsttk tsgpraapev
121 yafatpewpg srdkrtlacl iqnfmpedis vqwlhnevql pdarhsttqp rktkgsffv
181 fsrlevtrae weqkdeficr avheaaspsq tvqravsvnp gk
```

GenBank P01861
*Homo sapiens* IgG4 Fc (amino acids 100-327) (SEQ ID NO:59)
228 aa

```
  1 astkgpsvfp lapcsrstse staalgclvk dyfpepvtvs wnsgaltsgv htfpavlqss
 61 glyslssvvt vpssslgtkt ytcnvdhkps ntkvdkrves kygppcpscp apeflggpsv
121 flfppkpkdt lmisrtpevt cvvvdvsqed pevqfnwyvd gvevhnaktk preeqfnsty
181 rvvsvltvlh qdwlngkeyk ckvsnkglps siektiskak gqprepqvyt lppsqeemtk
241 nqvsltclvk gfypsdiave wesngqpenn ykttppvlds dgsfflysrl tvdksrwqeg
301 nvfscsvmhe alhnhytqks lslslgk
```

Figure 7A
*Homo sapiens*
GenBank NP_001229687
HLA-A
Amino acids 25-365 (SEQ ID NO:60)

```
  1 mavmaprtll lllsgalalt qtwagshsmr yfftsvsrpg rgeprfiavg yvddtqfvrf
 61 dsdaasqkme prapwieqeg peywdqetrn mkahsqtdra nlgtlrgyyn qsedgshtiq
121 imygcdvgpd grflrgyrqd aydgkdyial nedlrswtaa dmaaqitkrk weavhaaeqr
181 rvylegrcvd glrrylengk etlqrtdppk thmthhpisd heatlrcwal gfypaeitlt
241 wqrdgedqtq dtelvetrpa gdgtfqkwaa vvvpsgeeqr ytchvqhegl pkpltlrwel
301 ssqptipivg iiaglvllga vitgavvaav mwrrkssdrk ggsytqaass dsaggsdvsl
361 tackv
```

Figure 7B
*Homo sapiens*
GenBank NP_005505
HLA-B
Amino acids 25-362 (SEQ ID NO:61)

```
  1 mlvmaprtvl lllsaalalt etwagshsmr yfytsvsrpg rgeprfisvg yvddtqfvrf
 61 dsdaaspree prapwieqeg peywdrntqi ykaqaqtdre slrnlrgyyn qseagshtlq
121 smygcdvgpd grllrghdqy aydgkdyial nedlrswtaa dtaaqitqrk weaareaeqr
181 raylegecve wlrrylengk dkleradppk thvthhpisd heatlrcwal gfypaeitlt
241 wqrdgedqtq dtelvetrpa gdrtfqkwaa vvvpsgeeqr ytchvqhegl pkpltlrwep
301 ssqstvpivg ivaglavlav vvigavvaav mcrrkssggk ggsysqaacs dsaggsdvsl
361 ta
```

Figure 7C
*Homo sapiens*
GenBank NP_001229971
HLA-C
Amino acids 25-366 (SEQ ID NO:62)

```
  1 mrvmaprall lllsgglalt etwacsshsmr yfdtavsrpg rgeprfisvg yvddtqfvrf
 61 dsdaasprge prapwveqeg peywdretqn ykrqaqadrv slrnlrgyyn qsedgshtlq
121 rmygcdlgpd grlrgydqs aydgkdyial nedlrswtaa dtaaqitqrk leaaraaeql
181 raylegtcve wlrrylengk etlqraeppk thvthhplsd heatlrcwal gfypaeitlt
241 wqrdgedqtq dtelvetrpa gdgtfqkwaa vvvpsgqeqr ytchmqhegl qepltlswep
301 ssqptipimg ivaglavlvv lavlgavvta mmcrrkssgg kggscsqaac snsaggsdes
361 litcka
```

FIG. 8

```
NP_004039.1      MSRSVALAVLALLSLSGLEAIQRTPKIQVYSRHPAENGKSNFLNCYVSGFHPSDIEVDLL  60
NP_001009066.1   MSRSVALAVLALLSLSGLEAIQRTPKIQVYSRHPAENGKSNFLNCYVSGFHPSDIEVDLL  60
NP_001040602.1   MSRSVALAVLALLSLSGLEAIQRTPKIQVYSRHPPENGKPNFLNCYVSGFHPSDIEVDLL  60
NP_776318.1      MARFVALVLIGLLSLSGLDAIQRPKIQVYSRHPPEDGKPNYLNCYVYGFHPPQIEIDLL  60
NP_033865.2      MARSVTLVFLVLVSLTGLYAIQKTPQIQVYSRHPFENGKPNILNCYVTQFHPFHIEIQML  60
                 *:  *::*.::: *: .**  **. *:****:**  :.*:.*:****.. **:**::*

NP_004039.1      KNGERIEKVEHSDLSFSKDWSFYLLYYTEFTPTEKDEYACRVNHVTLSQEKIVWDRDM   119
NP_001009066.1   KNGERIEKVEHSDLSFSKDWSFYLLYYTEFTPTEKDEYACRVNHVTLSQEKIVWDRDM   119
NP_001040602.1   KNGERIEKMGKVEHSDLSFSKDWSFYLLYTEFTPNEKDEYACRVNHVTLSGPRTVWDRDM  119
NP_776318.1      KMGEKI-KSEQSDLSFSKDWSFYLLSHAEFTPMSKDQYSCRVHVTLEQPRIVWDRDLL  118
NP_033865.2      KNGKKIPKVEMSDMSFSKDWSFYILAHTEFTPTETDTYACRVKHASMAEPRTVYWDRDM  119
                 * *::  *  .**:***:*****: :. ***   * *:***:: : :  *  :***
```

FIG. 10A

>290
atgtctcgctccgtggccttagctgtgctcgcgctactctctctttctggcctggaggccGTTATCCACGTGACCAAGGAA
GTGAAAGAAGTGGCAACGCTGTCCTGTGGTCACAATGTTTCTGTTGAAGAGCTGGCA
CAAACTCGCATCTACTGGCAAAAGGAGAAGAAAATGGTGCTGACTATGATGTCTGG
GGACATGAATATATGGCCCGAGTACAAGAACCGGACCATCTTTGATATCACTAATAA
CCTCTCCATTGTGATCCTGGCTCTGCGCCCATCTGACGAGGGCACATACGAGTGTGTT
GTTCTGAAGTATGAAAAGACGCTTTCAAGCGGGAACACCTGGCTGAAGTGACGTTA
TCAGTCAAAGCTGACTTCCCTACACCTAGTATATCTGACTTTGAAATTCCAACTTCTA
ATATTAGAAGGATAATTTGCTCAACCTCTGGAGGTTTTCCAGAGCCTCACCTCTCCTG
GTTGGAAAATGGAGAAGAATTAAATGCCATCAACACAACAGTTTCCCAAGATCCTGA
AACTGAGCTCTATGCTGTTAGCAGCAAACTGGATTTCAATATGACAACCAACCACAG
CTTCATGTGTCTCATCAAGTATGGACATTTAAGAGTGAATCAGACCTTCAACTGGAA
TACAACCAAGCAAGAGCATTTTCCTGATAACGGAGGCGGAGGATCTGGTGGTGGAG
GTTCTGGTGGTGGGGGATCTGGAGGCGGAGGATCTGGCCCGCATTCCCTGCGCTACT
TTGTGACCGCTGTTAGCCGCCCGGGCCTGGGTGAACCGCGTTACATGGAGGTCGGTT
ATGTGGATGACACGGAGTTTGTGCGTTTCGATTCAGACGCTGAGAACCCGCGTTACG
AACCGCGTGCAAGATGGATGGAACAGGAAGGCCCGGAATATTGGGAAAGAGAGACC
CAAAAGGCAAAAGGCAACGAACAAAGCTTCCGTGTGGACCTGCGTACCCTGCTGGG
CGCCTACAACCAATCAAAAGGTGGCTCGCACACGATCCAGGTGATCAGCGGCTGCG
AGGTTGGTAGCGATGGCCGTCTGCTGCGCGGCTATCAGCAATACGCCTACGACGGTT
GCGATTATATCGCACTGAATGAAGACCTGAAAACCTGGACGGCGGCCGATATGGCA
GCTCTGATTACGAAGCACAAATGGGAACAGGCTGGCGAGGCGGAAAGACTGCGCGC
CTACCTGGAGGGTACCTGCGTGGAATGGCTGCGTCGCTATCTGAAGAACGGCAATGC
CACCTTGCTGCGTACGGATAGCCCGAAAGCACATGTTACCCACCACAGCCGCCCCGA
GGACAAGGTTACGCTGCGTTGTTGGGCTCTGGGCTTTTATCCGGCGGATATTACCCTG
ACGTGGCAGCTGAACGGTGAAGAGCTGATCCAAGATATGGAACTGGTGGAAACCCG
TCCGTGCGGCGATGGCACGTTCCAGAAATGGGCAAGCGTGGTTGTCCCGCTGGGTAA
AGAACAATACTACACCTGTCATGTTTACCACCAGGGTCTGCCGGAACCGCTGACGCT
GCGTTGGGCAGCTGCGGGTGGCCCCAGAGGGCCCACAATCAAGCCCTGTCCTCCATG
CAAATGCCCAGCACCTAACCTCTTGGGTGGACCATCCGTCTTCATCTTCCCTCCAAAG
ATCAAGGATGTACTCATGATCTCCCTGAGCCCCATAGTCACATGTGTGGTGGTGGAT
GTGAGCGAGGATGACCCAGATGTCCAGATCAGCTGGTTTGTGAACAACGTGGAAGT
ACACACAGCTCAGACACAAACCCATAGAGAGGATTACAACAGTACTCTCCGGGTGG
TCAGTGCCCTCCCCATCCAGCACCAGGACTGGATGAGTGGCAAGGAGTTCAAATGCA
AGGTCAACAACAAAGACCTCCCAGCGCCCATCGAGAGAACCATCTCAAAACCCAAA
GGGTCAGTAAGAGCTCCACAGGTATATGTCTTGCCTCCACCAGAAGAAGAGATGACT
AAGAAACAGGTCACTCTGACCTGCATGGTCACAGACTTCATGCCTGAAGACATTTAC
GTGGAGTGGACCAACAACGGGAAAACAGAGCTAAACTACAAGAACACTGAACCAGT
CCTGGACTCTGATGGTTCTTACTTCATGTACAGCAAGCTGAGAGTGGAAAAGAAGAA
CTGGGTGGAAAGAAATAGCTACTCCTGTTCAGTGGTCCACGAGGGTCTGCACAATCA
CCACACGACTAAGAGCTTCTCCCGGACTCCGGGTAAAGGCGGATCACATCACCATCA
CCATCACCATCACTAGTGA (SEQ ID NO:68)

FIG. 10B

<u>290</u> (wild-type CD80; linker; MHC Class I heavy chain; γ2a Fc)

MSRSVALAVLALLSLSGLEA<u>VIHVTKEVKEVATLSCGHNVSVEELAQTRIYWQKEKKM
VLTMMSGDMNIWPEYKNRTIFDITNNLSIVILALRPSDEGTYECVVLKYEKDAFKREHLA
EVTLSVKADFPTPSISDFEIPTSNIRRIICSTSGGFPEPHLSWLENGEELNAINTTVSQDPETE
LYAVSSKLDFNMTTNHSFMCLIKYGHLRVNQTFNWNTTKQEHFPDN</u>**GGGGSGGGGSG
GGGSGGGGSG**<u>PHS</u>LRYFVTAVSRPGLGEPRYMEVGYVDDTEFVRFDSDAENPRYEPRA
RWMEQEGPEYWERETQKAKGNEQSFRVDLRTLLGAYNQSKGGSHTIQVISGCEVGSDG
RLLRGYQQYAYDGCDYIALNEDLKTWTAADMAALITKHKWEQAGEAERLRAYLEGTC
VEWLRRYLKNGNATLLRTDSPKAHVTHHSRPEDKVTLRCWALGFYPADITLTWQLNGE
ELIQDMELVETRPCGDGTFQKWASVVVPLGKEQYYTCHVYHQGLPEPL<u>TLRW</u>AAA*GGP
RGPTIKPCPPCKCPAPNLLGGPSVFIFPPKIKDVLMISLSPIVTCVVVDVSEDDPDVQISWF
VNNVEVHTAQTQTHREDYNSTLRVVSALPIQHQDWMSGKEFKCKVNNKDLPAPIERTIS
KPKGSVRAPQVYVLPPPEEEMTKKQVTLTCMVTDFMPEDIYVEWTNNGKTELNYKNTE
PVLDSDGSYFMYSKLRVEKKNWVERNSYSCSVVHEGLHNHHTTKSFSRTPGK*GGSHHH
HHHHH (SEQ ID NO:69)

FIG. 10C
>345
ATGTCCCGCTCCGTGGCGCTTGCGGTGCTGGCCCTGCTGTCGTTGTCCGGGCTGGAAG
CGTCCATTATCAACTTCGAGAAACTGGGGGGAGGAGCCTCAGGAGGAGGAGGATCC
GGGGGTGGAGGTAGCATGATTCAAAAGACCCCTCAAATCCAGGTCTACTCGTGCCAC
CCACCCGAGAACGGAAAGCCTAATATCCTGAACTGTTACGTGACCCAATTCCACCCG
CCGCATATCGAGATCCAGATGCTCAAGAACGGCAAGAAGATCCCCAAGGTGGAAAT
GTCCGACATGAGCTTTTCCAAGGATTGGTCGTTCTATATCCTGGCTCATACCGAGTTC
ACCCCCACCGAAACCGATACTTACGCCTGCCGCGTCAAGCACGCCTCAATGGCGGAG
CCTAAGACCGTGTACTGGGACCGGGACATGGGTGGCGGGGGGTCCGGAGGAGGTGG
ATCCGGCGGAGGGGGATCTGGCGGAGGCGGATCAGGAGGTGGCGGCTCTGACCCTG
CAGGCCTGCTGGATCTGCGGCAGGGCATGTTCGCACAACTCGTGGCCCAGAACGTGC
TGCTGATCGATGGACCGCTGTCCTGGTACTCCGACCCGGGACTTGCCGGAGTGTCAC
TGACTGGAGGATTGTCCTACAAGGAAGATACGAAGGAGCTCGTCGTGGCGAAGGCC
GGAGTGTACTATGTGTTCTTCCAGCTCGAACTCCGGAGAGTCGTGGCCGGGGAAGGC
TCCGGCTCCGTGTCACTTGCCCTGCACCTCCAGCCACTTCGGTCGGCCGCTGGAGCCG
CCGCACTGGCCCTGACCGTCGACCTCCCTCCTGCGTCCTCCGAGGCTCGCAACTCGGC
CTTCGGATTCCAAGGGCGCCTTCTGCACCTGTCCGCGGGACAGAGGCTGGGGGTGCA
TCTGCATACTGAAGCGCGGGCACGGCATGCTTGGCAGCTGACTCAGGGAGCAACTGT
CCTGGGTCTGTTCCGCGTGACTCCGGAAATCCCCGCCGGTGGAGGTGGCTCAGGAGG
CGGCGGCAGCGGTGGAGGAGGGAGCGGAGGAGGCGGATCCGGTGGAGGCGGAAGC
GACCCTGCCGGACTCCTGGATCTGCGGCAGGGCATGTTCGCCCAGTTGGTGGCGCAG
AACGTCCTGCTCATTGACGGGCCGCTGTCGTGGTACAGCGATCCGGGCTTGGCCGGA
GTCTCGCTGACCGGAGGACTCAGCTACAAGGAAGATACCAAGGAGCTGGTCGTGGC
CAAGGCCGGAGTGTACTACGTGTTCTTCCAACTGGAACTGCGCCGGGTGGTGGCTGG
CGAAGGATCCGGGTCGGTGTCCCTGGCCCTGCATCTGCAGCCTCTGCGCTCAGCCGC
AGGAGCAGCCGCCTTGGCGCTCACCGTGGACCTTCCGCCCGCCTCCTCGGAAGCCCG
GAACAGCGCCTTCGGCTTCCAAGGCAGACTCCTGCACTTGAGCGCGGGCCAGAGACT
GGGAGTGCACCTCCACACCGAAGCGCGCGCAAGGCACGCCTGGCAGCTCACCCAGG
GAGCCACCGTGCTGGGCTTGTTTCGAGTCACCCCCGAGATCCCAGCCGGCGGAGGAG
GTTCCGGTGGCGGTGGATCAGGCGGTGGAGGCTCGGGTGGAGGGGGTAGCGGAGGG
GGTGGTTCCGACCCCGCAGGACTGCTGGACCTCCGGCAGGGGATGTTCGCGCAACTG
GTGGCTCAGAATGTCCTGCTGATTGACGGCCCCCTGTCGTGGTACTCGGACCCTGGC
CTTGCCGGCGTGTCCTTGACTGGAGGGCTGTCGTACAAGGAGGACACTAAGGAGCTG
GTCGTGGCCAAAGCCGGCGTGTACTACGTGTTCTTTCAGCTGGAACTGAGGAGAGTG
GTGGCGGGAGAAGGCAGCGGCTCAGTGTCCCTCGCCCTGCACCTTCAACCACTCCGC
TCTGCCGCTGGTGCAGCTGCGCTCGCCCTCACTGTGGATCTTCCACCGGCAAGCTCCG
AGGCCAGAAACTCCGCCTTCGGGTTCCAGGGGAGGCTGCTGCATCTCTCCGCCGGCC
AGAGACTGGGCGTGCACTTGCACACTGAGGCTAGGGCTCGCCATGCCTGGCAGCTGA
CCCAGGGCGCCACTGTGCTGGGACTGTTCCGGGTGACCCCAGAAATCCCGGCCTCCT
GATAG (SEQ ID NO:70)

FIG. 10D 345 (β2M signal peptide; OVA epitope; β2M polypeptide; linker; wt 4-1BBL; linker; wt 4-1BBL; linker; wt 4-1BBL)

*MSRSVALAVLALLSLSGLEA*SIINFEKL*GGGASGGGGSGGGGSMIQKTPQIQVYSCHPPEN GKPNILNCYVTQFHPPHIEIQMLKNGKKIPKVEMSDMSFSKDWSFYILAHTEFTPTETDT YACRVKHASMAEPKTVYWDRDMGGGGSGGGGSGGGGSGGGGSGGGGS*DPAGLLDL RQGMFAQLVAQNVLLIDGPLSWYSDPGLAGVSLTGGLSYKEDTKELVVAKAGVYYVFF QLELRRVVAGEGSGSVSLALHLQPLRSAAGAAALALTVDLPPASSEARNSAFGFQGRLL HLSAGQRLGVHLHTEARARHAWQLTQGATVLGLFRVTPEIPAGGGGSGGGGSGGGGS GGGGSGGGGSDPAGLLDLRQGMFAQLVAQNVLLIDGPLSWYSDPGLAGVSLTGGLSY KEDTKELVVAKAGVYYVFFQLELRRVVAGEGSGSVSLALHLQPLRSAAGAAALALTVD LPPASSEARNSAFGFQGRLLHLSAGQRLGVHLHTEARARHAWQLTQGATVLGLFRVTPE IPAGGGGSGGGGSGGGGSGGGGSGGGGSDPAGLLDLRQGMFAQLVAQNVLLIDGPLS WYSDPGLAGVSLTGGLSYKEDTKELVVAKAGVYYVFFQLELRRVVAGEGSGSVSLALH LQPLRSAAGAAALALTVDLPPASSEARNSAFGFQGRLLHLSAGQRLGVHLHTEARARHA WQLTQGATVLGLFRVTPEIPAS (SEQ ID NO:71)

FIG. 10E

>348
ATGTCCCGCTCCGTGGCGCTTGCGGTGCTGGCCCTGCTGTCGTTGTCCGGGCTGGAAG
CGTCCATTATCAACTTCGAGAAACTGGGGGGAGGAGCCTCAGGAGGAGGAGGATCC
GGGGGTGGAGGTAGCATGATTCAAAAGACCCCTCAAATCCAGGTCTACTCGTGCCAC
CCACCCGAGAACGGAAAGCCTAATATCCTGAACTGTTACGTGACCCAATTCCACCCG
CCGCATATCGAGATCCAGATGCTCAAGAACGGCAAGAAGATCCCCAAGGTGGAAAT
GTCCGACATGAGCTTTTCCAAGGATTGGTCGTTCTATATCCTGGCTCATACCGAGTTC
ACCCCCACCGAAACCGATACTTACGCCTGCCGCGTCAAGCACGCCTCAATGGCGGAG
CCTAAGACCGTGTACTGGGACCGGGACATGGGTGGCGGGGGGTCCGGAGGAGGTGG
ATCCGGCGGAGGGGGATCTGGCGGAGGCGGATCAGGAGGTGGCGGCTCTGCCTGCC
CCTGGGCCGTGTCCGGGGCTCGCGCCTCGCCCGGCTCCGCGGCCAGCCCGAGACTCC
GCGAGGGTCCCGAGCTTTCGCCCGACGACCCTGCAGGCCTGCTGGATCTGCGGCAGG
GCATGTTCGCACAACTCGTGGCCCAGAACGTGCTGCTGATCGATGGACCGCTGTCCT
GGTACTCCGACCCGGGACTTGCCGGAGTGTCACTGACTGGAGGATTGTCCTACAAGG
AAGATACGAAGGAGCTCGTCGTGGCGAAGGCCGGAGTGTACTATGTGTTCTTCCAGC
TCGAACTCCGGAGAGTCGTGGCCGGGGAAGGCTCCGGCTCCGTGTCACTTGCCCTGC
ACCTCCAGCCACTTCGGTCGGCCGCTGGAGCCGCCGCACTGGCCCTGACCGTCGACC
TCCCTCCTGCGTCCTCCGAGGCTCGCAACTCGGCCTTCGGATTCCAAGGGCGCCTTCT
GCACCTGTCCGCGGGACAGAGGCTGGGGGTGCATCTGCATACTGAAGCGCGGGCAC
GGCATGCTTGGCAGCTGACTCAGGGAGCAACTGTCCTGGGTCTGTTCCGCGTGACTC
CGGAAATCCCCGCCGGTGGAGGTGGCTCAGGAGGCGGCGGCAGCGGTGGAGGAGGG
AGCGGAGGAGGCGGATCCGGTGGAGGCGGAAGCGACCCTGCCGGACTCCTGGATCT
GCGGCAGGGCATGTTCGCCCAGTTGGTGGCGCAGAACGTCCTGCTCATTGACGGGCC
GCTGTCGTGGTACAGCGATCCGGGCTTGGCCGGAGTCTCGCTGACCGGAGGACTCAG
CTACAAGGAAGATACCAAGGAGCTGGTCGTGGCCAAGGCCGGAGTGTACTACGTGT
TCTTCCAACTGGAACTGCGCCGGGTGGTGGCTGGCGAAGGATCCGGGTCGGTGTCCC
TGGCCCTGCATCTGCAGCCTCTGCGCTCAGCCGCAGGAGCAGCCGCCTTGGCGCTCA
CCGTGGACCTTCCGCCCGCCTCCTCGGAAGCCCGGAACAGCGCCTTCGGCTTCCAAG
GCAGACTCCTGCACTTGAGCGCGGGCCAGAGACTGGGAGTGCACCTCCACACCGAA
GCGCGCGCAAGGCACGCCTGGCAGCTCACCCAGGGAGCCACCGTGCTGGGCTTGTTT
CGAGTCACCCCCGAGATCCCAGCCGGCGGAGGAGGTTCCGGTGGCGGTGGATCAGG
CGGTGGAGGCTCGGGTGGAGGGGGTAGCGGAGGGGGTGGTTCCGACCCCGCAGGAC
TGCTGGACCTCCGGCAGGGGATGTTCGCGCAACTGGTGGCTCAGAATGTCCTGCTGA
TTGACGGCCCCCTGTCGTGGTACTCGGACCCTGGCCTTGCCGGCGTGTCCTTGACTGG
AGGGCTGTCGTACAAGGAGGACACTAAGGAGCTGGTCGTGGCCAAAGCCGGCGTGT
ACTACGTGTTCTTTCAGCTGGAACTGAGGAGAGTGGTGGCGGGAGAAGGCAGCGGC
TCAGTGTCCCTCGCCCTGCACCTTCAACCACTCCGCTCTGCCGCTGGTGCAGCTGCGC
TCGCCCTCACTGTGGATCTTCCACCGGCAAGCTCCGAGGCCAGAAACTCCGCCTTCG
GGTTCCAGGGGAGGCTGCTGCATCTCTCCGCCGGCCAGAGACTGGGCGTGCACTTGC
ACACTGAGGCTAGGGCTCGCCATGCCTGGCAGCTGACCCAGGGCGCCACTGTGCTGG
GACTGTTCCGGGTGACCCCAGAAATCCCGGCCTCCTGATAG (SEQ ID NO:72)

FIG. 10F

348 (β2M signal peptide; OVA epitope; β2M polypeptide; linker; wild-type 4-1BBL; linker; wild-type 4-1BBL; linker; and wild-type 4-1BBL)

*MSRSVALAVLALLSLSGLEA*SIINFEKL*GGGASGGGGSGGGGSMIQKTPQIQVYSCHPPEN GKPNILNCYVTQFHPPHIEIQMLKNGKKIPKVEMSDMSFSKDWSFYILAHTEFTPTETDT YACRVKHASMAEPKTVYWDRDMGGGGSGGGGSGGGGSGGGGSGGGGS*ACPWAVSG ARASPGSAASPRLREGPELSPDDPAGLLDLRQGMFAQLVAQNVLLIDGPLSWYSDPGLA GVSLTGGLSYKEDTKELVVAKAGVYYVFFQLELRRVVAGEGSGSVSLALHLQPLRSAA GAAALALTVDLPPASSEARNSAFGFQGRLLHLSAGQRLGVHLHTEARARHAWQLTQGA TVLGLFRVTPEIPAGGGGSGGGGSGGGGSGGGGSGGGGSDPAGLLDLRQGMFAQLV AQNVLLIDGPLSWYSDPGLAGVSLTGGLSYKEDTKELVVAKAGVYYVFFQLELRRVVA GEGSGSVSLALHLQPLRSAAGAAALALTVDLPPASSEARNSAFGFQGRLLHLSAGQRLG VHLHTEARARHAWQLTQGATVLGLFRVTPEIPAGGGGSGGGGSGGGGSGGGGSGGG GSDPAGLLDLRQGMFAQLVAQNVLLIDGPLSWYSDPGLAGVSLTGGLSYKEDTKELVV AKAGVYYVFFQLELRRVVAGEGSGSVSLALHLQPLRSAAGAAALALTVDLPPASSEARN SAFGFQGRLLHLSAGQRLGVHLHTEARARHAWQLTQGATVLGLFRVTPEIPAS (SEQ ID NO:73)

FIG. 10G

>639
atgtctcgctccgtggccttagctgtgctcgcgctactctctctttctggcctggaggccGTTATCCACGTGACCAAGGAA
GTGAAAGAAGTGGCAACGCTGTCCTGTGGTCACAATGTTTCTGTTGAAGAGCTGGCA
CAAACTCGCATCTACTGGCAAAAGGAGAAGAAATGGTGCTGACTATGATGTCTGG
GGACATGAATATATGGCCCGAGTACAAGAACCGGACCATCTTTGATATCACTAATAA
CCTCTCCATTGTGATCCTGGCTCTGCGCCCATCTGACGAGGGCACATACGAGTGTGTT
GTTCTGGCCTATGAAAAGACGCTTTCAAGCGGGAACACCTGGCTGAAGTGACGTTA
TCAGTCAAAGCTGACTTCCCTACACCTAGTATATCTGACTTTGAAATTCCAACTTCTA
ATATTAGAAGGATAATTTGCTCAACCTCTGGAGGTTTTCCAGAGCCTCACCTCTCCTG
GTTGGAAAATGGAGAAGAATTAAATGCCATCAACACAACAGTTTCCCAAGATCCTGA
AACTGAGCTCTATGCTGTTAGCAGCAAACTGGATTTCAATATGACAACCAACCACAG
CTTCATGTGTCTCATCAAGTATGGACATTTAAGAGTGAATCAGACCTTCAACTGGAA
TACAACCAAGCAAGAGCATTTTCCTGATAACGGAGGCGGAGGATCTGGTGGTGGAG
GTTCTGGTGGTGGGGGATCTGGAGGCGGAGGATCTGGCCCGCATTCCCTGCGCTACT
TTGTGACCGCTGTTAGCCGCCCGGGCCTGGGTGAACCGCGTTACATGGAGGTCGGTT
ATGTGGATGACACGGAGTTTGTGCGTTTCGATTCAGACGCTGAGAACCCGCGTTACG
AACCGCGTGCAAGATGGATGGAACAGGAAGGCCCGGAATATTGGGAAAGAGAGACC
CAAAAGGCAAAAGGCAACGAACAAAGCTTCCGTGTGGACCTGCGTACCCTGCTGGG
CGCCTACAACCAATCAAAAGGTGGCTCGCACACGATCCAGGTGATCAGCGGCTGCG
AGGTTGGTAGCGATGGCCGTCTGCTGCGCGGCTATCAGCAATACGCCTACGACGGTT
GCGATTATATCGCACTGAATGAAGACCTGAAAACCTGGACGGCGGCCGATATGGCA
GCTCTGATTACGAAGCACAAATGGGAACAGGCTGGCGAGGCGGAAAGACTGCGCGC
CTACCTGGAGGGTACCTGCGTGGAATGGCTGCGTCGCTATCTGAAGAACGGCAATGC
CACCTTGCTGCGTACGGATAGCCCGAAAGCACATGTTACCACCACAGCCGCCCCGA
GGACAAGGTTACGCTGCGTTGTTGGGCTCTGGGCTTTTATCCGGCGGATATTACCCTG
ACGTGGCAGCTGAACGGTGAAGAGCTGATCCAAGATATGGAACTGGTGGAAACCCG
TCCGTGCGGCGATGGCACGTTCCAGAAATGGGCAAGCGTGGTTGTCCCGCTGGGTAA
AGAACAATACTACACCTGTCATGTTTACCACCAGGGTCTGCCGGAACCGCTGACGCT
GCGTTGGGCAGCTGCGGGTGGCCCCAGAGGGCCCACAATCAAGCCCTGTCCTCCATG
CAAATGCCCAGCACCTAACGCCGCCGGTGGACCATCCGTCTTCATCTTCCCTCCAAA
GATCAAGGATGTACTCATGATCTCCCTGAGCCCCATAGTCACATGTGTGGTGGTGGA
TGTGAGCGAGGATGACCCAGATGTCCAGATCAGCTGGTTTGTGAACAACGTGGAAGT
ACACACAGCTCAGACACAAACCCATAGAGAGGATTACAACAGTACTCTCCGGGTGG
TCAGTGCCCTCCCCATCCAGCACCAGGACTGGATGAGTGGCAAGGAGTTCAAATGCA
AGGTCAACAACAAAGACCTCCCAGCGCCCATCGAGAGAACCATCTCAAAACCCAAA
GGGTCAGTAAGAGCTCCACAGGTATATGTCTTGCCTCCACCAGAAGAAGAGATGACT
AAGAAACAGGTCACTCTGACCTGCATGGTCACAGACTTCATGCCTGAAGACATTTAC
GTGGAGTGGACCAACAACGGGAAAACAGAGCTAAACTACAAGAACACTGAACCAGT
CCTGGACTCTGATGGTTCTTACTTCATGTACAGCAAGCTGAGAGTGGAAAAGAAGAA
CTGGGTGGAAAGAAATAGCTACTCCTGTTCAGTGGTCCACGAGGGTCTGCACAATCA
CCACACGACTAAGAGCTTCTCCCGGACTCCGGGTAAAGGCGGATCACATCACCATCA
CCATCACCATCACTAGTGA (SEQ ID NO:74)

FIG. 10H

639 (β2M signal peptide; CD80 variant K86A; linker; MHC Class I H chain; variant γ2a Fc)

MSRSVALAVLALLSLSGLEA<u>VIHVTKEVKEVATLSCGHNVSVEELAQTRIYWQKEKKM
VLTMMSGDMNIWPEYKNRTIFDITNNLSIVILALRPSDEGTYECVVLA̲YEKDAFKREHLA
EVTLSVKADFPTPSISDFEIPTSNIRRIICSTSGGFPEPHLSWLENGEELNAINTTVSQDPETE
LYAVSSKLDFNMTTNHSFMCLIKYGHLRVNQTFNWNTTKQEHFPDN</u>*GGGGSGGGGSG
GGGSGGGGSG*<u>PHS</u>LRYFVTAVSRPGLGEPRYMEVGYVDDTEFVRFDSDAENPRYEPRA
RWMEQEGPEYWERETQKAKGNEQSFRVDLRTLLGAYNQSKGGSHTIQVISGCEVGSDG
RLLRGYQQYAYDGCDYIALNEDLKTWTAADMAALITKHKWEQAGEAERLRAYLEGTC
VEWLRRYLKNGNATLLRTDSPKAHVTHHSRPEDKVTLRCWALGFYPADITLTWQLNGE
ELIQDMELVETRPCGDGTFQKWASVVVPLGKEQYYTCHVYHQGLPEPL<u>TLRW</u>AAA*GGP
RGPTIKPCPPCKCPAPN<u>AA</u>GGPSVFIFPPKIKDVLMISLSPIVTCVVVDVSEDDPDVQISW
FVNNVEVHTAQTQTHREDYNSTLRVVSALPIQHQDWMSGKEFKCKVNNKDLPAPIERTI
SKPKGSVRAPQVYVLPPPEEEMTKKQVTLTCMVTDFMPEDIYVEWTNNGKTELNYKNTE
PVLDSDGSYFMYSKLRVEKKNWVERNSYSCSVVHEGLHNHHTTKSFSRTPGK*GGSHHH
HHHHH (SEQ ID NO:75)

FIG. 10I
>349
ATGTCCCGCTCCGTGGCGCTTGCGGTGCTGGCCCTGCTGTCGTTGTCCGGGCTGGAAG
CGTCCATTATCAACTTCGAGAAACTGGGGGGAGGAGCCTCAGGAGGAGGAGGATCC
GGGGGTGGAGGTAGCATGATTCAAAAGACCCCTCAAATCCAGGTCTACTCGTGCCAC
CCACCCGAGAACGGAAAGCCTAATATCCTGAACTGTTACGTGACCCAATTCCACCCG
CCGCATATCGAGATCCAGATGCTCAAGAACGGCAAGAAGATCCCCAAGGTGGAAAT
GTCCGACATGAGCTTTTCCAAGGATTGGTCGTTCTATATCCTGGCTCATACCGAGTTC
ACCCCCACCGAAACCGATACTTACGCCTGCCGCGTCAAGCACGCCTCAATGGCGGAG
CCTAAGACCGTGTACTGGGACCGGGACATGGGTGGCGGGGGGTCCGGAGGAGGTGG
ATCCGGCGGAGGGGGATCTGGCGGAGGCGGATCAGGAGGTGGCGGCTCTGACCCTG
CAGGCCTGCTGGATCTGCGGCAGGGCATGTTCGCACAACTCGTGGCCCAGAACGTGC
TGCTGATCGATGGACCGCTGTCCTGGTACTCCGACCCGGGACTTGCCGGAGTGTCAC
TGACTGGAGGATTGTCCTACGCCGAAGATACGAAGGAGCTCGTCGTGGCGAAGGCC
GGAGTGTACTATGTGTTCTTCCAGCTCGAACTCCGGAGAGTCGTGGCCGGGGAAGGC
TCCGGCTCCGTGTCACTTGCCCTGCACCTCCAGCCACTTCGGTCGGCCGCTGGAGCCG
CCGCACTGGCCCTGACCGTCGACCTCCCTCCTGCGTCCTCCGAGGCTCGCAACTCGGC
CTTCGGATTCCAAGGGCGCCTTCTGCACCTGTCCGCGGGACAGAGGCTGGGGGTGCA
TCTGCATACTGAAGCGCGGGCACGGCATGCTTGGCAGCTGACTCAGGGAGCAACTGT
CCTGGGTCTGTTCCGCGTGACTCCGGAAATCCCCGCCGGTGGAGGTGGCTCAGGAGG
CGGCGGCAGCGGTGGAGGAGGGAGCGGAGGAGGCGGATCCGGTGGAGGCGGAAGC
GACCCTGCCGGACTCCTGGATCTGCGGCAGGGCATGTTCGCCCAGTTGGTGGCGCAG
AACGTCCTGCTCATTGACGGGCCGCTGTCGTGGTACAGCGATCCGGGCTTGGCCGGA
GTCTCGCTGACCGGAGGACTCAGCTACGCCGAAGATACCAAGGAGCTGGTCGTGGCC
AAGGCCGGAGTGTACTACGTGTTCTTCCAACTGGAACTGCGCCGGGTGGTGGCTGGC
GAAGGATCCGGGTCGGTGTCCCTGGCCCTGCATCTGCAGCCTCTGCGCTCAGCCGCA
GGAGCAGCCGCCTTGGCGCTCACCGTGGACCTTCCGCCCGCCTCCTCGGAAGCCCGG
AACAGCGCCTTCGGCTTCCAAGGCAGACTCCTGCACTTGAGCGCGGGCCAGAGACTG
GGAGTGCACCTCCACACCGAAGCGCGCGCAAGGCACGCCTGGCAGCTCACCCAGGG
AGCCACCGTGCTGGGCTTGTTTCGAGTCACCCCCGAGATCCCAGCCGGCGGAGGAGG
TTCCGGTGGCGGTGGATCAGGCGGTGGAGGCTCGGGTGGAGGGGGTAGCGGAGGGG
GTGGTTCCGACCCCGCAGGACTGCTGGACCTCCGGCAGGGGATGTTCGCGCAACTGG
TGGCTCAGAATGTCCTGCTGATTGACGGCCCCTGTCGTGGTACTCGGACCCTGGCCT
TGCCGGCGTGTCCTTGACTGGAGGGCTGTCGTACGCCGAGGACACTAAGGAGCTGGT
CGTGGCCAAAGCCGGCGTGTACTACGTGTTCTTTCAGCTGGAACTGAGGAGAGTGGT
GGCGGGAGAAGGCAGCGGCTCAGTGTCCCTCGCCCTGCACCTTCAACCACTCCGCTC
TGCCGCTGGTGCAGCTGCGCTCGCCCTCACTGTGGATCTTCCACCGGCAAGCTCCGA
GGCCAGAAACTCCGCCTTCGGGTTCCAGGGGAGGCTGCTGCATCTCTCCGCCGGCCA
GAGACTGGGCGTGCACTTGCACACTGAGGCTAGGGCTCGCCATGCCTGGCAGCTGAC
CCAGGGCGCCACTGTGCTGGGACTGTTCCGGGTGACCCCAGAAATCCCGGCCTCCTG
ATAG (SEQ ID NO:76)

FIG. 10J 349 (β2M; linker; variant 4-1BBL (K127A); linker; variant 4-1BBL (K127A); linker; variant 4-1BBL (K127A))

*MSRSVALAVLALLSLSGLEA*SIINFEKL*GGGASGGGGSGGGGSMIQKTPQIQVYSCHPPEN GKPNILNCYVTQFHPPHIEIQMLKNGKKIPKVEMSDMSFSKDWSFYILAHTEFTPTETDT YACRVKHASMAEPKTVYWDRDM*GGGGSGGGGSGGGGSGGGGSGGGGSDPAGLLDL RQGMFAQLVAQNVLLIDGPLSWYSDPGLAGVSLTGGLSYAEDTKELVVAKAGVYYVFF QLELRRVVAGEGSGSVSLALHLQPLRSAAGAAALALTVDLPPASSEARNSAFGFQGRLL HLSAGQRLGVHLHTEARARHAWQLTQGATVLGLFRVTPEIPAGGGGSGGGGSGGGGS GGGGSGGGGSDPAGLLDLRQGMFAQLVAQNVLLIDGPLSWYSDPGLAGVSLTGGLSY AEDTKELVVAKAGVYYVFFQLELRRVVAGEGSGSVSLALHLQPLRSAAGAAALALTVD LPPASSEARNSAFGFQGRLLHLSAGQRLGVHLHTEARARHAWQLTQGATVLGLFRVTPE IPAGGGGSGGGGSGGGGSGGGGSGGGGSDPAGLLDLRQGMFAQLVAQNVLLIDGPLS WYSDPGLAGVSLTGGLSYAEDTKELVVAKAGVYYVFFQLELRRVVAGEGSGSVSLALH LQPLRSAAGAAALALTVDLPPASSEARNSAFGFQGRLLHLSAGQRLGVHLHTEARARHA WQLTQGATVLGLFRVTPEIPAS (SEQ ID NO:77)

FIG. 10K

>617
atgtctcgctccgtggccttagctgtgctcgcgctactctctctttctggcctggaggccGTTATCCACGTGACCAAGGAA
GTGAAAGAAGTGGCAACGCTGTCCTGTGGTCACAATGTTTCTGTTGAAGAGCTGGCA
CAAACTCGCATCTACTGGCAAAAGGAGAAGAAAATGGTGCTGACTATGATGTCTGG
GGACATGAATATATGGCCCGAGTACAAGAACCGGACCATCTTTGATATCACTAATAA
CCTCTCCATTGTGATCCTGGCTCTGCGCCCATCTGACGAGGGCACATACGAGTGTGTT
GTTCTGGCCTATGAAAAGACGCTTTCAAGCGGGAACACCTGGCTGAAGTGACGTTA
TCAGTCAAAGCTGACTTCCCTACACCTAGTATATCTGACTTTGAAATTCCAACTTCTA
ATATTAGAAGGATAATTTGCTCAACCTCTGGAGGTTTTCCAGAGCCTCACCTCTCCTG
GTTGGAAAATGGAGAAGAATTAAATGCCATCAACACAACAGTTTCCCAAGATCCTGA
AACTGAGCTCTATGCTGTTAGCAGCAAACTGGATTTCAATATGACAACCAACCACAG
CTTCATGTGTCTCATCAAGTATGGACATTTAAGAGTGAATCAGACCTTCAACTGGAA
TACAACCAAGCAAGAGCATTTTCCTGATAACGGAGGCGGAGGATCTGGTGGTGGAG
GTTCTGGTGGTGGGGGATCTGGAGGCGGAGGATCTGGCCCACACTCGATGCGGTATT
TCGAGACCGCCGTGTCCCGGCCCGGCCTCGAGGAGCCCCGGTACATCTCTGTCGGCT
ATGTGGACAACAAGGAGTTCGTGCGCTTCGACAGCGACGCGGAGAATCCGAGATAT
GAGCCGCGGGCGCCGTGGATGGAGCAGGAGGGGCCGGAGTATTGGGAGCGGGAAA
CACAGAAAGCCAAGGGCCAAGAGCAGTGGTTCCGAGTGAGCCTGAGGAACCTGCTC
GGCgccTACAACCAGAGCGCGGGCGGCTCTCACACACTCCAGCAGATGTCTGGCTGTG
ACTTGGGGTCGGACTGGCGCCTCCTCCGCGGGTACCTGCAGTTCGCCTATGAAGGCC
GCGATTACATCGCCCTGAACGAAGACCTGAAAACGTGGACGGCGGCGGACATGGCG
GCGCAGATCACCCGACGCAAGTGGGAGCAGAGTGGTGCTGCAGAGCATTACAAGGC
CTACCTGGAGGGCGAGTGCGTGGAGTGGCTCCACAGATACCTGAAGAACGGGAACG
CGACGCTGCTGCGCACAGATTCCCCAAAGGCACATGTGACCCATCACCCCAGATCTA
AAGGTGAAGTCACCCTGAGGTGCTGGGCCCTGGGCTTCTACCCTGCTGACATCACCC
TGACCTGGCAGTTGAATGGGGAGGAGCTGACCCAGGACATGGAGCTTGTGGAGACC
AGGCCTtGCGGGGATGGAACCTTCCAGAAGTGGGCATCTGTGGTGGTGCCTCTTGGG
AAGGAGCAGAATTACACATGCCGTGTGTACCATGAGGGGCTGCCTGAGCCCCTCACC
CTGAGATGGGCAGCTGCGGGTGGCCCCAGAGGGCCCACAATCAAGCCCTGTCCTCCA
TGCAAATGCCCAGCACCTAACGCCGCCGGTGGACCATCCGTCTTCATCTTCCCTCCAA
AGATCAAGGATGTACTCATGATCTCCCTGAGCCCCATAGTCACATGTGTGGTGGTGG
ATGTGAGCGAGGATGACCCAGATGTCCAGATCAGCTGGTTTGTGAACAACGTGGAA
GTACACACAGCTCAGACACAAACCCATAGAGAGGATTACAACAGTACTCTCCGGGT
GGTCAGTGCCCTCCCCATCCAGCACCAGGACTGGATGAGTGGCAAGGAGTTCAAATG
CAAGGTCAACAACAAAGACCTCCCAGCGCCCATCGAGAGAACCATCTCAAAACCCA
AAGGGTCAGTAAGAGCTCCACAGGTATATGTCTTGCCTCCACCAGAAGAAGAGATG
ACTAAGAAACAGGTCACTCTGACCTGCATGGTCACAGACTTCATGCCTGAAGACATT
TACGTGGAGTGGACCAACAACGGGAAAACAGAGCTAAACTACAAGAACACTGAACC
AGTCCTGGACTCTGATGGTTCTTACTTCATGTACAGCAAGCTGAGAGTGGAAAAGAA
GAACTGGGTGGAAAGAAATAGCTACTCCTGTTCAGTGGTCCACGAGGGTCTGCACAA
TCACCACACGACTAAGAGCTTCTCCCGGACTCCGGGTAAAGGCGGATCACATCACCA
TCACCATCACCATCACTAGTGA (SEQ ID NO:78)

FIG. 10L

617 (β2M signal peptide; variant CD80 (K86A); linker; MHC Class I H Chain; variant γ2a Fc)

MSRSVALAVLALLSLSGLEA<u>VIHVTKEVKEVATLSCGHNVSVEELAQTRIYWQKEKKM
VLTMMSGDMNIWPEYKNRTIFDITNNLSIVILALRPSDEGTYECVVL<u>A</u>YEKDAFKREHLA
EVTLSVKADFPTPSISDFEIPTSNIRRIICSTSGGFPEPHLSWLENGEELNAINTTVSQDPETE
LYAVSSKLDFNMTTNHSFMCLIKYGHLRVNQTFNWNTTKQEHFPDN</u>GGGGSGGGGSG
GGGSGGGGSG<u>PHS</u>MRYFETAVSRPGLEEPRYISVGYVDNKEFVRFDSDAENPRYEPRAP
WMEQEGPEYWERETQKAKGQEQWFRVSLRNLLGAYNQSAGGSHTLQQMSGCDLGSD
WRLLRGYLQFAYEGRDYIALNEDLKTWTAADMAAQITRRKWEQSGAAEHYKAYLEGE
CVEWLHRYLKNGNATLLRTDSPKAHVTHHPRSKGEVTLRCWALGFYPADITLTWQLNG
EELTQDMELVETRPCGDGTFQKWASVVVPLGKEQNYTCRVYHEGLPEPL<u>TLRW</u>AAA*GG
PRGPTIKPCPPCKCPAPN<u>AA</u>GGPSVFIFPPKIKDVLMISLSPIVTCVVVDVSEDDPDVQISW
FVNNVEVHTAQTQTHREDYNSTLRVVSALPIQHQDWMSGKEFKCKVNNKDLPAPIERTI
SKPKGSVRAPQVYVLPPPEEEMTKKQVTLTCMVTDFMPEDIYVEWTNNGKTELNYKNTE
PVLDSDGSYFMYSKLRVEKKNWVERNSYSCSVVHEGLHNHHTTKSFSRTPGK*GGSHHH
HHHHH (SEQ ID NO:79)

FIG. 10M

\>632
ATGTCCCGCTCCGTGGCGCTTGCGGTGCTGGCCCTGCTGTCGTTGTCCGGGCTGGAAG
CGCGAGCCCACTACAACATTGTGACATTTGGGGGAGGAGCCTCAGGAGGAGGAGGA
TCCGGGGGTGGAGGTAGCATGATTCAAAAGACCCCTCAAATCCAGGTCTACTCGTGC
CACCCACCCGAGAACGGAAAGCCTAATATCCTGAACTGTTACGTGACCCAATTCCAC
CCGCCGCATATCGAGATCCAGATGCTCAAGAACGGCAAGAAGATCCCCAAGGTGGA
AATGTCCGACATGAGCTTTTCCAAGGATTGGTCGTTCTATATCCTGGCTCATACCGAG
TTCACCCCCACCGAAACCGATACTTACGCCTGCCGCGTCAAGCACGCCTCAATGGCG
GAGCCTAAGACCGTGTACTGGGACCGGGACATGGGTGGCGGGGGGTCCGGAGGAGG
TGGATCCGGCGGAGGGGGATCTGGCGGAGGCGGATCAGGAGGTGGCGGCTCTGACC
CTGCAGGCCTGCTGGATCTGCGGCAGGGCATGTTCGCACAACTCGTGGCCCAGAACG
TGCTGCTGATCGATGGACCGCTGTCCTGGTACTCCGACCCGGGACTTGCCGGAGTGT
CACTGACTGGAGGATTGTCCTACGCCGAAGATACGAAGGAGCTCGTCGTGGCGAAG
GCCGGAGTGTACTATGTGTTCTTCCAGCTCGAACTCCGGAGAGTCGTGGCCGGGGAA
GGCTCCGGCTCCGTGTCACTTGCCCTGCACCTCCAGCCACTTCGGTCGGCCGCTGGAG
CCGCCGCACTGGCCCTGACCGTCGACCTCCCTCCTGCGTCCTCCGAGGCTCGCAACTC
GGCCTTCGGATTCCAAGGGCGCCTTCTGCACCTGTCCGCGGGACAGAGGCTGGGGGT
GCATCTGCATACTGAAGCGCGGGCACGGCATGCTTGGCAGCTGACTCAGGGAGCAA
CTGTCCTGGGTCTGTTCCGCGTGACTCCGGAAATCCCCGCCGGTGGAGGTGGCTCAG
GAGGCGGCGGCAGCGGTGGAGGAGGGAGCGGAGGAGGCGGATCCGGTGGAGGCGG
AAGCGACCCTGCCGGACTCCTGGATCTGCGGCAGGGCATGTTCGCCCAGTTGGTGGC
GCAGAACGTCCTGCTCATTGACGGGCCGCTGTCGTGGTACAGCGATCCGGGCTTGGC
CGGAGTCTCGCTGACCGGAGGACTCAGCTACGCCGAAGATACCAAGGAGCTGGTCG
TGGCCAAGGCCGGAGTGTACTACGTGTTCTTCCAACTGGAACTGCGCCGGGTGGTGG
CTGGCGAAGGATCCGGGTCGGTGTCCCTGGCCCTGCATCTGCAGCCTCTGCGCTCAG
CCGCAGGAGCAGCCGCCTTGGCGCTCACCGTGGACCTTCCGCCCGCCTCCTCGGAAG
CCCGGAACAGCGCCTTCGGCTTCCAAGGCAGACTCCTGCACTTGAGCGCGGGCCAGA
GACTGGGAGTGCACCTCCACACCGAAGCGCGCGCAAGGCACGCCTGGCAGCTCACC
CAGGGAGCCACCGTGCTGGGCTTGTTTCGAGTCACCCCCGAGATCCCAGCCGGCGGA
GGAGGTTCCGGTGGCGGTGGATCAGGCGGTGGAGGCTCGGGTGGAGGGGGTAGCGG
AGGGGGTGGTTCCGACCCCGCAGGACTGCTGGACCTCCGGCAGGGGATGTTCGCGCA
ACTGGTGGCTCAGAATGTCCTGCTGATTGACGGCCCCCTGTCGTGGTACTCGGACCCT
GGCCTTGCCGGCGTGTCCTTGACTGGAGGGCTGTCGTACAAGGAGGACACTAAGGAG
CTGGTCGTGGCCAAAGCCGGCGTGTACTACGTGTTCTTTCAGCTGGAACTGAGGAGA
GTGGTGGCGGGAGAAGGCAGCGGCTCAGTGTCCCTCGCCCTGCACCTTCAACCACTC
CGCTCTGCCGCTGGTGCAGCTGCGCTCGCCCTCACTGTGGATCTTCCACCGGCAAGCT
CCGAGGCCAGAAACTCCGCCTTCGGGTTCCAGGGGAGGCTGCTGCATCTCTCCGCCG
GCCAGAGACTGGGCGTGCACTTGCACACTGAGGCTAGGGCTCGCCATGCCTGGCAGC
TGACCCAGGGCGCCACTGTGCTGGGACTGTTCCGGGTGACCCCAGAAATCCCGGCCT
CCTGATAG (SEQ ID NO:80)

FIG. 10N 632 (β2M signal peptide; E7 epitope; β2M; linker; variant 4-1BBL (K127A); linker; variant 4-1BBL (K127A); linker; variant 4-1BBL (K127A)

SRSVALAVLALLSLSGLEA<u>RAHYNIVTF</u>*GGGASGGGGSGGGGSMIQKTPQIQVYSCHPPE NGKPNILNCYVTQFHPPHIEIQMLKNGKKIPKVEMSDMSFSKDWSFYILAHTEFTPTETD TYACRVKHASMAEPKTVYWDRDM*GGGGSGGGGSGGGGSGGGGSGGGGS<u>DPAGLLD LRQGMFAQLVAQNVLLIDGPLSWYSDPGLAGVSLTGGLSYAEDTKELVVAKAGVYYVF FQLELRRVVAGEGSGSVSLALHLQPLRSAAGAAALALTVDLPPASSEARNSAFGFQGRLL HLSAGQRLGVHLHTEARARHAWQLTQGATVLGLFRVTPEIPA</u>GGGGSGGGGSGGGGS GGGGSGGGGS<u>DPAGLLDLRQGMFAQLVAQNVLLIDGPLSWYSDPGLAGVSLTGGLSY AEDTKELVVAKAGVYYVFFQLELRRVVAGEGSGSVSLALHLQPLRSAAGAAALALTVD LPPASSEARNSAFGFQGRLLHLSAGQRLGVHLHTEARARHAWQLTQGATVLGLFRVTPE IPA</u>GGGGSGGGGSGGGGSGGGGSGGGGS<u>DPAGLLDLRQGMFAQLVAQNVLLIDGPLS WYSDPGLAGVSLTGGLSYKEDTKELVVAKAGVYYVFFQLELRRVVAGEGSGSVSLALH LQPLRSAAGAAALALTVDLPPASSEARNSAFGFQGRLLHLSAGQRLGVHLHTEARARHA WQLTQGATVLGLFRVTPEIPAS</u> (SEQ ID NO:81)

T-CELL MODULATORY MULTIMERIC POLYPEPTIDES AND METHODS OF USE THEREOF

CROSS-REFERENCE

This application claims the benefit of U.S. Provisional Patent Application No. 62/338,410, filed May 18, 2016, which application is incorporated herein by reference in its entirety.

INTRODUCTION

An adaptive immune response involves the engagement of the T cell receptor (TCR), present on the surface of a T cell, with a small peptide antigen non-covalently presented on the surface of an antigen presenting cell (APC) by a major histocompatibility complex (MHC; also referred to in humans as a human leukocyte antigen (HLA) complex). This engagement represents the immune system's targeting mechanism and is a requisite molecular interaction for T cell modulation (activation or inhibition) and effector function. Following epitope-specific cell targeting, the targeted T cells are activated through engagement of costimulatory proteins found on the APC with counterpart costimulatory proteins the T cells. Both signals—epitope/TCR binding and engagement of APC costimulatory proteins with T cell costimulatory proteins—are required to drive T cell specificity and activation or inhibition. The TCR is specific for a given epitope; however, the costimulatory protein not epitope specific and instead is generally expressed on all T cells or on large T cell subsets.

SUMMARY

The present disclosure provides T-cell modulatory multimeric polypeptides comprising two different immunomodulatory polypeptides, at least one of which is a variant immunomodulatory polypeptide. The present disclosure provides nucleic acids comprising nucleotide sequences encoding the T-cell modulatory multimeric polypeptides, and host cells comprising the nucleic acids. The present disclosure provides methods of modulating the activity of a T cell; the methods comprise contacting the T cell with a T-cell modulatory multimeric polypeptide of the present disclosure.

BRIEF DESCRIPTION OF THE DRAWINGS

FIG. 2 provides an amino acid sequence of a wild-type CD80 polypeptide.

FIG. 3 provides an amino acid sequence of a wild-type 4-1BBL polypeptide.

FIG. 4A-4C provide amino acid sequences of wild-type CD86 polypeptides.

FIG. 5 provides an amino acid sequence of a wild-type 4-1BB polypeptide.

FIG. 6A-6C provide amino acid sequences of immunoglobulin Fc polypeptides.

FIG. 7A-7C provide amino acid sequences of human leukocyte antigen (HLA) Class I heavy chain polypeptides. Signal sequences are underlined.

FIG. 8 provides a multiple amino acid sequence alignment of beta-2 microglobulin (β2M) precursors (i.e., including the leader sequence) from *Homo sapiens* (NP_004039.1; SEQ ID NO:63), *Pan troglodytes* (NP_001009066.1; SEQ ID NO:64), *Macaca mulatta* (NP_001040602.1; SEQ ID NO:65), *Bos Taurus* (NP_776318.1; SEQ ID NO:66) and *Mus musculus* (NP_033865.2; SEQ ID NO:67). Amino acids 1-20 are a signal peptide.

FIG. 10A-10N provide amino acid sequences of exemplary synTac polypeptides disclosed herein, and nucleotide sequences encoding same.

DEFINITIONS

Figure 1A:
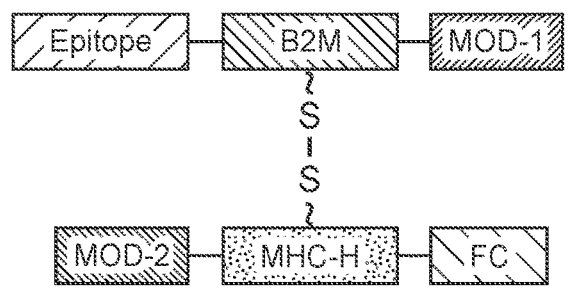
FIG. 1A-1C schematically depict various embodiments of a T-cell modulatory multimeric polypeptide of the present disclosure. In these embodiments, disulfide bonds are formed between MHC (e.g., HLA) polypeptides present in separate polypeptides.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

"Binding" as used herein (e.g. with reference to binding of a T-cell modulatory multimeric polypeptide of the present disclosure to a polypeptide (e.g., a T-cell receptor) on a T cell) refers to a non-covalent interaction between. Binding interactions are generally characterized by a dissociation constant ($K_D$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_D$.

The term "immunological synapse" or "immune synapse" as used herein generally refers to the natural interface between two interacting immune cells of an adaptive immune response including, e.g., the interface between an antigen-presenting cell (APC) or target cell and an effector cell, e.g., a lymphocyte, an effector T cell, a natural killer cell, and the like. An immunological synapse between an APC and a T cell is generally initiated by the interaction of a T cell antigen receptor and major histocompatibility complex molecules, e.g., as described in Bromley et al., Annu Rev Immunol. 2001; 19:375-96; the disclosure of which is incorporated herein by reference in its entirety.

"T cell" includes all types of immune cells expressing CD3, including T-helper cells (CD4+ cells), cytotoxic T-cells (CD8+ cells), T-regulatory cells (Treg), and NK-T cells.

"Co-stimulatory polypeptide," as the term is used herein, includes a polypeptide on an antigen presenting cell (APC) (e.g., a dendritic cell, a B cell, and the like) that specifically binds a cognate co-stimulatory polypeptide on a T cell, thereby providing a signal which, in addition to the primary signal provided by, for instance, binding of a TCR/CD3 complex with a major histocompatibility complex (MHC) polypeptide loaded with peptide, mediates a T cell response, including, but not limited to, proliferation, activation, differentiation, and the like.

A "modulatory domain" or "immunomodulatory domain" of a T-cell modulatory multimeric polypeptide of the present disclosure comprises a co-stimulatory polypeptide.

"Heterologous," as used herein, means a nucleotide or polypeptide that is not found in the native nucleic acid or protein, respectively.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells, for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication.

A "host cell," as used herein, denotes an in vivo or in vitro eukaryotic cell or a cell from a multicellular organism (e.g., a cell line) cultured as a unicellular entity, which eukaryotic cells can be, or have been, used as recipients for a nucleic acid (e.g., an expression vector that comprises a nucleotide sequence encoding a multimeric polypeptide of the present disclosure), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a genetically modified eukaryotic host cell is genetically modified by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired. Mammals include, e.g., humans, non-human primates, rodents (e.g., rats; mice), lagomorphs (e.g., rabbits), ungulates (e.g., cows, sheep, pigs, horses, goats, and the like), etc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a multimeric polypeptide" includes a plurality of such multimeric polypeptides and reference to "the modulatory domain" includes reference to one or more modulatory domains and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides T-cell modulatory multimeric polypeptides comprising two different immunomodulatory polypeptides, at least one of which is a variant immunomodulatory polypeptide. The present disclosure provides nucleic acids comprising nucleotide sequences encoding the T-cell modulatory multimeric polypeptides, and host cells comprising the nucleic acids. The present disclosure provides methods of modulating the activity of a T cell; the methods comprise contacting the T cell with a T-cell modulatory multimeric polypeptide of the present disclosure.

T-Cell Modulatory Multimeric Polypeptides

Figure 1B:
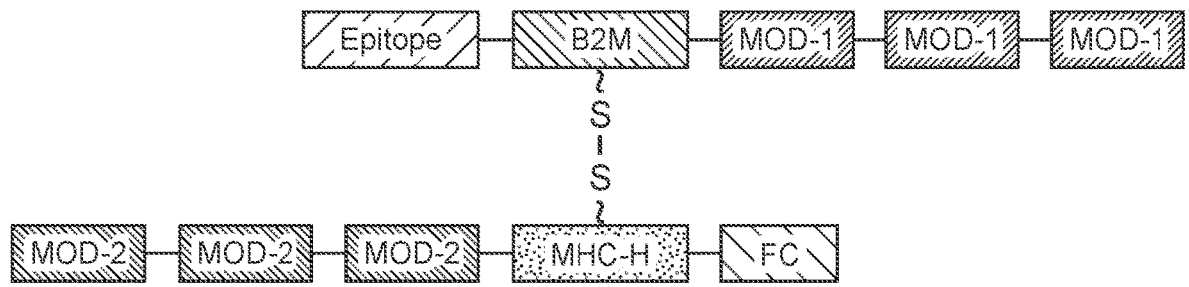
Figure 1C:
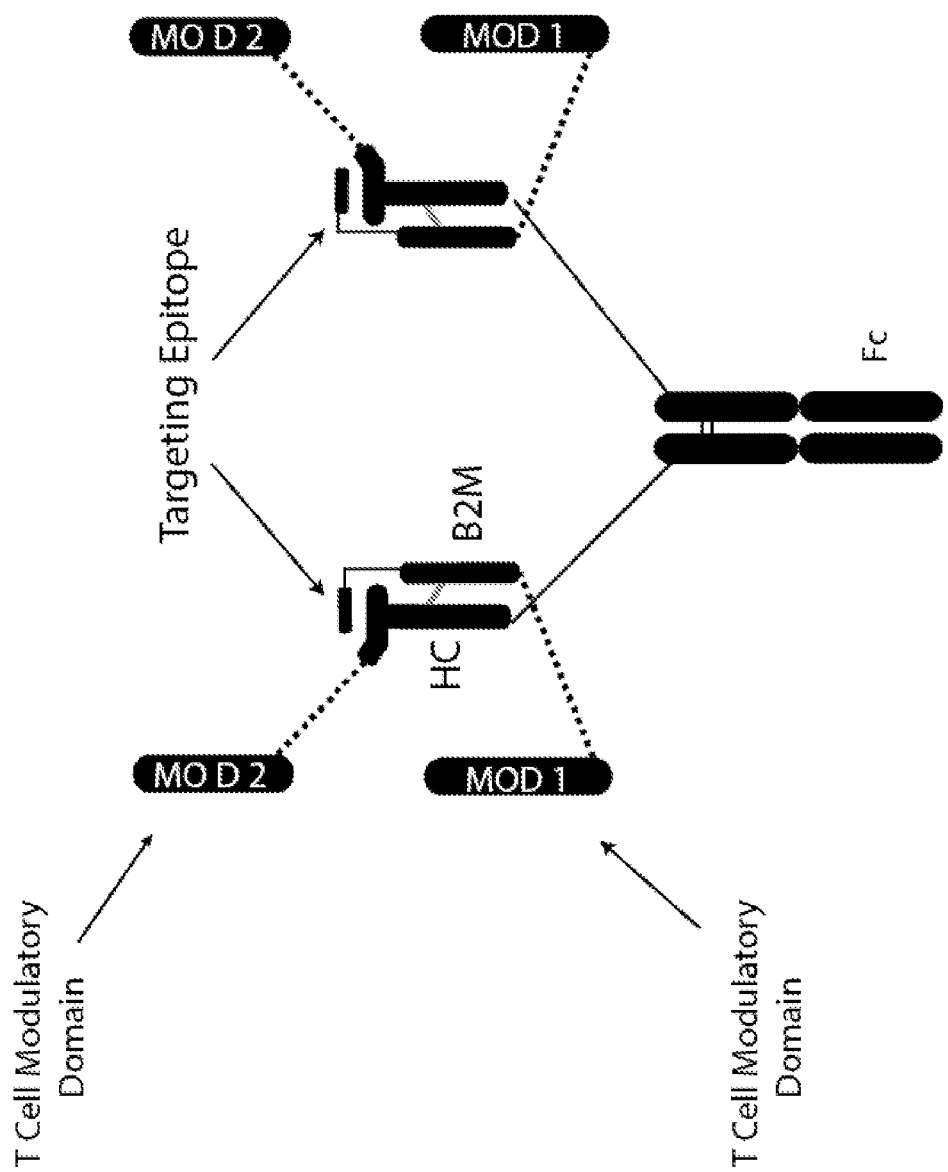

The present disclosure provides multimeric (e.g., heterodimeric, heterotrimeric) polypeptides. The multimeric polypeptides are T cell modulatory polypeptides, and are also referred to herein as "T-cell modulatory multimeric polypeptides," or "synTac" (for "immunological synapse for T cell activation"). FIG. 1A-1C provide schematic depictions of T-cell modulatory multimeric polypeptides of the present disclosure. A T-cell modulatory multimeric polypeptide of the present disclosure is also referred to as a "synTac polypeptide" or a "multimeric polypeptide."

A T-cell modulatory multimeric polypeptide of the present disclosure is also referred to as a "synTac polypeptide." A synTac polypeptide of the present disclosure comprises at least two modulatory domains, at least one of which is a variant modulatory domain, where the variant modulatory domain exhibits reduced binding affinity to an immunomodulatory polypeptide, compared to the affinity of a wild-type modulatory domain for the immunomodulatory polypeptide. A synTac polypeptide of the present disclosure can modulate the activity of a target T-cell. A synTac polypeptide of the present disclosure provides for enhanced target cell specificity.

The present disclosure provides a T-cell multimeric polypeptide that comprises a first immunomodulatory polypeptide and a second immunomodulatory polypeptide, where the first and the second immunomodulatory polypeptides have different amino acid sequences and bind different co-immunomodulatory polypeptides. Examples of immunomodulatory:co-immunomodulatory polypeptides include: a) 4-1BBL:4-1BB; b) CD80:CD28; and c) CD80:CTLA4. Those skilled in the art are familiar with other immunomodulatory:co-immunomodulatory polypeptide pairs.

In some cases, a synTac polypeptide of the present disclosure comprises a first immunomodulatory polypeptide that comprises a wild-type amino acid sequence; and a second immunomodulatory polypeptide that comprises a variant amino acid sequence (an amino acid sequence that differs from a corresponding wild-type amino acid sequence, e.g., a variant 4-1BBL polypeptide comprises an amino acid sequence that differs from a wild-type 4-1BBL amino acid sequence). Immunomodulatory polypeptides comprising a variant amino acid sequence can be non-naturally-occurring, i.e., do not occur in nature. Variant immunomodulatory polypeptides include immunomodulatory polypeptides having an amino acid sequence that has at least 80%, at least 85%, at least 90%, at least 95%, or at least 99% amino acid sequence identity to a corresponding wild-type immunomodulatory polypeptide, and include immunomodulatory polypeptides that differ by 1, 2, 3, 4 5, 6, 7, 8, 9, 10, 11, 12, 13, 14, or 15 amino acids or more relative to a corresponding wild-type immunomodulatory polypeptide. In some cases, a synTac polypeptide of the present disclosure comprises a first immunomodulatory polypeptide that comprises a variant amino acid sequence; and a second immunomodulatory polypeptide that comprises a wild-type amino acid sequence. In some cases, a synTac polypeptide of the present disclosure comprises a first immunomodulatory polypeptide that comprises a variant amino acid sequence; and a second immunomodulatory polypeptide that comprises a variant amino acid sequence.

In some cases, a T-cell multimeric polypeptide of the present disclosure comprises: a) a first polypeptide comprising, in order from N-terminus to C-terminus: i) an epitope; ii) a first major histocompatibility complex (MHC) polypeptide; and b) a second polypeptide comprising, in order from N-terminus to C-terminus: i) a second MHC polypeptide; and ii) optionally an immunoglobulin (Ig) Fc polypeptide or a non-Ig scaffold, wherein the multimeric polypeptide comprises at least a first and a second immunomodulatory domain, wherein the first and the second immunomodulatory domains are each independently: A) at the C-terminus of the first polypeptide; B) at the N-terminus of the second polypeptide; C) at the C-terminus of the second polypeptide; or D) at the C-terminus of the first polypeptide and at the N-terminus of the second polypeptide, wherein the first and the second immunomodulatory polypeptides bind different co-immunomodulatory polypeptides, and wherein one of the first and second immunomodulatory domains binds more than one co-immunomodulatory polypeptide and is a variant that has a bias for binding to one co-immunomodulatory polypeptide over another co-immunomodulatory polypeptide.

In some cases, an immunomodulatory polypeptide that binds more than one co-immunomodulatory polypeptide and is a variant that has a bias for binding to one co-immunomodulatory polypeptide over another co-immunomodulatory polypeptide binds to a first co-immunomodulatory polypeptide and a second co-immunomodulatory polypeptide. In some cases, an immunomodulatory polypeptide that binds to a first co-immunomodulatory polypeptide and a second co-immunomodulatory polypeptide binds to the first co-immunomodulatory polypeptide with an affinity that is at least at least 10%, at least 25%, at least 50%, at least 75%, at least 2-fold, at least 2.5-fold, at least 5-fold, at least 10-fold, at least 15-fold, at least 20-fold, at least 25-fold, at least 50-fold, or at least 100-fold, greater than the binding affinity of the immunomodulatory polypeptide for the second co-immunomodulatory polypeptide. In some cases, the immunomodulatory polypeptide that exhibits such preferential binding to a first co-immunomodulatory polypeptide over a second co-immunomodulatory polypeptide is a variant immunomodulatory polypeptide. A T-cell modulatory multimeric polypeptide of the present disclosure that comprises such an immunomodulatory polypeptide also exhibits preferential binding to a first co-immunomodulatory polypeptide over a second co-immunomodulatory polypeptide.

In some cases, the ratio of the binding affinity of an immunomodulatory polypeptide present in a T-cell modulatory multimeric polypeptide of the present disclosure for a first co-immunomodulatory polypeptide to the binding affinity of the immunomodulatory polypeptide for a second co-immunomodulatory polypeptide is greater than 1:1. In some cases, the ratio of binding of an immunomodulatory polypeptide present in a T-cell modulatory multimeric polypeptide of the present disclosure for a first co-immunomodulatory polypeptide to the binding affinity of the immunomodulatory polypeptide for a second co-immunomodulatory polypeptide is from about 1.1:1 to about 100:1. For example, in some cases, the ratio of binding of an immunomodulatory polypeptide present in a T-cell modulatory multimeric polypeptide of the present disclosure for a first co-immunomodulatory polypeptide to the binding affinity of the immunomodulatory polypeptide for a second co-immunomodulatory polypeptide is from about 1.1:1 to about 1.5:1, from about 1.5:1 to about 2:1, from about 2:1 to about 3:1, from about 3:1 to about 4:1, from about 4:1 to about 5:1, from about 5:1 to about 7.5:1, from about 7.5:1 to about 10:1, from about 10:1 to about 15:1, from about 15:1 to about 20:1, from about 20:1 to about 25:1, from about 25:1 to about 30:1, from about 30:1 to about 40:1, from about 40:1 to about 50:1, from about 50:1 to about 75:1, or from about 75:1 to about 100:1. In some cases, the ratio of binding of an immunomodulatory polypeptide present in a T-cell modulatory multimeric polypeptide of the present disclosure for a first co-immunomodulatory polypeptide to the binding affinity of the immunomodulatory polypeptide for a second co-immunomodulatory polypeptide is from 2:1 to 10:1.

A T-cell modulatory multimeric polypeptide of the present disclosure that comprises such an immunomodulatory polypeptide also exhibits a ratio of binding affinity for a first co-immunomodulatory polypeptide to the binding affinity of the T-cell modulatory multimeric polypeptide for a second co-immunomodulatory polypeptide is greater than 1:1. For example, in some cases, the ratio of the binding affinity of a T-cell modulatory multimeric polypeptide of the present disclosure to a first co-immunomodulatory polypeptide to the binding affinity of the T-cell modulatory multimeric polypeptide to a second co-immunomodulatory polypeptide is from about 1.1:1 to about 100:1. For example, in some cases, the ratio of the binding affinity of a T-cell modulatory multimeric polypeptide of the present disclosure to a first co-immunomodulatory polypeptide to the binding affinity of the T-cell modulatory multimeric polypeptide to a second co-immunomodulatory polypeptide is from about 1.1:1 to about 1.5:1, from about 1.5:1 to about 2:1, from about 2:1 to about 3:1, from about 3:1 to about 4:1, from about 4:1 to about 5:1, from about 5:1 to about 7.5:1, from about 7.5:1 to about 10:1, from about 10:1 to about 15:1, from about 15:1 to about 20:1, from about 20:1 to about 25:1, from about 25:1 to about 30:1, from about 30:1 to about 40:1, from about 40:1 to about 50:1, from about 50:1 to about 75:1, or from about 75:1 to about 100:1. In some cases, the ratio of the binding affinity of a T-cell modulatory multimeric polypeptide of the present disclosure to a first co-immunomodulatory polypeptide to the binding affinity of the T-cell modulatory multimeric polypeptide to a second co-immunomodulatory polypeptide is from about 2:1 to about 10:1.

A T-cell modulatory multimeric polypeptide of the present disclosure that comprises at least one immunomodulatory polypeptide that exhibits greater affinity for a first co-immunomodulatory polypeptide than to a second co-immunomodulatory polypeptide, when administered to an individual in need thereof, induces fewer adverse side effects associated with binding to the second co-immunomodulatory polypeptide.

A T-cell modulatory multimeric polypeptide of the present disclosure that comprises at least one immunomodulatory polypeptide that exhibits greater affinity for a first co-immunomodulatory polypeptide than to a second co-immunomodulatory polypeptide, when administered to an individual in need thereof, induces cytokine release syndrome (hypercytokinemia), if at all, to a degree that is at least 10%, at least 15%, at least 20%, at least 25%, at least 30%, at least 35%, at least 40%, at least 50%, at least 55%, at least 60%, at least 65%, at least 70%, at least 75%, at least 80%, or at least 90%, less than the cytokine release syndrome that is induced by, e.g., administration of an anti-CTLA antibody (e.g., ipilimumab; tremelimumab) or an anti-T cell antibody. For example, a T-cell modulatory multimeric polypeptide of the present disclosure that comprises at least one immunomodulatory polypeptide that exhibits greater affinity for a first co-immunomodulatory polypeptide than to a second co-immunomodulatory polypeptide, when administered to an individual in need thereof, induces cytokine release syndrome, if at all, to a degree that is at least 10%, at least 15%, at least 20%, at least 25%, at least 30%, at least 35%, at least 40%, at least 50%, at least 55%, at least 60%, at least 65%, at least 70%, at least 75%, at least 80%, or at least 90%, less than the cytokine release syndrome that is induced by, e.g., administration of ipilimumab at a dosage of 3 mg/kg every 3 weeks for 4 cycles, or administration of tremelimumab at a dosage of 15 mg/kg every 90 days.

A T-cell modulatory multimeric polypeptide of the present disclosure that comprises at least one immunomodulatory polypeptide that exhibits greater affinity for a first co-immunomodulatory polypeptide than to a second co-immunomodulatory polypeptide, when administered to an individual in need thereof, induces complement activation, if at all, to a degree that is at least 10%, at least 15%, at least 20%, at least 25%, at least 30%, at least 35%, at least 40%, at least 50%, at least 55%, at least 60%, at least 65%, at least 70%, at least 75%, at least 80%, or at least 90%, less than the degree of complement activation that is induced by, e.g., administration of an anti-CTLA antibody (e.g., ipilimumab; tremelimumab) or an anti-T cell antibody. For example, a T-cell modulatory multimeric polypeptide of the present disclosure that comprises at least one immunomodulatory polypeptide that exhibits greater affinity for a first co-immunomodulatory polypeptide than to a second co-immunomodulatory polypeptide, when administered to an individual in need thereof, induces complement activation, if at all, to a degree that is at least 10%, at least 15%, at least 20%, at least 25%, at least 30%, at least 35%, at least 40%, at least 50%, at least 55%, at least 60%, at least 65%, at least 70%, at least 75%, at least 80%, or at least 90%, less than the degree of complement activation that is induced by, e.g., administration of ipilimumab at a dosage of 3 mg/kg every 3 weeks for 4 cycles, or administration of tremelimumab at a dosage of 15 mg/kg every 90 days.

Targeting CTLA-4 is a strategic approach in cancer control; blocking CTLA4 can enhance anti-tumor immunity by promoting T-cell activation and cytotoxic T-lymphocyte proliferation. Consistent with this approach, in some treatment regimens, an anti-CTLA4 antibody is administered in combination therapy with an anti-cancer therapy. However, administration of an anti-CTLA4 antibody can give rise to immune-related adverse events (irAEs).

In some cases, a T-cell modulatory multimeric polypeptide of the present disclosure is administered to an individual in need thereof in the treatment of cancer. Where a T-cell modulatory multimeric polypeptide of the present disclosure exhibits greater affinity for a first co-immunomodulatory polypeptide than for a second co-immunomodulatory polypeptide, administration of such a T-cell modulatory multimeric polypeptide can reduce the amount and/or duration of administration of an anti-CTLA4 antibody, thereby reducing irAEs. For example, where a T-cell modulatory multimeric polypeptide of the present disclosure is administered in combination therapy with an anti-CTLA4 antibody, the incidence and/or severeity of irAEs is reduced by at least 10%, at least 15%, at least 20%, at least 25%, at least 30%, at least 35%, at least 40%, at least 50%, at least 55%, at least 60%, at least 65%, at least 70%, at least 75%, at least 80%, or more than 80%, compared to incidence and/or severity of the irAEs following co-administration of a control T-cell modulatory multimeric polypeptide comprising an immunomodulatory polypeptide that does not exhibit the binding affinity bias and the anti-CTLA4. Possible irAEs include skin toxicity, gastrointestinal tract toxicity, hepatotoxicity, and endocrinopathies. Possible irAEs include skin lesions (rash, pruritus, and vitiligo), colitis, hepatitis, hypophysitis, thyroiditis, sarcoidosis, uveitis, Guillain-Barré syndrome, immune-mediated cytopenia, and polymyalgia rheumatic/Horton.

In some cases, the amount of anti-CTLA4 antibody that is co-administered with a T-cell modulatory multimeric polypeptide of the present disclosure is less than the amount of anti-CTLA4 antibody that would need to be co-administered with another anti-cancer agent to achieve an anti-cancer effect. For example, in some cases, the amount of anti-CTLA4 antibody that is co-administered with a T-cell modulatory multimeric polypeptide of the present disclosure is at least 10%, at least 15%, at least 20%, at least 25%, at least 30%, at least 35%, at least 40%, at least 50%, at least 55%, at least 60%, at least 65%, at least 70%, at least 75%, or at least 80%, less than the amount of anti-CTLA4 antibody that would need to be co-administered with another anti-cancer agent to achieve an anti-cancer effect. For example, the humanized anti-CTLA4 antibody ipilimumab is administered in some current cancer treatment regimens at 3 mg/kg every 3 weeks for four cycles. In some current cancer treatment regimens, the anti-CTLA4 antibody tremelimumab is administered at 15 mg/kg every 90 days. The amount of anti-CTLA4 antibody that would be co-administered with a T-cell modulatory multimeric polypeptide of the present disclosure would be reduced by at least 10%, at least 15%, at least 20%, at least 25%, at least 30%, at least 35%, at least 40%, at least 50%, at least 55%, at least 60%, at least 65%, at least 70%, at least 75%, or at least 80%, compared to the 3 mg/kg dosage for ipilimumab or 15 mg/kg dosage for tremelimumab. In some cases, a T-cell modulatory multimeric polypeptide of the present disclosure is administered to an individual in need thereof without co-administration of an anti-CTLA4 antibody.

CD80/4-1BBL synTac Polypeptides

The present disclosure provides synTac polypeptides comprising a CD80 immunomodulatory polypeptide and a 4-1BBL immunomodulatory polypeptide. In some cases, a synTac polypeptide of the present disclosure comprises a wild-type CD80 immunomodulatory polypeptide; and a wild-type 4-1BBL immunomodulatory polypeptide. In some cases, a synTac polypeptide of the present disclosure comprises a wild-type CD80 immunomodulatory polypeptide; and a variant 4-1BBL immunomodulatory polypeptide. In some cases, a synTac polypeptide of the present disclosure comprises a variant CD80 immunomodulatory polypeptide; and a wild-type 4-1BBL immunomodulatory polypeptide. In some cases, a synTac polypeptide of the present disclosure comprises a variant CD80 immunomodulatory polypeptide;

and a variant 4-1BBL immunomodulatory polypeptide. Variant 4-1BBL polypeptides include those having an amino acid sequence that has at least 80%, at least 85%, at least 90%, at least 95%, or at least 99% amino acid sequence identity to a corresponding wild-type 4-1BBL polypeptide, and include variant 4-1BBL polypeptides that differ by 1, 2, 3, 4 5, 6, 7, 8, 9, 10, 11, 12, 13, 14, or 15 amino acids or more relative to a corresponding wild-type 4-1BBL polypeptide. Variant CD80 polypeptides include those having an amino acid sequence that has at least 80%, at least 85%, at least 90%, at least 95%, or at least 99% amino acid sequence identity to a corresponding wild-type CD80 polypeptide, and include variant CD80 polypeptides that differ by 1, 2, 3, 4 5, 6, 7, 8, 9, 10, 11, 12, 13, 14, or 15 amino acids or more relative to a corresponding wild-type CD80 polypeptide.

In some cases, a synTac polypeptide of the present disclosure comprises: a) a first polypeptide comprising, in order from N-terminus to C-terminus: i) an epitope; ii) a first major histocompatibility complex (MHC) polypeptide; and b) a second polypeptide comprising, in order from N-terminus to C-terminus: i) a second MHC polypeptide; and ii) optionally an immunoglobulin (Ig) Fc polypeptide or a non-Ig scaffold, where: 1) the multimeric polypeptide comprises a first and a second immunomodulatory domain; 2) the first and the second immunomodulatory domains are each independently: A) at the C-terminus of the first polypeptide; B) at the N-terminus of the second polypeptide; C) at the C-terminus of the second polypeptide; or D) at the C-terminus of the first polypeptide and at the N-terminus of the second polypeptide; and 3) at least one of the immunomodulatory domains is a variant immunomodulatory polypeptide having at least one amino acid substitution relative to SEQ ID NO:1 or relative to one of SEQ ID NOs:2-4. The multimeric polypeptide exhibits: a) reduced binding affinity to a CD28 polypeptide having an amino acid sequence depicted in one of FIG. 4A-4C, compared to the binding affinity of a control multimeric polypeptide comprising an immunomodulatory domain comprising the CD80 amino acid sequence depicted in FIG. 2, or compared to the binding affinity of a control multimeric polypeptide comprising an immunomodulatory domain comprising the CD80 amino acid sequence as set forth in SEQ ID NO:1, for the CD28 polypeptide; and/or b) reduced binding affinity to a 4-1BB polypeptide having an amino acid sequence depicted in FIG. 5, compared to the binding affinity of a control multimeric polypeptide comprising an immunomodulatory domain comprising the 4-1BBL amino acid sequence depicted in FIG. 3 or set forth in one of SEQ ID NOs:2-4 for the 4-1BB polypeptide.

In some cases, a synTac polypeptide of the present disclosure comprises: a) a first polypeptide comprising, in order from N-terminus to C-terminus: i) an epitope; ii) a first MHC polypeptide; and iii) a first immunomodulatory domain; and b) a second polypeptide comprising, in order from N-terminus to C-terminus: i) a second immunomodulatory domain; ii) a second MHC polypeptide; and iii) an Ig Fc polypeptide, where: at least one of the immunomodulatory domains is a variant immunomodulatory polypeptide having at least one amino acid substitution relative to SEQ ID NO:1 or relative to one of SEQ ID NOs:2-4.

In some cases, a synTac polypeptide of the present disclosure comprises: a) a first polypeptide comprising, in order from N-terminus to C-terminus: i) an epitope; ii) a first MHC polypeptide; and iii) a variant CD80 polypeptide comprising at least one amino acid substitution relative to SEQ ID NO:1; and b) a second polypeptide comprising, in order from N-terminus to C-terminus: i) a variant 4-1BBL polypeptide comprising at least one amino acid substitution relative to one of SEQ ID NOs:2-4; ii) a second MHC polypeptide; and iii) an Ig Fc polypeptide, where the synTac polypeptide exhibits: a) reduced binding affinity to a CD28 polypeptide having an amino acid sequence depicted in one of FIG. 4A-4C, compared to the binding affinity of a control synTac polypeptide comprising an immunomodulatory domain comprising the CD80 amino acid sequence depicted in FIG. 2, or compared to the binding affinity of a control synTac polypeptide comprising an immunomodulatory domain comprising the CD80 amino acid sequence as set forth in SEQ ID NO:1, for the CD28 polypeptide; and/or b) reduced binding affinity to a 4-1BB polypeptide having an amino acid sequence depicted in FIG. 5, compared to the binding affinity of a control synTac polypeptide comprising an immunomodulatory domain comprising the 4-1BBL amino acid sequence depicted in FIG. 3 or set forth in one of SEQ ID NOs:2-4 for the 4-1BB polypeptide.

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising at least one amino acid substitution relative to SEQ ID NO:1; and b) a second polypeptide comprising, in order from N-terminus to C-terminus: i) a variant 4-1BBL polypeptide comprising at least one amino acid substitution relative to one of SEQ ID NOs:2-4; ii) an MHC heavy polypeptide; and iii) an Ig Fc polypeptide, where the synTac polypeptide exhibits: a) reduced binding affinity to a CD28 polypeptide having an amino acid sequence depicted in one of FIG. 4A-4C, compared to the binding affinity of a control synTac polypeptide comprising an immunomodulatory domain comprising the CD80 amino acid sequence depicted in FIG. 2, or compared to the binding affinity of a control synTac polypeptide comprising an immunomodulatory domain comprising the CD80 amino acid sequence as set forth in SEQ ID NO:1, for the CD28 polypeptide; and/or b) reduced binding affinity to a 4-1BB polypeptide having an amino acid sequence depicted in FIG. 5, compared to the binding affinity of a control synTac polypeptide comprising an immunomodulatory domain comprising the 4-1BBL amino acid sequence depicted in FIG. 3 or set forth in one of SEQ ID NOs:2-4 for the 4-1BB polypeptide.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising at least one amino acid substitution relative to one of SEQ ID NOs:2-4; and b) a second polypeptide comprising, in order from N-terminus to C-terminus: i) a variant CD80 polypeptide comprising at least one amino acid substitution relative to SEQ ID NO:1; ii) an MHC heavy polypeptide; and iii) an Ig Fc polypeptide, where the synTac polypeptide exhibits: a) reduced binding affinity to a CD28 polypeptide having an amino acid sequence depicted in one of FIG. 4A-4C, compared to the binding affinity of a control synTac polypeptide comprising an immunomodulatory domain comprising the CD80 amino acid sequence depicted in FIG. 2, or compared to the binding affinity of a control synTac polypeptide comprising an immunomodulatory domain comprising the CD80 amino acid sequence as set forth in SEQ ID NO:1, for the CD28 polypeptide; and/or b) reduced binding affinity to a 4-1BB polypeptide having an amino acid sequence depicted in FIG. 5, compared to the binding affinity of a control synTac polypeptide comprising an immunomodulatory domain comprising the 4-1BBL amino acid sequence depicted in FIG. 3 or set forth in one of SEQ ID NOs:2-4 for the 4-1BB polypeptide.

In some cases, a synTac polypeptide of the present disclosure comprises: a) a first polypeptide comprising, in order from N-terminus to C-terminus: i) an epitope; ii) a first MHC polypeptide; iii) a first variant CD80 polypeptide comprising at least one amino acid substitution relative to SEQ ID NO:1; iv) a second variant CD80 polypeptide comprising at least one amino acid substitution relative to SEQ ID NO:1; and v) a third variant CD80 polypeptide comprising at least one amino acid substitution relative to SEQ ID NO:1; and b) a second polypeptide comprising, in order from N-terminus to C-terminus: i) a variant 4-1BBL polypeptide comprising at least one amino acid substitution relative to one of SEQ ID NOs:2-4; ii) a second MHC polypeptide; and iii) an Ig Fc polypeptide, where the synTac polypeptide exhibits: a) reduced binding affinity to a CD28 polypeptide having an amino acid sequence depicted in one of FIG. 4A-4C, compared to the binding affinity of a control synTac polypeptide comprising an immunomodulatory domain comprising the CD80 amino acid sequence depicted in FIG. 2, or compared to the binding affinity of a control synTac polypeptide comprising an immunomodulatory domain comprising the CD80 amino acid sequence as set forth in SEQ ID NO:1, for the CD28 polypeptide; and/or b) reduced binding affinity to a 4-1BB polypeptide having an amino acid sequence depicted in FIG. 5, compared to the binding affinity of a control synTac polypeptide comprising an immunomodulatory domain comprising the 4-1BBL amino acid sequence depicted in FIG. 3 or set forth in one of SEQ ID NOs:2-4 for the 4-1BB polypeptide. In some cases, the first, second, and third variant CD80 polypeptide have identical amino acid sequences; i.e., the second and the third variant CD80 polypeptides both have an amino acid sequence that has 100% amino acid sequence identity to the amino acid sequence of the first variant CD80 polypeptide. In other cases, the first, second, and third variant CD80 polypeptides have less than 100% amino acid sequence identity to one another.

In some cases, a synTac polypeptide of the present disclosure comprises: a) a first polypeptide comprising, in order from N-terminus to C-terminus: i) an epitope; ii) a β2M polypeptide; iii) a first variant CD80 polypeptide comprising at least one amino acid substitution relative to SEQ ID NO:1; iv) a second variant CD80 polypeptide comprising at least one amino acid substitution relative to SEQ ID NO:1; and v) a third variant CD80 polypeptide comprising at least one amino acid substitution relative to SEQ ID NO:1; and b) a second polypeptide comprising, in order from N-terminus to C-terminus: i) a variant 4-1BBL polypeptide comprising at least one amino acid substitution relative to one of SEQ ID NOs:2-4; ii) an MHC heavy chain polypeptide; and iii) an Ig Fc polypeptide, where the synTac polypeptide exhibits: a) reduced binding affinity to a CD28 polypeptide having an amino acid sequence depicted in one of FIG. 4A-4C, compared to the binding affinity of a control synTac polypeptide comprising an immunomodulatory domain comprising the CD80 amino acid sequence depicted in FIG. 2, or compared to the binding affinity of a control synTac polypeptide comprising an immunomodulatory domain comprising the CD80 amino acid sequence as set forth in SEQ ID NO:1, for the CD28 polypeptide; and/or b) reduced binding affinity to a 4-1BB polypeptide having an amino acid sequence depicted in FIG. 5, compared to the binding affinity of a control synTac polypeptide comprising an immunomodulatory domain comprising the 4-1BBL amino acid sequence depicted in FIG. 3 or set forth in one of SEQ ID NOs:2-4 for the 4-1BB polypeptide. In some cases, the first, second, and third variant CD80 polypeptide have identical amino acid sequences; i.e., the second and the third variant CD80 polypeptides both have an amino acid sequence that has 100% amino acid sequence identity to the amino acid sequence of the first variant CD80 polypeptide. In other cases, the first, second, and third variant CD80 polypeptides have less than 100% amino acid sequence identity to one another.

In some cases, a synTac polypeptide of the present disclosure comprises: a) a first polypeptide comprising, in order from N-terminus to C-terminus: i) an epitope; ii) a first MHC polypeptide; and iii) a variant CD80 polypeptide comprising at least one amino acid substitution relative to SEQ ID NO:1; and b) a second polypeptide comprising, in order from N-terminus to C-terminus: i) a first variant 4-1BBL polypeptide comprising at least one amino acid substitution relative to one of SEQ ID NOs:2-4; ii) a second variant 4-1BBL polypeptide comprising at least one amino acid substitution relative to one of SEQ ID NOs:2-4; iii) a third variant 4-1BBL polypeptide comprising at least one amino acid substitution relative to one of SEQ ID NOs:2-4; iv) a second MHC polypeptide; and v) an Ig Fc polypeptide, where the synTac polypeptide exhibits: a) reduced binding affinity to a CD28 polypeptide having an amino acid sequence depicted in one of FIG. 4A-4C, compared to the binding affinity of a control synTac polypeptide comprising an immunomodulatory domain comprising the CD80 amino acid sequence depicted in FIG. 2, or compared to the binding affinity of a control synTac polypeptide comprising an immunomodulatory domain comprising the CD80 amino acid sequence as set forth in SEQ ID NO:1, for the CD28 polypeptide; and/or b) reduced binding affinity to a 4-1BB polypeptide having an amino acid sequence depicted in FIG. 5, compared to the binding affinity of a control synTac polypeptide comprising an immunomodulatory domain comprising the 4-1BBL amino acid sequence depicted in FIG. 3 or set forth in one of SEQ ID NOs:2-4 for the 4-1BB polypeptide. In some cases, the first, second, and third variant 4-1BBL polypeptide have identical amino acid sequences; i.e., the second and the third variant 4-1BBL polypeptides both have an amino acid sequence that has 100% amino acid sequence identity to the amino acid sequence of the first variant 4-1BBL polypeptide. In other cases, the first, second, and third variant 4-1BBL polypeptides have less than 100% amino acid sequence identity to one another.

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising at least one amino acid substitution relative to SEQ ID NO:1; and b) a second polypeptide comprising, in order from N-terminus to C-terminus: i) a first variant 4-1BBL polypeptide comprising at least one amino acid substitution relative to one of SEQ ID NOs:2-4; ii) a second variant 4-1BBL polypeptide comprising at least one amino acid substitution relative to one of SEQ ID NOs:2-4; iii) a third variant 4-1BBL polypeptide comprising at least one amino acid substitution relative to one of SEQ ID NOs:2-4; iv) an MHC heavy chain polypeptide; and v) an Ig Fc polypeptide, where the synTac polypeptide exhibits: a) reduced binding affinity to a CD28 polypeptide having an amino acid sequence depicted in one of FIG. 4A-4C, compared to the binding affinity of a control synTac polypeptide comprising an immunomodulatory domain comprising the CD80 amino acid sequence depicted in FIG. 2, or compared to the binding affinity of a control synTac polypeptide comprising an immunomodulatory domain comprising the CD80 amino acid sequence as set forth in SEQ ID NO:1, for the CD28 polypeptide; and/or b) reduced binding affinity to a 4-1BB polypeptide having an amino acid sequence depicted in FIG. 5, compared to the binding affinity of a control synTac polypeptide comprising an immunomodulatory domain comprising the 4-1BBL amino acid sequence depicted in FIG. 3 or set forth in one of SEQ ID NOs:2-4 for the 4-1BB polypeptide. In some cases, the first, second, and third variant 4-1BBL polypeptide have identical amino acid sequences; i.e., the second and the third variant 4-1BBL polypeptides both have an amino acid sequence that has 100% amino acid sequence identity to the amino acid sequence of the first variant 4-1BBL polypeptide. In other cases, the first, second, and third variant 4-1BBL polypeptides have less than 100% amino acid sequence identity to one another.

In some cases, a T-cell modulatory multimeric polypeptide of the present disclosure binds CD28 with an affinity that is at least 10%, at least 25%, at least 50%, at least 75%, at least 2-fold, at least 2.5-fold, at least 5-fold, at least 10-fold, at least 15-fold, at least 20-fold, at least 25-fold, at least 50-fold, or at least 100-fold, greater than the binding affinity of the T-cell modulatory multimeric polypeptide for CTLA4.

In some cases, the ratio of the binding affinity of a T-cell modulatory multimeric polypeptide of the present disclosure to CD28 to the binding affinity of the T-cell modulatory multimeric polypeptide to CTLA4 is from about 1.1:1 to about 100:1. For example, in some cases, the ratio of the binding affinity of a T-cell modulatory multimeric polypeptide of the present disclosure to CD28 to the binding affinity of the T-cell modulatory multimeric polypeptide to CTLA4 is from about 1.1:1 to about 1.5:1, from about 1.5:1 to about 2:1, from about 2:1 to about 3:1, from about 3:1 to about 4:1, from about 4:1 to about 5:1, from about 5:1 to about 7.5:1, from about 7.5:1 to about 10:1, from about 10:1 to about 15:1, from about 15:1 to about 20:1, from about 20:1 to about 25:1, from about 25:1 to about 30:1, from about 30:1 to about 40:1, from about 40:1 to about 50:1, from about 50:1 to about 75:1, or from about 75:1 to about 100:1. In some cases, the ratio of the binding affinity of a T-cell modulatory multimeric polypeptide of the present disclosure to CD28 to the binding affinity of the T-cell modulatory multimeric polypeptide to CTLA4 is from about 2:1 to about 10:1.

As a non-limiting example, in some cases, a T-cell modulatory multimeric polypeptide of the present disclosure comprises a variant CD80 polypeptide comprising a K86A substitution, and a variant 4-1BBL polypeptide comprising a K127A substitution, and binds CD28 with an affinity that is at least 10%, at least 25%, at least 50%, at least 75%, at least 2-fold, at least 2.5-fold, at least 5-fold, at least 10-fold, at least 15-fold, at least 20-fold, at least 25-fold, at least 50-fold, or at least 100-fold, greater than the binding affinity of the T-cell modulatory multimeric polypeptide for CTLA4.

As a non-limiting example, in some cases, a T-cell modulatory multimeric polypeptide of the present disclosure comprises a variant CD80 polypeptide comprising a K86A substitution, and a variant 4-1BBL polypeptide comprising a K127A substitution, and the ratio of the binding affinity of the T-cell modulatory multimeric polypeptide to CD28 to the binding affinity of the T-cell modulatory multimeric polypeptide to CTLA4 is from about 1.1:1 to about 100:1. For example, in some cases, the ratio of the binding affinity of the T-cell modulatory multimeric polypeptide to CD28 to the binding affinity of the T-cell modulatory multimeric polypeptide to CTLA4 is from about 1.1:1 to about 1.5:1, from about 1.5:1 to about 2:1, from about 2:1 to about 3:1, from about 3:1 to about 4:1, from about 4:1 to about 5:1, from about 5:1 to about 7.5:1, from about 7.5:1 to about 10:1, from about 10:1 to about 15:1, from about 15:1 to about 20:1, from about 20:1 to about 25:1, from about 25:1 to about 30:1, from about 30:1 to about 40:1, from about 40:1 to about 50:1, from about 50:1 to about 75:1, or from about 75:1 to about 100:1. In some cases, the ratio of the binding affinity of the T-cell modulatory multimeric polypeptide to CD28 to the binding affinity of the T-cell modulatory multimeric polypeptide to CTLA4 is from about 2:1 to about 10:1.

CD80

In some cases, a T-cell modulatory multimeric polypeptide of the present disclosure comprises a CD80 modulatory polypeptide, which in some cases is a variant CD80 modulatory polypeptide.

A wild-type amino acid sequence of human CD80 is provided in FIG. 2. The ectodomain of human CD80 comprises amino acids 1-208 of the amino acid sequence depicted in FIG. 2. Thus, a wild-type amino acid sequence of the ectodomain of human CD80 can be as follows:

```
                                           (SEQ ID NO: 1)
VIHVTK EVKEVATLSC GHNVSVEELA QTRIYWQKEK KMVLTMMSGD

MNIWPEYKNR TIFDITNNLS IVILALRPSD EGTYECVVLK

YEKDAFKREH LAEVTLSVKA DFPTPSISDF EIPTSNIRRI

ICSTSGGFPE PHLSWLENGE ELNAINTTVS QDPETELYAV

SSKLDFNMTT NHSFMCLIKY GHLRVNQTFN WNTTKQEHFP DN.
```

Wild-type CD80 binds to CD28. Amino acid sequences of CD28 are provided in FIG. 4A-4C. In some cases, a variant CD80 polypeptide present in a synTac polypeptide of the present disclosure exhibits reduced binding affinity to CD28, compared to the binding affinity of a CD80 polypeptide comprising the amino acid sequence depicted in FIG. 2 or SEQ ID NO:1 for CD28. For example, in some cases, a variant CD80 polypeptide present in a synTac polypeptide of the present disclosure binds CD28 with a binding affinity that is less than the binding affinity of a CD80 polypeptide comprising the amino acid sequence depicted in FIG. 2 or SEQ ID NO:1 for a CD28 polypeptide comprising the amino acid sequence depicted in one of FIG. 4A-4C. For example, in some cases, a variant CD80 polypeptide present in a synTac polypeptide of the present disclosure binds CD28 with a binding affinity that is at least 10%, at least 15%, at least 20%, at least 25%, at least 30%, at least 35%, at least 40%, at least 45%, at least 50% less, at least 55% less, at least 60% less, at least 65% less, at least 70% less, at least 75% less, at least 80% less, at least 85% less, at least 90% less, at least 95% less, or more than 95% less, than the binding affinity of a CD80 polypeptide comprising the amino acid sequence depicted in FIG. 2 or SEQ ID NO:1 for CD28 (e.g., a CD28 polypeptide comprising the amino acid sequence depicted in one of FIG. 4A-4C).

In some cases, a variant CD80 polypeptide present in a synTac polypeptide of the present disclosure has a binding affinity to CD28 that is from 100 nM to 100 μM. As another example, in some cases, a variant CD80 polypeptide present in a synTac polypeptide of the present disclosure has a binding affinity for CD28 (e.g., a CD28 polypeptide comprising the amino acid sequence depicted in one of FIG.

4A-4C) that is from about 100 nM to 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 µM, to about 1 µM to about 5 µM, from about 5 µM to about 10 µM, from about 10 µM to about 15 µM, from about 15 µM to about 20 µM, from about 20 µM to about 25 µM, from about 25 µM to about 50 µM, from about 50 µM to about 75 µM, or from about 75 µM to about 100 µM.

Variant CD80 Modulatory Polypeptides

In some cases, a variant CD80 modulatory polypeptide suitable for inclusion in a multimeric polypeptide of the present disclosure comprises an amino acid substitution of amino acid N19, N63, I67, K86, Q157, D158, L25, Y31, Q33, M38, V39, I49, Y53, D60, F108, or S156, where the amino acid numbering is based on the amino acid sequence depicted in FIG. 2. In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence depicted in FIG. 2 or as set forth in SEQ ID NO:1; and comprises an amino acid substitution of amino acid N19, N63, I67, K86, Q157, D158, L25, Y31, Q33, M38, V39, I49, Y53, D60, F108, or S156, where the amino acid numbering is based on the amino acid sequence depicted in FIG. 2.

In some cases, a variant CD80 modulatory polypeptide suitable for inclusion in a multimeric polypeptide of the present disclosure comprises a substitution of amino acid I67, where the amino acid numbering is based on the amino acid sequence depicted in FIG. 2. In some cases, the variant CD80 polypeptide comprises a substitution of amino acid K86, where the amino acid numbering is based on the amino acid sequence depicted in FIG. 2. In some cases, the variant CD80 polypeptide comprises a substitution of amino acid D158, where the amino acid numbering is based on the amino acid sequence depicted in FIG. 2.

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence set forth in SEQ ID NO:1; and comprises an amino acid substitution of amino acid I67, K86, or D158.

I67 Substitution

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence set forth in SEQ ID NO:1; and comprises an amino acid substitution of amino acid I67.

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence set forth in SEQ ID NO:1; and comprises an amino acid substitution of amino acid I67, where the substitution is Ala, Gly, Val, or Leu. In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence set forth in SEQ ID NO:1; and comprises an amino acid substitution of amino acid I67, where the substitution is Glu or Asp. In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence set forth in SEQ ID NO:1; and comprises an amino acid substitution of amino acid I67, where the substitution is Arg, His, or Lys. In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence set forth in SEQ ID NO:1; and comprises an amino acid substitution of amino acid I67, such that amino acid 67 is Ala.

In some cases, a variant CD80 polypeptide suitable for inclusion in a multimeric polypeptide of the present disclosure comprises the following amino acid sequence:

```
                                            (SEQ ID NO: 5)
VIHVTK EVKEVATLSC GHNVSVEELA QTRIYWQKEK KMVLTMMSGD

MNIWPEYKNR TIFDITNNLS XVILALRPSD EGTYECVVLK

YEKDAFKREH LAEVTLSVKA DFPTPSISDF EIPTSNIRRI

ICSTSGGFPE PHLSWLENGE ELNAINTTVS QDPETELYAV

SSKLDFNMTT NHSFMCLIKY GHLRVNQTFN WNTTKQEHFP DN,
``` where X is any amino acid other than isoleucine, e.g., where X is Gly, Ala, Val, Leu, Pro, Phe, Tyr, Trp, Ser, Thr, Cys, Met, Asn, Gln, Lys, Arg, His, Asp, or Glu. In some cases, X is Ala, Gly, Leu, or Val. In some cases, X is Glu or Asp. In some cases, X is Arg, His, or Lys. In some cases, X is Ala.

In some cases, a variant CD80 polypeptide suitable for inclusion in a multimeric polypeptide of the present disclosure comprises the following amino acid sequence:

```
                                            (SEQ ID NO: 6)
VIHVTK EVKEVATLSC GHNVSVEELA QTRIYWQKEK KMVLTMMSGD

MNIWPEYKNR TIFDITNNLS AVILALRPSD EGTYECVVLK

YEKDAFKREH LAEVTLSVKA DFPTPSISDF EIPTSNIRRI

ICSTSGGFPE PHLSWLENGE ELNAINTTVS QDPETELYAV

SSKLDFNMTT NHSFMCLIKY GHLRVNQTFN WNTTKQEHFP DN.
```

K86 Substitution

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence set forth in SEQ ID NO:1; and comprises an amino acid substitution of amino acid K86. In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence set forth in SEQ ID NO:1; and comprises an amino acid substitution of amino acid K86, where the substitution is Ala, Gly, Val, Ile, or Leu.

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence set forth in SEQ ID NO:1; and comprises an amino acid substitution of amino acid K86, where the substitution is Glu or Asp. In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence set forth in SEQ ID NO:1; and comprises an amino acid substitution of amino acid K86, where the substitution is Arg or His. In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence set forth in SEQ ID NO:1; and comprises an amino acid substitution of amino acid K86, such that amino acid 86 is Ala.

In some cases, a variant CD80 polypeptide suitable for inclusion in a multimeric polypeptide of the present disclosure comprises the following amino acid sequence:

```
                                      (SEQ ID NO: 7)
VIHVTK EVKEVATLSC GHNVSVEELA QTRIYWQKEK KMVLTMMSGD

MNIWPEYKNR TIFDITNNLS IVILALRPSD EGTYECVVLX

YEKDAFKREH LAEVTLSVKA DFPTPSISDF EIPTSNIRRI

ICSTSGGFPE PHLSWLENGE ELNAINTTVS QDPETELYAV

SSKLDFNMTT NHSFMCLIKY GHLRVNQTFN WNTTKQEHFP DN,
``` where X is any amino acid other than lysine, e.g., where X is Gly, Ala, Val, Leu, Ile, Pro, Phe, Tyr, Trp, Ser, Thr, Cys, Met, Asn, Gln, Arg, His, Asp, or Glu. In some cases, X is Ala, Gly, Leu, Ile, or Val. In some cases, X is Glu or Asp. In some cases, X is Arg or His. In some cases, X is Ala.

In some cases, a variant CD80 polypeptide suitable for inclusion in a multimeric polypeptide of the present disclosure comprises the following amino acid sequence:

```
                                      (SEQ ID NO: 8)
VIHVTK EVKEVATLSC GHNVSVEELA QTRIYWQKEK KMVLTMMSGD

MNIWPEYKNR TIFDITNNLS IVILALRPSD EGTYECVVLA

YEKDAFKREH LAEVTLSVKA DFPTPSISDF EIPTSNIRRI

ICSTSGGFPE PHLSWLENGE ELNAINTTVS QDPETELYAV

SSKLDFNMTT NHSFMCLIKY GHLRVNQTFN WNTTKQEHFP DN.
```

D158 Substitution

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence set forth in SEQ ID NO:1; and comprises an amino acid substitution of amino acid D158. In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence set forth in SEQ ID NO:1; and comprises an amino acid substitution of amino acid D158, where the substitution is Ala, Gly, Val, Ile, or Leu. In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence set forth in SEQ ID NO:1; and comprises an amino acid substitution of amino acid D158, where the substitution is Glu. In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence set forth in SEQ ID NO:1; and comprises an amino acid substitution of amino acid D158, where the substitution is Arg or His. In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence set forth in SEQ ID NO:1; and comprises an amino acid substitution of amino acid D158, such that amino acid 86 is Ala.

In some cases, a variant CD80 polypeptide suitable for inclusion in a multimeric polypeptide of the present disclosure comprises the following amino acid sequence:

```
                                      (SEQ ID NO: 9)
VIHVTK EVKEVATLSC GHNVSVEELA QTRIYWQKEK KMVLTMMSGD

MNIWPEYKNR TIFDITNNLS IVILALRPSD EGTYECVVLK

YEKDAFKREH LAEVTLSVKA DFPTPSISDF EIPTSNIRRI

ICSTSGGFPE PHLSWLENGE ELNAINTTVS QXPETELYAV

SSKLDFNMTT NHSFMCLIKY GHLRVNQTFN WNTTKQEHFP DN,
``` where X is any amino acid other than aspartic acid, e.g., where X is Gly, Ala, Val, Leu, Ile, Pro, Phe, Tyr, Trp, Ser, Thr, Cys, Met, Asn, Gln, Arg, His, Lys, or Glu. In some cases, X is Ala, Gly, Leu, Ile, or Val. In some cases, X is Glu. In some cases, X is Arg or Lys. In some cases, X is Ala.

In some cases, a variant CD80 polypeptide suitable for inclusion in a multimeric polypeptide of the present disclosure comprises the following amino acid sequence:

```
                                      (SEQ ID NO: 10)
VIHVTK EVKEVATLSC GHNVSVEELA QTRIYWQKEK KMVLTMMSGD

MNIWPEYKNR TIFDITNNLS IVILALRPSD EGTYECVVLK

YEKDAFKREH LAEVTLSVKA DFPTPSISDF EIPTSNIRRI

ICSTSGGFPE PHLSWLENGE ELNAINTTVS QAPETELYAV

SSKLDFNMTT NHSFMCLIKY GHLRVNQTFN WNTTKQEHFP DN.
```

Additional CD80 Variants

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence depicted in FIG. 2 or as set forth in SEQ ID NO:1; and comprises an amino acid substitution of amino acid N19, N63, I67, K86, Q157, D158, L25, Y31, Q33, M38, V39, I49, Y53, D60, F108, or S156, where the amino acid numbering is based on the amino acid sequence depicted in FIG. 2.

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence depicted in FIG. 2 or as set forth in SEQ ID NO:1; and comprises an amino acid substitution of amino acid N19, where the amino acid numbering is based on the amino acid sequence depicted in FIG. 2.

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence depicted in FIG. 2 or as set forth in SEQ ID NO:1; and comprises an amino acid substitution of amino acid N63, where the amino acid numbering is based on the amino acid sequence depicted in FIG. 2.

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence depicted in FIG. 2 or as set forth in SEQ ID NO:1; and comprises an amino acid substitution of amino acid Q157, where the amino acid numbering is based on the amino acid sequence depicted in FIG. 2.

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence depicted in FIG. 2 or as set forth in SEQ ID NO:1; and comprises an amino acid substitution of amino acid L25, where the amino acid numbering is based on the amino acid sequence depicted in FIG. 2. In some cases, the substitution is an L25A substitution. In some cases, the substitution is an L25V substitution. In some cases, the substitution is an L25G substitution. In some cases, the substitution is an L25S substitution.

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence depicted in FIG. 2 or as set forth in SEQ ID NO:1; and comprises an amino acid substitution of amino acid Y31, where the amino acid numbering is based on the amino acid sequence depicted in FIG. 2. In some cases, the substitution is a Y31A substitution. In some cases, the substitution is a Y31G substitution. In some cases, the substitution is a Y31V substitution. In some cases, the substitution is a Y31I substitution. In some cases, the substitution is a Y31L substitution. In some cases, the substitution is a Y31R substitution. In some cases, the substitution is a Y31W substitution.

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence depicted in FIG. 2 or as set forth in SEQ ID NO:1; and comprises an amino acid substitution of amino acid Q33, where the amino acid numbering is based on the amino acid sequence depicted in FIG. 2. In some cases, the substitution is a Q33A substitution. In some cases, the substitution is a Q33R substitution. In some cases, the substitution is a Q33E substitution. In some cases, the substitution is a Q33L substitution.

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence depicted in FIG. 2 or as set forth in SEQ ID NO:1; and comprises an amino acid substitution of amino acid M38, where the amino acid numbering is based on the amino acid sequence depicted in FIG. 2. In some cases, the substitution is an M38A substitution. In some cases, the substitution is an M38S substitution. In some cases, the substitution is an M38V substitution. In some cases, the substitution is an M38L substitution. In some cases, the substitution is an M38G substitution. In some cases, the substitution is an M38I substitution.

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence depicted in FIG. 2 or as set forth in SEQ ID NO:1; and comprises an amino acid substitution of amino acid V39, where the amino acid numbering is based on the amino acid sequence depicted in FIG. 2.

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence depicted in FIG. 2 or as set forth in SEQ ID NO:1; and comprises an amino acid substitution of amino acid I49, where the amino acid numbering is based on the amino acid sequence depicted in FIG. 2.

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence depicted in FIG. 2 or as set forth in SEQ ID NO:1; and comprises an amino acid substitution of amino acid Y53, where the amino acid numbering is based on the amino acid sequence depicted in FIG. 2.

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence depicted in FIG. 2 or as set forth in SEQ ID NO:1; and comprises an amino acid substitution of amino acid D60, where the amino acid numbering is based on the amino acid sequence depicted in FIG. 2.

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence depicted in FIG. 2 or as set forth in SEQ ID NO:1; and comprises an amino acid substitution of amino acid F108, where the amino acid numbering is based on the amino acid sequence depicted in FIG. 2.

In some cases, a variant CD80 polypeptide suitable for inclusion in a multimeric polypeptide of the present disclosure comprises an amino acid sequence having at least 90%, at least 95%, at least 98%, or at least 99%, amino acid sequence identity to the CD80 ectodomain amino acid sequence depicted in FIG. 2 or as set forth in SEQ ID NO:1; and comprises an amino acid substitution of amino acid S156, where the amino acid numbering is based on the amino acid sequence depicted in FIG. 2.

4-1BBL

In some cases, a T-cell modulatory multimeric polypeptide of the present disclosure comprises a 4-1BBL modulatory polypeptide, which in some cases is a variant 4-1BBL modulatory polypeptide. A wild-type human 4-1BBL amino acid sequence is provided in FIG. 3. The tumor necrosis factor (TNF) homology domain (THD) of human 4-1BBL comprises amino acids 81-254, amino acids 80-254, or amino acids 80-246 of the amino acid sequence depicted in FIG. 3. Thus, a wild-type amino acid sequence of the THD of human 4-1BBL can be, e.g., one of SEQ ID NOs:2-4, as follows:

```
                                          (SEQ ID NO: 2)
PAGLLDLRQG MFAQLVAQNV LLIDGPLSWY SDPGLAGVSL

TGGLSYKEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE.
                                          (SEQ ID NO: 3)
D PAGLLDLRQG MFAQLVAQNV LLIDGPLSWY SDPGLAGVSL

TGGLSYKEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE.
                                          (SEQ ID NO: 4)
D PAGLLDLRQG MFAQLVAQNV LLIDGPLSWY SDPGLAGVSL

TGGLSYKEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV TPEIPA.
```

Wild-type 4-1BBL binds to 4-1BB (CD137). An amino acid sequences of 4-1BB is provided in FIG. 5. In some cases, a variant 4-1BBL polypeptide present in a multimeric polypeptide of the present disclosure binds to 4-1BB with reduced affinity compared to binding of wild-type 4-1BBL to 4-1BB.

Variant 4-1BBL Modulatory Polypeptides

In some cases, a variant 4-1BBL modulatory polypeptide suitable for inclusion in a multimeric polypeptide of the present disclosure comprises a substitution of amino acid comprises a substitution of one of amino acids 91, 92, 94-115, 117-126, 128-132, 144-153, 155-158, 184-187, 189-191, 193-195, 197, 210-219, 221-224, 226, 228-231, 233, and 234, where the amino acid numbering is based on the amino acid sequence depicted in FIG. 3.

In some cases, a variant 4-1BBL modulatory polypeptide suitable for inclusion in a multimeric polypeptide of the present disclosure comprises a substitution of amino acid comprises a substitution of amino acid K127, where the amino acid numbering is based on the amino acid sequence depicted in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the 4-1BBL THD amino acid sequence set forth in one of SEQ ID NOs:2-4, or set forth in FIG. 3; and comprises an amino acid substitution of K127, where the amino acid numbering is based on the amino acid sequence depicted in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the following amino acid sequence:

```
                                          (SEQ ID NO: 11)
PAGLLDLRQG MFAQLVAQNV LLIDGPLSWY SDPGLAGVSL

TGGLSYXEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE,
``` where X is an amino acid other than lysine, e.g., where X is Gly, Ala, Val, Leu, Ile, Pro, Phe, Tyr, Trp, Ser, Thr, Cys, Met, Asn, Gln, Arg, His, Asp, or Glu. In some cases, X is Ala, Gly, Leu, Ile, or Val. In some cases, X is Glu or Asp. In some cases, X is Arg or His. In some cases, X is Ala.

In some cases, a variant 4-1BBL polypeptide suitable for inclusion in a multimeric polypeptide of the present disclosure comprises the following amino acid sequence:

```
                                          (SEQ ID NO: 12)
PAGLLDLRQG MFAQLVAQNV LLIDGPLSWY SDPGLAGVSL

TGGLSYAEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE.
```

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the following amino acid sequence:

```
                                          (SEQ ID NO: 13)
D PAGLLDLRQG MFAQLVAQNV LLIDGPLSWY SDPGLAGVSL

TGGLSYXEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE,
``` where X is an amino acid other than lysine, e.g., where X is Gly, Ala, Val, Leu, Ile, Pro, Phe, Tyr, Trp, Ser, Thr, Cys, Met, Asn, Gln, Arg, His, Asp, or Glu. In some cases, X is Ala, Gly, Leu, Ile, or Val. In some cases, X is Glu or Asp. In some cases, X is Arg or His. In some cases, X is Ala.

In some cases, a variant 4-1BBL polypeptide suitable for inclusion in a multimeric polypeptide of the present disclosure comprises the following amino acid sequence:

(SEQ ID NO: 14)
D PAGLLDLRQG MFAQLVAQNV LLIDGPLSWY SDPGLAGVSL
TGGLSYAEDT KELVVAKAGV YYVFFQLELR RVVAGEGSGS
VSLALHLQPL RSAAGAAALA LTVDLPPASS EARNSAFGFQ
GRLLHLSAGQ RLGVHLHTEA RARHAWQLTQ GATVLGLFRV
TPEIPAGLPS PRSE.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the following amino acid sequence:

(SEQ ID NO: 15)
D PAGLLDLRQG MFAQLVAQNV LLIDGPLSWY
SDPGLAGVSL TGGLSYXEDT KELVVAKAGV YYVFFQLELR
RVVAGEGSGS VSLALHLQPL RSAAGAAALA LTVDLPPASS
EARNSAFGFQ GRLLHLSAGQ RLGVHLHTEA RARHAWQLTQ
GATVLGLFRV TPEIPA, where where X is an amino acid other than lysine, e.g., where X is Gly, Ala, Val, Leu, Ile, Pro, Phe, Tyr, Trp, Ser, Thr, Cys, Met, Asn, Gln, Arg, His, Asp, or Glu. In some cases, X is Ala, Gly, Leu, Ile, or Val. In some cases, X is Glu or Asp. In some cases, X is Arg or His. In some cases, X is Ala.

In some cases, a variant 4-1BBL polypeptide suitable for inclusion in a multimeric polypeptide of the present disclosure comprises the following amino acid sequence:

(SEQ ID NO: 16)
D PAGLLDLRQG MFAQLVAQNV LLIDGPLSWY SDPGLAGVSL
TGGLSYAEDT KELVVAKAGV YYVFFQLELR RVVAGEGSGS
VSLALHLQPL RSAAGAAALA LTVDLPPASS EARNSAFGFQ
GRLLHLSAGQ RLGVHLHTEA RARHAWQLTQ GATVLGLFRV TPEIPA.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of one of amino acids 91, 92, 94-115, 117-126, 128-132, 144-153, 155-158, 184-187, 189-191, 193-195, 197, 210-219, 221-224, 226, 228-231, 233, and 234 based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid M91 (e.g., where amino acid 91 is Gly, Ala, Val, Leu, Ile, Pro, Phe, Tyr, Trp, Ser, Thr, Cys, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid F92 (e.g., where amino acid 92 is Gly, Ala, Val, Leu, Ile, Pro, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid Q94 (e.g., where amino acid 94 is Gly, Ala, Val, Leu, Ile, Pro, Phe, Tyr, Trp, Ser, Thr, Cys, Met, Asn, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid L95 (e.g., where amino acid 95 is Gly, Ala, Val, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid V96 (e.g., where amino acid 96 is Gly, Ala, Leu, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid Q98 (e.g., where amino acid 98 is Gly, Ala, Val, Leu, Ile, Pro, Phe, Tyr, Trp, Ser, Thr, Cys, Met, Asn, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid N99 (e.g., where amino acid 99 is Gly, Ala, Val, Leu, Ile, Pro, Phe, Tyr, Trp, Ser, Thr, Cys, Met, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid V100 (e.g., where amino acid 100 is Gly, Ala, Leu, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid L101 (e.g., where amino acid 101 is Gly, Ala, Val, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid L102 (e.g., where amino acid 102 is Gly, Ala, Val, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid L103 (e.g., where amino acid 103 is Gly, Ala, Val, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid I103 (e.g., where amino acid 103 is Gly, Ala, Val, Leu, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid D104 (e.g., where amino acid 104 is Gly, Ala, Val, Leu, Ile, Pro, Phe, Tyr, Trp, Ser, Thr, Cys, Met, Asn, Gln, Lys, Arg, His, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid G105 (e.g., where amino acid 105 is Ala, Val, Leu, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid P106 (e.g., where amino acid 106 is Gly, Ala, Val, Leu, Ile, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid L107 (e.g., where amino acid 107 is Gly, Ala, Val, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid S108 (e.g., where amino acid 108 is Gly, Ala, Val, Leu, Ile, Pro, Phe, Tyr, Trp, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid W109 (e.g., where amino acid 109 is Gly, Ala, Val, Leu, Ile, Pro, Phe, Tyr, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid Y110 (e.g., where amino acid 110 is Gly, Ala, Val, Leu, Ile, Pro, Phe, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid S111 (e.g., where amino acid 111 is Gly, Ala, Val, Leu, Ile, Pro, Phe, Tyr, Trp, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid D112 (e.g., where amino acid 112 is Gly, Ala, Val, Leu, Ile, Pro, Phe, Tyr, Trp, Ser, Thr, Cys, Met, Asn, Gln, Lys, Arg, His, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid P113 (e.g., where amino acid 113 is Gly, Ala, Val, Leu, Ile, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid G114 (e.g., where amino acid 114 is Ala, Val, Leu, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid L115 (e.g., where amino acid 115 is Gly, Ala, Val, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid G117 (e.g., where amino acid 117 is Ala, Val, Leu, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid V118 (e.g., where amino acid 118 is Gly, Ala, Leu, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid S119 (e.g., where amino acid 119 is Gly, Ala, Val, Leu, Ile, Pro, Phe, Tyr, Trp, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid L120 (e.g., where amino acid 120 is Gly, Ala, Val, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid T121 (e.g., where amino acid 121 is Gly, Ala, Val, Leu, Ile, Pro, Phe, Tyr, Trp, Ser, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid G122 (e.g., where amino acid 122 is Ala, Val, Leu, Ile, Pro, Phe, Tyr, Trp, Ser, Thr, Cys, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid G123 (e.g., where amino acid 123 is Ala, Val, Leu, Ile, Pro, Phe, Tyr, Trp, Ser, Thr, Cys, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid L124 (e.g., where amino acid 124 is Gly, Ala, Val, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid S125 (e.g., where amino acid 125 is Gly, Ala, Val, Leu, Ile, Pro, Phe, Tyr, Trp, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid Y126 (e.g., where amino acid 126 is Gly, Ala, Val, Leu, Ile, Pro, Phe, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid E128 (e.g., where amino acid 128 is Gly, Ala, Val, Leu, Ile, Pro, Phe, Tyr, Trp, Ser, Thr, Cys, Met, Asn, Gln, Lys, Arg, His, or Asp), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid D129 (e.g., where amino acid 129 is Gly, Ala, Val, Leu, Ile, Pro, Phe, Tyr, Trp, Ser, Thr, Cys, Met, Asn, Gln, Lys, Arg, His, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid T130 (e.g., where amino acid 130 is Gly, Ala, Val, Leu, Ile, Pro, Phe, Tyr, Trp, Ser, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid K131 (e.g., where amino acid 131 is Gly, Ala, Val, Leu, Ile, Pro, Phe, Tyr, Trp, Ser, Thr, Cys, Met, Asn, Gln, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid E132 (e.g., where amino acid 132 is Gly, Ala, Val, Leu, Ile, Pro, Phe, Tyr, Trp, Ser, Thr, Cys, Met, Asn, Gln, Lys, Arg, His, or Asp), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid F144 (e.g., where amino acid 144 is Gly, Ala, Val, Leu, Ile, Pro, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid F145 (e.g., where amino acid 145 is Gly, Ala, Val, Leu, Ile, Pro, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid Q146 (e.g., where amino acid 146 is Gly, Ala, Val, Leu, Ile, Pro, Phe, Tyr, Trp, Ser, Thr, Cys, Met, Asn, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid L147 (e.g., where amino acid 147 is Gly, Ala, Val, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid E148 (e.g., where amino acid 148 is Gly, Ala, Val, Leu, Ile, Pro, Phe, Tyr, Trp, Ser, Thr, Cys, Met, Asn, Gln, Lys, Arg, His, or Asp), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid L149 (e.g., where amino acid 149 is Gly, Ala, Val, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid R150 (e.g., where amino acid 150 is Gly, Ala, Val, Leu, Ile, Pro, Phe, Tyr, Trp, Ser, Thr, Cys, Met, Asn, Gln, Lys, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid R151 (e.g., where amino acid 151 is Gly, Ala, Val, Leu, Ile, Pro, Phe, Tyr, Trp, Ser, Thr, Cys, Met, Asn, Gln, Lys, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid V152 (e.g., where amino acid 152 is Gly, Ala, Leu, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid V153 (e.g., where amino acid 153 is Gly, Ala, Leu, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid G155 (e.g., where amino acid 155 is Ala, Val, Leu, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid E156 (e.g., where amino acid 156 is Gly, Ala, Val, Leu, Ile, Pro, Phe, Tyr, Trp, Ser, Thr, Cys, Met, Asn, Gln, Lys, Arg, His, or Asp), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid G157 (e.g., where amino acid 157 is Ala, Val, Leu, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid S158 (e.g., where amino acid 158 is Gly, Ala, Val, Leu, Ile, Pro, Phe, Tyr, Trp, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid D184 (e.g., where amino acid 184 is Gly, Ala, Val, Leu, Ile, Pro, Phe, Tyr, Trp, Ser, Thr, Cys, Met, Asn, Gln, Lys, Arg, His, or Asp), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid L185 (e.g., where amino acid 185 is Gly, Ala, Val, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid P186 (e.g., where amino acid 186 is Gly, Ala, Val, Leu, Ile, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid P187 (e.g., where amino acid 187 is Gly, Ala, Val, Leu, Ile, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid S189 (e.g., where amino acid 189 is Gly, Ala, Val, Leu, Ile, Pro, Phe, Tyr, Trp, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid S190 (e.g., where amino acid 190 is Gly, Ala, Val, Leu, Ile, Pro, Phe, Tyr, Trp, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid E191 (e.g., where amino acid 191 is Gly, Ala, Val, Leu, Ile, Pro, Phe, Tyr, Trp, Ser, Thr, Cys, Met, Asn, Gln, Lys, Arg, His, or Asp), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid R193 (e.g., where amino acid 155 is Gly, Ala, Val, Leu, Ile, Pro, Phe, Tyr, Trp, Ser, Thr, Cys, Met, Asn, Gln, Lys, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid N194 (e.g., where amino acid 194 is Gly, Ala, Val, Leu, Ile, Pro, Phe, Tyr, Trp, Ser, Thr, Cys, Met, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid S195 (e.g., where amino acid 195 is Gly, Ala, Val, Leu, Ile, Pro, Phe, Tyr, Trp, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid F197 (e.g., where amino acid 197 is Gly, Ala, Val, Leu, Ile, Pro, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid Q210 (e.g., where amino acid 210 is Gly, Ala, Val, Leu, Ile, Pro, Phe, Tyr, Trp, Ser, Thr, Cys, Met, Asn, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid R211 (e.g., where amino acid 211 is Gly, Ala, Val, Leu, Ile, Pro, Phe, Tyr, Trp, Ser, Thr, Cys, Met, Asn, Gln, Lys, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid L212 (e.g., where amino acid 212 is Gly, Ala, Val, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid G213 (e.g., where amino acid 213 is Ala, Val, Leu, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid V214 (e.g., where amino acid 214 is Gly, Ala, Leu, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid H215 (e.g., where amino acid 215 is Gly, Ala, Val, Leu, Ile, Pro, Phe, Tyr, Trp, Ser, Thr, Cys, Met, Asn, Gln, Lys, Arg, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid L216 (e.g., where amino acid 216 is Gly, Ala, Val, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid H217 (e.g., where amino acid 217 is Gly, Ala, Val, Leu, Ile, Pro, Phe, Tyr, Trp, Ser, Thr, Cys, Met, Asn, Gln, Lys, Arg, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid T218 (e.g., where amino acid 218 is Gly, Ala, Val, Leu, Ile, Pro, Phe, Tyr, Trp, Ser, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid E219 (e.g., where amino acid 219 is Gly, Ala, Val, Leu, Ile, Pro, Phe, Tyr, Trp, Ser, Thr, Cys, Met, Asn, Gln, Lys, Arg, His, or Asp), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid R221 (e.g., where amino acid 221 is Gly, Ala, Val, Leu, Ile, Pro, Phe, Tyr, Trp, Ser, Thr, Cys, Met, Asn, Gln, Lys, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid R223 (e.g., where amino acid 223 is Gly, Ala, Val, Leu, Ile, Pro, Phe, Tyr, Trp, Ser, Thr, Cys, Met, Asn, Gln, Lys, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid H224 (e.g., where amino acid 224 is Gly, Ala, Val, Leu, Ile, Pro, Phe, Tyr, Trp, Ser, Thr, Cys, Met, Asn, Gln, Lys, Arg, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid W226 (e.g., where amino acid 226 is Gly, Ala, Val, Leu, Ile, Pro, Phe, Tyr, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid Q227 (e.g., where amino acid 210 is Gly, Ala, Val, Leu, Ile, Pro, Phe, Tyr, Trp, Ser, Thr, Cys, Met, Asn, Lys, Arg, His, Asp, or Glu), based on the amino acid numbering set out in FIG. 3. In some cases, the substitution is a Q227A substitution. In some cases, the substitution is a Q227R substitution. In some cases, the substitution is a Q227E substitution. In some cases, the substitution is a Q227L substitution. In some cases, the substitution is a Q227G substitution. In some cases, the substitution is a Q227V substitution. In some cases, the substitution is a Q227I substitution. In some cases, the substitution is a Q227P substitution. In some cases, the substitution is a Q227F substitution. In some cases, the substitution is a Q227Y substitution. In some cases, the substitution is a Q227S substitution. In some cases, the substitution is a Q227T substitution. In some cases, the substitution is a Q227C substitution. In some cases, the substitution is a Q227M substitution. In some cases, the substitution is a Q227N substitution. In some cases, the substitution is a Q227K substitution. In some cases, the substitution is a Q227H substitution. In some cases, the substitution is a Q227D substitution.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid L228 (e.g., where amino acid 228 is Gly, Ala, Val, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid T229 (e.g., where amino acid 229 is Gly, Ala, Val, Leu, Ile, Pro, Phe, Tyr, Trp, Ser, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid Q230 (e.g., where amino acid 230 is Gly, Ala, Val, Leu, Ile, Pro, Phe, Tyr, Trp, Ser, Thr, Cys, Met, Asn, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid G231 (e.g., where amino acid 231 is Ala, Val, Leu, Ile, Pro, Phe, Tyr, Trp, Ser, Thr, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid T233 (e.g., where amino acid 233 is Gly, Ala, Val, Leu, Ile, Pro, Phe, Tyr, Trp, Ser, Cys, Met, Asn, Gln, Lys, Arg, His, Asp, or Glu), based on the amino acid numbering set out in FIG. 3.

In some cases, a variant 4-1BBL polypeptide suitable for inclusion in a multimeric polypeptide of the present disclosure comprises an amino acid sequence having at least 90%, at least 95%, at least 98%, or at least 99%, amino acid sequence identity to the amino acid sequence depicted in FIG. 3 or set forth in one of SEQ ID NOs:2-4, where the variant 4-1BBL polypeptide comprises a substitution of amino acid V234 (e.g., where amino acid 234 is Gly, Ala, Leu, Ile, Pro, Phe, Tyr, Trp, Ser, Thr, Cys, Met, Asn, Gln, Lys, Arg, His, Asp, or Glu), based on the amino acid numbering set out in FIG. 3.

Scaffold Polypeptides

A T-cell modulatory multimeric polypeptide of the present disclosure comprises an Fc polypeptide, or another suitable scaffold polypeptide.

Suitable scaffold polypeptides include antibody-based scaffold polypeptides and non-antibody-based scaffolds. Non-antibody-based scaffolds include, e.g., albumin, an XTEN (extended recombinant) polypeptide, transferrin, an Fc receptor polypeptide, an elastin-like polypeptide (see, e.g., Hassouneh et al. (2012) *Methods Enzymol.* 502:215; e.g., a polypeptide comprising a pentapeptide repeat unit of (Val-Pro-Gly-X-Gly), where X iany amino acid other than proline), an albumin-binding polypeptide, a silk-like polypeptide (see, e.g., Valluzzi et al. (2002) *Philos Trans R Soc Lond B Biol Sci.* 357:165), a silk-elastin-like polypeptide (SELP; see, e.g., Megeed et al. (2002) *Adv Drug Deliv Rev.* 54:1075), and the like. Suitable XTEN polypeptides include, e.g., those disclosed in WO 2009/023270, WO 2010/091122, WO 2007/103515, US 2010/0189682, and US 2009/0092582; see also Schellenberger et al. (2009) *Nat Biotechnol.* 27:1186). Suitable albumin polypeptides include, e.g., human serum albumin.

Suitable scaffold polypeptides will in some cases be a half-life extending polypeptides. Thus, in some cases, a suitable scaffold polypeptide increases the in vivo half-life (e.g., the serum half-life) of the multimeric polypeptide, compared to a control multimeric polypeptide lacking the scaffold polypeptide. For example, in some cases, a scaffold polypeptide increases the in vivo half-life (e.g., the serum half-life) of the multimeric polypeptide, compared to a control multimeric polypeptide lacking the scaffold polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold. As an example, in some cases, an Fc polypeptide increases the in vivo half-life (e.g., the serum half-life) of the multimeric polypeptide, compared to a control multimeric polypeptide lacking the Fc polypeptide, by at least about 10%, at least about 15%, at least about 20%, at least about 25%, at least about 50%, at least about 2-fold, at least about 2.5-fold, at least about 5-fold, at least about 10-fold, at least about 25-fold, at least about 50-fold, at least about 100-fold, or more than 100-fold.

Fc Polypeptides

In some cases, the first and/or the second polypeptide chain of a multimeric polypeptide of the present disclosure comprises an Fc polypeptide. The Fc polypeptide of a multimeric polypeptide of the present disclosure can be a human IgG1 Fc, a human IgG2 Fc, a human IgG3 Fc, a human IgG4 Fc, etc. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to an amino acid sequence of an Fc region depicted in FIGS. 6A-6C. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 6A. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 6A; and comprises a substitution of N77; e.g., the Fc polypeptide comprises an N77A substitution. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG2 Fc polypeptide depicted in FIG. 6A; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 99-325 of the human IgG2 Fc polypeptide depicted in FIG. 6A. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgG3 Fc polypeptide depicted in FIG. 6A; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 19-246 of the human IgG3 Fc polypeptide depicted in FIG. 6A. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgM Fc polypeptide depicted in FIG. 6B; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 1-276 to the human IgM Fc polypeptide depicted in FIG. 6B. In some cases, the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to the human IgA Fc polypeptide depicted in FIG. 6C; e.g., the Fc polypeptide comprises an amino acid sequence having at least about 70%, at least about 75%, at least about 80%, at least about 85%, at least about 90%, at least about 95%, at least about 98%, at least about 99%, or 100%, amino acid sequence identity to amino acids 1-234 to the human IgA Fc polypeptide depicted in FIG. 6C. In some cases, the Fc polypeptide comprises an amino acid substitution that provides for reduced effector function.

Additional Polypeptides

A polypeptide chain of a multimeric polypeptide of the present disclosure can include one or more polypeptides in addition to those described above. Suitable additional polypeptides include epitope tags and affinity domains. The one or more additional polypeptide can be included at the N-terminus of a polypeptide chain of a multimeric polypeptide of the present disclosure, at the C-terminus of a polypeptide chain of a multimeric polypeptide of the present disclosure, or internally within a polypeptide chain of a multimeric polypeptide of the present disclosure.

Epitope Tag

Suitable epitope tags include, but are not limited to, hemagglutinin (HA; e.g., YPYDVPDYA (SEQ ID NO:17); FLAG (e.g., DYKDDDDK (SEQ ID NO:18); c-myc (e.g., EQKLISEEDL; SEQ ID NO:19), and the like.

Affinity Domain

Affinity domains include peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel sepharose. Exemplary affinity domains include His5 (HHHHH) (SEQ ID NO:20), HisX6 (HHHHHH) (SEQ ID NO:21), C-myc (EQKLISEEDL) (SEQ ID NO:19), Flag (DYKDDDDK) (SEQ ID NO:18), StrepTag (WSHPQFEK) (SEQ ID NO:22), hemagglutinin, e.g., HA Tag (YPYDVPDYA) (SEQ ID NO:17), glutathione-S-transferase (GST), thioredoxin, cellulose binding domain, RYIRS (SEQ ID NO:23), Phe-His-His-Thr (SEQ ID NO:24), chitin binding domain, S-peptide, T7 peptide, SH2 domain, C-end RNA tag, WEAAAREACCRECCARA (SEQ ID NO:25), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, Id, leucine zipper sequences, and maltose binding protein.

Exemplary Multimeric Polypeptides

Exemplary multimeric polypeptides of the present disclosure are described below.

Variant 4-1BBL on First Polypeptide Chain; Variant CD-80 on Second Polypeptide Chain In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising an amino acid sequence having at least 90%, at least 95%, at least 98%, or at least 99%, amino acid sequence identity to the amino acid sequence of one of SEQ ID NOs:2-4, or set forth in FIG. 3, and comprises a substitution of amino acid K127, where the amino acid numbering is based on the 4-1BBL amino acid sequence depicted in FIG. 3; and b) a second polypeptide comprising, in order from N-terminus to C-terminus: i) a variant CD80 polypeptide comprising an amino acid sequence having at least 90%, at least 95%, at least 98%, or at least 99%, amino acid sequence identity to the amino acid sequence of SEQ ID NO:1, and comprising an amino acid substitution of amino acid I67, K86, or D158; ii) an MHC heavy chain polypeptide; and iii) an Ig Fc polypeptide. In some cases, the first polypeptide comprises a single variant 4-1BBL polypeptide; and the second polypeptide comprises a single variant CD80 polypeptide. In some cases, the first polypeptide comprises two variant 4-1BBL polypeptides (e.g., where the variants are in tandem); and the second polypeptide comprises a single variant CD80 polypeptide. In some cases, the first polypeptide comprises three variant 4-1BBL polypeptides (e.g., where the variants are in tandem); and the second polypeptide comprises a single variant CD80 polypeptide. In some cases, the first polypeptide comprises a single variant 4-1BBL polypeptide; and the second polypeptide comprises two variant CD80 polypeptides (e.g., where the variants are in tandem). In some cases, the first polypeptide comprises a single variant 4-1BBL polypeptide; and the second polypeptide comprises three variant CD80 polypeptides (e.g., where the variants are in tandem). In some cases, the first polypeptide comprises two variant 4-1BBL polypeptides (e.g., where the variants are in tandem); and the second polypeptide comprises two variant CD80 polypeptides (e.g., where the variants are in tandem). In some cases, the first polypeptide comprises three variant 4-1BBL polypeptides (e.g., where the variants are in tandem); and the second polypeptide comprises three variant CD80 polypeptides (e.g., where the variants are in tandem).

K127 (4-1BBL)+I67 (CD80)

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising an amino acid sequence having at least 90%, at least 95%, at least 98%, or at least 99%, amino acid sequence identity to the following amino acid sequence:

(SEQ ID NO: 11)
PAGLLDLRQG MFAQLVAQNV LLIDGPLSWY

SDPGLAGVSL TGGLSYXEDT KELVVAKAGV YYVFFQLELR

RVVAGEGSGS VSLALHLQPL RSAAGAAALA LTVDLPPASS

EARNSAFGFQ GRLLHLSAGQ RLGVHLHTEA RARHAWQLTQ

GATVLGLFRV TPEIPAGLPS PRSE, where X is not a lysine, e.g., where X is Ala, Gly, Val, or Leu, or where X is Glu or Asp, or where X is Arg or His, or where X is Ala; and b) a second polypeptide comprising, in order from N-terminus to C-terminus: i) a variant CD80 polypeptide comprising an amino acid sequence having at least 90%, at least 95%, at least 98%, or at least 99%, amino acid sequence identity to the following amino acid sequence:

(SEQ ID NO: 5)
VIHVTK EVKEVATLSC GHNVSVEELA

QTRIYWQKEK KMVLTMMSGD MNIWPEYKNR TIFDITNNLS

XVILALRPSD EGTYECVVLK YEKDAFKREH LAEVTLSVKA

DFPTPSISDF EIPTSNIRRI ICSTSGGFPE PHLSWLENGE

ELNAINTTVS QDPETELYAV SSKLDFNMTT NHSFMCLIKY

GHLRVNQTFN WNTTKQEHFP DN, where X is any amino acid other than isoleucine, e.g., where X is Gly, Ala, Val, Leu, Pro, Phe, Tyr, Trp, Ser, Thr, Cys, Met, Asn, Gln, Lys, Arg, His, Asp, or Glu, or where X is Ala, Gly, Val, or Leu, or where X is Glu or Asp, or where X is Arg, His, or Lys, or where X is Ala; ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising an amino acid sequence having at least 90%, at least 95%, at least 98%, or at least 99%, amino acid sequence identity to the following amino acid sequence:

(SEQ ID NO: 13)
D PAGLLDLRQG MFAQLVAQNV LLIDGPLSWY

SDPGLAGVSL TGGLSYXEDT KELVVAKAGV YYVFFQLELR

RVVAGEGSGS VSLALHLQPL RSAAGAAALA LTVDLPPASS

EARNSAFGFQ GRLLHLSAGQ RLGVHLHTEA RARHAWQLTQ

GATVLGLFRV TPEIPAGLPS PRSE, where X is not a lysine, e.g., where X is Ala, Gly, Val, or Leu, or where X is Glu or Asp, or where X is Arg or His, or where X is Ala; and b) a second polypeptide comprising, in order from N-terminus to C-terminus: i) a variant CD80 polypeptide comprising an amino acid sequence having at least 90%, at least 95%, at least 98%, or at least 99%, amino acid sequence identity to the following amino acid sequence:

(SEQ ID NO: 5)
VIHVTK EVKEVATLSC GHNVSVEELA

QTRIYWQKEK KMVLTMMSGD MNIWPEYKNR TIFDITNNLS

XVILALRPSD EGTYECVVLK YEKDAFKREH LAEVTLSVKA

DFPTPSISDF EIPTSNIRRI ICSTSGGFPE PHLSWLENGE

ELNAINTTVS QDPETELYAV SSKLDFNMTT NHSFMCLIKY

GHLRVNQTFN WNTTKQEHFP DN, where X is any amino acid other than isoleucine, e.g., where X is Gly, Ala, Val, Leu, Pro, Phe, Tyr, Trp, Ser, Thr, Cys, Met, Asn, Gln, Lys, Arg, His, Asp, or Glu, or where X is Ala, Gly, Val, or Leu, or where X is Glu or Asp, or where X is Arg, His, or Lys, or where X is Ala; ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising an amino acid sequence having at least 90%, at least 95%, at least 98%, or at least 99%, amino acid sequence identity to the following amino acid sequence:

(SEQ ID NO: 15)
D PAGLLDLRQG MFAQLVAQNV LLIDGPLSWY

SDPGLAGVSL TGGLSYXEDT KELVVAKAGV YYVFFQLELR

RVVAGEGSGS VSLALHLQPL RSAAGAAALA LTVDLPPASS

EARNSAFGFQ GRLLHLSAGQ RLGVHLHTEA RARHAWQLTQ

GATVLGLFRV TPEIPA, where X is not a lysine, e.g., where X is Ala, Gly, Val, or Leu, or where X is Glu or Asp, or where X is Arg or His, or where X is Ala; and b) a second polypeptide comprising, in order from N-terminus to C-terminus: i) a variant CD80 polypeptide comprising an amino acid sequence having at least 90%, at least 95%, at least 98%, or at least 99%, amino acid sequence identity to the following amino acid sequence:

```
                                           (SEQ ID NO: 5)
VIHVTK EVKEVATLSC GHNVSVEELA QTRIYWQKEK KMVLTMMSGD

MNIWPEYKNR TIFDITNNLS XVILALRPSD EGTYECVVLK

YEKDAFKREH LAEVTLSVKA DFPTPSISDF EIPTSNIRRI

ICSTSGGFPE PHLSWLENGE ELNAINTTVS QDPETELYAV

SSKLDFNMTT NHSFMCLIKY GHLRVNQTFN WNTTKQEHFP DN,
``` where X is any amino acid other than isoleucine, e.g., where X is Gly, Ala, Val, Leu, Pro, Phe, Tyr, Trp, Ser, Thr, Cys, Met, Asn, Gln, Lys, Arg, His, Asp, or Glu, or where X is Ala, Gly, Val, or Leu, or where X is Glu or Asp, or where X is Arg, His, or Lys, or where X is Ala; ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising the amino acid sequence PAGLLDLRQG MFAQLVAQNV LLIDGPLSWY SDPGLAGVSL TGGLSYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:12); and b) a second polypeptide comprising, in order from N-terminus to C-terminus: i) a variant CD80 polypeptide comprising the amino acid sequence VIHVTK EVKEVATLSC GHNVSVEELA QTRIYWQKEK KMVLTMMSGD MNIWPEYKNR TIFDITNNLS A VILALRPSD EGTYECVVLK YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:6); ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising the amino acid sequence D PAGLLDLRQG MFAQLVAQNV LLIDGPLSWY SDPGLAGVSL TGGLSYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:14); and b) a second polypeptide comprising, in order from N-terminus to C-terminus: i) a variant CD80 polypeptide comprising the amino acid sequence VIHVTK EVKEVATLSC GHNVSVEELA QTRIYWQKEK KMVLTMMSGD MNIWPEYKNR TIFDITNNLS A VILALRPSD EGTYECVVLK YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:6); ii) an MHC heavy chain polypeptide; and iii) an Ig Fc polypeptide.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising the amino acid sequence PAGLLDLRQG MFAQLVAQNV LLIDGPLSWY SDPGLAGVSL TGGLSYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPA (SEQ ID NO:27); and b) a second polypeptide comprising, in order from N-terminus to C-terminus: i) a variant CD80 polypeptide comprising the amino acid sequence VIHVTK EVKEVATLSC GHNVSVEELA QTRIYWQKEK KMVLTMMSGD MNIWPEYKNR TIFDITNNLS A VILALRPSD EGTYECVVLK YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:6); ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

K127 (4-1BBL)+K86 (CD80)

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising an amino acid sequence having at least 90%, at least 95%, at least 98%, or at least 99%, amino acid sequence identity to the following amino acid sequence: PAGLLDLRQG MFAQLVAQNV LLIDGPLSWY SDPGLAGVSL TGGLSYXEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:11), where X is not a lysine, e.g., where X is Ala, Gly, Val, or Leu, or where X is Glu or Asp, or where X is Arg or His, or where X is Ala; and b) a second polypeptide comprising, in order from N-terminus to C-terminus: i) a variant CD80 polypeptide comprising an amino acid sequence having at least 90%, at least 95%, at least 98%, or at least 99%, amino acid sequence identity to the following amino acid sequence:

```
                                           (SEQ ID NO: 7)
VIHVTK EVKEVATLSC GHNVSVEELA

QTRIYWQKEK KMVLTMMSGD MNIWPEYKNR TIFDITNNLS

IVILALRPSD EGTYECVVLX YEKDAFKREH LAEVTLSVKA

DFPTPSISDF EIPTSNIRRI ICSTSGGFPE PHLSWLENGE

ELNAINTTVS QDPETELYAV SSKLDFNMTT NHSFMCLIKY

GHLRVNQTFN WNTTKQEHFP DN,
``` where X is any amino acid other than lysine, e.g., where X is Gly, Ala, Val, Leu, Ile, Pro, Phe, Tyr, Trp, Ser, Thr, Cys, Met, Asn, Gln, Arg, His, Asp, or Glu, or where X is Ala, Gly, Val, or Leu, or where X is Glu or Asp, or where X is Arg or His, or where X is Ala; ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising an amino acid sequence having at least 90%, at least 95%, at least 98%, or at least 99%, amino acid sequence identity to the following amino acid sequence:

(SEQ ID NO: 13)
D PAGLLDLRQG MFAQLVAQNV LLIDGPLSWY

SDPGLAGVSL TGGLSYXEDT KELVVAKAGV YYVFFQLELR

RVVAGEGSGS VSLALHLQPL RSAAGAAALA LTVDLPPASS

EARNSAFGFQ GRLLHLSAGQ RLGVHLHTEA RARHAWQLTQ

GATVLGLFRV TPEIPAGLPS PRSE, where X is not a lysine, e.g., where X is Ala, Gly, Val, or Leu, or where X is Glu or Asp, or where X is Arg or His, or where X is Ala; and b) a second polypeptide comprising, in order from N-terminus to C-terminus: i) a variant CD80 polypeptide comprising an amino acid sequence having at least 90%, at least 95%, at least 98%, or at least 99%, amino acid sequence identity to the following amino acid sequence:

(SEQ ID NO: 7)
VIHVTK EVKEVATLSC GHNVSVEELA QTRIYWQKEK KMVLTMMSGD

MNIWPEYKNR TIFDITNNLS IVILALRPSD EGTYECVVLX

YEKDAFKREH LAEVTLSVKA DFPTPSISDF EIPTSNIRRI

ICSTSGGFPE PHLSWLENGE ELNAINTTVS QDPETELYAV

SSKLDFNMTT NHSFMCLIKY GHLRVNQTFN WNTTKQEHFP DN, where X is any amino acid other than lysine, e.g., where X is Gly, Ala, Val, Leu, Ile, Pro, Phe, Tyr, Trp, Ser, Thr, Cys, Met, Asn, Gln, Arg, His, Asp, or Glu, or where X is Ala, Gly, Val, or Leu, or where X is Glu or Asp, or where X is Arg or His, or where X is Ala; ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising an amino acid sequence having at least 90%, at least 95%, at least 98%, or at least 99%, amino acid sequence identity to the following amino acid sequence:

(SEQ ID NO: 15)
D PAGLLDLRQG MFAQLVAQNV LLIDGPLSWY SDPGLAGVSL

TGGLSYXEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV TPEIPA, where X is not a lysine, e.g., where X is Ala, Gly, Val, or Leu, or where X is Glu or Asp, or where X is Arg or His, or where X is Ala; and b) a second polypeptide comprising, in order from N-terminus to C-terminus: i) a variant CD80 polypeptide comprising an amino acid sequence having at least 90%, at least 95%, at least 98%, or at least 99%, amino acid sequence identity to the following amino acid sequence:

(SEQ ID NO: 7)
VIHVTK EVKEVATLSC GHNVSVEELA QTRIYWQKEK KMVLTMMSGD

MNIWPEYKNR TIFDITNNLS IVILALRPSD EGTYECVVLX

YEKDAFKREH LAEVTLSVKA DFPTPSISDF EIPTSNIRRI

ICSTSGGFPE PHLSWLENGE ELNAINTTVS QDPETELYAV

SSKLDFNMTT NHSFMCLIKY GHLRVNQTFN WNTTKQEHFP DN, where X is any amino acid other than lysine, e.g., where X is Gly, Ala, Val, Leu, Ile, Pro, Phe, Tyr, Trp, Ser, Thr, Cys, Met, Asn, Gln, Arg, His, Asp, or Glu, or where X is Ala, Gly, Val, or Leu, or where X is Glu or Asp, or where X or His, or where X is Ala; ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising the amino acid sequence PAGLLDLRQG MFAQLVAQNV LLIDGPLSWY SDPGLAGVSL TGGLSYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:12); and b) a second polypeptide comprising, in order from N-terminus to C-terminus: i) a variant CD80 polypeptide comprising the amino acid sequence VIHVTK EVKEVATLSC GHNVSVEELA QTRIYWQKEK KMVLTMMSGD MNIWPEYKNR TIFDITNNLS IVILALRPSD EGTYECVVLA YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:8); ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising the amino acid sequence D PAGLLDLRQG MFAQLVAQNV LLIDGPLSWY SDPGLAGVSL TGGLSYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:14); and b) a second polypeptide comprising, in order from N-terminus to C-terminus: i) a variant CD80 polypeptide comprising the amino acid sequence VIHVTK EVKEVATLSC GHNVSVEELA QTRIYWQKEK KMVLTMMSGD MNIWPEYKNR TIFDITNNLS IVILALRPSD EGTYECVVLA YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:8); ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising the amino acid sequence D PAGLLDLRQG MFAQLVAQNV LLIDGPLSWY SDPGLAGVSL TGGL-SYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPA (SEQ ID NO:16); and b) a second polypeptide comprising, in order from N-terminus to C-terminus: i) a variant CD80 polypeptide comprising the amino acid sequence VIHVTK EVKEVATLSC GHNVSVEELA QTRIYWQKEK KMVLTMMSGD MNIWPEYKNR TIFDITNNLS IVILA-LRPSD EGTYECVVLA YEKDAFKREH LAEVTLSVKA DFPTPSISDF EIPTSNIRRI ICSTSGGFPE PHLSW-LENGE ELNAINTTVS QDPETELYAV SSKLDFNMTT NHSFMCLIKY GHLRVNQTFN WNTTKQEHFP DN (SEQ ID NO:8); ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.
K127 (4-1BBL)+D158 (CD80)

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising an amino acid sequence having at least 90%, at least 95%, at least 98%, or at least 99%, amino acid sequence identity to the following amino acid sequence:

```
                                      (SEQ ID NO: 11)
PAGLLDLRQG MFAQLVAQNV LLIDGPLSWY SDPGLAGVSL

TGGLSYXEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE,
``` where X is not a lysine, e.g., where X is Ala, Gly, Val, or Leu, or where X is Glu or Asp, or where X is Arg or His, or where X is Ala; and b) a second polypeptide comprising, in order from N-terminus to C-terminus: i) a variant CD80 polypeptide comprising an amino acid sequence having at least 90%, at least 95%, at least 98%, or at least 99%, amino acid sequence identity to the following amino acid sequence:

```
                                       (SEQ ID NO: 9)
VIHVTK EVKEVATLSC GHNVSVEELA QTRIYWQKEK KMVLTMMSGD

MNIWPEYKNR TIFDITNNLS IVILALRPSD EGTYECVVLK

YEKDAFKREH LAEVTLSVKA DFPTPSISDF EIPTSNIRRI

ICSTSGGFPE PHLSWLENGE ELNAINTTVS QXPETELYAV

SSKLDFNMTT NHSFMCLIKY GHLRVNQTFN WNTTKQEHFP DN,
``` where X is any amino acid other than aspartic acid, e.g., where X is Gly, Ala, Val, Leu, Ile, Pro, Phe, Tyr, Trp, Ser, Thr, Cys, Met, Asn, Gln, Arg, His, Lys, or Glu, or where X is Ala, Gly, Val, Ile, or Leu, or where amino acid 86 is Glu, or where X is Arg, Lys, or His, or where X is Ala; ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising an amino acid sequence having at least 90%, at least 95%, at least 98%, or at least 99%, amino acid sequence identity to the following amino acid sequence:

```
                                      (SEQ ID NO: 13)
D PAGLLDLRQG MFAQLVAQNV LLIDGPLSWY SDPGLAGVSL

TGGLSYXEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE,
``` where X is not a lysine, e.g., where X is Ala, Gly, Val, or Leu, or where X is Glu or Asp, or where X is Arg or His, or where X is Ala; and b) a second polypeptide comprising, in order from N-terminus to C-terminus: i) a variant CD80 polypeptide comprising an amino acid sequence having at least 90%, at least 95%, at least 98%, or at least 99%, amino acid sequence identity to the following amino acid sequence:

```
                                       (SEQ ID NO: 9)
VIHVTK EVKEVATLSC GHNVSVEELA QTRIYWQKEK KMVLTMMSGD

MNIWPEYKNR TIFDITNNLS IVILALRPSD EGTYECVVLK

YEKDAFKREH LAEVTLSVKA DFPTPSISDF EIPTSNIRRI

ICSTSGGFPE PHLSWLENGE ELNAINTTVS QXPETELYAV

SSKLDFNMTT NHSFMCLIKY GHLRVNQTFN WNTTKQEHFP DN,
``` where X is any amino acid other than aspartic acid, e.g., where X is Gly, Ala, Val, Leu, Ile, Pro, Phe, Tyr, Trp, Ser, Thr, Cys, Met, Asn, Gln, Arg, His, Lys, or Glu, or where X is Ala, Gly, Val, Ile, or Leu, or where X is Glu, or where X is Arg, Lys, or His, or where X is Ala; ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising an amino acid sequence having at least 90%, at least 95%, at least 98%, or at least 99%, amino acid sequence identity to the following amino acid sequence:

```
                                          (SEQ ID NO: 15)
D PAGLLDLRQG MFAQLVAQNV LLIDGPLSWY SDPGLAGVSL

TGGLSYXEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV TPEIPA,
``` where X is not a lysine, e.g., where X is Ala, Gly, Val, or Leu, or where X is Glu or Asp, or where X is Arg or His, or where X is Ala; and b) a second polypeptide comprising, in order from N-terminus to C-terminus: i) a variant CD80 polypeptide comprising an amino acid sequence having at least 90%, at least 95%, at least 98%, or at least 99%, amino acid sequence identity to the following amino acid sequence:

```
                                          (SEQ ID NO: 9)
VIHVTK EVKEVATLSC GHNVSVEELA QTRIYWQKEK KMVLTMMSGD

MNIWPEYKNR TIFDITNNLS IVILALRPSD EGTYECVVLK

YEKDAFKREH LAEVTLSVKA DFPTPSISDF EIPTSNIRRI

ICSTSGGFPE PHLSWLENGE ELNAINTTVS QXPETELYAV

SSKLDFNMTT NHSFMCLIKY GHLRVNQTFN WNTTKQEHFP DN,
``` where X is any amino acid other than aspartic acid, e.g., where X is Gly, Ala, Val, Leu, Ile, Pro, Phe, Tyr, Trp, Ser, Thr, Cys, Met, Asn, Gln, Arg, His, Lys, or Glu, or where X is Ala, Gly, Val, Ile, or Leu, or where X is Glu, or where X is Arg, Lys, or His, or where X is Ala; ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising the amino acid sequence PAGLLDLRQG MFAQLVAQNV LLIDGPLSWY SDPGLAGVSL TGGL-SYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEI-PAGLPS PRSE (SEQ ID NO:12); and b) a second polypeptide comprising, in order from N-terminus to C-terminus: i) a variant CD80 polypeptide comprising the amino acid sequence VIHVTK EVKEVATLSC GHNVSVEELA QTRIYWQKEK KMVLTMMSGD MNIWPEYKNR TIFDITNNLS IVILALRPSD EGTYECVVLK YEK-DAFKREH LAEVTLSVKA DFPTPSISDF EIPTSNIRRI ICSTSGGFPE PHLSWLENGE ELNAINTTVS QAPETE-LYAV SSKLDFNMTT NHSFMCLIKY GHLRVNQTFN WNTTKQEHFP DN (SEQ ID NO:10); ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising the amino acid sequence D PAGLLDLRQG MFAQLVAQNV LLIDGPLSWY SDPGLAGVSL TGGL-SYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEI-PAGLPS PRSE (SEQ ID NO:14); and b) a second polypeptide comprising, in order from N-terminus to C-terminus: i) a variant CD80 polypeptide comprising the amino acid sequence VIHVTK EVKEVATLSC GHNVSVEELA QTRIYWQKEK KMVLTMMSGD MNIWPEYKNR TIFDITNNLS IVILALRPSD EGTYECVVLK YEK-DAFKREH LAEVTLSVKA DFPTPSISDF EIPTSNIRRI ICSTSGGFPE PHLSWLENGE ELNAINTTVS QAPETE-LYAV SSKLDFNMTT NHSFMCLIKY GHLRVNQTFN WNTTKQEHFP DN (SEQ ID NO:10); ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising the amino acid sequence D PAGLLDLRQG MFAQLVAQNV LLIDGPLSWY SDPGLAGVSL TGGLSYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPA (SEQ ID NO:16); and b) a second polypeptide comprising, in order from N-terminus to C-terminus: i) a variant CD80 polypeptide comprising the amino acid sequence VIHVTK EVKEVATLSC GHNVSVEELA QTRIYWQKEK KMVLTMMSGD MNIWPEYKNR TIFDITNNLS IVILA-LRPSD EGTYECVVLK YEKDAFKREH LAEVTLSVKA DFPTPSISDF EIPTSNIRRI ICSTSGGFPE PHLSW-LENGE ELNAINTTVS QAPETELYAV SSKLDFNMTT NHSFMCLIKY GHLRVNQTFN WNTTKQEHFP DN (SEQ ID NO:10); ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising the amino acid sequence D PAGLLDLRQG MFAQLVAQNV LLIDGPLSWY SDPGLAGVSL TGGLSYX$_1$EDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWX$_2$LTQ GATVLGLFRV TPEIPA (SEQ ID NO:41), wherein X$_1$ is selected from A, D, and E and X$_2$ is selected from A, R, E, and L; and b) a second polypeptide comprising, in order from N-terminus to C-terminus: i) a variant CD80 polypeptide comprising the amino acid sequence VIHVTKEVKEVATLSCGHNVS-VEELAQTRIYWQKEKKMVLTMMSGDM-NIWPEYKNRT IFDITNNLSIVILALRPSDE-GTYECVVLA YEKDAFKREHLAEVTLSVKADFPTPSISDFEIPT SNIR-RIICSTSGGFPEPHLSWLENGEELNAINTTVSQDPETE- LYAVSSKLDFNMTTNHSFM CLIKYGHLRVNQTFNWNTTKQEHFPDN (SEQ ID NO:42); ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising the amino acid sequence D PAGLLDLRQG MFAQLVAQNV LLIDGPLSWY SDPGLAGVSL TGGL-SYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWALTQ GATVLGLFRV TPEIPA (SEQ ID NO:43); and b) a second polypeptide comprising, in order from N-terminus to C-terminus: i) a variant CD80 polypeptide comprising the amino acid sequence VIHVTKEVKEVATLSCGHNVS-VEELAQTRIYWQKEKKMVLTMMSGDM-NIWPEYKNRT IFDITNNLSIVILALRPSDEGTYECVV-LAYEKDAFKREHLAEVTLSVKADFPTPSISDFEIPT SNIRRIICSTSGGFPEPHLSWLENGEELNAINTTVSQD-PETELYAVSSKLDFNMTTNHSFM CLIKYGHLRVNQTFNWNTTKQEHFPDN (SEQ ID NO:42); ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising the amino acid sequence D PAGLLDLRQG MFAQLVAQNV LLIDGPLSWY SDPGLAGVSL TGGL-SYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWRLTQ GATVLGLFRV TPEIPA (SEQ ID NO:44); and b) a second polypeptide comprising, in order from N-terminus to C-terminus: i) a variant CD80 polypeptide comprising the amino acid sequence VIHVTKEVKEVATLSCGHNVS-VEELAQTRIYWQKEKKMVLTMMSGDM-NIWPEYKNRT IFDITNNLSIVILALRPSDEGTYECVV-LAYEKDAFKREHLAEVTLSVKADFPTPSISDFEIPT SNIRRIICSTSGGFPEPHLSWLENGEELNAINTTVSQD-PETELYAVSSKLDFNMTTNHSFM CLIKYGHLRVNQTFNWNTTKQEHFPDN (SEQ ID NO:42); ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising the amino acid sequence D PAGLLDLRQG MFAQLVAQNV LLIDGPLSWY SDPGLAGVSL TGGL-SYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWELTQ GATVLGLFRV TPEIPA (SEQ ID NO:45); and b) a second polypeptide comprising, in order from N-terminus to C-terminus: i) a variant CD80 polypeptide comprising the amino acid sequence VIHVTKEVKEVATLSCGHNVS-VEELAQTRIYWQKEKKMVLTMMSGDM-NIWPEYKNRT IFDITNNLSIVILALRPSDEGTYECVV-LAYEKDAFKREHLAEVTLSVKADFPTPSISDFEIPT SNIRRIICSTSGGFPEPHLSWLENGEELNAINTTVSQD-PETELYAVSSKLDFNMTTNHSFM CLIKYGHLRVNQTFNWNTTKQEHFPDN (SEQ ID NO:42); ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising the amino acid sequence D PAGLLDLRQG MFAQLVAQNV LLIDGPLSWY SDPGLAGVSL TGGL-SYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWLLTQ GATVLGLFRV TPEIPA (SEQ ID NO:46); and b) a second polypeptide comprising, in order from N-terminus to C-terminus: i) a variant CD80 polypeptide comprising the amino acid sequence VIHVTKEVKEVATLSCGHNVS-VEELAQTRIYWQKEKKMVLTMMSGDM-NIWPEYKNRT IFDITNNLSIVILALRPSDEGTYECVV-LAYEKDAFKREHLAEVTLSVKADFPTPSISDFEIPT SNIRRIICSTSGGFPEPHLSWLENGEELNAINTTVSQD-PETELYAVSSKLDFNMTTNHSFM CLIKYGHLRVNQTFNWNTTKQEHFPDN (SEQ ID NO:42); ii) an MHC heavy chain polypeptide; and iii) an Ig Fc polypeptide. In some cases, the first polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

Variant CD80 on First Polypeptide Chain; Variant 4-BBL on Second Polypeptide Chain In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising an amino acid sequence having at least 90%, at least 95%, at least 98%, or at least 99%, amino acid sequence identity to the amino acid sequence of SEQ ID NO:1, and comprising an amino acid substitution of amino acid I67, K86, or D158; and b) a second polypeptide comprising, in order from N-terminus to C-terminus: i) a variant 4-1BBL polypeptide comprising an amino acid sequence having at least 90%, at least 95%, at least 98%, or at least 99%, amino acid sequence identity to the amino acid sequence of one of SEQ ID NOs:2-4, and comprises a substitution of amino acid K127, where the amino acid numbering is based on the 4-1BBL amino acid sequence depicted in FIG. 3; ii) an MHC heavy chain polypeptide; and iii) an Ig Fc polypeptide. In some cases, the first polypeptide comprises a single variant CD80 polypeptide; and the second polypeptide comprises a single variant 4-1BBL polypeptide. In some cases, the first polypeptide comprises two variant CD80 polypeptides (e.g., where the variants are in tandem); and the second polypeptide comprises a single variant 4-1BBL polypeptide. In some cases, the first polypeptide comprises three variant CD80 polypeptides (e.g., where the variants are in tandem); and the second polypeptide comprises a single variant 4-1BBL polypeptide. In some cases, the first polypeptide comprises a single variant CD80 polypeptide; and the second polypeptide comprises two variant 4-1BBL polypeptides (e.g., where the variants are in tandem). In some cases, the first polypeptide comprises a single variant CD80 polypeptide; and the second polypeptide comprises three variant 4-1BBL polypeptides (e.g., where the variants are in tandem). In some cases, the first polypeptide comprises two variant CD80 polypeptides (e.g., where the variants are in tandem); and the second polypeptide comprises two variant 4-1BBL polypeptides (e.g., where the variants are in tandem). In some cases, the first polypeptide comprises three variant CD80 polypeptides (e.g., where the variants are in tandem); and the second polypeptide comprises three variant 4-1BBL polypeptides (e.g., where the variants are in tandem).

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising an amino acid sequence having at least 90%, at least 95%, at least 98%, or at least 99%, amino acid sequence identity to the amino acid sequence of SEQ ID NO:1, and comprising an amino acid substitution of amino acid I67, K86, or D158; and b) a second polypeptide comprising, in order from N-terminus to C-terminus: i) a variant 4-1BBL polypeptide comprising an amino acid sequence having at least 90%, at least 95%, at least 98%, or at least 99%, amino acid sequence identity to the amino acid sequence of one of SEQ ID NOs:2-4, and comprises a substitution of amino acid K127, where the amino acid numbering is based on the 4-1BBL amino acid sequence depicted in FIG. 3; ii) an MHC heavy chain polypeptide; and iii) an Ig Fc polypeptide.

I67 (CD80)+K127 (4-1BBL)

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising an amino acid sequence having at least 90%, at least 95%, at least 98%, or at least 99%, amino acid sequence identity to the following amino acid sequence: VIHVTK EVKEVATLSC GHNVSVEELA QTRIYWQKEK KMVLTMMSGD MNIWPEYKNR TIFDITNNLS XVILALRPSD EGTYECVVLK YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:5), where X is any amino acid other than isoleucine, e.g., where X is Gly, Ala, Val, Leu, Pro, Phe, Tyr, Trp, Ser, Thr, Cys, Met, Asn, Gln, Lys, Arg, His, Asp, or Glu, or where X is Ala, Gly, Val, or Leu, or where X is Glu or Asp, or where X is Arg, His, or Lys, or where X is Ala; and b) a second polypeptide comprising, in order from N-terminus to C-terminus: i) a variant 4-1BBL polypeptide comprising an amino acid sequence having at least 90%, at least 95%, at least 98%, or at least 99%, amino acid sequence identity to the following amino acid sequence:

```
                                       (SEQ ID NO: 11)
PAGLLDLRQG MFAQLVAQNV LLIDGPLSWY SDPGLAGVSL

TGGLSYXEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE,
``` where X is not a lysine, e.g., where X is Ala, Gly, Val, or Leu, or where X is Glu or Asp, or where X is Arg or His, or where X is Ala; ii) an MHC heavy chain polypeptide; and iii) an Ig Fc polypeptide. In some cases, the second polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising an amino acid sequence having at least 90%, at least 95%, at least 98%, or at least 99%, amino acid sequence identity to the following amino acid sequence:

```
                                        (SEQ ID NO: 5)
VIHVTK EVKEVATLSC GHNVSVEELA QTRIYWQKEK KMVLTMMSGD

MNIWPEYKNR TIFDITNNLS XVILALRPSD EGTYECVVLK

YEKDAFKREH LAEVTLSVKA DFPTPSISDF EIPTSNIRRI

ICSTSGGFPE PHLSWLENGE ELNAINTTVS QDPETELYAV

SSKLDFNMTT NHSFMCLIKY GHLRVNQTFN WNTTKQEHFP DN,
``` where X is any amino acid other than isoleucine, e.g., where X is Gly, Ala, Val, Leu, Pro, Phe, Tyr, Trp, Ser, Thr, Cys, Met, Asn, Gln, Lys, Arg, His, Asp, or Glu, or where X is Ala, Gly, Val, or Leu, or where X is Glu or Asp, or where X is Arg, His, or Lys, or where X is Ala; and b) a second polypeptide comprising, in order from N-terminus to C-terminus: i) a variant 4-1BBL polypeptide comprising an amino acid sequence having at least 90%, at least 95%, at least 98%, or at least 99%, amino acid sequence identity to the following amino acid sequence: D PAGLLDLRQG MFAQLVAQNV LLIDGPLSWY SDPGLAGVSL TGGLSYXEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:13), where X is not a lysine, e.g., where X is Ala, Gly, Val, or Leu, or where X is Glu or Asp, or where X is Arg or His, or where X is Ala; ii) an MHC heavy chain polypeptide; and iii) an Ig Fc polypeptide. In some cases, the second polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising an amino acid sequence having at least 90%, at least 95%, at least 98%, or at least 99%, amino acid sequence identity to the following amino acid sequence:

(SEQ ID NO: 5)
VIHVTK EVKEVATLSC GHNVSVEELA QTRIYWQKEK KMVLTMMSGD

MNIWPEYKNR TIFDITNNLS XVILALRPSD EGTYECVVLK

YEKDAFKREH LAEVTLSVKA DFPTPSISDF EIPTSNIRRI

ICSTSGGFPE PHLSWLENGE ELNAINTTVS QDPETELYAV

SSKLDFNMTT NHSFMCLIKY GHLRVNQTFN WNTTKQEHFP DN, where X is any amino acid other than isoleucine, e.g., where X is Gly, Ala, Val, Leu, Pro, Phe, Tyr, Trp, Ser, Thr, Cys, Met, Asn, Gln, Lys, Arg, His, Asp, or Glu, or where X is Ala, Gly, Val, or Leu, or where X is Glu or Asp, or where X is Arg, His, or Lys, or where X is Ala; and b) a second polypeptide comprising, in order from N-terminus to C-terminus: i) a variant 4-1BBL polypeptide comprising an amino acid sequence having at least 90%, at least 95%, at least 98%, or at least 99%, amino acid sequence identity to the following amino acid sequence:

(SEQ ID NO: 15)
D PAGLLDLRQG MFAQLVAQNV LLIDGPLSWY SDPGLAGVSL

TGGLSYXEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV TPEIPA, where X is not a lysine, e.g., where X is Ala, Gly, Val, or Leu, or where X is Glu or Asp, or where X is Arg or His, or where X is Ala; ii) an MHC heavy chain polypeptide; and iii) an Ig Fc polypeptide. In some cases, the second polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising the amino acid sequence VIHVTK EVKEVATLSC GHNVSVEELA QTRIYWQKEK KMVLTMMSGD MNIWPEYKNR TIFDITNNLS A VILALRPSD EGTYECVVLK YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:6); and b) a second polypeptide comprising, in order from N-terminus to C-terminus: i) a variant 4-1BBL polypeptide comprising the amino acid sequence PAGLLDLRQG MFAQLVAQNV LLIDGPLSWY SDPGLAGVSL TGGLSYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:12); ii) an MHC heavy chain polypeptide; and iii) an Ig Fc polypeptide.

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising the amino acid sequence VIHVTK EVKEVATLSC GHNVSVEELA QTRIYWQKEK KMVLTMMSGD MNIWPEYKNR TIFDITNNLS A VILALRPSD EGTYECVVLK YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:6); and b) a second polypeptide comprising, in order from N-terminus to C-terminus: i) a variant 4-1BBL polypeptide comprising the amino acid sequence D PAGLLDLRQG MFAQLVAQNV LLIDGPLSWY SDPGLAGVSL TGGLSYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:14); ii) an MHC heavy chain polypeptide; and iii) an Ig Fc polypeptide. In some cases, the second polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii); a variant CD80 polypeptide comprising the amino acid sequence VIHVTK EVKEVATLSC GHNVSVEELA QTRIYWQKEK KMVLTMMSGD MNIWPEYKNR TIFDITNNLS A VILALRPSD EGTYECVVLK YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:6) and b) a second polypeptide comprising, in order from N-terminus to C-terminus: i) a variant 4-1BBL polypeptide comprising the amino acid sequence PAGLLDLRQG MFAQLVAQNV LLIDGPLSWY SDPGLAGVSL TGGLSYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPA (SEQ ID NO:27); ii) an MHC heavy chain polypeptide; and iii) an Ig Fc polypeptide. In some cases, the second polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

K86 (CD80)+K127 (4-1BBL)

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising an amino acid sequence having at least 90%, at least 95%, at least 98%, or at least 99%, amino acid sequence identity to the following amino acid sequence:

(SEQ ID NO: 7)
VIHVTK EVKEVATLSC GHNVSVEELA QTRIYWQKEK KMVLTMMSGD

MNIWPEYKNR TIFDITNNLS IVILALRPSD EGTYECVVLX

YEKDAFKREH LAEVTLSVKA DFPTPSISDF EIPTSNIRRI

ICSTSGGFPE PHLSWLENGE ELNAINTTVS QDPETELYAV

SSKLDFNMTT NHSFMCLIKY GHLRVNQTFN WNTTKQEHFP DN, where X is any amino acid other than lysine, e.g., where X is Gly, Ala, Val, Leu, Ile, Pro, Phe, Tyr, Trp, Ser, Thr, Cys, Met, Asn, Gln, Arg, His, Asp, or Glu, or where X is Ala, Gly, Val, or Leu, or where X is Glu or Asp, or where X is Arg or His, or where X is Ala; and b) a second polypeptide comprising, in order from N-terminus to C-terminus: i) a variant 4-1BBL polypeptide comprising an amino acid sequence having at least 90%, at least 95%, at least 98%, or at least 99%, amino acid sequence identity to the following amino acid sequence:

(SEQ ID NO: 11)
PAGLLDLRQG MFAQLVAQNV LLIDGPLSWY SDPGLAGVSL

TGGLSYXEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE, where X is not a lysine, e.g., where X is Ala, Gly, Val, or Leu, or where X is Glu or Asp, or where X is Arg or His, or where X is Ala; ii) an MHC heavy chain polypeptide; and iii) an Ig Fc polypeptide. In some cases, the second polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising an amino acid sequence having at least 90%, at least 95%, at least 98%, or at least 99%, amino acid sequence identity to the following amino acid sequence:

(SEQ ID NO: 7)
VIHVTK EVKEVATLSC GHNVSVEELA QTRIYWQKEK

KMVLTMMSGD MNIWPEYKNR TIFDITNNLS IVILALRPSD

EGTYECVVLX YEKDAFKREH LAEVTLSVKA DFPTPSISDF

EIPTSNIRRI ICSTSGGFPE PHLSWLENGE ELNAINTTVS

QDPETELYAV SSKLDFNMTT NHSFMCLIKY GHLRVNQTFN

WNTTKQEHFP DN, where X is any amino acid other than lysine, e.g., where X is Gly, Ala, Val, Leu, Ile, Pro, Phe, Tyr, Trp, Ser, Thr, Cys, Met, Asn, Gln, Arg, His, Asp, or Glu, or where X is Ala, Gly, Val, or Leu, or where X is Glu or Asp, or where X or His, or where X is Ala; and b) a second polypeptide comprising, in order from N-terminus to C-terminus: i) a variant 4-1BBL polypeptide comprising an amino acid sequence having at least 90%, at least 95%, at least 98%, or at least 99%, amino acid sequence identity to the following amino acid sequence:

(SEQ ID NO: 15)
D PAGLLDLRQG MFAQLVAQNV LLIDGPLSWY

SDPGLAGVSL TGGLSYXEDT KELVVAKAGV YYVFFQLELR

RVVAGEGSGS VSLALHLQPL RSAAGAAALA LTVDLPPASS

EARNSAFGFQ GRLLHLSAGQ RLGVHLHTEA RARHAWQLTQ

GATVLGLFRV TPEIPA, where X is not a lysine, e.g., where X is Ala, Gly, Val, or Leu, or where X is Glu or Asp, or where X is Arg or His, or where X is Ala; ii) an MHC heavy chain polypeptide; and iii) an Ig Fc polypeptide. In some cases, the second polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising an amino acid sequence having at least 90%, at least 95%, at least 98%, or at least 99%, amino acid sequence identity to the following amino acid sequence:

(SEQ ID NO: 7)
VIHVTK EVKEVATLSC GHNVSVEELA QTRIYWQKEK

KMVLTMMSGD MNIWPEYKNR TIFDITNNLS IVILALRPSD

EGTYECVVLX YEKDAFKREH LAEVTLSVKA DFPTPSISDF

EIPTSNIRRI ICSTSGGFPE PHLSWLENGE ELNAINTTVS

QDPETELYAV SSKLDFNMTT NHSFMCLIKY GHLRVNQTFN

WNTTKQEHFP DN, where X is any amino acid other than lysine, e.g., where X is Gly, Ala, Val, Leu, Ile, Pro, Phe, Tyr, Trp, Ser, Thr, Cys, Met, Asn, Gln, Arg, His, Asp, or Glu, or where X is Ala, Gly, Val, or Leu, or where X is Glu or Asp, or where X is Arg or His, or where X is Ala; and b) a second polypeptide comprising, in order from N-terminus to C-terminus: i) a variant 4-1BBL polypeptide comprising an amino acid sequence having at least 90%, at least 95%, at least 98%, or at least 99%, amino acid sequence identity to the following amino acid sequence:

(SEQ ID NO: 13)
D PAGLLDLRQG MFAQLVAQNV LLIDGPLSWY SDPGLAGVSL

TGGLSYXEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE, where X is not a lysine, e.g., where X is Ala, Gly, Val, or Leu, or where X is Glu or Asp, or where X is Arg or His, or where X is Ala; ii) an MHC heavy chain polypeptide; and iii) an Ig Fc polypeptide. In some cases, the second polypeptide comprises 3 copies of the variant 4-1BBL polypeptide; in some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising the amino acid sequence VIHVTK EVKEVATLSC GHNVSVEELA QTRIYWQKEK KMVLTMMSGD MNIWPEYKNR TIFDITNNLS IVILALRPSD EGTYECVVLA YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:8); and b) a second polypeptide comprising, in order from N-terminus to C-terminus: i) a variant 4-1BBL polypeptide comprising the amino acid sequence PAGLLD-LRQG MFAQLVAQNV LLIDGPLSWY SDPGLAGVSL TGGLSYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:12); ii) an MHC heavy chain polypeptide; and iii) an Ig Fc polypeptide. In some cases, the second polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising the amino acid sequence VIHVTK EVKEVATLSC GHNVSVEELA QTRIYWQKEK KMVLTMMSGD MNIWPEYKNR TIFDITNNLS IVILALRPSD EGTYECVVLA YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:8); and b) a second polypeptide comprising, in order from N-terminus to C-terminus: i) a variant 4-1BBL polypeptide comprising the amino acid sequence D PAGLLDLRQG MFAQLVAQNV LLIDGPLSWY SDPGLAGVSL TGGLSYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:14); ii) an MHC heavy chain polypeptide; and iii) an Ig Fc polypeptide. In some cases, the second polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising the amino acid sequence VIHVTK EVKEVATLSC GHNVSVEELA QTRIYWQKEK KMVLTMMSGD MNIWPEYKNR TIFDITNNLS IVILALRPSD EGTYECVVLA YEKDAFKREH LAEVTLSVKA DFPTPSISDF EIPTSNIRRI ICSTSGGFPE PHLSWLENGE ELNAINTTVS QDPETELYAV SSKLDFNMTT NHSFMCLIKY GHLRVNQTFN WNTTKQEHFP DN (SEQ ID NO:8); and b) a second polypeptide comprising, in order from N-terminus to C-terminus: i) a variant 4-1BBL polypeptide comprising the amino acid sequence D PAGLLDLRQG MFAQLVAQNV LLIDGPLSWY SDPGLAGVSL TGGLSYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPA (SEQ ID NO:16); ii) an MHC heavy chain polypeptide; and iii) an Ig Fc polypeptide. In some cases, the second polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

D158 (CD80)+K127 (4-1BBL)

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising an amino acid sequence having at least 90%, at least 95%, at least 98%, or at least 99%, amino acid sequence identity to the following amino acid sequence:

```
                                          (SEQ ID NO: 9)
VIHVTK EVKEVATLSC GHNVSVEELA QTRIYWQKEK

KMVLTMMSGD MNIWPEYKNR TIFDITNNLS IVILALRPSD

EGTYECVVLK YEKDAFKREH LAEVTLSVKA DFPTPSISDF

EIPTSNIRRI ICSTSGGFPE PHLSWLENGE ELNAINTTVS

QXPETELYAV SSKLDFNMTT NHSFMCLIKY GHLRVNQTFN

WNTTKQEHFP DN,
``` where X is any amino acid other than aspartic acid, e.g., where X is Gly, Ala, Val, Leu, Ile, Pro, Phe, Tyr, Trp, Ser, Thr, Cys, Met, Asn, Gln, Arg, His, Lys, or Glu, or where X is Ala, Gly, Val, Ile, or Leu, or where amino acid 86 is Glu, or where X is Arg, Lys, or His, or where X is Ala; ii) an MHC heavy chain polypeptide; and b) a second polypeptide comprising, in order from N-terminus to C-terminus: i) a variant 4-1BBL polypeptide comprising an amino acid sequence having at least 90%, at least 95%, at least 98%, or at least 99%, amino acid sequence identity to the following amino acid sequence:

```
                                         (SEQ ID NO: 11)
PAGLLDLRQG MFAQLVAQNV LLIDGPLSWY SDPGLAGVSL

TGGLSYXEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE,
``` where X is not a lysine, e.g., where X is Ala, Gly, Val, or Leu, or where X is Glu or Asp, or where X is Arg or His, or where X is Ala; and iii) an Ig Fc polypeptide. In some cases, the second polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising an amino acid sequence having at least 90%, at least 95%, at least 98%, or at least 99%, amino acid sequence identity to the following amino acid sequence:

```
                                          (SEQ ID NO: 9)
VIHVTK EVKEVATLSC GHNVSVEELA QTRIYWQKEK

KMVLTMMSGD MNIWPEYKNR TIFDITNNLS IVILALRPSD

EGTYECVVLK YEKDAFKREH LAEVTLSVKA DFPTPSISDF

EIPTSNIRRI ICSTSGGFPE PHLSWLENGE ELNAINTTVS

QXPETELYAV SSKLDFNMTT NHSFMCLIKY GHLRVNQTFN

WNTTKQEHFP DN,
``` where X is any amino acid other than aspartic acid, e.g., where X is Gly, Ala, Val, Leu, Ile, Pro, Phe, Tyr, Trp, Ser, Thr, Cys, Met, Asn, Gln, Arg, His, Lys, or Glu, or where X is Ala, Gly, Val, Ile, or Leu, or where X is Glu, or where X is Arg, Lys, or His, or where X is Ala; and b) a second polypeptide comprising, in order from N-terminus to C-terminus: i) a variant 4-1BBL polypeptide comprising an amino acid sequence having at least 90%, at least 95%, at least 98%, or at least 99%, amino acid sequence identity to the following amino acid sequence:

```
                                          (SEQ ID NO: 13)
D PAGLLDLRQG MFAQLVAQNV LLIDGPLSWY SDPGLAGVSL

TGGLSYXEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPAGLPS PRSE,
``` where X is not a lysine, e.g., where X is Ala, Gly, Val, or Leu, or where X is Glu or Asp, or where X is Arg or His, or where X is Ala; ii) an MHC heavy chain polypeptide; and iii) an Ig Fc polypeptide. In some cases, the second polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising an amino acid sequence having at least 90%, at least 95%, at least 98%, or at least 99%, amino acid sequence identity to the following amino acid sequence:

```
                                          (SEQ ID NO: 9)
VIHVTK EVKEVATLSC GHNVSVEELA QTRIYWQKEK

KMVLTMMSGD MNIWPEYKNR TIFDITNNLS IVILALRPSD

EGTYECVVLK YEKDAFKREH LAEVTLSVKA DFPTPSISDF

EIPTSNIRRI ICSTSGGFPE PHLSWLENGE ELNAINTTVS

QXPETELYAV SSKLDFNMTT NHSFMCLIKY GHLRVNQTFN

WNTTKQEHFP DN,
``` where X is any amino acid other than aspartic acid, e.g., where X is Gly, Ala, Val, Leu, Ile, Pro, Phe, Tyr, Trp, Ser, Thr, Cys, Met, Asn, Gln, Arg, His, Lys, or Glu, or where X is Ala, Gly, Val, Ile, or Leu, or where X is Glu, or where X is Arg, Lys, or His, or where X is Ala; and b) a second polypeptide comprising, in order from N-terminus to C-terminus: i) a variant 4-1BBL polypeptide comprising an amino acid sequence having at least 90%, at least 95%, at least 98%, or at least 99%, amino acid sequence identity to the following amino acid sequence:

```
                                          (SEQ ID NO: 15)
D PAGLLDLRQG MFAQLVAQNV LLIDGPLSWY SDPGLAGVSL

TGGLSYXEDT KELVVAKAGV YYVFFQLELR RVVAGEGSGS

VSLALHLQPL RSAAGAAALA LTVDLPPASS EARNSAFGFQ

GRLLHLSAGQ RLGVHLHTEA RARHAWQLTQ GATVLGLFRV

TPEIPA,
``` where X is not a lysine, e.g., where X is Ala, Gly, Val, or Leu, or where X is Glu or Asp, or where X is Arg or His, or where X is Ala; ii) an MHC heavy chain polypeptide; and iii) an Ig Fc polypeptide. In some cases, the second polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising the amino acid sequence VIHVTK EVKEVATLSC GHNVSVEELA QTRIYWQKEK KMVLTMMSGD MNIWPEYKNR TIFDITNNLS IVILALRPSD EGTYECVVLK YEKDAFKREH LAEVTLSVKA DFPTPSISDF EIPTSNIRRI ICSTSGGFPE PHLSWLENGE ELNAINTTVS QAPETELYAV SSKLDFNMTT NHSFMCLIKY GHLRVNQTFN WNTTKQEHFP DN (SEQ ID NO:10); and b) a second polypeptide comprising, in order from N-terminus to C-terminus: i) a variant 4-1BBL polypeptide comprising the amino acid sequence PAGLLDLRQG MFAQLVAQNV LLIDGPLSWY SDPGLAGVSL TGGLSYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:12); ii) an MHC heavy chain polypeptide; and iii) an Ig Fc polypeptide. In some cases, the second polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising the amino acid sequence VIHVTK EVKEVATLSC GHNVSVEELA QTRIYWQKEK KMVLTMMSGD MNIWPEYKNR TIFDITNNLS IVILALRPSD EGTYECVVLK YEKDAFKREH LAEVTLSVKA DFPTPSISDF EIPTSNIRRI ICSTSGGFPE PHLSWLENGE ELNAINTTVS QAPETELYAV SSKLDFNMTT NHSFMCLIKY GHLRVNQTFN WNTTKQEHFP DN (SEQ ID NO:10); and b) a second polypeptide comprising, in order from N-terminus to C-terminus: i) a variant 4-1BBL polypeptide comprising the amino acid sequence D PAGLLDLRQG MFAQLVAQNV LLIDGPLSWY SDPGLAGVSL TGGLSYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPAGLPS PRSE (SEQ ID NO:14); ii) an MHC heavy chain polypeptide; and iii) an Ig Fc polypeptide. In some cases, the second polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising the amino acid sequence VIHVTK EVKEVATLSC GHNVSVEELA QTRIYWQKEK KMVLTMMSGD MNIWPEYKNR TIFDITNNLS IVILALRPSD EGTYECVVLK YEKDAFKREH LAEVTLSVKA DFPTPSISDF EIPTSNIRRI ICSTSGGFPE PHLSWLENGE ELNAINTTVS QAPETELYAV SSKLDFNMTT NHSFMCLIKY GHLRVNQTFN WNTTKQEHFP DN (SEQ ID NO:10); and b) a second polypeptide comprising, in order from N-terminus to C-terminus: i) a variant 4-1BBL polypeptide comprising the amino acid sequence D PAGLLDLRQG MFAQLVAQNV LLIDGPLSWY SDPGLAGVSL TGGLSYAEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEIPA (SEQ ID NO:16); ii) an MHC heavy chain polypeptide; and iii) an Ig Fc polypeptide. In some cases, the second polypeptide comprises 3 copies of the variant 4-1BBL polypeptide; in some cases, a linker (e.g., GGGGSGGGGSGGGGSGGGGSGGGGS; SEQ ID NO:26) is interposed between the copies.

Additional synTacs

In some cases, a synTac polypeptide of the present disclosure comprises: a) a first polypeptide comprising, in order from N-terminus to C-terminus: i) an epitope; ii) a β2M polypeptide; and iii) a variant 4-1BBL polypeptide comprising an amino acid sequence having at least 90%, at least 95%, at least 98%, or at least 99%, amino acid sequence identity to the amino acid sequence depicted in FIG. 3 or as set forth in one of SEQ ID NOs:2-4, where the variant 4-1BBL comprises substitution of one of amino acids 91, 92, 94-115, 117-126, 128-132, 144-153, 155-158, 184-187, 189-191, 193-195, 197, 210-219, 221-224, 226, 228-231, 233, and 234 based on the amino acid numbering set out in FIG. 3; and b) a second polypeptide comprising, in order from N-terminus to C-terminus: i) a variant CD80 polypeptide comprising an amino acid sequence having at least 90%, at least 95%, at least 98%, or at least 99%, amino acid sequence identity to the amino acid sequence depicted in FIG. 2 or as set forth in SEQ ID NO:1, wherein the variant CD80 polypeptide comprises a substitution of amino acid N19, N63, I67, K86, Q157, D158, L25, Y31, Q33, M38, V39, I49, Y53, D60, F108, or S156, based on the amino acid numbering set out in FIG. 2; and iii) an Ig Fc polypeptide.

In some cases, a synTac polypeptide of the present disclosure comprises: a) a first polypeptide comprising, in order from N-terminus to C-terminus: i) an epitope; ii) a β2M polypeptide; and iii) a variant CD80 polypeptide comprising an amino acid sequence having at least 90%, at least 95%, at least 98%, or at least 99%, amino acid sequence identity to the amino acid sequence depicted in FIG. 2 or as set forth in SEQ ID NO:1, wherein the variant CD80 polypeptide comprises a substitution of amino acid N19, N63, I67, K86, Q157, D158, L25, Y31, Q33, M38, V39, I49, Y53, D60, F108, or S156, based on the amino acid numbering set out in FIG. 2; and b) a second polypeptide comprising, in order from N-terminus to C-terminus: i) a variant 4-1BBL polypeptide comprising an amino acid sequence having at least 90%, at least 95%, at least 98%, or at least 99%, amino acid sequence identity to the amino acid sequence depicted in FIG. 3 or as set forth in one of SEQ ID NOs:2-4, where the variant 4-1BBL comprises substitution of one of amino acids 91, 92, 94-115, 117-126, 128-132, 144-153, 155-158, 184-187, 189-191, 193-195, 197, 210-219, 221-224, 226, 228-231, 233, and 234 based on the amino acid numbering set out in FIG. 3; and iii) an Ig Fc polypeptide.

In some cases, the CD80 variant polypeptide comprises a substitution at N19; and the 4-1BBL variant comprises a substitution at M91. In some cases, the CD80 variant polypeptide comprises a substitution at N19; and the 4-1BBL variant comprises a substitution at F92. In some cases, the CD80 variant polypeptide comprises a substitution at N19; and the 4-1BBL variant comprises a substitution at Q94. In some cases, the CD80 variant polypeptide comprises a substitution at N19; and the 4-1BBL variant comprises a substitution at L95. In some cases, the CD80 variant polypeptide comprises a substitution at N19; and the 4-1BBL variant comprises a substitution at V96. In some cases, the CD80 variant polypeptide comprises a substitution at N19; and the 4-1BBL variant comprises a substitution at Q98. In some cases, the CD80 variant polypeptide comprises a substitution at N19; and the 4-1BBL variant comprises a substitution at N99. In some cases, the CD80 variant polypeptide comprises a substitution at N19; and the 4-1BBL variant comprises a substitution at V100. In some cases, the CD80 variant polypeptide comprises a substitution at N19; and the 4-1BBL variant comprises a substitution at L101. In some cases, the CD80 variant polypeptide comprises a substitution at N19; and the 4-1BBL variant comprises a substitution at L102. In some cases, the CD80 variant polypeptide comprises a substitution at N19; and the 4-1BBL variant comprises a substitution at I103. In some cases, the CD80 variant polypeptide comprises a substitution at N19; and the 4-1BBL variant comprises a substitution at D104. In some cases, the CD80 variant polypeptide comprises a substitution at N19; and the 4-1BBL variant comprises a substitution at G105. In some cases, the CD80 variant polypeptide comprises a substitution at N19; and the 4-1BBL variant comprises a substitution at P106. In some cases, the CD80 variant polypeptide comprises a substitution at N19; and the 4-1BBL variant comprises a substitution at L107. In some cases, the CD80 variant polypeptide comprises a substitution at N19; and the 4-1BBL variant comprises a substitution at S108. In some cases, the CD80 variant polypeptide comprises a substitution at N19; and the 4-1BBL variant comprises a substitution at W109. In some cases, the CD80 variant polypeptide comprises a substitution at N19; and the 4-1BBL variant comprises a substitution at Y110. In some cases, the CD80 variant polypeptide comprises a substitution at N19; and the 4-1BBL variant comprises a substitution at S111. In some cases, the CD80 variant polypeptide comprises a substitution at N19; and the 4-1BBL variant comprises a substitution at D112. In some cases, the CD80 variant polypeptide comprises a substitution at N19; and the 4-1BBL variant comprises a substitution at P113. In some cases, the CD80 variant polypeptide comprises a substitution at N19; and the 4-1BBL variant comprises a substitution at G114. In some cases, the CD80 variant polypeptide comprises a substitution at N19; and the 4-1BBL variant comprises a substitution at L115. In some cases, the CD80 variant polypeptide comprises a substitution at N19; and the 4-1BBL variant comprises a substitution at G117. In some cases, the CD80 variant polypeptide comprises a substitution at N19; and the 4-1BBL variant comprises a substitution at V118. In some cases, the CD80 variant polypeptide comprises a substitution at N19; and the 4-1BBL variant comprises a substitution at S119. In some cases, the CD80 variant polypeptide comprises a substitution at N19; and the 4-1BBL variant comprises a substitution at L120. In some cases, the CD80 variant polypeptide comprises a substitution at N19; and the 4-1BBL variant comprises a substitution at T121. In some cases, the CD80 variant polypeptide comprises a substitution at N19; and the 4-1BBL variant comprises a substitution at G122. In some cases, the CD80 variant polypeptide comprises a substitution at N19; and the 4-1BBL variant comprises a substitution at G123. In some cases, the CD80 variant polypeptide comprises a substitution at N19; and the 4-1BBL variant comprises a substitution at L124. In some cases, the CD80 variant polypeptide comprises a substitution at N19; and the 4-1BBL variant comprises a substitution at S125. In some cases, the CD80 variant polypeptide comprises a substitution at N19; and the 4-1BBL variant comprises a substitution at Y126. In some cases, the CD80 variant polypeptide comprises a substitution at N19; and the 4-1BBL variant comprises a substitution at E128. In some cases, the CD80 variant polypeptide comprises a substitution at N19; and the 4-1BBL variant comprises a substitution at D129. In some cases, the CD80 variant polypeptide comprises a substitution at N19; and the 4-1BBL variant comprises a substitution at T130. In some cases, the CD80 variant polypeptide comprises a substitution at N19; and the 4-1BBL variant comprises a substitution at K131. In some cases, the CD80 variant polypeptide comprises a substitution at N19; and the 4-1BBL variant comprises a substitution at E132. In some cases, the CD80 variant polypeptide comprises a substitution at N19; and the 4-1BBL variant comprises a substitution at F144. In some cases, the CD80 variant polypeptide comprises a substitution at N19; and the 4-1BBL variant comprises a substitution at F145. In some cases, the CD80 variant polypeptide comprises a substitution at N19; and the 4-1BBL variant comprises a substitution at Q146. In some cases, the CD80 variant polypeptide comprises a substitution at N19; and the 4-1BBL variant comprises a substitution at L147. In some cases, the CD80 variant polypeptide comprises a substitution at N19; and the 4-1BBL variant comprises a substitution at E148. In some cases, the CD80 variant polypeptide comprises a substitution at N19; and the 4-1BBL variant comprises a substitution at L149. In some cases, the CD80 variant polypeptide comprises a substitution at N19; and the 4-1BBL variant comprises a substitution at R150. In some cases, the CD80 variant polypeptide comprises a substitution at N19; and the 4-1BBL variant comprises a substitution at R151. In some cases, the CD80 variant polypeptide comprises a substitution at N19; and the 4-1BBL variant comprises a substitution at V152. In some cases, the CD80 variant polypeptide comprises a substitution at N19; and the 4-1BBL variant comprises a substitution at V153. In some cases, the CD80 variant polypeptide comprises a substitution at N19; and the 4-1BBL variant comprises a substitution at G155. In some cases, the CD80 variant polypeptide comprises a substitution at N19; and the 4-1BBL variant comprises a substitution at E156. In some cases, the CD80 variant polypeptide comprises a substitution at N19; and the 4-1BBL variant comprises a substitution at G157. In some cases, the CD80 variant polypeptide comprises a substitution at N19; and the 4-1BBL variant comprises a substitution at S158. In some cases, the CD80 variant polypeptide comprises a substitution at N19; and the 4-1BBL variant comprises a substitution at D184. In some cases, the CD80 variant polypeptide comprises a substitution at N19; and the 4-1BBL variant comprises a substitution at L185. In some cases, the CD80 variant polypeptide comprises a substitution at N19; and the 4-1BBL variant comprises a substitution at P186. In some cases, the CD80 variant polypeptide comprises a substitution at N19; and the 4-1BBL variant comprises a substitution at P187. In some cases, the CD80 variant polypeptide comprises a substitution at N19; and the 4-1BBL variant comprises a substitution at S189. In some cases, the CD80 variant polypeptide comprises a substitution at N19; and the 4-1BBL variant comprises a substitution at S190. In some cases, the CD80 variant polypeptide comprises a substitution at N19; and the 4-1BBL variant comprises a substitution at E191. In some cases, the CD80 variant polypeptide comprises a substitution at N19; and the 4-1BBL variant comprises a substitution at R193. In some cases, the CD80 variant polypeptide comprises a substitution at N19; and the 4-1BBL variant comprises a substitution at N194. In some cases, the CD80 variant polypeptide comprises a substitution at N19; and the 4-1BBL variant comprises a substitution at S195. In some cases, the CD80 variant polypeptide comprises a substitution at N19; and the 4-1BBL variant comprises a substitution at F197. In some cases, the CD80 variant polypeptide comprises a substitution at N19; and the 4-1BBL variant comprises a substitution at Q210. In some cases, the CD80 variant polypeptide comprises a substitution at N19; and the 4-1BBL variant comprises a substitution at R211. In some cases, the CD80 variant polypeptide comprises a substitution at N19; and the 4-1BBL variant comprises a substitution at L212. In some cases, the CD80 variant polypeptide comprises a substitution at N19; and the 4-1BBL variant comprises a substitution at G213. In some cases, the CD80 variant polypeptide comprises a substitution at N19; and the 4-1BBL variant comprises a substitution at V214. In some cases, the CD80 variant polypeptide comprises a substitution at N19; and the 4-1BBL variant comprises a substitution at H215. In some cases, the CD80 variant polypeptide comprises a substitution at N19; and the 4-1BBL variant comprises a substitution at L216. In some cases, the CD80 variant polypeptide comprises a substitution at N19; and the 4-1BBL variant comprises a substitution at H217. In some cases, the CD80 variant polypeptide comprises a substitution at N19; and the 4-1BBL variant comprises a substitution at T218. In some cases, the CD80 variant polypeptide comprises a substitution at N19; and the 4-1BBL variant comprises a substitution at E219. In some cases, the CD80 variant polypeptide comprises a substitution at N19; and the 4-1BBL variant comprises a substitution at R221. In some cases, the CD80 variant polypeptide comprises a substitution at N19; and the 4-1BBL variant comprises a substitution at R223. In some cases, the CD80 variant polypeptide comprises a substitution at N19; and the 4-1BBL variant comprises a substitution at H224. In some cases, the CD80 variant polypeptide comprises a substitution at N19; and the 4-1BBL variant comprises a substitution at W226. In some cases, the CD80 variant polypeptide comprises a substitution at N19; and the 4-1BBL variant comprises a substitution at L228. In some cases, the CD80 variant polypeptide comprises a substitution at N19; and the 4-1BBL variant comprises a substitution at T229. In some cases, the CD80 variant polypeptide comprises a substitution at N19; and the 4-1BBL variant comprises a substitution at Q230. In some cases, the CD80 variant polypeptide comprises a substitution at N19; and the 4-1BBL variant comprises a substitution at G231. In some cases, the CD80 variant polypeptide comprises a substitution at N19; and the 4-1BBL variant comprises a substitution at T233. In some cases, the CD80 variant polypeptide comprises a substitution at N19; and the 4-1BBL variant comprises a substitution at V234. The amino acid numbering for CD80 is based on the numbering set out in FIG. 2. The amino acid numbering for 4-1BBL is based on the numbering set out in FIG. 3.

In some cases, the CD80 variant polypeptide comprises a substitution at N63; and the 4-1BBL variant comprises a substitution at M91. In some cases, the CD80 variant polypeptide comprises a substitution at N63; and the 4-1BBL variant comprises a substitution at F92. In some cases, the CD80 variant polypeptide comprises a substitution at N63; and the 4-1BBL variant comprises a substitution at Q94. In some cases, the CD80 variant polypeptide comprises a substitution at N63; and the 4-1BBL variant comprises a substitution at L95. In some cases, the CD80 variant polypeptide comprises a substitution at N63; and the 4-1BBL variant comprises a substitution at V96. In some cases, the CD80 variant polypeptide comprises a substitution at N63; and the 4-1BBL variant comprises a substitution at Q98. In some cases, the CD80 variant polypeptide comprises a substitution at N63; and the 4-1BBL variant comprises a substitution at N99. In some cases, the CD80 variant polypeptide comprises a substitution at N63; and the 4-1BBL variant comprises a substitution at V100. In some cases, the CD80 variant polypeptide comprises a substitution at N63; and the 4-1BBL variant comprises a substitution at L101. In some cases, the CD80 variant polypeptide comprises a substitution at N63; and the 4-1BBL variant comprises a substitution at L102. In some cases, the CD80 variant polypeptide comprises a substitution at N63; and the 4-1BBL variant comprises a substitution at I103. In some cases, the CD80 variant polypeptide comprises a substitution at N63; and the 4-1BBL variant comprises a substitution at D104. In some cases, the CD80 variant polypeptide comprises a substitution at N63; and the 4-1BBL variant comprises a substitution at G105. In some cases, the CD80 variant polypeptide comprises a substitution at N63; and the 4-1BBL variant comprises a substitution at P106. In some cases, the CD80 variant polypeptide comprises a substitution at N63; and the 4-1BBL variant comprises a substitution at L107. In some cases, the CD80 variant polypeptide comprises a substitution at N63; and the 4-1BBL variant comprises a substitution at S108. In some cases, the CD80 variant polypeptide comprises a substitution at N63; and the 4-1BBL variant comprises a substitution at W109. In some cases, the CD80 variant polypeptide comprises a substitution at N63; and the 4-1BBL variant comprises a substitution at Y110. In some cases, the CD80 variant polypeptide comprises a substitution at N63; and the 4-1BBL variant comprises a substitution at S111. In some cases, the CD80 variant polypeptide comprises a substitution at N63; and the 4-1BBL variant comprises a substitution at D112. In some cases, the CD80 variant polypeptide comprises a substitution at N63; and the 4-1BBL variant comprises a substitution at P113. In some cases, the CD80 variant polypeptide comprises a substitution at N63; and the 4-1BBL variant comprises a substitution at G114. In some cases, the CD80 variant polypeptide comprises a substitution at N63; and the 4-1BBL variant comprises a substitution at L115. In some cases, the CD80 variant polypeptide comprises a substitution at N63; and the 4-1BBL variant comprises a substitution at G117. In some cases, the CD80 variant polypeptide comprises a substitution at N63; and the 4-1BBL variant comprises a substitution at V118. In some cases, the CD80 variant polypeptide comprises a substitution at N63; and the 4-1BBL variant comprises a substitution at S119. In some cases, the CD80 variant polypeptide comprises a substitution at N63; and the 4-1BBL variant comprises a substitution at L120. In some cases, the CD80 variant polypeptide comprises a substitution at N63; and the 4-1BBL variant comprises a substitution at T121. In some cases, the CD80 variant polypeptide comprises a substitution at N63; and the 4-1BBL variant comprises a substitution at G122. In some cases, the CD80 variant polypeptide comprises a substitution at N63; and the 4-1BBL variant comprises a substitution at G123. In some cases, the CD80 variant polypeptide comprises a substitution at N63; and the 4-1BBL variant comprises a substitution at L124. In some cases, the CD80 variant polypeptide comprises a substitution at N63; and the 4-1BBL variant comprises a substitution at S125. In some cases, the CD80 variant polypeptide comprises a substitution at N63; and the 4-1BBL variant comprises a substitution at Y126. In some cases, the CD80 variant polypeptide comprises a substitution at N63; and the 4-1BBL variant comprises a substitution at E128. In some cases, the CD80 variant polypeptide comprises a substitution at N63; and the 4-1BBL variant comprises a substitution at D129. In some cases, the CD80 variant polypeptide comprises a substitution at N63; and the 4-1BBL variant comprises a substitution at T130. In some cases, the CD80 variant polypeptide comprises a substitution at N63; and the 4-1BBL variant comprises a substitution at K131. In some cases, the CD80 variant polypeptide comprises a substitution at N63; and the 4-1BBL variant comprises a substitution at E132. In some cases, the CD80 variant polypeptide comprises a substitution at N63; and the 4-1BBL variant comprises a substitution at F144. In some cases, the CD80 variant polypeptide comprises a substitution at N63; and the 4-1BBL variant comprises a substitution at F145. In some cases, the CD80 variant polypeptide comprises a substitution at N63; and the 4-1BBL variant comprises a substitution at Q146. In some cases, the CD80 variant polypeptide comprises a substitution at N63; and the 4-1BBL variant comprises a substitution at L147. In some cases, the CD80 variant polypeptide comprises a substitution at N63; and the 4-1BBL variant comprises a substitution at E148. In some cases, the CD80 variant polypeptide comprises a substitution at N63; and the 4-1BBL variant comprises a substitution at L149. In some cases, the CD80 variant polypeptide comprises a substitution at N63; and the 4-1BBL variant comprises a substitution at R150. In some cases, the CD80 variant polypeptide comprises a substitution at N63; and the 4-1BBL variant comprises a substitution at R151. In some cases, the CD80 variant polypeptide comprises a substitution at N63; and the 4-1BBL variant comprises a substitution at V152. In some cases, the CD80 variant polypeptide comprises a substitution at N63; and the 4-1BBL variant comprises a substitution at V153. In some cases, the CD80 variant polypeptide comprises a substitution at N63; and the 4-1BBL variant comprises a substitution at G155. In some cases, the CD80 variant polypeptide comprises a substitution at N63; and the 4-1BBL variant comprises a substitution at E156. In some cases, the CD80 variant polypeptide comprises a substitution at N63; and the 4-1BBL variant comprises a substitution at G157. In some cases, the CD80 variant polypeptide comprises a substitution at N63; and the 4-1BBL variant comprises a substitution at S158. In some cases, the CD80 variant polypeptide comprises a substitution at N63; and the 4-1BBL variant comprises a substitution at D184. In some cases, the CD80 variant polypeptide comprises a substitution at N63; and the 4-1BBL variant comprises a substitution at L185. In some cases, the CD80 variant polypeptide comprises a substitution at N63; and the 4-1BBL variant comprises a substitution at P186. In some cases, the CD80 variant polypeptide comprises a substitution at N63; and the 4-1BBL variant comprises a substitution at P187. In some cases, the CD80 variant polypeptide comprises a substitution at N63; and the 4-1BBL variant comprises a substitution at S189. In some cases, the CD80 variant polypeptide comprises a substitution at N63; and the 4-1BBL variant comprises a substitution at S190. In some cases, the CD80 variant polypeptide comprises a substitution at N63; and the 4-1BBL variant comprises a substitution at E191. In some cases, the CD80 variant polypeptide comprises a substitution at N63; and the 4-1BBL variant comprises a substitution at R193. In some cases, the CD80 variant polypeptide comprises a substitution at N63; and the 4-1BBL variant comprises a substitution at N634. In some cases, the CD80 variant polypeptide comprises a substitution at N63; and the 4-1BBL variant comprises a substitution at S195. In some cases, the CD80 variant polypeptide comprises a substitution at N63; and the 4-1BBL variant comprises a substitution at F197. In some cases, the CD80 variant polypeptide comprises a substitution at N63; and the 4-1BBL variant comprises a substitution at Q210. In some cases, the CD80 variant polypeptide comprises a substitution at N63; and the 4-1BBL variant comprises a substitution at R211. In some cases, the CD80 variant polypeptide comprises a substitution at N63; and the 4-1BBL variant comprises a substitution at L212. In some cases, the CD80 variant polypeptide comprises a substitution at N63; and the 4-1BBL variant comprises a substitution at G213. In some cases, the CD80 variant polypeptide comprises a substitution at N63; and the 4-1BBL variant comprises a substitution at V214. In some cases, the CD80 variant polypeptide comprises a substitution at N63; and the 4-1BBL variant comprises a substitution at H215. In some cases, the CD80 variant polypeptide comprises a substitution at N63; and the 4-1BBL variant comprises a substitution at L216. In some cases, the CD80 variant polypeptide comprises a substitution at N63; and the 4-1BBL variant comprises a substitution at H217. In some cases, the CD80 variant polypeptide comprises a substitution at N63; and the 4-1BBL variant comprises a substitution at T218. In some cases, the CD80 variant polypeptide comprises a substitution at N63; and the 4-1BBL variant comprises a substitution at E219. In some cases, the CD80 variant polypeptide comprises a substitution at N63; and the 4-1BBL variant comprises a substitution at R221. In some cases, the CD80 variant polypeptide comprises a substitution at N63; and the 4-1BBL variant comprises a substitution at R223. In some cases, the CD80 variant polypeptide comprises a substitution at N63; and the 4-1BBL variant comprises a substitution at H224. In some cases, the CD80 variant polypeptide comprises a substitution at N63; and the 4-1BBL variant comprises a substitution at W226. In some cases, the CD80 variant polypeptide comprises a substitution at N63; and the 4-1BBL variant comprises a substitution at L228. In some cases, the CD80 variant polypeptide comprises a substitution at N63; and the 4-1BBL variant comprises a substitution at T229. In some cases, the CD80 variant polypeptide comprises a substitution at N63; and the 4-1BBL variant comprises a substitution at Q230. In some cases, the CD80 variant polypeptide comprises a substitution at N63; and the 4-1BBL variant comprises a substitution at G231. In some cases, the CD80 variant polypeptide comprises a substitution at N63; and the 4-1BBL variant comprises a substitution at T233. In some cases, the CD80 variant polypeptide comprises a substitution at N63; and the 4-1BBL variant comprises a substitution at V234. The amino acid numbering for CD80 is based on the numbering set out in FIG. 2. The amino acid numbering for 4-1BBL is based on the numbering set out in FIG. 3.

In some cases, the CD80 variant polypeptide comprises a substitution at I67; and the 4-1BBL variant comprises a substitution at M91. In some cases, the CD80 variant polypeptide comprises a substitution at I67; and the 4-1BBL variant comprises a substitution at F92. In some cases, the CD80 variant polypeptide comprises a substitution at I67; and the 4-1BBL variant comprises a substitution at Q94. In some cases, the CD80 variant polypeptide comprises a substitution at I67; and the 4-1BBL variant comprises a substitution at L95. In some cases, the CD80 variant polypeptide comprises a substitution at I67; and the 4-1BBL variant comprises a substitution at V96. In some cases, the CD80 variant polypeptide comprises a substitution at I67; and the 4-1BBL variant comprises a substitution at Q98. In some cases, the CD80 variant polypeptide comprises a substitution at I67; and the 4-1BBL variant comprises a substitution at N99. In some cases, the CD80 variant polypeptide comprises a substitution at I67; and the 4-1BBL variant comprises a substitution at V100. In some cases, the CD80 variant polypeptide comprises a substitution at I67; and the 4-1BBL variant comprises a substitution at L101. In some cases, the CD80 variant polypeptide comprises a substitution at I67; and the 4-1BBL variant comprises a substitution at L102. In some cases, the CD80 variant polypeptide comprises a substitution at I67; and the 4-1BBL variant comprises a substitution at I103. In some cases, the CD80 variant polypeptide comprises a substitution at I67; and the 4-1BBL variant comprises a substitution at D104. In some cases, the CD80 variant polypeptide comprises a substitution at I67; and the 4-1BBL variant comprises a substitution at G105. In some cases, the CD80 variant polypeptide comprises a substitution at I67; and the 4-1BBL variant comprises a substitution at P106. In some cases, the CD80 variant polypeptide comprises a substitution at I67; and the 4-1BBL variant comprises a substitution at L107. In some cases, the CD80 variant polypeptide comprises a substitution at I67; and the 4-1BBL variant comprises a substitution at S108. In some cases, the CD80 variant polypeptide comprises a substitution at I67; and the 4-1BBL variant comprises a substitution at W109. In some cases, the CD80 variant polypeptide comprises a substitution at I67; and the 4-1BBL variant comprises a substitution at Y110. In some cases, the CD80 variant polypeptide comprises a substitution at I67; and the 4-1BBL variant comprises a substitution at S111. In some cases, the CD80 variant polypeptide comprises a substitution at I67; and the 4-1BBL variant comprises a substitution at D112. In some cases, the CD80 variant polypeptide comprises a substitution at I67; and the 4-1BBL variant comprises a substitution at P113. In some cases, the CD80 variant polypeptide comprises a substitution at I67; and the 4-1BBL variant comprises a substitution at G114. In some cases, the CD80 variant polypeptide comprises a substitution at I67; and the 4-1BBL variant comprises a substitution at L115. In some cases, the CD80 variant polypeptide comprises a substitution at I67; and the 4-1BBL variant comprises a substitution at G117. In some cases, the CD80 variant polypeptide comprises a substitution at I67; and the 4-1BBL variant comprises a substitution at V118. In some cases, the CD80 variant polypeptide comprises a substitution at I67; and the 4-1BBL variant comprises a substitution at S119. In some cases, the CD80 variant polypeptide comprises a substitution at I67; and the 4-1BBL variant comprises a substitution at L120. In some cases, the CD80 variant polypeptide comprises a substitution at I67; and the 4-1BBL variant comprises a substitution at T121. In some cases, the CD80 variant polypeptide comprises a substitution at I67; and the 4-1BBL variant comprises a substitution at G122. In some cases, the CD80 variant polypeptide comprises a substitution at I67; and the 4-1BBL variant comprises a substitution at G123. In some cases, the CD80 variant polypeptide comprises a substitution at I67; and the 4-1BBL variant comprises a substitution at L124. In some cases, the CD80 variant polypeptide comprises a substitution at I67; and the 4-1BBL variant comprises a substitution at S125. In some cases, the CD80 variant polypeptide comprises a substitution at I67; and the 4-1BBL variant comprises a substitution at Y126. In some cases, the CD80 variant polypeptide comprises a substitution at I67; and the 4-1BBL variant comprises a substitution at E128. In some cases, the CD80 variant polypeptide comprises a substitution at I67; and the 4-1BBL variant comprises a substitution at D129. In some cases, the CD80 variant polypeptide comprises a substitution at I67; and the 4-1BBL variant comprises a substitution at T130. In some cases, the CD80 variant polypeptide comprises a substitution at I67; and the 4-1BBL variant comprises a substitution at K131. In some cases, the CD80 variant polypeptide comprises a substitution at I67; and the 4-1BBL variant comprises a substitution at E132. In some cases, the CD80 variant polypeptide comprises a substitution at I67; and the 4-1BBL variant comprises a substitution at F144. In some cases, the CD80 variant polypeptide comprises a substitution at I67; and the 4-1BBL variant comprises a substitution at F145. In some cases, the CD80 variant polypeptide comprises a substitution at I67; and the 4-1BBL variant comprises a substitution at Q146. In some cases, the CD80 variant polypeptide comprises a substitution at I67; and the 4-1BBL variant comprises a substitution at L147. In some cases, the CD80 variant polypeptide comprises a substitution at I67; and the 4-1BBL variant comprises a substitution at E148. In some cases, the CD80 variant polypeptide comprises a substitution at I67; and the 4-1BBL variant comprises a substitution at L149. In some cases, the CD80 variant polypeptide comprises a substitution at I67; and the 4-1BBL variant comprises a substitution at R150. In some cases, the CD80 variant polypeptide comprises a substitution at I67; and the 4-1BBL variant comprises a substitution at R151. In some cases, the CD80 variant polypeptide comprises a substitution at I67; and the 4-1BBL variant comprises a substitution at V152. In some cases, the CD80 variant polypeptide comprises a substitution at I67; and the 4-1BBL variant comprises a substitution at V153. In some cases, the CD80 variant polypeptide comprises a substitution at I67; and the 4-1BBL variant comprises a substitution at G155. In some cases, the CD80 variant polypeptide comprises a substitution at I67; and the 4-1BBL variant comprises a substitution at E156. In some cases, the CD80 variant polypeptide comprises a substitution at I67; and the 4-1BBL variant comprises a substitution at G157. In some cases, the CD80 variant polypeptide comprises a substitution at I67; and the 4-1BBL variant comprises a substitution at S158. In some cases, the CD80 variant polypeptide comprises a substitution at I67; and the 4-1BBL variant comprises a substitution at D184. In some cases, the CD80 variant polypeptide comprises a substitution at I67; and the 4-1BBL variant comprises a substitution at L185. In some cases, the CD80 variant polypeptide comprises a substitution at I67; and the 4-1BBL variant comprises a substitution at P186. In some cases, the CD80 variant polypeptide comprises a substitution at I67; and the 4-1BBL variant comprises a substitution at P187. In some cases, the CD80 variant polypeptide comprises a substitution at I67; and the 4-1BBL variant comprises a substitution at S189. In some cases, the CD80 variant polypeptide comprises a substitution at I67; and the 4-1BBL variant comprises a substitution at S190. In some cases, the CD80 variant polypeptide comprises a substitution at I67; and the 4-1BBL variant comprises a substitution at E191. In some cases, the CD80 variant polypeptide comprises a substitution at I67; and the 4-1BBL variant comprises a substitution at R193. In some cases, the CD80 variant polypeptide comprises a substitution at I67; and the 4-1BBL variant comprises a substitution at I674. In some cases, the CD80 variant polypeptide comprises a substitution at I67; and the 4-1BBL variant comprises a substitution at S195. In some cases, the CD80 variant polypeptide comprises a substitution at I67; and the 4-1BBL variant comprises a substitution at F197. In some cases, the CD80 variant polypeptide comprises a substitution at I67; and the 4-1BBL variant comprises a substitution at Q210. In some cases, the CD80 variant polypeptide comprises a substitution at I67; and the 4-1BBL variant comprises a substitution at R211. In some cases, the CD80 variant polypeptide comprises a substitution at I67; and the 4-1BBL variant comprises a substitution at L212. In some cases, the CD80 variant polypeptide comprises a substitution at I67; and the 4-1BBL variant comprises a substitution at G213. In some cases, the CD80 variant polypeptide comprises a substitution at I67; and the 4-1BBL variant comprises a substitution at V214. In some cases, the CD80 variant polypeptide comprises a substitution at I67; and the 4-1BBL variant comprises a substitution at H215. In some cases, the CD80 variant polypeptide comprises a substitution at I67; and the 4-1BBL variant comprises a substitution at L216. In some cases, the CD80 variant polypeptide comprises a substitution at I67; and the 4-1BBL variant comprises a substitution at H217. In some cases, the CD80 variant polypeptide comprises a substitution at I67; and the 4-1BBL variant comprises a substitution at T218. In some cases, the CD80 variant polypeptide comprises a substitution at I67; and the 4-1BBL variant comprises a substitution at E219. In some cases, the CD80 variant polypeptide comprises a substitution at I67; and the 4-1BBL variant comprises a substitution at R221. In some cases, the CD80 variant polypeptide comprises a substitution at I67; and the 4-1BBL variant comprises a substitution at R223. In some cases, the CD80 variant polypeptide comprises a substitution at I67; and the 4-1BBL variant comprises a substitution at H224. In some cases, the CD80 variant polypeptide comprises a substitution at I67; and the 4-1BBL variant comprises a substitution at W226. In some cases, the CD80 variant polypeptide comprises a substitution at I67; and the 4-1BBL variant comprises a substitution at L228. In some cases, the CD80 variant polypeptide comprises a substitution at I67; and the 4-1BBL variant comprises a substitution at T229. In some cases, the CD80 variant polypeptide comprises a substitution at I67; and the 4-1BBL variant comprises a substitution at Q230. In some cases, the CD80 variant polypeptide comprises a substitution at I67; and the 4-1BBL variant comprises a substitution at G231. In some cases, the CD80 variant polypeptide comprises a substitution at I67; and the 4-1BBL variant comprises a substitution at T233. In some cases, the CD80 variant polypeptide comprises a substitution at I67; and the 4-1BBL variant comprises a substitution at V234. The amino acid numbering for CD80 is based on the numbering set out in FIG. 2. The amino acid numbering for 4-1BBL is based on the numbering set out in FIG. 3.

In some cases, the CD80 variant polypeptide comprises a substitution at K86; and the 4-1BBL variant comprises a substitution at M91. In some cases, the CD80 variant polypeptide comprises a substitution at K86; and the 4-1BBL variant comprises a substitution at F92. In some cases, the CD80 variant polypeptide comprises a substitution at K86; and the 4-1BBL variant comprises a substitution at Q94. In some cases, the CD80 variant polypeptide comprises a substitution at K86; and the 4-1BBL variant comprises a substitution at L95. In some cases, the CD80 variant polypeptide comprises a substitution at K86; and the 4-1BBL variant comprises a substitution at V96. In some cases, the CD80 variant polypeptide comprises a substitution at K86; and the 4-1BBL variant comprises a substitution at Q98. In some cases, the CD80 variant polypeptide comprises a substitution at K86; and the 4-1BBL variant comprises a substitution at N99. In some cases, the CD80 variant polypeptide comprises a substitution at K86; and the 4-1BBL variant comprises a substitution at V100. In some cases, the CD80 variant polypeptide comprises a substitution at K86; and the 4-1BBL variant comprises a substitution at L101. In some cases, the CD80 variant polypeptide comprises a substitution at K86; and the 4-1BBL variant comprises a substitution at L102. In some cases, the CD80 variant polypeptide comprises a substitution at K86; and the 4-1BBL variant comprises a substitution at I103. In some cases, the CD80 variant polypeptide comprises a substitution at K86; and the 4-1BBL variant comprises a substitution at D104. In some cases, the CD80 variant polypeptide comprises a substitution at K86; and the 4-1BBL variant comprises a substitution at G105. In some cases, the CD80 variant polypeptide comprises a substitution at K86; and the 4-1BBL variant comprises a substitution at P106. In some cases, the CD80 variant polypeptide comprises a substitution at K86; and the 4-1BBL variant comprises a substitution at L107. In some cases, the CD80 variant polypeptide comprises a substitution at K86; and the 4-1BBL variant comprises a substitution at S108. In some cases, the CD80 variant polypeptide comprises a substitution at K86; and the 4-1BBL variant comprises a substitution at W109. In some cases, the CD80 variant polypeptide comprises a substitution at K86; and the 4-1BBL variant comprises a substitution at Y110. In some cases, the CD80 variant polypeptide comprises a substitution at K86; and the 4-1BBL variant comprises a substitution at S111. In some cases, the CD80 variant polypeptide comprises a substitution at K86; and the 4-1BBL variant comprises a substitution at D112. In some cases, the CD80 variant polypeptide comprises a substitution at K86; and the 4-1BBL variant comprises a substitution at P113. In some cases, the CD80 variant polypeptide comprises a substitution at K86; and the 4-1BBL variant comprises a substitution at G114. In some cases, the CD80 variant polypeptide comprises a substitution at K86; and the 4-1BBL variant comprises a substitution at L115. In some cases, the CD80 variant polypeptide comprises a substitution at K86; and the 4-1BBL variant comprises a substitution at G117. In some cases, the CD80 variant polypeptide comprises a substitution at K86; and the 4-1BBL variant comprises a substitution at V118. In some cases, the CD80 variant polypeptide comprises a substitution at K86; and the 4-1BBL variant comprises a substitution at S119. In some cases, the CD80 variant polypeptide comprises a substitution at K86; and the 4-1BBL variant comprises a substitution at L120. In some cases, the CD80 variant polypeptide comprises a substitution at K86; and the 4-1BBL variant comprises a substitution at T121. In some cases, the CD80 variant polypeptide comprises a substitution at K86; and the 4-1BBL variant comprises a substitution at G122. In some cases, the CD80 variant polypeptide comprises a substitution at K86; and the 4-1BBL variant comprises a substitution at G123. In some cases, the CD80 variant polypeptide comprises a substitution at K86; and the 4-1BBL variant comprises a substitution at L124. In some cases, the CD80 variant polypeptide comprises a substitution at K86; and the 4-1BBL variant comprises a substitution at S125. In some cases, the CD80 variant polypeptide comprises a substitution at K86; and the 4-1BBL variant comprises a substitution at Y126. In some cases, the CD80 variant polypeptide comprises a substitution at K86; and the 4-1BBL variant comprises a substitution at E128. In some cases, the CD80 variant polypeptide comprises a substitution at K86; and the 4-1BBL variant comprises a substitution at D129. In some cases, the CD80 variant polypeptide comprises a substitution at K86; and the 4-1BBL variant comprises a substitution at T130. In some cases, the CD80 variant polypeptide comprises a substitution at K86; and the 4-1BBL variant comprises a substitution at K131. In some cases, the CD80 variant polypeptide comprises a substitution at K86; and the 4-1BBL variant comprises a substitution at E132. In some cases, the CD80 variant polypeptide comprises a substitution at K86; and the 4-1BBL variant comprises a substitution at F144. In some cases, the CD80 variant polypeptide comprises a substitution at K86; and the 4-1BBL variant comprises a substitution at F145. In some cases, the CD80 variant polypeptide comprises a substitution at K86; and the 4-1BBL variant comprises a substitution at Q146. In some cases, the CD80 variant polypeptide comprises a substitution at K86; and the 4-1BBL variant comprises a substitution at L147. In some cases, the CD80 variant polypeptide comprises a substitution at K86; and the 4-1BBL variant comprises a substitution at E148. In some cases, the CD80 variant polypeptide comprises a substitution at K86; and the 4-1BBL variant comprises a substitution at L149. In some cases, the CD80 variant polypeptide comprises a substitution at K86; and the 4-1BBL variant comprises a substitution at R150. In some cases, the CD80 variant polypeptide comprises a substitution at K86; and the 4-1BBL variant comprises a substitution at R151. In some cases, the CD80 variant polypeptide comprises a substitution at K86; and the 4-1BBL variant comprises a substitution at V152. In some cases, the CD80 variant polypeptide comprises a substitution at K86; and the 4-1BBL variant comprises a substitution at V153. In some cases, the CD80 variant polypeptide comprises a substitution at K86; and the 4-1BBL variant comprises a substitution at G155. In some cases, the CD80 variant polypeptide comprises a substitution at K86; and the 4-1BBL variant comprises a substitution at E156. In some cases, the CD80 variant polypeptide comprises a substitution at K86; and the 4-1BBL variant comprises a substitution at G157. In some cases, the CD80 variant polypeptide comprises a substitution at K86; and the 4-1BBL variant comprises a substitution at S158. In some cases, the CD80 variant polypeptide comprises a substitution at K86; and the 4-1BBL variant comprises a substitution at D184. In some cases, the CD80 variant polypeptide comprises a substitution at K86; and the 4-1BBL variant comprises a substitution at L185. In some cases, the CD80 variant polypeptide comprises a substitution at K86; and the 4-1BBL variant comprises a substitution at P186. In some cases, the CD80 variant polypeptide comprises a substitution at K86; and the 4-1BBL variant comprises a substitution at P187. In some cases, the CD80 variant polypeptide comprises a substitution at K86; and the 4-1BBL variant comprises a substitution at S189. In some cases, the CD80 variant polypeptide comprises a substitution at K86; and the 4-1BBL variant comprises a substitution at S190. In some cases, the CD80 variant polypeptide comprises a substitution at K86; and the 4-1BBL variant comprises a substitution at E191. In some cases, the CD80 variant polypeptide comprises a substitution at K86; and the 4-1BBL variant comprises a substitution at R193. In some cases, the CD80 variant polypeptide comprises a substitution at K86; and the 4-1BBL variant comprises a substitution at K864. In some cases, the CD80 variant polypeptide comprises a substitution at K86; and the 4-1BBL variant comprises a substitution at S195. In some cases, the CD80 variant polypeptide comprises a substitution at K86; and the 4-1BBL variant comprises a substitution at F197. In some cases, the CD80 variant polypeptide comprises a substitution at K86; and the 4-1BBL variant comprises a substitution at Q210. In some cases, the CD80 variant polypeptide comprises a substitution at K86; and the 4-1BBL variant comprises a substitution at R211. In some cases, the CD80 variant polypeptide comprises a substitution at K86; and the 4-1BBL variant comprises a substitution at L212. In some cases, the CD80 variant polypeptide comprises a substitution at K86; and the 4-1BBL variant comprises a substitution at G213. In some cases, the CD80 variant polypeptide comprises a substitution at K86; and the 4-1BBL variant comprises a substitution at V214. In some cases, the CD80 variant polypeptide comprises a substitution at K86; and the 4-1BBL variant comprises a substitution at H215. In some cases, the CD80 variant polypeptide comprises a substitution at K86; and the 4-1BBL variant comprises a substitution at L216. In some cases, the CD80 variant polypeptide comprises a substitution at K86; and the 4-1BBL variant comprises a substitution at H217. In some cases, the CD80 variant polypeptide comprises a substitution at K86; and the 4-1BBL variant comprises a substitution at T218. In some cases, the CD80 variant polypeptide comprises a substitution at K86; and the 4-1BBL variant comprises a substitution at E219. In some cases, the CD80 variant polypeptide comprises a substitution at K86; and the 4-1BBL variant comprises a substitution at R221. In some cases, the CD80 variant polypeptide comprises a substitution at K86; and the 4-1BBL variant comprises a substitution at R223. In some cases, the CD80 variant polypeptide comprises a substitution at K86; and the 4-1BBL variant comprises a substitution at H224. In some cases, the CD80 variant polypeptide comprises a substitution at K86; and the 4-1BBL variant comprises a substitution at W226. In some cases, the CD80 variant polypeptide comprises a substitution at K86; and the 4-1BBL variant comprises a substitution at L228. In some cases, the CD80 variant polypeptide comprises a substitution at K86; and the 4-1BBL variant comprises a substitution at T229. In some cases, the CD80 variant polypeptide comprises a substitution at K86; and the 4-1BBL variant comprises a substitution at Q230. In some cases, the CD80 variant polypeptide comprises a substitution at K86; and the 4-1BBL variant comprises a substitution at G231. In some cases, the CD80 variant polypeptide comprises a substitution at K86; and the 4-1BBL variant comprises a substitution at T233. In some cases, the CD80 variant polypeptide comprises a substitution at K86; and the 4-1BBL variant comprises a substitution at V234. The amino acid numbering for CD80 is based on the numbering set out in FIG. 2. The amino acid numbering for 4-1BBL is based on the numbering set out in FIG. 3.

In some cases, the CD80 variant polypeptide comprises a substitution at Q157; and the 4-1BBL variant comprises a substitution at M91. In some cases, the CD80 variant polypeptide comprises a substitution at Q157; and the 4-1BBL variant comprises a substitution at F92. In some cases, the CD80 variant polypeptide comprises a substitution at Q157; and the 4-1BBL variant comprises a substitution at Q94. In some cases, the CD80 variant polypeptide comprises a substitution at Q157; and the 4-1BBL variant comprises a substitution at L95. In some cases, the CD80 variant polypeptide comprises a substitution at Q157; and the 4-1BBL variant comprises a substitution at V96. In some cases, the CD80 variant polypeptide comprises a substitution at Q157; and the 4-1BBL variant comprises a substitution at Q98. In some cases, the CD80 variant polypeptide comprises a substitution at Q157; and the 4-1BBL variant comprises a substitution at N99. In some cases, the CD80 variant polypeptide comprises a substitution at Q157; and the 4-1BBL variant comprises a substitution at V100. In some cases, the CD80 variant polypeptide comprises a substitution at Q157; and the 4-1BBL variant comprises a substitution at L101. In some cases, the CD80 variant polypeptide comprises a substitution at Q157; and the 4-1BBL variant comprises a substitution at L102. In some cases, the CD80 variant polypeptide comprises a substitution at Q157; and the 4-1BBL variant comprises a substitution at I103. In some cases, the CD80 variant polypeptide comprises a substitution at Q157; and the 4-1BBL variant comprises a substitution at D104. In some cases, the CD80 variant polypeptide comprises a substitution at Q157; and the 4-1BBL variant comprises a substitution at G105. In some cases, the CD80 variant polypeptide comprises a substitution at Q157; and the 4-1BBL variant comprises a substitution at P106. In some cases, the CD80 variant polypeptide comprises a substitution at Q157; and the 4-1BBL variant comprises a substitution at L107. In some cases, the CD80 variant polypeptide comprises a substitution at Q157; and the 4-1BBL variant comprises a substitution at S108. In some cases, the CD80 variant polypeptide comprises a substitution at Q157; and the 4-1BBL variant comprises a substitution at W109. In some cases, the CD80 variant polypeptide comprises a substitution at Q157; and the 4-1BBL variant comprises a substitution at Y110. In some cases, the CD80 variant polypeptide comprises a substitution at Q157; and the 4-1BBL variant comprises a substitution at S111. In some cases, the CD80 variant polypeptide comprises a substitution at Q157; and the 4-1BBL variant comprises a substitution at D112. In some cases, the CD80 variant polypeptide comprises a substitution at Q157; and the 4-1BBL variant comprises a substitution at P113. In some cases, the CD80 variant polypeptide comprises a substitution at Q157; and the 4-1BBL variant comprises a substitution at G114. In some cases, the CD80 variant polypeptide comprises a substitution at Q157; and the 4-1BBL variant comprises a substitution at L115. In some cases, the CD80 variant polypeptide comprises a substitution at Q157; and the 4-1BBL variant comprises a substitution at G117. In some cases, the CD80 variant polypeptide comprises a substitution at Q157; and the 4-1BBL variant comprises a substitution at V118. In some cases, the CD80 variant polypeptide comprises a substitution at Q157; and the 4-1BBL variant comprises a substitution at S119. In some cases, the CD80 variant polypeptide comprises a substitution at Q157; and the 4-1BBL variant comprises a substitution at L120. In some cases, the CD80 variant polypeptide comprises a substitution at Q157; and the 4-1BBL variant comprises a substitution at T121. In some cases, the CD80 variant polypeptide comprises a substitution at Q157; and the 4-1BBL variant comprises a substitution at G122. In some cases, the CD80 variant polypeptide comprises a substitution at Q157; and the 4-1BBL variant comprises a substitution at G123. In some cases, the CD80 variant polypeptide comprises a substitution at Q157; and the 4-1BBL variant comprises a substitution at L124. In some cases, the CD80 variant polypeptide comprises a substitution at Q157; and the 4-1BBL variant comprises a substitution at S125. In some cases, the CD80 variant polypeptide comprises a substitution at Q157; and the 4-1BBL variant comprises a substitution at Y126. In some cases, the CD80 variant polypeptide comprises a substitution at Q157; and the 4-1BBL variant comprises a substitution at E128. In some cases, the CD80 variant polypeptide comprises a substitution at Q157; and the 4-1BBL variant comprises a substitution at D129. In some cases, the CD80 variant polypeptide comprises a substitution at Q157; and the 4-1BBL variant comprises a substitution at T130. In some cases, the CD80 variant polypeptide comprises a substitution at Q157; and the 4-1BBL variant comprises a substitution at K131. In some cases, the CD80 variant polypeptide comprises a substitution at Q157; and the 4-1BBL variant comprises a substitution at E132. In some cases, the CD80 variant polypeptide comprises a substitution at Q157; and the 4-1BBL variant comprises a substitution at F144. In some cases, the CD80 variant polypeptide comprises a substitution at Q157; and the 4-1BBL variant comprises a substitution at F145. In some cases, the CD80 variant polypeptide comprises a substitution at Q157; and the 4-1BBL variant comprises a substitution at Q146. In some cases, the CD80 variant polypeptide comprises a substitution at Q157; and the 4-1BBL variant comprises a substitution at L147. In some cases, the CD80 variant polypeptide comprises a substitution at Q157; and the 4-1BBL variant comprises a substitution at E148. In some cases, the CD80 variant polypeptide comprises a substitution at Q157; and the 4-1BBL variant comprises a substitution at L149. In some cases, the CD80 variant polypeptide comprises a substitution at Q157; and the 4-1BBL variant comprises a substitution at R150. In some cases, the CD80 variant polypeptide comprises a substitution at Q157; and the 4-1BBL variant comprises a substitution at R151. In some cases, the CD80 variant polypeptide comprises a substitution at Q157; and the 4-1BBL variant comprises a substitution at V152. In some cases, the CD80 variant polypeptide comprises a substitution at Q157; and the 4-1BBL variant comprises a substitution at V153. In some cases, the CD80 variant polypeptide comprises a substitution at Q157; and the 4-1BBL variant comprises a substitution at G155. In some cases, the CD80 variant polypeptide comprises a substitution at Q157; and the 4-1BBL variant comprises a substitution at E156. In some cases, the CD80 variant polypeptide comprises a substitution at Q157; and the 4-1BBL variant comprises a substitution at G157. In some cases, the CD80 variant polypeptide comprises a substitution at Q157; and the 4-1BBL variant comprises a substitution at S158. In some cases, the CD80 variant polypeptide comprises a substitution at Q157; and the 4-1BBL variant comprises a substitution at D184. In some cases, the CD80 variant polypeptide comprises a substitution at Q157; and the 4-1BBL variant comprises a substitution at L185. In some cases, the CD80 variant polypeptide comprises a substitution at Q157; and the 4-1BBL variant comprises a substitution at P186. In some cases, the CD80 variant polypeptide comprises a substitution at Q157; and the 4-1BBL variant comprises a substitution at P187. In some cases, the CD80 variant polypeptide comprises a substitution at Q157; and the 4-1BBL variant comprises a substitution at S189. In some cases, the CD80 variant polypeptide comprises a substitution at Q157; and the 4-1BBL variant comprises a substitution at S190. In some cases, the CD80 variant polypeptide comprises a substitution at Q157; and the 4-1BBL variant comprises a substitution at E191. In some cases, the CD80 variant polypeptide comprises a substitution at Q157; and the 4-1BBL variant comprises a substitution at R193. In some cases, the CD80 variant polypeptide comprises a substitution at Q157; and the 4-1BBL variant comprises a substitution at Q1574. In some cases, the CD80 variant polypeptide comprises a substitution at Q157; and the 4-1BBL variant comprises a substitution at S195. In some cases, the CD80 variant polypeptide comprises a substitution at Q157; and the 4-1BBL variant comprises a substitution at F197. In some cases, the CD80 variant polypeptide comprises a substitution at Q157; and the 4-1BBL variant comprises a substitution at Q210. In some cases, the CD80 variant polypeptide comprises a substitution at Q157; and the 4-1BBL variant comprises a substitution at R211. In some cases, the CD80 variant polypeptide comprises a substitution at Q157; and the 4-1BBL variant comprises a substitution at L212. In some cases, the CD80 variant polypeptide comprises a substitution at Q157; and the 4-1BBL variant comprises a substitution at G213. In some cases, the CD80 variant polypeptide comprises a substitution at Q157; and the 4-1BBL variant comprises a substitution at V214. In some cases, the CD80 variant polypeptide comprises a substitution at Q157; and the 4-1BBL variant comprises a substitution at H215. In some cases, the CD80 variant polypeptide comprises a substitution at Q157; and the 4-1BBL variant comprises a substitution at L216. In some cases, the CD80 variant polypeptide comprises a substitution at Q157; and the 4-1BBL variant comprises a substitution at H217. In some cases, the CD80 variant polypeptide comprises a substitution at Q157; and the 4-1BBL variant comprises a substitution at T218. In some cases, the CD80 variant polypeptide comprises a substitution at Q157; and the 4-1BBL variant comprises a substitution at E219. In some cases, the CD80 variant polypeptide comprises a substitution at Q157; and the 4-1BBL variant comprises a substitution at R221. In some cases, the CD80 variant polypeptide comprises a substitution at Q157; and the 4-1BBL variant comprises a substitution at R223. In some cases, the CD80 variant polypeptide comprises a substitution at Q157; and the 4-1BBL variant comprises a substitution at H224. In some cases, the CD80 variant polypeptide comprises a substitution at Q157; and the 4-1BBL variant comprises a substitution at W226. In some cases, the CD80 variant polypeptide comprises a substitution at Q157; and the 4-1BBL variant comprises a substitution at L228. In some cases, the CD80 variant polypeptide comprises a substitution at Q157; and the 4-1BBL variant comprises a substitution at T229. In some cases, the CD80 variant polypeptide comprises a substitution at Q157; and the 4-1BBL variant comprises a substitution at Q230. In some cases, the CD80 variant polypeptide comprises a substitution at Q157; and the 4-1BBL variant comprises a substitution at G231. In some cases, the CD80 variant polypeptide comprises a substitution at Q157; and the 4-1BBL variant comprises a substitution at T233. In some cases, the CD80 variant polypeptide comprises a substitution at Q157; and the 4-1BBL variant comprises a substitution at V234. The amino acid numbering for CD80 is based on the numbering set out in FIG. 2. The amino acid numbering for 4-1BBL is based on the numbering set out in FIG. 3.

In some cases, the CD80 variant polypeptide comprises a substitution at D158; and the 4-1BBL variant comprises a substitution at M91. In some cases, the CD80 variant polypeptide comprises a substitution at D158; and the 4-1BBL variant comprises a substitution at F92. In some cases, the CD80 variant polypeptide comprises a substitution at D158; and the 4-1BBL variant comprises a substitution at Q94. In some cases, the CD80 variant polypeptide comprises a substitution at D158; and the 4-1BBL variant comprises a substitution at L95. In some cases, the CD80 variant polypeptide comprises a substitution at D158; and the 4-1BBL variant comprises a substitution at V96. In some cases, the CD80 variant polypeptide comprises a substitution at D158; and the 4-1BBL variant comprises a substitution at Q98. In some cases, the CD80 variant polypeptide comprises a substitution at D158; and the 4-1BBL variant comprises a substitution at N99. In some cases, the CD80 variant polypeptide comprises a substitution at D158; and the 4-1BBL variant comprises a substitution at V100. In some cases, the CD80 variant polypeptide comprises a substitution at D158; and the 4-1BBL variant comprises a substitution at L101. In some cases, the CD80 variant polypeptide comprises a substitution at D158; and the 4-1BBL variant comprises a substitution at L102. In some cases, the CD80 variant polypeptide comprises a substitution at D158; and the 4-1BBL variant comprises a substitution at I103. In some cases, the CD80 variant polypeptide comprises a substitution at D158; and the 4-1BBL variant comprises a substitution at D104. In some cases, the CD80 variant polypeptide comprises a substitution at D158; and the 4-1BBL variant comprises a substitution at G105. In some cases, the CD80 variant polypeptide comprises a substitution at D158; and the 4-1BBL variant comprises a substitution at P106. In some cases, the CD80 variant polypeptide comprises a substitution at D158; and the 4-1BBL variant comprises a substitution at L107. In some cases, the CD80 variant polypeptide comprises a substitution at D158; and the 4-1BBL variant comprises a substitution at S108. In some cases, the CD80 variant polypeptide comprises a substitution at D158; and the 4-1BBL variant comprises a substitution at W109. In some cases, the CD80 variant polypeptide comprises a substitution at D158; and the 4-1BBL variant comprises a substitution at Y110. In some cases, the CD80 variant polypeptide comprises a substitution at D158; and the 4-1BBL variant comprises a substitution at S111. In some cases, the CD80 variant polypeptide comprises a substitution at D158; and the 4-1BBL variant comprises a substitution at D112. In some cases, the CD80 variant polypeptide comprises a substitution at D158; and the 4-1BBL variant comprises a substitution at P113. In some cases, the CD80 variant polypeptide comprises a substitution at D158; and the 4-1BBL variant comprises a substitution at G114. In some cases, the CD80 variant polypeptide comprises a substitution at D158; and the 4-1BBL variant comprises a substitution at L115. In some cases, the CD80 variant polypeptide comprises a substitution at D158; and the 4-1BBL variant comprises a substitution at G117. In some cases, the CD80 variant polypeptide comprises a substitution at D158; and the 4-1BBL variant comprises a substitution at V118. In some cases, the CD80 variant polypeptide comprises a substitution at D158; and the 4-1BBL variant comprises a substitution at S119. In some cases, the CD80 variant polypeptide comprises a substitution at D158; and the 4-1BBL variant comprises a substitution at L120. In some cases, the CD80 variant polypeptide comprises a substitution at D158; and the 4-1BBL variant comprises a substitution at T121. In some cases, the CD80 variant polypeptide comprises a substitution at D158; and the 4-1BBL variant comprises a substitution at G122. In some cases, the CD80 variant polypeptide comprises a substitution at D158; and the 4-1BBL variant comprises a substitution at G123. In some cases, the CD80 variant polypeptide comprises a substitution at D158; and the 4-1BBL variant comprises a substitution at L124. In some cases, the CD80 variant polypeptide comprises a substitution at D158; and the 4-1BBL variant comprises a substitution at S125. In some cases, the CD80 variant polypeptide comprises a substitution at D158; and the 4-1BBL variant comprises a substitution at Y126. In some cases, the CD80 variant polypeptide comprises a substitution at D158; and the 4-1BBL variant comprises a substitution at E128. In some cases, the CD80 variant polypeptide comprises a substitution at D158; and the 4-1BBL variant comprises a substitution at D129. In some cases, the CD80 variant polypeptide comprises a substitution at D158; and the 4-1BBL variant comprises a substitution at T130. In some cases, the CD80 variant polypeptide comprises a substitution at D158; and the 4-1BBL variant comprises a substitution at K131. In some cases, the CD80 variant polypeptide comprises a substitution at D158; and the 4-1BBL variant comprises a substitution at E132. In some cases, the CD80 variant polypeptide comprises a substitution at D158; and the 4-1BBL variant comprises a substitution at F144. In some cases, the CD80 variant polypeptide comprises a substitution at D158; and the 4-1BBL variant comprises a substitution at F145. In some cases, the CD80 variant polypeptide comprises a substitution at D158; and the 4-1BBL variant comprises a substitution at Q146. In some cases, the CD80 variant polypeptide comprises a substitution at D158; and the 4-1BBL variant comprises a substitution at L147. In some cases, the CD80 variant polypeptide comprises a substitution at D158; and the 4-1BBL variant comprises a substitution at E148. In some cases, the CD80 variant polypeptide comprises a substitution at D158; and the 4-1BBL variant comprises a substitution at L149. In some cases, the CD80 variant polypeptide comprises a substitution at D158; and the 4-1BBL variant comprises a substitution at R150. In some cases, the CD80 variant polypeptide comprises a substitution at D158; and the 4-1BBL variant comprises a substitution at R151. In some cases, the CD80 variant polypeptide comprises a substitution at D158; and the 4-1BBL variant comprises a substitution at V152. In some cases, the CD80 variant polypeptide comprises a substitution at D158; and the 4-1BBL variant comprises a substitution at V153. In some cases, the CD80 variant polypeptide comprises a substitution at D158; and the 4-1BBL variant comprises a substitution at G155. In some cases, the CD80 variant polypeptide comprises a substitution at D158; and the 4-1BBL variant comprises a substitution at E156. In some cases, the CD80 variant polypeptide comprises a substitution at D158; and the 4-1BBL variant comprises a substitution at G157. In some cases, the CD80 variant polypeptide comprises a substitution at D158; and the 4-1BBL variant comprises a substitution at S158. In some cases, the CD80 variant polypeptide comprises a substitution at D158; and the 4-1BBL variant comprises a substitution at D184. In some cases, the CD80 variant polypeptide comprises a substitution at D158; and the 4-1BBL variant comprises a substitution at L185. In some cases, the CD80 variant polypeptide comprises a substitution at D158; and the 4-1BBL variant comprises a substitution at P186. In some cases, the CD80 variant polypeptide comprises a substitution at D158; and the 4-1BBL variant comprises a substitution at P187. In some cases, the CD80 variant polypeptide comprises a substitution at D158; and the 4-1BBL variant comprises a substitution at S189. In some cases, the CD80 variant polypeptide comprises a substitution at D158; and the 4-1BBL variant comprises a substitution at S190. In some cases, the CD80 variant polypeptide comprises a substitution at D158; and the 4-1BBL variant comprises a substitution at E191. In some cases, the CD80 variant polypeptide comprises a substitution at D158; and the 4-1BBL variant comprises a substitution at R193. In some cases, the CD80 variant polypeptide comprises a substitution at D158; and the 4-1BBL variant comprises a substitution at D1584. In some cases, the CD80 variant polypeptide comprises a substitution at D158; and the 4-1BBL variant comprises a substitution at S195. In some cases, the CD80 variant polypeptide comprises a substitution at D158; and the 4-1BBL variant comprises a substitution at F197. In some cases, the CD80 variant polypeptide comprises a substitution at D158; and the 4-1BBL variant comprises a substitution at Q210. In some cases, the CD80 variant polypeptide comprises a substitution at D158; and the 4-1BBL variant comprises a substitution at R211. In some cases, the CD80 variant polypeptide comprises a substitution at D158; and the 4-1BBL variant comprises a substitution at L212. In some cases, the CD80 variant polypeptide comprises a substitution at D158; and the 4-1BBL variant comprises a substitution at G213. In some cases, the CD80 variant polypeptide comprises a substitution at D158; and the 4-1BBL variant comprises a substitution at V214. In some cases, the CD80 variant polypeptide comprises a substitution at D158; and the 4-1BBL variant comprises a substitution at H215. In some cases, the CD80 variant polypeptide comprises a substitution at D158; and the 4-1BBL variant comprises a substitution at L216. In some cases, the CD80 variant polypeptide comprises a substitution at D158; and the 4-1BBL variant comprises a substitution at H217. In some cases, the CD80 variant polypeptide comprises a substitution at D158; and the 4-1BBL variant comprises a substitution at T218. In some cases, the CD80 variant polypeptide comprises a substitution at D158; and the 4-1BBL variant comprises a substitution at E219. In some cases, the CD80 variant polypeptide comprises a substitution at D158; and the 4-1BBL variant comprises a substitution at R221. In some cases, the CD80 variant polypeptide comprises a substitution at D158; and the 4-1BBL variant comprises a substitution at R223. In some cases, the CD80 variant polypeptide comprises a substitution at D158; and the 4-1BBL variant comprises a substitution at H224. In some cases, the CD80 variant polypeptide comprises a substitution at D158; and the 4-1BBL variant comprises a substitution at W226. In some cases, the CD80 variant polypeptide comprises a substitution at D158; and the 4-1BBL variant comprises a substitution at L228. In some cases, the CD80 variant polypeptide comprises a substitution at D158; and the 4-1BBL variant comprises a substitution at T229. In some cases, the CD80 variant polypeptide comprises a substitution at D158; and the 4-1BBL variant comprises a substitution at Q230. In some cases, the CD80 variant polypeptide comprises a substitution at D158; and the 4-1BBL variant comprises a substitution at G231. In some cases, the CD80 variant polypeptide comprises a substitution at D158; and the 4-1BBL variant comprises a substitution at T233. In some cases, the CD80 variant polypeptide comprises a substitution at D158; and the 4-1BBL variant comprises a substitution at V234. The amino acid numbering for CD80 is based on the numbering set out in FIG. 2. The amino acid numbering for 4-1BBL is based on the numbering set out in FIG. 3.

In some cases, the CD80 variant polypeptide comprises a substitution at L25; and the 4-1BBL variant comprises a substitution at M91. In some cases, the CD80 variant polypeptide comprises a substitution at L25; and the 4-1BBL variant comprises a substitution at F92. In some cases, the CD80 variant polypeptide comprises a substitution at L25; and the 4-1BBL variant comprises a substitution at Q94. In some cases, the CD80 variant polypeptide comprises a substitution at L25; and the 4-1BBL variant comprises a substitution at L95. In some cases, the CD80 variant polypeptide comprises a substitution at L25; and the 4-1BBL variant comprises a substitution at V96. In some cases, the CD80 variant polypeptide comprises a substitution at L25; and the 4-1BBL variant comprises a substitution at Q98. In some cases, the CD80 variant polypeptide comprises a substitution at L25; and the 4-1BBL variant comprises a substitution at N99. In some cases, the CD80 variant polypeptide comprises a substitution at L25; and the 4-1BBL variant comprises a substitution at V100. In some cases, the CD80 variant polypeptide comprises a substitution at L25; and the 4-1BBL variant comprises a substitution at L101. In some cases, the CD80 variant polypeptide comprises a substitution at L25; and the 4-1BBL variant comprises a substitution at L102. In some cases, the CD80 variant polypeptide comprises a substitution at L25; and the 4-1BBL variant comprises a substitution at I103. In some cases, the CD80 variant polypeptide comprises a substitution at L25; and the 4-1BBL variant comprises a substitution at D104. In some cases, the CD80 variant polypeptide comprises a substitution at L25; and the 4-1BBL variant comprises a substitution at G105. In some cases, the CD80 variant polypeptide comprises a substitution at L25; and the 4-1BBL variant comprises a substitution at P106. In some cases, the CD80 variant polypeptide comprises a substitution at L25; and the 4-1BBL variant comprises a substitution at L107. In some cases, the CD80 variant polypeptide comprises a substitution at L25; and the 4-1BBL variant comprises a substitution at S108. In some cases, the CD80 variant polypeptide comprises a substitution at L25; and the 4-1BBL variant comprises a substitution at W109. In some cases, the CD80 variant polypeptide comprises a substitution at L25; and the 4-1BBL variant comprises a substitution at Y110. In some cases, the CD80 variant polypeptide comprises a substitution at L25; and the 4-1BBL variant comprises a substitution at S111. In some cases, the CD80 variant polypeptide comprises a substitution at L25; and the 4-1BBL variant comprises a substitution at D112. In some cases, the CD80 variant polypeptide comprises a substitution at L25; and the 4-1BBL variant comprises a substitution at P113. In some cases, the CD80 variant polypeptide comprises a substitution at L25; and the 4-1BBL variant comprises a substitution at G114. In some cases, the CD80 variant polypeptide comprises a substitution at L25; and the 4-1BBL variant comprises a substitution at L115. In some cases, the CD80 variant polypeptide comprises a substitution at L25; and the 4-1BBL variant comprises a substitution at G117. In some cases, the CD80 variant polypeptide comprises a substitution at L25; and the 4-1BBL variant comprises a substitution at V118. In some cases, the CD80 variant polypeptide comprises a substitution at L25; and the 4-1BBL variant comprises a substitution at S119. In some cases, the CD80 variant polypeptide comprises a substitution at L25; and the 4-1BBL variant comprises a substitution at L120. In some cases, the CD80 variant polypeptide comprises a substitution at L25; and the 4-1BBL variant comprises a substitution at T121. In some cases, the CD80 variant polypeptide comprises a substitution at L25; and the 4-1BBL variant comprises a substitution at G122. In some cases, the CD80 variant polypeptide comprises a substitution at L25; and the 4-1BBL variant comprises a substitution at G123. In some cases, the CD80 variant polypeptide comprises a substitution at L25; and the 4-1BBL variant comprises a substitution at L124. In some cases, the CD80 variant polypeptide comprises a substitution at L25; and the 4-1BBL variant comprises a substitution at S125. In some cases, the CD80 variant polypeptide comprises a substitution at L25; and the 4-1BBL variant comprises a substitution at Y126. In some cases, the CD80 variant polypeptide comprises a substitution at L25; and the 4-1BBL variant comprises a substitution at E128. In some cases, the CD80 variant polypeptide comprises a substitution at L25; and the 4-1BBL variant comprises a substitution at D129. In some cases, the CD80 variant polypeptide comprises a substitution at L25; and the 4-1BBL variant comprises a substitution at T130. In some cases, the CD80 variant polypeptide comprises a substitution at L25; and the 4-1BBL variant comprises a substitution at K131. In some cases, the CD80 variant polypeptide comprises a substitution at L25; and the 4-1BBL variant comprises a substitution at E132. In some cases, the CD80 variant polypeptide comprises a substitution at L25; and the 4-1BBL variant comprises a substitution at F144. In some cases, the CD80 variant polypeptide comprises a substitution at L25; and the 4-1BBL variant comprises a substitution at F145. In some cases, the CD80 variant polypeptide comprises a substitution at L25; and the 4-1BBL variant comprises a substitution at Q146. In some cases, the CD80 variant polypeptide comprises a substitution at L25; and the 4-1BBL variant comprises a substitution at L147. In some cases, the CD80 variant polypeptide comprises a substitution at L25; and the 4-1BBL variant comprises a substitution at E148. In some cases, the CD80 variant polypeptide comprises a substitution at L25; and the 4-1BBL variant comprises a substitution at L149. In some cases, the CD80 variant polypeptide comprises a substitution at L25; and the 4-1BBL variant comprises a substitution at R150. In some cases, the CD80 variant polypeptide comprises a substitution at L25; and the 4-1BBL variant comprises a substitution at R151. In some cases, the CD80 variant polypeptide comprises a substitution at L25; and the 4-1BBL variant comprises a substitution at V152. In some cases, the CD80 variant polypeptide comprises a substitution at L25; and the 4-1BBL variant comprises a substitution at V153. In some cases, the CD80 variant polypeptide comprises a substitution at L25; and the 4-1BBL variant comprises a substitution at G155. In some cases, the CD80 variant polypeptide comprises a substitution at L25; and the 4-1BBL variant comprises a substitution at E156. In some cases, the CD80 variant polypeptide comprises a substitution at L25; and the 4-1BBL variant comprises a substitution at G157. In some cases, the CD80 variant polypeptide comprises a substitution at L25; and the 4-1BBL variant comprises a substitution at S158. In some cases, the CD80 variant polypeptide comprises a substitution at L25; and the 4-1BBL variant comprises a substitution at D184. In some cases, the CD80 variant polypeptide comprises a substitution at L25; and the 4-1BBL variant comprises a substitution at L185. In some cases, the CD80 variant polypeptide comprises a substitution at L25; and the 4-1BBL variant comprises a substitution at P186. In some cases, the CD80 variant polypeptide comprises a substitution at L25; and the 4-1BBL variant comprises a substitution at P187. In some cases, the CD80 variant polypeptide comprises a substitution at L25; and the 4-1BBL variant comprises a substitution at S189. In some cases, the CD80 variant polypeptide comprises a substitution at L25; and the 4-1BBL variant comprises a substitution at S190. In some cases, the CD80 variant polypeptide comprises a substitution at L25; and the 4-1BBL variant comprises a substitution at E191. In some cases, the CD80 variant polypeptide comprises a substitution at L25; and the 4-1BBL variant comprises a substitution at R193. In some cases, the CD80 variant polypeptide comprises a substitution at L25; and the 4-1BBL variant comprises a substitution at L254. In some cases, the CD80 variant polypeptide comprises a substitution at L25; and the 4-1BBL variant comprises a substitution at S195. In some cases, the CD80 variant polypeptide comprises a substitution at L25; and the 4-1BBL variant comprises a substitution at F197. In some cases, the CD80 variant polypeptide comprises a substitution at L25; and the 4-1BBL variant comprises a substitution at Q210. In some cases, the CD80 variant polypeptide comprises a substitution at L25; and the 4-1BBL variant comprises a substitution at R211. In some cases, the CD80 variant polypeptide comprises a substitution at L25; and the 4-1BBL variant comprises a substitution at L212. In some cases, the CD80 variant polypeptide comprises a substitution at L25; and the 4-1BBL variant comprises a substitution at G213. In some cases, the CD80 variant polypeptide comprises a substitution at L25; and the 4-1BBL variant comprises a substitution at V214. In some cases, the CD80 variant polypeptide comprises a substitution at L25; and the 4-1BBL variant comprises a substitution at H215. In some cases, the CD80 variant polypeptide comprises a substitution at L25; and the 4-1BBL variant comprises a substitution at L216. In some cases, the CD80 variant polypeptide comprises a substitution at L25; and the 4-1BBL variant comprises a substitution at H217. In some cases, the CD80 variant polypeptide comprises a substitution at L25; and the 4-1BBL variant comprises a substitution at T218. In some cases, the CD80 variant polypeptide comprises a substitution at L25; and the 4-1BBL variant comprises a substitution at E219. In some cases, the CD80 variant polypeptide comprises a substitution at L25; and the 4-1BBL variant comprises a substitution at R221. In some cases, the CD80 variant polypeptide comprises a substitution at L25; and the 4-1BBL variant comprises a substitution at R223. In some cases, the CD80 variant polypeptide comprises a substitution at L25; and the 4-1BBL variant comprises a substitution at H224. In some cases, the CD80 variant polypeptide comprises a substitution at L25; and the 4-1BBL variant comprises a substitution at W226. In some cases, the CD80 variant polypeptide comprises a substitution at L25; and the 4-1BBL variant comprises a substitution at L228. In some cases, the CD80 variant polypeptide comprises a substitution at L25; and the 4-1BBL variant comprises a substitution at T229. In some cases, the CD80 variant polypeptide comprises a substitution at L25; and the 4-1BBL variant comprises a substitution at Q230. In some cases, the CD80 variant polypeptide comprises a substitution at L25; and the 4-1BBL variant comprises a substitution at G231. In some cases, the CD80 variant polypeptide comprises a substitution at L25; and the 4-1BBL variant comprises a substitution at T233. In some cases, the CD80 variant polypeptide comprises a substitution at L25; and the 4-1BBL variant comprises a substitution at V234. The amino acid numbering for CD80 is based on the numbering set out in FIG. 2. The amino acid numbering for 4-1BBL is based on the numbering set out in FIG. 3.

In some cases, the CD80 variant polypeptide comprises a substitution at Y31; and the 4-1BBL variant comprises a substitution at M91. In some cases, the CD80 variant polypeptide comprises a substitution at Y31; and the 4-1BBL variant comprises a substitution at F92. In some cases, the CD80 variant polypeptide comprises a substitution at Y31; and the 4-1BBL variant comprises a substitution at Q94. In some cases, the CD80 variant polypeptide comprises a substitution at Y31; and the 4-1BBL variant comprises a substitution at L95. In some cases, the CD80 variant polypeptide comprises a substitution at Y31; and the 4-1BBL variant comprises a substitution at V96. In some cases, the CD80 variant polypeptide comprises a substitution at Y31; and the 4-1BBL variant comprises a substitution at Q98. In some cases, the CD80 variant polypeptide comprises a substitution at Y31; and the 4-1BBL variant comprises a substitution at N99. In some cases, the CD80 variant polypeptide comprises a substitution at Y31; and the 4-1BBL variant comprises a substitution at V100. In some cases, the CD80 variant polypeptide comprises a substitution at Y31; and the 4-1BBL variant comprises a substitution at L101. In some cases, the CD80 variant polypeptide comprises a substitution at Y31; and the 4-1BBL variant comprises a substitution at L102. In some cases, the CD80 variant polypeptide comprises a substitution at Y31; and the 4-1BBL variant comprises a substitution at I103. In some cases, the CD80 variant polypeptide comprises a substitution at Y31; and the 4-1BBL variant comprises a substitution at D104. In some cases, the CD80 variant polypeptide comprises a substitution at Y31; and the 4-1BBL variant comprises a substitution at G105. In some cases, the CD80 variant polypeptide comprises a substitution at Y31; and the 4-1BBL variant comprises a substitution at P106. In some cases, the CD80 variant polypeptide comprises a substitution at Y31; and the 4-1BBL variant comprises a substitution at L107. In some cases, the CD80 variant polypeptide comprises a substitution at Y31; and the 4-1BBL variant comprises a substitution at S108. In some cases, the CD80 variant polypeptide comprises a substitution at Y31; and the 4-1BBL variant comprises a substitution at W109. In some cases, the CD80 variant polypeptide comprises a substitution at Y31; and the 4-1BBL variant comprises a substitution at Y110. In some cases, the CD80 variant polypeptide comprises a substitution at Y31; and the 4-1BBL variant comprises a substitution at S111. In some cases, the CD80 variant polypeptide comprises a substitution at Y31; and the 4-1BBL variant comprises a substitution at D112. In some cases, the CD80 variant polypeptide comprises a substitution at Y31; and the 4-1BBL variant comprises a substitution at P113. In some cases, the CD80 variant polypeptide comprises a substitution at Y31; and the 4-1BBL variant comprises a substitution at G114. In some cases, the CD80 variant polypeptide comprises a substitution at Y31; and the 4-1BBL variant comprises a substitution at L115. In some cases, the CD80 variant polypeptide comprises a substitution at Y31; and the 4-1BBL variant comprises a substitution at G117. In some cases, the CD80 variant polypeptide comprises a substitution at Y31; and the 4-1BBL variant comprises a substitution at V118. In some cases, the CD80 variant polypeptide comprises a substitution at Y31; and the 4-1BBL variant comprises a substitution at S119. In some cases, the CD80 variant polypeptide comprises a substitution at Y31; and the 4-1BBL variant comprises a substitution at L120. In some cases, the CD80 variant polypeptide comprises a substitution at Y31; and the 4-1BBL variant comprises a substitution at T121. In some cases, the CD80 variant polypeptide comprises a substitution at Y31; and the 4-1BBL variant comprises a substitution at G122. In some cases, the CD80 variant polypeptide comprises a substitution at Y31; and the 4-1BBL variant comprises a substitution at G123. In some cases, the CD80 variant polypeptide comprises a substitution at Y31; and the 4-1BBL variant comprises a substitution at L124. In some cases, the CD80 variant polypeptide comprises a substitution at Y31; and the 4-1BBL variant comprises a substitution at S125. In some cases, the CD80 variant polypeptide comprises a substitution at Y31; and the 4-1BBL variant comprises a substitution at Y126. In some cases, the CD80 variant polypeptide comprises a substitution at Y31; and the 4-1BBL variant comprises a substitution at E128. In some cases, the CD80 variant polypeptide comprises a substitution at Y31; and the 4-1BBL variant comprises a substitution at D129. In some cases, the CD80 variant polypeptide comprises a substitution at Y31; and the 4-1BBL variant comprises a substitution at T130. In some cases, the CD80 variant polypeptide comprises a substitution at Y31; and the 4-1BBL variant comprises a substitution at K131. In some cases, the CD80 variant polypeptide comprises a substitution at Y31; and the 4-1BBL variant comprises a substitution at E132. In some cases, the CD80 variant polypeptide comprises a substitution at Y31; and the 4-1BBL variant comprises a substitution at F144. In some cases, the CD80 variant polypeptide comprises a substitution at Y31; and the 4-1BBL variant comprises a substitution at F145. In some cases, the CD80 variant polypeptide comprises a substitution at Y31; and the 4-1BBL variant comprises a substitution at Q146. In some cases, the CD80 variant polypeptide comprises a substitution at Y31; and the 4-1BBL variant comprises a substitution at L147. In some cases, the CD80 variant polypeptide comprises a substitution at Y31; and the 4-1BBL variant comprises a substitution at E148. In some cases, the CD80 variant polypeptide comprises a substitution at Y31; and the 4-1BBL variant comprises a substitution at L149. In some cases, the CD80 variant polypeptide comprises a substitution at Y31; and the 4-1BBL variant comprises a substitution at R150. In some cases, the CD80 variant polypeptide comprises a substitution at Y31; and the 4-1BBL variant comprises a substitution at R151. In some cases, the CD80 variant polypeptide comprises a substitution at Y31; and the 4-1BBL variant comprises a substitution at V152. In some cases, the CD80 variant polypeptide comprises a substitution at Y31; and the 4-1BBL variant comprises a substitution at V153. In some cases, the CD80 variant polypeptide comprises a substitution at Y31; and the 4-1BBL variant comprises a substitution at G155. In some cases, the CD80 variant polypeptide comprises a substitution at Y31; and the 4-1BBL variant comprises a substitution at E156. In some cases, the CD80 variant polypeptide comprises a substitution at Y31; and the 4-1BBL variant comprises a substitution at G157. In some cases, the CD80 variant polypeptide comprises a substitution at Y31; and the 4-1BBL variant comprises a substitution at S158. In some cases, the CD80 variant polypeptide comprises a substitution at Y31; and the 4-1BBL variant comprises a substitution at D184. In some cases, the CD80 variant polypeptide comprises a substitution at Y31; and the 4-1BBL variant comprises a substitution at L185. In some cases, the CD80 variant polypeptide comprises a substitution at Y31; and the 4-1BBL variant comprises a substitution at P186. In some cases, the CD80 variant polypeptide comprises a substitution at Y31; and the 4-1BBL variant comprises a substitution at P187. In some cases, the CD80 variant polypeptide comprises a substitution at Y31; and the 4-1BBL variant comprises a substitution at S189. In some cases, the CD80 variant polypeptide comprises a substitution at Y31; and the 4-1BBL variant comprises a substitution at S190. In some cases, the CD80 variant polypeptide comprises a substitution at Y31; and the 4-1BBL variant comprises a substitution at E191. In some cases, the CD80 variant polypeptide comprises a substitution at Y31; and the 4-1BBL variant comprises a substitution at R193. In some cases, the CD80 variant polypeptide comprises a substitution at Y31; and the 4-1BBL variant comprises a substitution at Y314. In some cases, the CD80 variant polypeptide comprises a substitution at Y31; and the 4-1BBL variant comprises a substitution at S195. In some cases, the CD80 variant polypeptide comprises a substitution at Y31; and the 4-1BBL variant comprises a substitution at F197. In some cases, the CD80 variant polypeptide comprises a substitution at Y31; and the 4-1BBL variant comprises a substitution at Q210. In some cases, the CD80 variant polypeptide comprises a substitution at Y31; and the 4-1BBL variant comprises a substitution at R211. In some cases, the CD80 variant polypeptide comprises a substitution at Y31; and the 4-1BBL variant comprises a substitution at L212. In some cases, the CD80 variant polypeptide comprises a substitution at Y31; and the 4-1BBL variant comprises a substitution at G213. In some cases, the CD80 variant polypeptide comprises a substitution at Y31; and the 4-1BBL variant comprises a substitution at V214. In some cases, the CD80 variant polypeptide comprises a substitution at Y31; and the 4-1BBL variant comprises a substitution at H215. In some cases, the CD80 variant polypeptide comprises a substitution at Y31; and the 4-1BBL variant comprises a substitution at L216. In some cases, the CD80 variant polypeptide comprises a substitution at Y31; and the 4-1BBL variant comprises a substitution at H217. In some cases, the CD80 variant polypeptide comprises a substitution at Y31; and the 4-1BBL variant comprises a substitution at T218. In some cases, the CD80 variant polypeptide comprises a substitution at Y31; and the 4-1BBL variant comprises a substitution at E219. In some cases, the CD80 variant polypeptide comprises a substitution at Y31; and the 4-1BBL variant comprises a substitution at R221. In some cases, the CD80 variant polypeptide comprises a substitution at Y31; and the 4-1BBL variant comprises a substitution at R223. In some cases, the CD80 variant polypeptide comprises a substitution at Y31; and the 4-1BBL variant comprises a substitution at H224. In some cases, the CD80 variant polypeptide comprises a substitution at Y31; and the 4-1BBL variant comprises a substitution at W226. In some cases, the CD80 variant polypeptide comprises a substitution at Y31; and the 4-1BBL variant comprises a substitution at L228. In some cases, the CD80 variant polypeptide comprises a substitution at Y31; and the 4-1BBL variant comprises a substitution at T229. In some cases, the CD80 variant polypeptide comprises a substitution at Y31; and the 4-1BBL variant comprises a substitution at Q230. In some cases, the CD80 variant polypeptide comprises a substitution at Y31; and the 4-1BBL variant comprises a substitution at G231. In some cases, the CD80 variant polypeptide comprises a substitution at Y31; and the 4-1BBL variant comprises a substitution at T233. In some cases, the CD80 variant polypeptide comprises a substitution at Y31; and the 4-1BBL variant comprises a substitution at V234. The amino acid numbering for CD80 is based on the numbering set out in FIG. 2. The amino acid numbering for 4-1BBL is based on the numbering set out in FIG. 3.

In some cases, the CD80 variant polypeptide comprises a substitution at Q33; and the 4-1BBL variant comprises a substitution at M91. In some cases, the CD80 variant polypeptide comprises a substitution at Q33; and the 4-1BBL variant comprises a substitution at F92. In some cases, the CD80 variant polypeptide comprises a substitution at Q33; and the 4-1BBL variant comprises a substitution at Q94. In some cases, the CD80 variant polypeptide comprises a substitution at Q33; and the 4-1BBL variant comprises a substitution at L95. In some cases, the CD80 variant polypeptide comprises a substitution at Q33; and the 4-1BBL variant comprises a substitution at V96. In some cases, the CD80 variant polypeptide comprises a substitution at Q33; and the 4-1BBL variant comprises a substitution at Q98. In some cases, the CD80 variant polypeptide comprises a substitution at Q33; and the 4-1BBL variant comprises a substitution at N99. In some cases, the CD80 variant polypeptide comprises a substitution at Q33; and the 4-1BBL variant comprises a substitution at V100. In some cases, the CD80 variant polypeptide comprises a substitution at Q33; and the 4-1BBL variant comprises a substitution at L101. In some cases, the CD80 variant polypeptide comprises a substitution at Q33; and the 4-1BBL variant comprises a substitution at L102. In some cases, the CD80 variant polypeptide comprises a substitution at Q33; and the 4-1BBL variant comprises a substitution at I103. In some cases, the CD80 variant polypeptide comprises a substitution at Q33; and the 4-1BBL variant comprises a substitution at D104. In some cases, the CD80 variant polypeptide comprises a substitution at Q33; and the 4-1BBL variant comprises a substitution at G105. In some cases, the CD80 variant polypeptide comprises a substitution at Q33; and the 4-1BBL variant comprises a substitution at P106. In some cases, the CD80 variant polypeptide comprises a substitution at Q33; and the 4-1BBL variant comprises a substitution at L107. In some cases, the CD80 variant polypeptide comprises a substitution at Q33; and the 4-1BBL variant comprises a substitution at S108. In some cases, the CD80 variant polypeptide comprises a substitution at Q33; and the 4-1BBL variant comprises a substitution at W109. In some cases, the CD80 variant polypeptide comprises a substitution at Q33; and the 4-1BBL variant comprises a substitution at Y110. In some cases, the CD80 variant polypeptide comprises a substitution at Q33; and the 4-1BBL variant comprises a substitution at S111. In some cases, the CD80 variant polypeptide comprises a substitution at Q33; and the 4-1BBL variant comprises a substitution at D112. In some cases, the CD80 variant polypeptide comprises a substitution at Q33; and the 4-1BBL variant comprises a substitution at P113. In some cases, the CD80 variant polypeptide comprises a substitution at Q33; and the 4-1BBL variant comprises a substitution at G114. In some cases, the CD80 variant polypeptide comprises a substitution at Q33; and the 4-1BBL variant comprises a substitution at L115. In some cases, the CD80 variant polypeptide comprises a substitution at Q33; and the 4-1BBL variant comprises a substitution at G117. In some cases, the CD80 variant polypeptide comprises a substitution at Q33; and the 4-1BBL variant comprises a substitution at V118. In some cases, the CD80 variant polypeptide comprises a substitution at Q33; and the 4-1BBL variant comprises a substitution at S119. In some cases, the CD80 variant polypeptide comprises a substitution at Q33; and the 4-1BBL variant comprises a substitution at L120. In some cases, the CD80 variant polypeptide comprises a substitution at Q33; and the 4-1BBL variant comprises a substitution at T121. In some cases, the CD80 variant polypeptide comprises a substitution at Q33; and the 4-1BBL variant comprises a substitution at G122. In some cases, the CD80 variant polypeptide comprises a substitution at Q33; and the 4-1BBL variant comprises a substitution at G123. In some cases, the CD80 variant polypeptide comprises a substitution at Q33; and the 4-1BBL variant comprises a substitution at L124. In some cases, the CD80 variant polypeptide comprises a substitution at Q33; and the 4-1BBL variant comprises a substitution at S125. In some cases, the CD80 variant polypeptide comprises a substitution at Q33; and the 4-1BBL variant comprises a substitution at Y126. In some cases, the CD80 variant polypeptide comprises a substitution at Q33; and the 4-1BBL variant comprises a substitution at E128. In some cases, the CD80 variant polypeptide comprises a substitution at Q33; and the 4-1BBL variant comprises a substitution at D129. In some cases, the CD80 variant polypeptide comprises a substitution at Q33; and the 4-1BBL variant comprises a substitution at T130. In some cases, the CD80 variant polypeptide comprises a substitution at Q33; and the 4-1BBL variant comprises a substitution at K131. In some cases, the CD80 variant polypeptide comprises a substitution at Q33; and the 4-1BBL variant comprises a substitution at E132. In some cases, the CD80 variant polypeptide comprises a substitution at Q33; and the 4-1BBL variant comprises a substitution at F144. In some cases, the CD80 variant polypeptide comprises a substitution at Q33; and the 4-1BBL variant comprises a substitution at F145. In some cases, the CD80 variant polypeptide comprises a substitution at Q33; and the 4-1BBL variant comprises a substitution at Q146. In some cases, the CD80 variant polypeptide comprises a substitution at Q33; and the 4-1BBL variant comprises a substitution at L147. In some cases, the CD80 variant polypeptide comprises a substitution at Q33; and the 4-1BBL variant comprises a substitution at E148. In some cases, the CD80 variant polypeptide comprises a substitution at Q33; and the 4-1BBL variant comprises a substitution at L149. In some cases, the CD80 variant polypeptide comprises a substitution at Q33; and the 4-1BBL variant comprises a substitution at R150. In some cases, the CD80 variant polypeptide comprises a substitution at Q33; and the 4-1BBL variant comprises a substitution at R151. In some cases, the CD80 variant polypeptide comprises a substitution at Q33; and the 4-1BBL variant comprises a substitution at V152. In some cases, the CD80 variant polypeptide comprises a substitution at Q33; and the 4-1BBL variant comprises a substitution at V153. In some cases, the CD80 variant polypeptide comprises a substitution at Q33; and the 4-1BBL variant comprises a substitution at G155. In some cases, the CD80 variant polypeptide comprises a substitution at Q33; and the 4-1BBL variant comprises a substitution at E156. In some cases, the CD80 variant polypeptide comprises a substitution at Q33; and the 4-1BBL variant comprises a substitution at G157. In some cases, the CD80 variant polypeptide comprises a substitution at Q33; and the 4-1BBL variant comprises a substitution at S158. In some cases, the CD80 variant polypeptide comprises a substitution at Q33; and the 4-1BBL variant comprises a substitution at D184. In some cases, the CD80 variant polypeptide comprises a substitution at Q33; and the 4-1BBL variant comprises a substitution at L185. In some cases, the CD80 variant polypeptide comprises a substitution at Q33; and the 4-1BBL variant comprises a substitution at P186. In some cases, the CD80 variant polypeptide comprises a substitution at Q33; and the 4-1BBL variant comprises a substitution at P187. In some cases, the CD80 variant polypeptide comprises a substitution at Q33; and the 4-1BBL variant comprises a substitution at S189. In some cases, the CD80 variant polypeptide comprises a substitution at Q33; and the 4-1BBL variant comprises a substitution at S190. In some cases, the CD80 variant polypeptide comprises a substitution at Q33; and the 4-1BBL variant comprises a substitution at E191. In some cases, the CD80 variant polypeptide comprises a substitution at Q33; and the 4-1BBL variant comprises a substitution at R193. In some cases, the CD80 variant polypeptide comprises a substitution at Q33; and the 4-1BBL variant comprises a substitution at Q334. In some cases, the CD80 variant polypeptide comprises a substitution at Q33; and the 4-1BBL variant comprises a substitution at S195. In some cases, the CD80 variant polypeptide comprises a substitution at Q33; and the 4-1BBL variant comprises a substitution at F197. In some cases, the CD80 variant polypeptide comprises a substitution at Q33; and the 4-1BBL variant comprises a substitution at Q210. In some cases, the CD80 variant polypeptide comprises a substitution at Q33; and the 4-1BBL variant comprises a substitution at R211. In some cases, the CD80 variant polypeptide comprises a substitution at Q33; and the 4-1BBL variant comprises a substitution at L212. In some cases, the CD80 variant polypeptide comprises a substitution at Q33; and the 4-1BBL variant comprises a substitution at G213. In some cases, the CD80 variant polypeptide comprises a substitution at Q33; and the 4-1BBL variant comprises a substitution at V214. In some cases, the CD80 variant polypeptide comprises a substitution at Q33; and the 4-1BBL variant comprises a substitution at H215. In some cases, the CD80 variant polypeptide comprises a substitution at Q33; and the 4-1BBL variant comprises a substitution at L216. In some cases, the CD80 variant polypeptide comprises a substitution at Q33; and the 4-1BBL variant comprises a substitution at H217. In some cases, the CD80 variant polypeptide comprises a substitution at Q33; and the 4-1BBL variant comprises a substitution at T218. In some cases, the CD80 variant polypeptide comprises a substitution at Q33; and the 4-1BBL variant comprises a substitution at E219. In some cases, the CD80 variant polypeptide comprises a substitution at Q33; and the 4-1BBL variant comprises a substitution at R221. In some cases, the CD80 variant polypeptide comprises a substitution at Q33; and the 4-1BBL variant comprises a substitution at R223. In some cases, the CD80 variant polypeptide comprises a substitution at Q33; and the 4-1BBL variant comprises a substitution at H224. In some cases, the CD80 variant polypeptide comprises a substitution at Q33; and the 4-1BBL variant comprises a substitution at W226. In some cases, the CD80 variant polypeptide comprises a substitution at Q33; and the 4-1BBL variant comprises a substitution at L228. In some cases, the CD80 variant polypeptide comprises a substitution at Q33; and the 4-1BBL variant comprises a substitution at T229. In some cases, the CD80 variant polypeptide comprises a substitution at Q33; and the 4-1BBL variant comprises a substitution at Q230. In some cases, the CD80 variant polypeptide comprises a substitution at Q33; and the 4-1BBL variant comprises a substitution at G231. In some cases, the CD80 variant polypeptide comprises a substitution at Q33; and the 4-1BBL variant comprises a substitution at T233. In some cases, the CD80 variant polypeptide comprises a substitution at Q33; and the 4-1BBL variant comprises a substitution at V234. The amino acid numbering for CD80 is based on the numbering set out in FIG. 2. The amino acid numbering for 4-1BBL is based on the numbering set out in FIG. 3.

In some cases, the CD80 variant polypeptide comprises a substitution at M38; and the 4-1BBL variant comprises a substitution at M91. In some cases, the CD80 variant polypeptide comprises a substitution at M38; and the 4-1BBL variant comprises a substitution at F92. In some cases, the CD80 variant polypeptide comprises a substitution at M38; and the 4-1BBL variant comprises a substitution at Q94. In some cases, the CD80 variant polypeptide comprises a substitution at M38; and the 4-1BBL variant comprises a substitution at L95. In some cases, the CD80 variant polypeptide comprises a substitution at M38; and the 4-1BBL variant comprises a substitution at V96. In some cases, the CD80 variant polypeptide comprises a substitution at M38; and the 4-1BBL variant comprises a substitution at Q98. In some cases, the CD80 variant polypeptide comprises a substitution at M38; and the 4-1BBL variant comprises a substitution at N99. In some cases, the CD80 variant polypeptide comprises a substitution at M38; and the 4-1BBL variant comprises a substitution at V100. In some cases, the CD80 variant polypeptide comprises a substitution at M38; and the 4-1BBL variant comprises a substitution at L101. In some cases, the CD80 variant polypeptide comprises a substitution at M38; and the 4-1BBL variant comprises a substitution at L102. In some cases, the CD80 variant polypeptide comprises a substitution at M38; and the 4-1BBL variant comprises a substitution at I103. In some cases, the CD80 variant polypeptide comprises a substitution at M38; and the 4-1BBL variant comprises a substitution at D104. In some cases, the CD80 variant polypeptide comprises a substitution at M38; and the 4-1BBL variant comprises a substitution at G105. In some cases, the CD80 variant polypeptide comprises a substitution at M38; and the 4-1BBL variant comprises a substitution at P106. In some cases, the CD80 variant polypeptide comprises a substitution at M38; and the 4-1BBL variant comprises a substitution at L107. In some cases, the CD80 variant polypeptide comprises a substitution at M38; and the 4-1BBL variant comprises a substitution at S108. In some cases, the CD80 variant polypeptide comprises a substitution at M38; and the 4-1BBL variant comprises a substitution at W109. In some cases, the CD80 variant polypeptide comprises a substitution at M38; and the 4-1BBL variant comprises a substitution at Y110. In some cases, the CD80 variant polypeptide comprises a substitution at M38; and the 4-1BBL variant comprises a substitution at S111. In some cases, the CD80 variant polypeptide comprises a substitution at M38; and the 4-1BBL variant comprises a substitution at D112. In some cases, the CD80 variant polypeptide comprises a substitution at M38; and the 4-1BBL variant comprises a substitution at P113. In some cases, the CD80 variant polypeptide comprises a substitution at M38; and the 4-1BBL variant comprises a substitution at G114. In some cases, the CD80 variant polypeptide comprises a substitution at M38; and the 4-1BBL variant comprises a substitution at L115. In some cases, the CD80 variant polypeptide comprises a substitution at M38; and the 4-1BBL variant comprises a substitution at G117. In some cases, the CD80 variant polypeptide comprises a substitution at M38; and the 4-1BBL variant comprises a substitution at V118. In some cases, the CD80 variant polypeptide comprises a substitution at M38; and the 4-1BBL variant comprises a substitution at S119. In some cases, the CD80 variant polypeptide comprises a substitution at M38; and the 4-1BBL variant comprises a substitution at L120. In some cases, the CD80 variant polypeptide comprises a substitution at M38; and the 4-1BBL variant comprises a substitution at T121. In some cases, the CD80 variant polypeptide comprises a substitution at M38; and the 4-1BBL variant comprises a substitution at G122. In some cases, the CD80 variant polypeptide comprises a substitution at M38; and the 4-1BBL variant comprises a substitution at G123. In some cases, the CD80 variant polypeptide comprises a substitution at M38; and the 4-1BBL variant comprises a substitution at L124. In some cases, the CD80 variant polypeptide comprises a substitution at M38; and the 4-1BBL variant comprises a substitution at S125. In some cases, the CD80 variant polypeptide comprises a substitution at M38; and the 4-1BBL variant comprises a substitution at Y126. In some cases, the CD80 variant polypeptide comprises a substitution at M38; and the 4-1BBL variant comprises a substitution at E128. In some cases, the CD80 variant polypeptide comprises a substitution at M38; and the 4-1BBL variant comprises a substitution at D129. In some cases, the CD80 variant polypeptide comprises a substitution at M38; and the 4-1BBL variant comprises a substitution at T130. In some cases, the CD80 variant polypeptide comprises a substitution at M38; and the 4-1BBL variant comprises a substitution at K131. In some cases, the CD80 variant polypeptide comprises a substitution at M38; and the 4-1BBL variant comprises a substitution at E132. In some cases, the CD80 variant polypeptide comprises a substitution at M38; and the 4-1BBL variant comprises a substitution at F144. In some cases, the CD80 variant polypeptide comprises a substitution at M38; and the 4-1BBL variant comprises a substitution at F145. In some cases, the CD80 variant polypeptide comprises a substitution at M38; and the 4-1BBL variant comprises a substitution at Q146. In some cases, the CD80 variant polypeptide comprises a substitution at M38; and the 4-1BBL variant comprises a substitution at L147. In some cases, the CD80 variant polypeptide comprises a substitution at M38; and the 4-1BBL variant comprises a substitution at E148. In some cases, the CD80 variant polypeptide comprises a substitution at M38; and the 4-1BBL variant comprises a substitution at L149. In some cases, the CD80 variant polypeptide comprises a substitution at M38; and the 4-1BBL variant comprises a substitution at R150. In some cases, the CD80 variant polypeptide comprises a substitution at M38; and the 4-1BBL variant comprises a substitution at R151. In some cases, the CD80 variant polypeptide comprises a substitution at M38; and the 4-1BBL variant comprises a substitution at V152. In some cases, the CD80 variant polypeptide comprises a substitution at M38; and the 4-1BBL variant comprises a substitution at V153. In some cases, the CD80 variant polypeptide comprises a substitution at M38; and the 4-1BBL variant comprises a substitution at G155. In some cases, the CD80 variant polypeptide comprises a substitution at M38; and the 4-1BBL variant comprises a substitution at E156. In some cases, the CD80 variant polypeptide comprises a substitution at M38; and the 4-1BBL variant comprises a substitution at G157. In some cases, the CD80 variant polypeptide comprises a substitution at M38; and the 4-1BBL variant comprises a substitution at S158. In some cases, the CD80 variant polypeptide comprises a substitution at M38; and the 4-1BBL variant comprises a substitution at D184. In some cases, the CD80 variant polypeptide comprises a substitution at M38; and the 4-1BBL variant comprises a substitution at L185. In some cases, the CD80 variant polypeptide comprises a substitution at M38; and the 4-1BBL variant comprises a substitution at P186. In some cases, the CD80 variant polypeptide comprises a substitution at M38; and the 4-1BBL variant comprises a substitution at P187. In some cases, the CD80 variant polypeptide comprises a substitution at M38; and the 4-1BBL variant comprises a substitution at S189. In some cases, the CD80 variant polypeptide comprises a substitution at M38; and the 4-1BBL variant comprises a substitution at S190. In some cases, the CD80 variant polypeptide comprises a substitution at M38; and the 4-1BBL variant comprises a substitution at E191. In some cases, the CD80 variant polypeptide comprises a substitution at M38; and the 4-1BBL variant comprises a substitution at R193. In some cases, the CD80 variant polypeptide comprises a substitution at M38; and the 4-1BBL variant comprises a substitution at M384. In some cases, the CD80 variant polypeptide comprises a substitution at M38; and the 4-1BBL variant comprises a substitution at S195. In some cases, the CD80 variant polypeptide comprises a substitution at M38; and the 4-1BBL variant comprises a substitution at F197. In some cases, the CD80 variant polypeptide comprises a substitution at M38; and the 4-1BBL variant comprises a substitution at Q210. In some cases, the CD80 variant polypeptide comprises a substitution at M38; and the 4-1BBL variant comprises a substitution at R211. In some cases, the CD80 variant polypeptide comprises a substitution at M38; and the 4-1BBL variant comprises a substitution at L212. In some cases, the CD80 variant polypeptide comprises a substitution at M38; and the 4-1BBL variant comprises a substitution at G213. In some cases, the CD80 variant polypeptide comprises a substitution at M38; and the 4-1BBL variant comprises a substitution at V214. In some cases, the CD80 variant polypeptide comprises a substitution at M38; and the 4-1BBL variant comprises a substitution at H215. In some cases, the CD80 variant polypeptide comprises a substitution at M38; and the 4-1BBL variant comprises a substitution at L216. In some cases, the CD80 variant polypeptide comprises a substitution at M38; and the 4-1BBL variant comprises a substitution at H217. In some cases, the CD80 variant polypeptide comprises a substitution at M38; and the 4-1BBL variant comprises a substitution at T218. In some cases, the CD80 variant polypeptide comprises a substitution at M38; and the 4-1BBL variant comprises a substitution at E219. In some cases, the CD80 variant polypeptide comprises a substitution at M38; and the 4-1BBL variant comprises a substitution at R221. In some cases, the CD80 variant polypeptide comprises a substitution at M38; and the 4-1BBL variant comprises a substitution at R223. In some cases, the CD80 variant polypeptide comprises a substitution at M38; and the 4-1BBL variant comprises a substitution at H224. In some cases, the CD80 variant polypeptide comprises a substitution at M38; and the 4-1BBL variant comprises a substitution at W226. In some cases, the CD80 variant polypeptide comprises a substitution at M38; and the 4-1BBL variant comprises a substitution at L228. In some cases, the CD80 variant polypeptide comprises a substitution at M38; and the 4-1BBL variant comprises a substitution at T229. In some cases, the CD80 variant polypeptide comprises a substitution at M38; and the 4-1BBL variant comprises a substitution at Q230. In some cases, the CD80 variant polypeptide comprises a substitution at M38; and the 4-1BBL variant comprises a substitution at G231. In some cases, the CD80 variant polypeptide comprises a substitution at M38; and the 4-1BBL variant comprises a substitution at T233. In some cases, the CD80 variant polypeptide comprises a substitution at M38; and the 4-1BBL variant comprises a substitution at V234. The amino acid numbering for CD80 is based on the numbering set out in FIG. 2. The amino acid numbering for 4-1BBL is based on the numbering set out in FIG. 3.

In some cases, the CD80 variant polypeptide comprises a substitution at V39; and the 4-1BBL variant comprises a substitution at M91. In some cases, the CD80 variant polypeptide comprises a substitution at V39; and the 4-1BBL variant comprises a substitution at F92. In some cases, the CD80 variant polypeptide comprises a substitution at V39; and the 4-1BBL variant comprises a substitution at Q94. In some cases, the CD80 variant polypeptide comprises a substitution at V39; and the 4-1BBL variant comprises a substitution at L95. In some cases, the CD80 variant polypeptide comprises a substitution at V39; and the 4-1BBL variant comprises a substitution at V96. In some cases, the CD80 variant polypeptide comprises a substitution at V39; and the 4-1BBL variant comprises a substitution at Q98. In some cases, the CD80 variant polypeptide comprises a substitution at V39; and the 4-1BBL variant comprises a substitution at N99. In some cases, the CD80 variant polypeptide comprises a substitution at V39; and the 4-1BBL variant comprises a substitution at V100. In some cases, the CD80 variant polypeptide comprises a substitution at V39; and the 4-1BBL variant comprises a substitution at L101. In some cases, the CD80 variant polypeptide comprises a substitution at V39; and the 4-1BBL variant comprises a substitution at L102. In some cases, the CD80 variant polypeptide comprises a substitution at V39; and the 4-1BBL variant comprises a substitution at I103. In some cases, the CD80 variant polypeptide comprises a substitution at V39; and the 4-1BBL variant comprises a substitution at D104. In some cases, the CD80 variant polypeptide comprises a substitution at V39; and the 4-1BBL variant comprises a substitution at G105. In some cases, the CD80 variant polypeptide comprises a substitution at V39; and the 4-1BBL variant comprises a substitution at P106. In some cases, the CD80 variant polypeptide comprises a substitution at V39; and the 4-1BBL variant comprises a substitution at L107. In some cases, the CD80 variant polypeptide comprises a substitution at V39; and the 4-1BBL variant comprises a substitution at S108. In some cases, the CD80 variant polypeptide comprises a substitution at V39; and the 4-1BBL variant comprises a substitution at W109. In some cases, the CD80 variant polypeptide comprises a substitution at V39; and the 4-1BBL variant comprises a substitution at Y110. In some cases, the CD80 variant polypeptide comprises a substitution at V39; and the 4-1BBL variant comprises a substitution at S111. In some cases, the CD80 variant polypeptide comprises a substitution at V39; and the 4-1BBL variant comprises a substitution at D112. In some cases, the CD80 variant polypeptide comprises a substitution at V39; and the 4-1BBL variant comprises a substitution at P113. In some cases, the CD80 variant polypeptide comprises a substitution at V39; and the 4-1BBL variant comprises a substitution at G114. In some cases, the CD80 variant polypeptide comprises a substitution at V39; and the 4-1BBL variant comprises a substitution at L115. In some cases, the CD80 variant polypeptide comprises a substitution at V39; and the 4-1BBL variant comprises a substitution at G117. In some cases, the CD80 variant polypeptide comprises a substitution at V39; and the 4-1BBL variant comprises a substitution at V118. In some cases, the CD80 variant polypeptide comprises a substitution at V39; and the 4-1BBL variant comprises a substitution at S119. In some cases, the CD80 variant polypeptide comprises a substitution at V39; and the 4-1BBL variant comprises a substitution at L120. In some cases, the CD80 variant polypeptide comprises a substitution at V39; and the 4-1BBL variant comprises a substitution at T121. In some cases, the CD80 variant polypeptide comprises a substitution at V39; and the 4-1BBL variant comprises a substitution at G122. In some cases, the CD80 variant polypeptide comprises a substitution at V39; and the 4-1BBL variant comprises a substitution at G123. In some cases, the CD80 variant polypeptide comprises a substitution at V39; and the 4-1BBL variant comprises a substitution at L124. In some cases, the CD80 variant polypeptide comprises a substitution at V39; and the 4-1BBL variant comprises a substitution at S125. In some cases, the CD80 variant polypeptide comprises a substitution at V39; and the 4-1BBL variant comprises a substitution at Y126. In some cases, the CD80 variant polypeptide comprises a substitution at V39; and the 4-1BBL variant comprises a substitution at E128. In some cases, the CD80 variant polypeptide comprises a substitution at V39; and the 4-1BBL variant comprises a substitution at D129. In some cases, the CD80 variant polypeptide comprises a substitution at V39; and the 4-1BBL variant comprises a substitution at T130. In some cases, the CD80 variant polypeptide comprises a substitution at V39; and the 4-1BBL variant comprises a substitution at K131. In some cases, the CD80 variant polypeptide comprises a substitution at V39; and the 4-1BBL variant comprises a substitution at E132. In some cases, the CD80 variant polypeptide comprises a substitution at V39; and the 4-1BBL variant comprises a substitution at F144. In some cases, the CD80 variant polypeptide comprises a substitution at V39; and the 4-1BBL variant comprises a substitution at F145. In some cases, the CD80 variant polypeptide comprises a substitution at V39; and the 4-1BBL variant comprises a substitution at Q146. In some cases, the CD80 variant polypeptide comprises a substitution at V39; and the 4-1BBL variant comprises a substitution at L147. In some cases, the CD80 variant polypeptide comprises a substitution at V39; and the 4-1BBL variant comprises a substitution at E148. In some cases, the CD80 variant polypeptide comprises a substitution at V39; and the 4-1BBL variant comprises a substitution at L149. In some cases, the CD80 variant polypeptide comprises a substitution at V39; and the 4-1BBL variant comprises a substitution at R150. In some cases, the CD80 variant polypeptide comprises a substitution at V39; and the 4-1BBL variant comprises a substitution at R151. In some cases, the CD80 variant polypeptide comprises a substitution at V39; and the 4-1BBL variant comprises a substitution at V152. In some cases, the CD80 variant polypeptide comprises a substitution at V39; and the 4-1BBL variant comprises a substitution at V153. In some cases, the CD80 variant polypeptide comprises a substitution at V39; and the 4-1BBL variant comprises a substitution at G155. In some cases, the CD80 variant polypeptide comprises a substitution at V39; and the 4-1BBL variant comprises a substitution at E156. In some cases, the CD80 variant polypeptide comprises a substitution at V39; and the 4-1BBL variant comprises a substitution at G157. In some cases, the CD80 variant polypeptide comprises a substitution at V39; and the 4-1BBL variant comprises a substitution at S158. In some cases, the CD80 variant polypeptide comprises a substitution at V39; and the 4-1BBL variant comprises a substitution at D184. In some cases, the CD80 variant polypeptide comprises a substitution at V39; and the 4-1BBL variant comprises a substitution at L185. In some cases, the CD80 variant polypeptide comprises a substitution at V39; and the 4-1BBL variant comprises a substitution at P186. In some cases, the CD80 variant polypeptide comprises a substitution at V39; and the 4-1BBL variant comprises a substitution at P187. In some cases, the CD80 variant polypeptide comprises a substitution at V39; and the 4-1BBL variant comprises a substitution at S189. In some cases, the CD80 variant polypeptide comprises a substitution at V39; and the 4-1BBL variant comprises a substitution at S190. In some cases, the CD80 variant polypeptide comprises a substitution at V39; and the 4-1BBL variant comprises a substitution at E191. In some cases, the CD80 variant polypeptide comprises a substitution at V39; and the 4-1BBL variant comprises a substitution at R193. In some cases, the CD80 variant polypeptide comprises a substitution at V39; and the 4-1BBL variant comprises a substitution at V394. In some cases, the CD80 variant polypeptide comprises a substitution at V39; and the 4-1BBL variant comprises a substitution at S195. In some cases, the CD80 variant polypeptide comprises a substitution at V39; and the 4-1BBL variant comprises a substitution at F197. In some cases, the CD80 variant polypeptide comprises a substitution at V39; and the 4-1BBL variant comprises a substitution at Q210. In some cases, the CD80 variant polypeptide comprises a substitution at V39; and the 4-1BBL variant comprises a substitution at R211. In some cases, the CD80 variant polypeptide comprises a substitution at V39; and the 4-1BBL variant comprises a substitution at L212. In some cases, the CD80 variant polypeptide comprises a substitution at V39; and the 4-1BBL variant comprises a substitution at G213. In some cases, the CD80 variant polypeptide comprises a substitution at V39; and the 4-1BBL variant comprises a substitution at V214. In some cases, the CD80 variant polypeptide comprises a substitution at V39; and the 4-1BBL variant comprises a substitution at H215. In some cases, the CD80 variant polypeptide comprises a substitution at V39; and the 4-1BBL variant comprises a substitution at L216. In some cases, the CD80 variant polypeptide comprises a substitution at V39; and the 4-1BBL variant comprises a substitution at H217. In some cases, the CD80 variant polypeptide comprises a substitution at V39; and the 4-1BBL variant comprises a substitution at T218. In some cases, the CD80 variant polypeptide comprises a substitution at V39; and the 4-1BBL variant comprises a substitution at E219. In some cases, the CD80 variant polypeptide comprises a substitution at V39; and the 4-1BBL variant comprises a substitution at R221. In some cases, the CD80 variant polypeptide comprises a substitution at V39; and the 4-1BBL variant comprises a substitution at R223. In some cases, the CD80 variant polypeptide comprises a substitution at V39; and the 4-1BBL variant comprises a substitution at H224. In some cases, the CD80 variant polypeptide comprises a substitution at V39; and the 4-1BBL variant comprises a substitution at W226. In some cases, the CD80 variant polypeptide comprises a substitution at V39; and the 4-1BBL variant comprises a substitution at L228. In some cases, the CD80 variant polypeptide comprises a substitution at V39; and the 4-1BBL variant comprises a substitution at T229. In some cases, the CD80 variant polypeptide comprises a substitution at V39; and the 4-1BBL variant comprises a substitution at Q230. In some cases, the CD80 variant polypeptide comprises a substitution at V39; and the 4-1BBL variant comprises a substitution at G231. In some cases, the CD80 variant polypeptide comprises a substitution at V39; and the 4-1BBL variant comprises a substitution at T233. In some cases, the CD80 variant polypeptide comprises a substitution at V39; and the 4-1BBL variant comprises a substitution at V234. The amino acid numbering for CD80 is based on the numbering set out in FIG. 2. The amino acid numbering for 4-1BBL is based on the numbering set out in FIG. 3.

In some cases, the CD80 variant polypeptide comprises a substitution at I49; and the 4-1BBL variant comprises a substitution at M91. In some cases, the CD80 variant polypeptide comprises a substitution at I49; and the 4-1BBL variant comprises a substitution at F92. In some cases, the CD80 variant polypeptide comprises a substitution at I49; and the 4-1BBL variant comprises a substitution at Q94. In some cases, the CD80 variant polypeptide comprises a substitution at I49; and the 4-1BBL variant comprises a substitution at L95. In some cases, the CD80 variant polypeptide comprises a substitution at I49; and the 4-1BBL variant comprises a substitution at V96. In some cases, the CD80 variant polypeptide comprises a substitution at I49; and the 4-1BBL variant comprises a substitution at Q98. In some cases, the CD80 variant polypeptide comprises a substitution at I49; and the 4-1BBL variant comprises a substitution at N99. In some cases, the CD80 variant polypeptide comprises a substitution at I49; and the 4-1BBL variant comprises a substitution at V100. In some cases, the CD80 variant polypeptide comprises a substitution at I49; and the 4-1BBL variant comprises a substitution at L101. In some cases, the CD80 variant polypeptide comprises a substitution at I49; and the 4-1BBL variant comprises a substitution at L102. In some cases, the CD80 variant polypeptide comprises a substitution at I49; and the 4-1BBL variant comprises a substitution at I103. In some cases, the CD80 variant polypeptide comprises a substitution at I49; and the 4-1BBL variant comprises a substitution at D104. In some cases, the CD80 variant polypeptide comprises a substitution at I49; and the 4-1BBL variant comprises a substitution at G105. In some cases, the CD80 variant polypeptide comprises a substitution at I49; and the 4-1BBL variant comprises a substitution at P106. In some cases, the CD80 variant polypeptide comprises a substitution at I49; and the 4-1BBL variant comprises a substitution at L107. In some cases, the CD80 variant polypeptide comprises a substitution at I49; and the 4-1BBL variant comprises a substitution at S108. In some cases, the CD80 variant polypeptide comprises a substitution at I49; and the 4-1BBL variant comprises a substitution at W109. In some cases, the CD80 variant polypeptide comprises a substitution at I49; and the 4-1BBL variant comprises a substitution at Y110. In some cases, the CD80 variant polypeptide comprises a substitution at I49; and the 4-1BBL variant comprises a substitution at S111. In some cases, the CD80 variant polypeptide comprises a substitution at I49; and the 4-1BBL variant comprises a substitution at D112. In some cases, the CD80 variant polypeptide comprises a substitution at I49; and the 4-1BBL variant comprises a substitution at P113. In some cases, the CD80 variant polypeptide comprises a substitution at I49; and the 4-1BBL variant comprises a substitution at G114. In some cases, the CD80 variant polypeptide comprises a substitution at I49; and the 4-1BBL variant comprises a substitution at L115. In some cases, the CD80 variant polypeptide comprises a substitution at I49; and the 4-1BBL variant comprises a substitution at G117. In some cases, the CD80 variant polypeptide comprises a substitution at I49; and the 4-1BBL variant comprises a substitution at V118. In some cases, the CD80 variant polypeptide comprises a substitution at I49; and the 4-1BBL variant comprises a substitution at S119. In some cases, the CD80 variant polypeptide comprises a substitution at I49; and the 4-1BBL variant comprises a substitution at L120. In some cases, the CD80 variant polypeptide comprises a substitution at I49; and the 4-1BBL variant comprises a substitution at T121. In some cases, the CD80 variant polypeptide comprises a substitution at I49; and the 4-1BBL variant comprises a substitution at G122. In some cases, the CD80 variant polypeptide comprises a substitution at I49; and the 4-1BBL variant comprises a substitution at G123. In some cases, the CD80 variant polypeptide comprises a substitution at I49; and the 4-1BBL variant comprises a substitution at L124. In some cases, the CD80 variant polypeptide comprises a substitution at I49; and the 4-1BBL variant comprises a substitution at S125. In some cases, the CD80 variant polypeptide comprises a substitution at I49; and the 4-1BBL variant comprises a substitution at Y126. In some cases, the CD80 variant polypeptide comprises a substitution at I49; and the 4-1BBL variant comprises a substitution at E128. In some cases, the CD80 variant polypeptide comprises a substitution at I49; and the 4-1BBL variant comprises a substitution at D129. In some cases, the CD80 variant polypeptide comprises a substitution at I49; and the 4-1BBL variant comprises a substitution at T130. In some cases, the CD80 variant polypeptide comprises a substitution at I49; and the 4-1BBL variant comprises a substitution at K131. In some cases, the CD80 variant polypeptide comprises a substitution at I49; and the 4-1BBL variant comprises a substitution at E132. In some cases, the CD80 variant polypeptide comprises a substitution at I49; and the 4-1BBL variant comprises a substitution at F144. In some cases, the CD80 variant polypeptide comprises a substitution at I49; and the 4-1BBL variant comprises a substitution at F145. In some cases, the CD80 variant polypeptide comprises a substitution at I49; and the 4-1BBL variant comprises a substitution at Q146. In some cases, the CD80 variant polypeptide comprises a substitution at I49; and the 4-1BBL variant comprises a substitution at L147. In some cases, the CD80 variant polypeptide comprises a substitution at I49; and the 4-1BBL variant comprises a substitution at E148. In some cases, the CD80 variant polypeptide comprises a substitution at I49; and the 4-1BBL variant comprises a substitution at L149. In some cases, the CD80 variant polypeptide comprises a substitution at I49; and the 4-1BBL variant comprises a substitution at R150. In some cases, the CD80 variant polypeptide comprises a substitution at I49; and the 4-1BBL variant comprises a substitution at R151. In some cases, the CD80 variant polypeptide comprises a substitution at I49; and the 4-1BBL variant comprises a substitution at V152. In some cases, the CD80 variant polypeptide comprises a substitution at I49; and the 4-1BBL variant comprises a substitution at V153. In some cases, the CD80 variant polypeptide comprises a substitution at I49; and the 4-1BBL variant comprises a substitution at G155. In some cases, the CD80 variant polypeptide comprises a substitution at I49; and the 4-1BBL variant comprises a substitution at E156. In some cases, the CD80 variant polypeptide comprises a substitution at I49; and the 4-1BBL variant comprises a substitution at G157. In some cases, the CD80 variant polypeptide comprises a substitution at I49; and the 4-1BBL variant comprises a substitution at S158. In some cases, the CD80 variant polypeptide comprises a substitution at I49; and the 4-1BBL variant comprises a substitution at D184. In some cases, the CD80 variant polypeptide comprises a substitution at I49; and the 4-1BBL variant comprises a substitution at L185. In some cases, the CD80 variant polypeptide comprises a substitution at I49; and the 4-1BBL variant comprises a substitution at P186. In some cases, the CD80 variant polypeptide comprises a substitution at I49; and the 4-1BBL variant comprises a substitution at P187. In some cases, the CD80 variant polypeptide comprises a substitution at I49; and the 4-1BBL variant comprises a substitution at S189. In some cases, the CD80 variant polypeptide comprises a substitution at I49; and the 4-1BBL variant comprises a substitution at S190. In some cases, the CD80 variant polypeptide comprises a substitution at I49; and the 4-1BBL variant comprises a substitution at E191. In some cases, the CD80 variant polypeptide comprises a substitution at I49; and the 4-1BBL variant comprises a substitution at R193. In some cases, the CD80 variant polypeptide comprises a substitution at I49; and the 4-1BBL variant comprises a substitution at I494. In some cases, the CD80 variant polypeptide comprises a substitution at I49; and the 4-1BBL variant comprises a substitution at S195. In some cases, the CD80 variant polypeptide comprises a substitution at I49; and the 4-1BBL variant comprises a substitution at F197. In some cases, the CD80 variant polypeptide comprises a substitution at I49; and the 4-1BBL variant comprises a substitution at Q210. In some cases, the CD80 variant polypeptide comprises a substitution at I49; and the 4-1BBL variant comprises a substitution at R211. In some cases, the CD80 variant polypeptide comprises a substitution at I49; and the 4-1BBL variant comprises a substitution at L212. In some cases, the CD80 variant polypeptide comprises a substitution at I49; and the 4-1BBL variant comprises a substitution at G213. In some cases, the CD80 variant polypeptide comprises a substitution at I49; and the 4-1BBL variant comprises a substitution at V214. In some cases, the CD80 variant polypeptide comprises a substitution at I49; and the 4-1BBL variant comprises a substitution at H215. In some cases, the CD80 variant polypeptide comprises a substitution at I49; and the 4-1BBL variant comprises a substitution at L216. In some cases, the CD80 variant polypeptide comprises a substitution at I49; and the 4-1BBL variant comprises a substitution at H217. In some cases, the CD80 variant polypeptide comprises a substitution at I49; and the 4-1BBL variant comprises a substitution at T218. In some cases, the CD80 variant polypeptide comprises a substitution at I49; and the 4-1BBL variant comprises a substitution at E219. In some cases, the CD80 variant polypeptide comprises a substitution at I49; and the 4-1BBL variant comprises a substitution at R221. In some cases, the CD80 variant polypeptide comprises a substitution at I49; and the 4-1BBL variant comprises a substitution at R223. In some cases, the CD80 variant polypeptide comprises a substitution at I49; and the 4-1BBL variant comprises a substitution at H224. In some cases, the CD80 variant polypeptide comprises a substitution at I49; and the 4-1BBL variant comprises a substitution at W226. In some cases, the CD80 variant polypeptide comprises a substitution at I49; and the 4-1BBL variant comprises a substitution at L228. In some cases, the CD80 variant polypeptide comprises a substitution at I49; and the 4-1BBL variant comprises a substitution at T229. In some cases, the CD80 variant polypeptide comprises a substitution at I49; and the 4-1BBL variant comprises a substitution at Q230. In some cases, the CD80 variant polypeptide comprises a substitution at I49; and the 4-1BBL variant comprises a substitution at G231. In some cases, the CD80 variant polypeptide comprises a substitution at I49; and the 4-1BBL variant comprises a substitution at T233. In some cases, the CD80 variant polypeptide comprises a substitution at I49; and the 4-1BBL variant comprises a substitution at V234. The amino acid numbering for CD80 is based on the numbering set out in FIG. 2. The amino acid numbering for 4-1BBL is based on the numbering set out in FIG. 3.

In some cases, the CD80 variant polypeptide comprises a substitution at Y53; and the 4-1BBL variant comprises a substitution at M91. In some cases, the CD80 variant polypeptide comprises a substitution at Y53; and the 4-1BBL variant comprises a substitution at F92. In some cases, the CD80 variant polypeptide comprises a substitution at Y53; and the 4-1BBL variant comprises a substitution at Q94. In some cases, the CD80 variant polypeptide comprises a substitution at Y53; and the 4-1BBL variant comprises a substitution at L95. In some cases, the CD80 variant polypeptide comprises a substitution at Y53; and the 4-1BBL variant comprises a substitution at V96. In some cases, the CD80 variant polypeptide comprises a substitution at Y53; and the 4-1BBL variant comprises a substitution at Q98. In some cases, the CD80 variant polypeptide comprises a substitution at Y53; and the 4-1BBL variant comprises a substitution at N99. In some cases, the CD80 variant polypeptide comprises a substitution at Y53; and the 4-1BBL variant comprises a substitution at V100. In some cases, the CD80 variant polypeptide comprises a substitution at Y53; and the 4-1BBL variant comprises a substitution at L101. In some cases, the CD80 variant polypeptide comprises a substitution at Y53; and the 4-1BBL variant comprises a substitution at L102. In some cases, the CD80 variant polypeptide comprises a substitution at Y53; and the 4-1BBL variant comprises a substitution at I103. In some cases, the CD80 variant polypeptide comprises a substitution at Y53; and the 4-1BBL variant comprises a substitution at D104. In some cases, the CD80 variant polypeptide comprises a substitution at Y53; and the 4-1BBL variant comprises a substitution at G105. In some cases, the CD80 variant polypeptide comprises a substitution at Y53; and the 4-1BBL variant comprises a substitution at P106. In some cases, the CD80 variant polypeptide comprises a substitution at Y53; and the 4-1BBL variant comprises a substitution at L107. In some cases, the CD80 variant polypeptide comprises a substitution at Y53; and the 4-1BBL variant comprises a substitution at S108. In some cases, the CD80 variant polypeptide comprises a substitution at Y53; and the 4-1BBL variant comprises a substitution at W109. In some cases, the CD80 variant polypeptide comprises a substitution at Y53; and the 4-1BBL variant comprises a substitution at Y110. In some cases, the CD80 variant polypeptide comprises a substitution at Y53; and the 4-1BBL variant comprises a substitution at S111. In some cases, the CD80 variant polypeptide comprises a substitution at Y53; and the 4-1BBL variant comprises a substitution at D112. In some cases, the CD80 variant polypeptide comprises a substitution at Y53; and the 4-1BBL variant comprises a substitution at P113. In some cases, the CD80 variant polypeptide comprises a substitution at Y53; and the 4-1BBL variant comprises a substitution at G114. In some cases, the CD80 variant polypeptide comprises a substitution at Y53; and the 4-1BBL variant comprises a substitution at L115. In some cases, the CD80 variant polypeptide comprises a substitution at Y53; and the 4-1BBL variant comprises a substitution at G117. In some cases, the CD80 variant polypeptide comprises a substitution at Y53; and the 4-1BBL variant comprises a substitution at V118. In some cases, the CD80 variant polypeptide comprises a substitution at Y53; and the 4-1BBL variant comprises a substitution at S119. In some cases, the CD80 variant polypeptide comprises a substitution at Y53; and the 4-1BBL variant comprises a substitution at L120. In some cases, the CD80 variant polypeptide comprises a substitution at Y53; and the 4-1BBL variant comprises a substitution at T121. In some cases, the CD80 variant polypeptide comprises a substitution at Y53; and the 4-1BBL variant comprises a substitution at G122. In some cases, the CD80 variant polypeptide comprises a substitution at Y53; and the 4-1BBL variant comprises a substitution at G123. In some cases, the CD80 variant polypeptide comprises a substitution at Y53; and the 4-1BBL variant comprises a substitution at L124. In some cases, the CD80 variant polypeptide comprises a substitution at Y53; and the 4-1BBL variant comprises a substitution at S125. In some cases, the CD80 variant polypeptide comprises a substitution at Y53; and the 4-1BBL variant comprises a substitution at Y126. In some cases, the CD80 variant polypeptide comprises a substitution at Y53; and the 4-1BBL variant comprises a substitution at E128. In some cases, the CD80 variant polypeptide comprises a substitution at Y53; and the 4-1BBL variant comprises a substitution at D129. In some cases, the CD80 variant polypeptide comprises a substitution at Y53; and the 4-1BBL variant comprises a substitution at T130. In some cases, the CD80 variant polypeptide comprises a substitution at Y53; and the 4-1BBL variant comprises a substitution at K131. In some cases, the CD80 variant polypeptide comprises a substitution at Y53; and the 4-1BBL variant comprises a substitution at E132. In some cases, the CD80 variant polypeptide comprises a substitution at Y53; and the 4-1BBL variant comprises a substitution at F144. In some cases, the CD80 variant polypeptide comprises a substitution at Y53; and the 4-1BBL variant comprises a substitution at F145. In some cases, the CD80 variant polypeptide comprises a substitution at Y53; and the 4-1BBL variant comprises a substitution at Q146. In some cases, the CD80 variant polypeptide comprises a substitution at Y53; and the 4-1BBL variant comprises a substitution at L147. In some cases, the CD80 variant polypeptide comprises a substitution at Y53; and the 4-1BBL variant comprises a substitution at E148. In some cases, the CD80 variant polypeptide comprises a substitution at Y53; and the 4-1BBL variant comprises a substitution at L149. In some cases, the CD80 variant polypeptide comprises a substitution at Y53; and the 4-1BBL variant comprises a substitution at R150. In some cases, the CD80 variant polypeptide comprises a substitution at Y53; and the 4-1BBL variant comprises a substitution at R151. In some cases, the CD80 variant polypeptide comprises a substitution at Y53; and the 4-1BBL variant comprises a substitution at V152. In some cases, the CD80 variant polypeptide comprises a substitution at Y53; and the 4-1BBL variant comprises a substitution at V153. In some cases, the CD80 variant polypeptide comprises a substitution at Y53; and the 4-1BBL variant comprises a substitution at G155. In some cases, the CD80 variant polypeptide comprises a substitution at Y53; and the 4-1BBL variant comprises a substitution at E156. In some cases, the CD80 variant polypeptide comprises a substitution at Y53; and the 4-1BBL variant comprises a substitution at G157. In some cases, the CD80 variant polypeptide comprises a substitution at Y53; and the 4-1BBL variant comprises a substitution at S158. In some cases, the CD80 variant polypeptide comprises a substitution at Y53; and the 4-1BBL variant comprises a substitution at D184. In some cases, the CD80 variant polypeptide comprises a substitution at Y53; and the 4-1BBL variant comprises a substitution at L185. In some cases, the CD80 variant polypeptide comprises a substitution at Y53; and the 4-1BBL variant comprises a substitution at P186. In some cases, the CD80 variant polypeptide comprises a substitution at Y53; and the 4-1BBL variant comprises a substitution at P187. In some cases, the CD80 variant polypeptide comprises a substitution at Y53; and the 4-1BBL variant comprises a substitution at S189. In some cases, the CD80 variant polypeptide comprises a substitution at Y53; and the 4-1BBL variant comprises a substitution at S190. In some cases, the CD80 variant polypeptide comprises a substitution at Y53; and the 4-1BBL variant comprises a substitution at E191. In some cases, the CD80 variant polypeptide comprises a substitution at Y53; and the 4-1BBL variant comprises a substitution at R193. In some cases, the CD80 variant polypeptide comprises a substitution at Y53; and the 4-1BBL variant comprises a substitution at Y534. In some cases, the CD80 variant polypeptide comprises a substitution at Y53; and the 4-1BBL variant comprises a substitution at S195. In some cases, the CD80 variant polypeptide comprises a substitution at Y53; and the 4-1BBL variant comprises a substitution at F197. In some cases, the CD80 variant polypeptide comprises a substitution at Y53; and the 4-1BBL variant comprises a substitution at Q210. In some cases, the CD80 variant polypeptide comprises a substitution at Y53; and the 4-1BBL variant comprises a substitution at R211. In some cases, the CD80 variant polypeptide comprises a substitution at Y53; and the 4-1BBL variant comprises a substitution at L212. In some cases, the CD80 variant polypeptide comprises a substitution at Y53; and the 4-1BBL variant comprises a substitution at G213. In some cases, the CD80 variant polypeptide comprises a substitution at Y53; and the 4-1BBL variant comprises a substitution at V214. In some cases, the CD80 variant polypeptide comprises a substitution at Y53; and the 4-1BBL variant comprises a substitution at H215. In some cases, the CD80 variant polypeptide comprises a substitution at Y53; and the 4-1BBL variant comprises a substitution at L216. In some cases, the CD80 variant polypeptide comprises a substitution at Y53; and the 4-1BBL variant comprises a substitution at H217. In some cases, the CD80 variant polypeptide comprises a substitution at Y53; and the 4-1BBL variant comprises a substitution at T218. In some cases, the CD80 variant polypeptide comprises a substitution at Y53; and the 4-1BBL variant comprises a substitution at E219. In some cases, the CD80 variant polypeptide comprises a substitution at Y53; and the 4-1BBL variant comprises a substitution at R221. In some cases, the CD80 variant polypeptide comprises a substitution at Y53; and the 4-1BBL variant comprises a substitution at R223. In some cases, the CD80 variant polypeptide comprises a substitution at Y53; and the 4-1BBL variant comprises a substitution at H224. In some cases, the CD80 variant polypeptide comprises a substitution at Y53; and the 4-1BBL variant comprises a substitution at W226. In some cases, the CD80 variant polypeptide comprises a substitution at Y53; and the 4-1BBL variant comprises a substitution at L228. In some cases, the CD80 variant polypeptide comprises a substitution at Y53; and the 4-1BBL variant comprises a substitution at T229. In some cases, the CD80 variant polypeptide comprises a substitution at Y53; and the 4-1BBL variant comprises a substitution at Q230. In some cases, the CD80 variant polypeptide comprises a substitution at Y53; and the 4-1BBL variant comprises a substitution at G231. In some cases, the CD80 variant polypeptide comprises a substitution at Y53; and the 4-1BBL variant comprises a substitution at T233. In some cases, the CD80 variant polypeptide comprises a substitution at Y53; and the 4-1BBL variant comprises a substitution at V234. The amino acid numbering for CD80 is based on the numbering set out in FIG. 2. The amino acid numbering for 4-1BBL is based on the numbering set out in FIG. 3.

In some cases, the CD80 variant polypeptide comprises a substitution at D60; and the 4-1BBL variant comprises a substitution at M91. In some cases, the CD80 variant polypeptide comprises a substitution at D60; and the 4-1BBL variant comprises a substitution at F92. In some cases, the CD80 variant polypeptide comprises a substitution at D60; and the 4-1BBL variant comprises a substitution at Q94. In some cases, the CD80 variant polypeptide comprises a substitution at D60; and the 4-1BBL variant comprises a substitution at L95. In some cases, the CD80 variant polypeptide comprises a substitution at D60; and the 4-1BBL variant comprises a substitution at V96. In some cases, the CD80 variant polypeptide comprises a substitution at D60; and the 4-1BBL variant comprises a substitution at Q98. In some cases, the CD80 variant polypeptide comprises a substitution at D60; and the 4-1BBL variant comprises a substitution at N99. In some cases, the CD80 variant polypeptide comprises a substitution at D60; and the 4-1BBL variant comprises a substitution at V100. In some cases, the CD80 variant polypeptide comprises a substitution at D60; and the 4-1BBL variant comprises a substitution at L101. In some cases, the CD80 variant polypeptide comprises a substitution at D60; and the 4-1BBL variant comprises a substitution at L102. In some cases, the CD80 variant polypeptide comprises a substitution at D60; and the 4-1BBL variant comprises a substitution at I103. In some cases, the CD80 variant polypeptide comprises a substitution at D60; and the 4-1BBL variant comprises a substitution at D104. In some cases, the CD80 variant polypeptide comprises a substitution at D60; and the 4-1BBL variant comprises a substitution at G105. In some cases, the CD80 variant polypeptide comprises a substitution at D60; and the 4-1BBL variant comprises a substitution at P106. In some cases, the CD80 variant polypeptide comprises a substitution at D60; and the 4-1BBL variant comprises a substitution at L107. In some cases, the CD80 variant polypeptide comprises a substitution at D60; and the 4-1BBL variant comprises a substitution at S108. In some cases, the CD80 variant polypeptide comprises a substitution at D60; and the 4-1BBL variant comprises a substitution at W109. In some cases, the CD80 variant polypeptide comprises a substitution at D60; and the 4-1BBL variant comprises a substitution at Y110. In some cases, the CD80 variant polypeptide comprises a substitution at D60; and the 4-1BBL variant comprises a substitution at S111. In some cases, the CD80 variant polypeptide comprises a substitution at D60; and the 4-1BBL variant comprises a substitution at D112. In some cases, the CD80 variant polypeptide comprises a substitution at D60; and the 4-1BBL variant comprises a substitution at P113. In some cases, the CD80 variant polypeptide comprises a substitution at D60; and the 4-1BBL variant comprises a substitution at G114. In some cases, the CD80 variant polypeptide comprises a substitution at D60; and the 4-1BBL variant comprises a substitution at L115. In some cases, the CD80 variant polypeptide comprises a substitution at D60; and the 4-1BBL variant comprises a substitution at G117. In some cases, the CD80 variant polypeptide comprises a substitution at D60; and the 4-1BBL variant comprises a substitution at V118. In some cases, the CD80 variant polypeptide comprises a substitution at D60; and the 4-1BBL variant comprises a substitution at S119. In some cases, the CD80 variant polypeptide comprises a substitution at D60; and the 4-1BBL variant comprises a substitution at L120. In some cases, the CD80 variant polypeptide comprises a substitution at D60; and the 4-1BBL variant comprises a substitution at T121. In some cases, the CD80 variant polypeptide comprises a substitution at D60; and the 4-1BBL variant comprises a substitution at G122. In some cases, the CD80 variant polypeptide comprises a substitution at D60; and the 4-1BBL variant comprises a substitution at G123. In some cases, the CD80 variant polypeptide comprises a substitution at D60; and the 4-1BBL variant comprises a substitution at L124. In some cases, the CD80 variant polypeptide comprises a substitution at D60; and the 4-1BBL variant comprises a substitution at S125. In some cases, the CD80 variant polypeptide comprises a substitution at D60; and the 4-1BBL variant comprises a substitution at Y126. In some cases, the CD80 variant polypeptide comprises a substitution at D60; and the 4-1BBL variant comprises a substitution at E128. In some cases, the CD80 variant polypeptide comprises a substitution at D60; and the 4-1BBL variant comprises a substitution at D129. In some cases, the CD80 variant polypeptide comprises a substitution at D60; and the 4-1BBL variant comprises a substitution at T130. In some cases, the CD80 variant polypeptide comprises a substitution at D60; and the 4-1BBL variant comprises a substitution at K131. In some cases, the CD80 variant polypeptide comprises a substitution at D60; and the 4-1BBL variant comprises a substitution at E132. In some cases, the CD80 variant polypeptide comprises a substitution at D60; and the 4-1BBL variant comprises a substitution at F144. In some cases, the CD80 variant polypeptide comprises a substitution at D60; and the 4-1BBL variant comprises a substitution at F145. In some cases, the CD80 variant polypeptide comprises a substitution at D60; and the 4-1BBL variant comprises a substitution at Q146. In some cases, the CD80 variant polypeptide comprises a substitution at D60; and the 4-1BBL variant comprises a substitution at L147. In some cases, the CD80 variant polypeptide comprises a substitution at D60; and the 4-1BBL variant comprises a substitution at E148. In some cases, the CD80 variant polypeptide comprises a substitution at D60; and the 4-1BBL variant comprises a substitution at L149. In some cases, the CD80 variant polypeptide comprises a substitution at D60; and the 4-1BBL variant comprises a substitution at R150. In some cases, the CD80 variant polypeptide comprises a substitution at D60; and the 4-1BBL variant comprises a substitution at R151. In some cases, the CD80 variant polypeptide comprises a substitution at D60; and the 4-1BBL variant comprises a substitution at V152. In some cases, the CD80 variant polypeptide comprises a substitution at D60; and the 4-1BBL variant comprises a substitution at V153. In some cases, the CD80 variant polypeptide comprises a substitution at D60; and the 4-1BBL variant comprises a substitution at G155. In some cases, the CD80 variant polypeptide comprises a substitution at D60; and the 4-1BBL variant comprises a substitution at E156. In some cases, the CD80 variant polypeptide comprises a substitution at D60; and the 4-1BBL variant comprises a substitution at G157. In some cases, the CD80 variant polypeptide comprises a substitution at D60; and the 4-1BBL variant comprises a substitution at S158. In some cases, the CD80 variant polypeptide comprises a substitution at D60; and the 4-1BBL variant comprises a substitution at D184. In some cases, the CD80 variant polypeptide comprises a substitution at D60; and the 4-1BBL variant comprises a substitution at L185. In some cases, the CD80 variant polypeptide comprises a substitution at D60; and the 4-1BBL variant comprises a substitution at P186. In some cases, the CD80 variant polypeptide comprises a substitution at D60; and the 4-1BBL variant comprises a substitution at P187. In some cases, the CD80 variant polypeptide comprises a substitution at D60; and the 4-1BBL variant comprises a substitution at S189. In some cases, the CD80 variant polypeptide comprises a substitution at D60; and the 4-1BBL variant comprises a substitution at S190. In some cases, the CD80 variant polypeptide comprises a substitution at D60; and the 4-1BBL variant comprises a substitution at E191. In some cases, the CD80 variant polypeptide comprises a substitution at D60; and the 4-1BBL variant comprises a substitution at R193. In some cases, the CD80 variant polypeptide comprises a substitution at D60; and the 4-1BBL variant comprises a substitution at D604. In some cases, the CD80 variant polypeptide comprises a substitution at D60; and the 4-1BBL variant comprises a substitution at S195. In some cases, the CD80 variant polypeptide comprises a substitution at D60; and the 4-1BBL variant comprises a substitution at F197. In some cases, the CD80 variant polypeptide comprises a substitution at D60; and the 4-1BBL variant comprises a substitution at Q210. In some cases, the CD80 variant polypeptide comprises a substitution at D60; and the 4-1BBL variant comprises a substitution at R211. In some cases, the CD80 variant polypeptide comprises a substitution at D60; and the 4-1BBL variant comprises a substitution at L212. In some cases, the CD80 variant polypeptide comprises a substitution at D60; and the 4-1BBL variant comprises a substitution at G213. In some cases, the CD80 variant polypeptide comprises a substitution at D60; and the 4-1BBL variant comprises a substitution at V214. In some cases, the CD80 variant polypeptide comprises a substitution at D60; and the 4-1BBL variant comprises a substitution at H215. In some cases, the CD80 variant polypeptide comprises a substitution at D60; and the 4-1BBL variant comprises a substitution at L216. In some cases, the CD80 variant polypeptide comprises a substitution at D60; and the 4-1BBL variant comprises a substitution at H217. In some cases, the CD80 variant polypeptide comprises a substitution at D60; and the 4-1BBL variant comprises a substitution at T218. In some cases, the CD80 variant polypeptide comprises a substitution at D60; and the 4-1BBL variant comprises a substitution at E219. In some cases, the CD80 variant polypeptide comprises a substitution at D60; and the 4-1BBL variant comprises a substitution at R221. In some cases, the CD80 variant polypeptide comprises a substitution at D60; and the 4-1BBL variant comprises a substitution at R223. In some cases, the CD80 variant polypeptide comprises a substitution at D60; and the 4-1BBL variant comprises a substitution at H224. In some cases, the CD80 variant polypeptide comprises a substitution at D60; and the 4-1BBL variant comprises a substitution at W226. In some cases, the CD80 variant polypeptide comprises a substitution at D60; and the 4-1BBL variant comprises a substitution at L228. In some cases, the CD80 variant polypeptide comprises a substitution at D60; and the 4-1BBL variant comprises a substitution at T229. In some cases, the CD80 variant polypeptide comprises a substitution at D60; and the 4-1BBL variant comprises a substitution at Q230. In some cases, the CD80 variant polypeptide comprises a substitution at D60; and the 4-1BBL variant comprises a substitution at G231. In some cases, the CD80 variant polypeptide comprises a substitution at D60; and the 4-1BBL variant comprises a substitution at T233. In some cases, the CD80 variant polypeptide comprises a substitution at D60; and the 4-1BBL variant comprises a substitution at V234. The amino acid numbering for CD80 is based on the numbering set out in FIG. 2. The amino acid numbering for 4-1BBL is based on the numbering set out in FIG. 3.

In some cases, the CD80 variant polypeptide comprises a substitution at F108; and the 4-1BBL variant comprises a substitution at M91. In some cases, the CD80 variant polypeptide comprises a substitution at F108; and the 4-1BBL variant comprises a substitution at F92. In some cases, the CD80 variant polypeptide comprises a substitution at F108; and the 4-1BBL variant comprises a substitution at Q94. In some cases, the CD80 variant polypeptide comprises a substitution at F108; and the 4-1BBL variant comprises a substitution at L95. In some cases, the CD80 variant polypeptide comprises a substitution at F108; and the 4-1BBL variant comprises a substitution at V96. In some cases, the CD80 variant polypeptide comprises a substitution at F108; and the 4-1BBL variant comprises a substitution at Q98. In some cases, the CD80 variant polypeptide comprises a substitution at F108; and the 4-1BBL variant comprises a substitution at N99. In some cases, the CD80 variant polypeptide comprises a substitution at F108; and the 4-1BBL variant comprises a substitution at V100. In some cases, the CD80 variant polypeptide comprises a substitution at F108; and the 4-1BBL variant comprises a substitution at L101. In some cases, the CD80 variant polypeptide comprises a substitution at F108; and the 4-1BBL variant comprises a substitution at L102. In some cases, the CD80 variant polypeptide comprises a substitution at F108; and the 4-1BBL variant comprises a substitution at I103. In some cases, the CD80 variant polypeptide comprises a substitution at F108; and the 4-1BBL variant comprises a substitution at D104. In some cases, the CD80 variant polypeptide comprises a substitution at F108; and the 4-1BBL variant comprises a substitution at G105. In some cases, the CD80 variant polypeptide comprises a substitution at F108; and the 4-1BBL variant comprises a substitution at P106. In some cases, the CD80 variant polypeptide comprises a substitution at F108; and the 4-1BBL variant comprises a substitution at L107. In some cases, the CD80 variant polypeptide comprises a substitution at F108; and the 4-1BBL variant comprises a substitution at S108. In some cases, the CD80 variant polypeptide comprises a substitution at F108; and the 4-1BBL variant comprises a substitution at W109. In some cases, the CD80 variant polypeptide comprises a substitution at F108; and the 4-1BBL variant comprises a substitution at Y110. In some cases, the CD80 variant polypeptide comprises a substitution at F108; and the 4-1BBL variant comprises a substitution at S111. In some cases, the CD80 variant polypeptide comprises a substitution at F108; and the 4-1BBL variant comprises a substitution at D112. In some cases, the CD80 variant polypeptide comprises a substitution at F108; and the 4-1BBL variant comprises a substitution at P113. In some cases, the CD80 variant polypeptide comprises a substitution at F108; and the 4-1BBL variant comprises a substitution at G114. In some cases, the CD80 variant polypeptide comprises a substitution at F108; and the 4-1BBL variant comprises a substitution at L115. In some cases, the CD80 variant polypeptide comprises a substitution at F108; and the 4-1BBL variant comprises a substitution at G117. In some cases, the CD80 variant polypeptide comprises a substitution at F108; and the 4-1BBL variant comprises a substitution at V118. In some cases, the CD80 variant polypeptide comprises a substitution at F108; and the 4-1BBL variant comprises a substitution at S119. In some cases, the CD80 variant polypeptide comprises a substitution at F108; and the 4-1BBL variant comprises a substitution at L120. In some cases, the CD80 variant polypeptide comprises a substitution at F108; and the 4-1BBL variant comprises a substitution at T121. In some cases, the CD80 variant polypeptide comprises a substitution at F108; and the 4-1BBL variant comprises a substitution at G122. In some cases, the CD80 variant polypeptide comprises a substitution at F108; and the 4-1BBL variant comprises a substitution at G123. In some cases, the CD80 variant polypeptide comprises a substitution at F108; and the 4-1BBL variant comprises a substitution at L124. In some cases, the CD80 variant polypeptide comprises a substitution at F108; and the 4-1BBL variant comprises a substitution at S125. In some cases, the CD80 variant polypeptide comprises a substitution at F108; and the 4-1BBL variant comprises a substitution at Y126. In some cases, the CD80 variant polypeptide comprises a substitution at F108; and the 4-1BBL variant comprises a substitution at E128. In some cases, the CD80 variant polypeptide comprises a substitution at F108; and the 4-1BBL variant comprises a substitution at D129. In some cases, the CD80 variant polypeptide comprises a substitution at F108; and the 4-1BBL variant comprises a substitution at T130. In some cases, the CD80 variant polypeptide comprises a substitution at F108; and the 4-1BBL variant comprises a substitution at K131. In some cases, the CD80 variant polypeptide comprises a substitution at F108; and the 4-1BBL variant comprises a substitution at E132. In some cases, the CD80 variant polypeptide comprises a substitution at F108; and the 4-1BBL variant comprises a substitution at F144. In some cases, the CD80 variant polypeptide comprises a substitution at F108; and the 4-1BBL variant comprises a substitution at F145. In some cases, the CD80 variant polypeptide comprises a substitution at F108; and the 4-1BBL variant comprises a substitution at Q146. In some cases, the CD80 variant polypeptide comprises a substitution at F108; and the 4-1BBL variant comprises a substitution at L147. In some cases, the CD80 variant polypeptide comprises a substitution at F108; and the 4-1BBL variant comprises a substitution at E148. In some cases, the CD80 variant polypeptide comprises a substitution at F108; and the 4-1BBL variant comprises a substitution at L149. In some cases, the CD80 variant polypeptide comprises a substitution at F108; and the 4-1BBL variant comprises a substitution at R150. In some cases, the CD80 variant polypeptide comprises a substitution at F108; and the 4-1BBL variant comprises a substitution at R151. In some cases, the CD80 variant polypeptide comprises a substitution at F108; and the 4-1BBL variant comprises a substitution at V152. In some cases, the CD80 variant polypeptide comprises a substitution at F108; and the 4-1BBL variant comprises a substitution at V153. In some cases, the CD80 variant polypeptide comprises a substitution at F108; and the 4-1BBL variant comprises a substitution at G155. In some cases, the CD80 variant polypeptide comprises a substitution at F108; and the 4-1BBL variant comprises a substitution at E156. In some cases, the CD80 variant polypeptide comprises a substitution at F108; and the 4-1BBL variant comprises a substitution at G157. In some cases, the CD80 variant polypeptide comprises a substitution at F108; and the 4-1BBL variant comprises a substitution at S158. In some cases, the CD80 variant polypeptide comprises a substitution at F108; and the 4-1BBL variant comprises a substitution at D184. In some cases, the CD80 variant polypeptide comprises a substitution at F108; and the 4-1BBL variant comprises a substitution at L185. In some cases, the CD80 variant polypeptide comprises a substitution at F108; and the 4-1BBL variant comprises a substitution at P186. In some cases, the CD80 variant polypeptide comprises a substitution at F108; and the 4-1BBL variant comprises a substitution at P187. In some cases, the CD80 variant polypeptide comprises a substitution at F108; and the 4-1BBL variant comprises a substitution at S189. In some cases, the CD80 variant polypeptide comprises a substitution at F108; and the 4-1BBL variant comprises a substitution at S190. In some cases, the CD80 variant polypeptide comprises a substitution at F108; and the 4-1BBL variant comprises a substitution at E191. In some cases, the CD80 variant polypeptide comprises a substitution at F108; and the 4-1BBL variant comprises a substitution at R193. In some cases, the CD80 variant polypeptide comprises a substitution at F108; and the 4-1BBL variant comprises a substitution at F1084. In some cases, the CD80 variant polypeptide comprises a substitution at F108; and the 4-1BBL variant comprises a substitution at S195. In some cases, the CD80 variant polypeptide comprises a substitution at F108; and the 4-1BBL variant comprises a substitution at F197. In some cases, the CD80 variant polypeptide comprises a substitution at F108; and the 4-1BBL variant comprises a substitution at Q210. In some cases, the CD80 variant polypeptide comprises a substitution at F108; and the 4-1BBL variant comprises a substitution at R211. In some cases, the CD80 variant polypeptide comprises a substitution at F108; and the 4-1BBL variant comprises a substitution at L212. In some cases, the CD80 variant polypeptide comprises a substitution at F108; and the 4-1BBL variant comprises a substitution at G213. In some cases, the CD80 variant polypeptide comprises a substitution at F108; and the 4-1BBL variant comprises a substitution at V214. In some cases, the CD80 variant polypeptide comprises a substitution at F108; and the 4-1BBL variant comprises a substitution at H215. In some cases, the CD80 variant polypeptide comprises a substitution at F108; and the 4-1BBL variant comprises a substitution at L216. In some cases, the CD80 variant polypeptide comprises a substitution at F108; and the 4-1BBL variant comprises a substitution at H217. In some cases, the CD80 variant polypeptide comprises a substitution at F108; and the 4-1BBL variant comprises a substitution at T218. In some cases, the CD80 variant polypeptide comprises a substitution at F108; and the 4-1BBL variant comprises a substitution at E219. In some cases, the CD80 variant polypeptide comprises a substitution at F108; and the 4-1BBL variant comprises a substitution at R221. In some cases, the CD80 variant polypeptide comprises a substitution at F108; and the 4-1BBL variant comprises a substitution at R223. In some cases, the CD80 variant polypeptide comprises a substitution at F108; and the 4-1BBL variant comprises a substitution at H224. In some cases, the CD80 variant polypeptide comprises a substitution at F108; and the 4-1BBL variant comprises a substitution at W226. In some cases, the CD80 variant polypeptide comprises a substitution at F108; and the 4-1BBL variant comprises a substitution at L228. In some cases, the CD80 variant polypeptide comprises a substitution at F108; and the 4-1BBL variant comprises a substitution at T229. In some cases, the CD80 variant polypeptide comprises a substitution at F108; and the 4-1BBL variant comprises a substitution at Q230. In some cases, the CD80 variant polypeptide comprises a substitution at F108; and the 4-1BBL variant comprises a substitution at G231. In some cases, the CD80 variant polypeptide comprises a substitution at F108; and the 4-1BBL variant comprises a substitution at T233. In some cases, the CD80 variant polypeptide comprises a substitution at F108; and the 4-1BBL variant comprises a substitution at V234. The amino acid numbering for CD80 is based on the numbering set out in FIG. 2. The amino acid numbering for 4-1BBL is based on the numbering set out in FIG. 3.

In some cases, the CD80 variant polypeptide comprises a substitution at S156; and the 4-1BBL variant comprises a substitution at M91. In some cases, the CD80 variant polypeptide comprises a substitution at S156; and the 4-1BBL variant comprises a substitution at F92. In some cases, the CD80 variant polypeptide comprises a substitution at S156; and the 4-1BBL variant comprises a substitution at Q94. In some cases, the CD80 variant polypeptide comprises a substitution at S156; and the 4-1BBL variant comprises a substitution at L95. In some cases, the CD80 variant polypeptide comprises a substitution at S156; and the 4-1BBL variant comprises a substitution at V96. In some cases, the CD80 variant polypeptide comprises a substitution at S156; and the 4-1BBL variant comprises a substitution at Q98. In some cases, the CD80 variant polypeptide comprises a substitution at S156; and the 4-1BBL variant comprises a substitution at N99. In some cases, the CD80 variant polypeptide comprises a substitution at S156; and the 4-1BBL variant comprises a substitution at V100. In some cases, the CD80 variant polypeptide comprises a substitution at S156; and the 4-1BBL variant comprises a substitution at L101. In some cases, the CD80 variant polypeptide comprises a substitution at S156; and the 4-1BBL variant comprises a substitution at L102. In some cases, the CD80 variant polypeptide comprises a substitution at S156; and the 4-1BBL variant comprises a substitution at I103. In some cases, the CD80 variant polypeptide comprises a substitution at S156; and the 4-1BBL variant comprises a substitution at D104. In some cases, the CD80 variant polypeptide comprises a substitution at S156; and the 4-1BBL variant comprises a substitution at G105. In some cases, the CD80 variant polypeptide comprises a substitution at S156; and the 4-1BBL variant comprises a substitution at P106. In some cases, the CD80 variant polypeptide comprises a substitution at S156; and the 4-1BBL variant comprises a substitution at L107. In some cases, the CD80 variant polypeptide comprises a substitution at S156; and the 4-1BBL variant comprises a substitution at S108. In some cases, the CD80 variant polypeptide comprises a substitution at S156; and the 4-1BBL variant comprises a substitution at W109. In some cases, the CD80 variant polypeptide comprises a substitution at S156; and the 4-1BBL variant comprises a substitution at Y110. In some cases, the CD80 variant polypeptide comprises a substitution at S156; and the 4-1BBL variant comprises a substitution at S111. In some cases, the CD80 variant polypeptide comprises a substitution at S156; and the 4-1BBL variant comprises a substitution at D112. In some cases, the CD80 variant polypeptide comprises a substitution at S156; and the 4-1BBL variant comprises a substitution at P113. In some cases, the CD80 variant polypeptide comprises a substitution at S156; and the 4-1BBL variant comprises a substitution at G114. In some cases, the CD80 variant polypeptide comprises a substitution at S156; and the 4-1BBL variant comprises a substitution at L115. In some cases, the CD80 variant polypeptide comprises a substitution at S156; and the 4-1BBL variant comprises a substitution at G117. In some cases, the CD80 variant polypeptide comprises a substitution at S156; and the 4-1BBL variant comprises a substitution at V118. In some cases, the CD80 variant polypeptide comprises a substitution at S156; and the 4-1BBL variant comprises a substitution at S119. In some cases, the CD80 variant polypeptide comprises a substitution at S156; and the 4-1BBL variant comprises a substitution at L120. In some cases, the CD80 variant polypeptide comprises a substitution at S156; and the 4-1BBL variant comprises a substitution at T121. In some cases, the CD80 variant polypeptide comprises a substitution at S156; and the 4-1BBL variant comprises a substitution at G122. In some cases, the CD80 variant polypeptide comprises a substitution at S156; and the 4-1BBL variant comprises a substitution at G123. In some cases, the CD80 variant polypeptide comprises a substitution at S156; and the 4-1BBL variant comprises a substitution at L124. In some cases, the CD80 variant polypeptide comprises a substitution at S156; and the 4-1BBL variant comprises a substitution at S125. In some cases, the CD80 variant polypeptide comprises a substitution at S156; and the 4-1BBL variant comprises a substitution at Y126. In some cases, the CD80 variant polypeptide comprises a substitution at S156; and the 4-1BBL variant comprises a substitution at E128. In some cases, the CD80 variant polypeptide comprises a substitution at S156; and the 4-1BBL variant comprises a substitution at D129. In some cases, the CD80 variant polypeptide comprises a substitution at S156; and the 4-1BBL variant comprises a substitution at T130. In some cases, the CD80 variant polypeptide comprises a substitution at S156; and the 4-1BBL variant comprises a substitution at K131. In some cases, the CD80 variant polypeptide comprises a substitution at S156; and the 4-1BBL variant comprises a substitution at E132. In some cases, the CD80 variant polypeptide comprises a substitution at S156; and the 4-1BBL variant comprises a substitution at F144. In some cases, the CD80 variant polypeptide comprises a substitution at S156; and the 4-1BBL variant comprises a substitution at F145. In some cases, the CD80 variant polypeptide comprises a substitution at S156; and the 4-1BBL variant comprises a substitution at Q146. In some cases, the CD80 variant polypeptide comprises a substitution at S156; and the 4-1BBL variant comprises a substitution at L147. In some cases, the CD80 variant polypeptide comprises a substitution at S156; and the 4-1BBL variant comprises a substitution at E148. In some cases, the CD80 variant polypeptide comprises a substitution at S156; and the 4-1BBL variant comprises a substitution at L149. In some cases, the CD80 variant polypeptide comprises a substitution at S156; and the 4-1BBL variant comprises a substitution at R150. In some cases, the CD80 variant polypeptide comprises a substitution at S156; and the 4-1BBL variant comprises a substitution at R151. In some cases, the CD80 variant polypeptide comprises a substitution at S156; and the 4-1BBL variant comprises a substitution at V152. In some cases, the CD80 variant polypeptide comprises a substitution at S156; and the 4-1BBL variant comprises a substitution at V153. In some cases, the CD80 variant polypeptide comprises a substitution at S156; and the 4-1BBL variant comprises a substitution at G155. In some cases, the CD80 variant polypeptide comprises a substitution at S156; and the 4-1BBL variant comprises a substitution at E156. In some cases, the CD80 variant polypeptide comprises a substitution at S156; and the 4-1BBL variant comprises a substitution at G157. In some cases, the CD80 variant polypeptide comprises a substitution at S156; and the 4-1BBL variant comprises a substitution at S158. In some cases, the CD80 variant polypeptide comprises a substitution at S156; and the 4-1BBL variant comprises a substitution at D184. In some cases, the CD80 variant polypeptide comprises a substitution at S156; and the 4-1BBL variant comprises a substitution at L185. In some cases, the CD80 variant polypeptide comprises a substitution at S156; and the 4-1BBL variant comprises a substitution at P186. In some cases, the CD80 variant polypeptide comprises a substitution at S156; and the 4-1BBL variant comprises a substitution at P187. In some cases, the CD80 variant polypeptide comprises a substitution at S156; and the 4-1BBL variant comprises a substitution at S189. In some cases, the CD80 variant polypeptide comprises a substitution at S156; and the 4-1BBL variant comprises a substitution at S190. In some cases, the CD80 variant polypeptide comprises a substitution at S156; and the 4-1BBL variant comprises a substitution at E191. In some cases, the CD80 variant polypeptide comprises a substitution at S156; and the 4-1BBL variant comprises a substitution at R193. In some cases, the CD80 variant polypeptide comprises a substitution at S156; and the 4-1BBL variant comprises a substitution at S1564. In some cases, the CD80 variant polypeptide comprises a substitution at S156; and the 4-1BBL variant comprises a substitution at S195. In some cases, the CD80 variant polypeptide comprises a substitution at S156; and the 4-1BBL variant comprises a substitution at F197. In some cases, the CD80 variant polypeptide comprises a substitution at S156; and the 4-1BBL variant comprises a substitution at Q210. In some cases, the CD80 variant polypeptide comprises a substitution at S156; and the 4-1BBL variant comprises a substitution at R211. In some cases, the CD80 variant polypeptide comprises a substitution at S156; and the 4-1BBL variant comprises a substitution at L212. In some cases, the CD80 variant polypeptide comprises a substitution at S156; and the 4-1BBL variant comprises a substitution at G213. In some cases, the CD80 variant polypeptide comprises a substitution at S156; and the 4-1BBL variant comprises a substitution at V214. In some cases, the CD80 variant polypeptide comprises a substitution at S156; and the 4-1BBL variant comprises a substitution at H215. In some cases, the CD80 variant polypeptide comprises a substitution at S156; and the 4-1BBL variant comprises a substitution at L216. In some cases, the CD80 variant polypeptide comprises a substitution at S156; and the 4-1BBL variant comprises a substitution at H217. In some cases, the CD80 variant polypeptide comprises a substitution at S156; and the 4-1BBL variant comprises a substitution at T218. In some cases, the CD80 variant polypeptide comprises a substitution at S156; and the 4-1BBL variant comprises a substitution at E219. In some cases, the CD80 variant polypeptide comprises a substitution at S156; and the 4-1BBL variant comprises a substitution at R221. In some cases, the CD80 variant polypeptide comprises a substitution at S156; and the 4-1BBL variant comprises a substitution at R223. In some cases, the CD80 variant polypeptide comprises a substitution at S156; and the 4-1BBL variant comprises a substitution at H224. In some cases, the CD80 variant polypeptide comprises a substitution at S156; and the 4-1BBL variant comprises a substitution at W226. In some cases, the CD80 variant polypeptide comprises a substitution at S156; and the 4-1BBL variant comprises a substitution at L228. In some cases, the CD80 variant polypeptide comprises a substitution at S156; and the 4-1BBL variant comprises a substitution at T229. In some cases, the CD80 variant polypeptide comprises a substitution at S156; and the 4-1BBL variant comprises a substitution at Q230. In some cases, the CD80 variant polypeptide comprises a substitution at S156; and the 4-1BBL variant comprises a substitution at G231. In some cases, the CD80 variant polypeptide comprises a substitution at S156; and the 4-1BBL variant comprises a substitution at T233. In some cases, the CD80 variant polypeptide comprises a substitution at S156; and the 4-1BBL variant comprises a substitution at V234. The amino acid numbering for CD80 is based on the numbering set out in FIG. 2. The amino acid numbering for 4-1BBL is based on the numbering set out in FIG. 3.

In some cases, the variant CD80 polypeptide is in the first polypeptide chain of a synTac of the present disclosure; and the variant 4-1BBL polypeptide is in the second polypeptide chain of a synTac of the present disclosure. In some cases, the variant 4-1BBL polypeptide is in the first polypeptide chain of a synTac of the present disclosure; and the variant CD80 polypeptide is in the second polypeptide chain of a synTac of the present disclosure. In some cases, the substituted amino acid is substituted with an Ala. In some cases, the substituted amino acid is substituted with a Gly (where the original amino acid is not a Gly). In some cases, the substituted amino acid is substituted with a Val (where the original amino acid is not a Val). In some cases, the substituted amino acid is substituted with a Leu (where the original amino acid is not a Leu). In some cases, the substituted amino acid is substituted with an Ile (where the original amino acid is not an Ile). In some cases, the substituted amino acid is substituted with a Pro (where the original amino acid is not a Pro). In some cases, the substituted amino acid is substituted with a Phe (where the original amino acid is not a Phe). In some cases, the substituted amino acid is substituted with a Tyr (where the original amino acid is not a Tyr). In some cases, the substituted amino acid is substituted with a Trp (where the original amino acid is not a Trp). In some cases, the substituted amino acid is substituted with a Ser (where the original amino acid is not a Ser). In some cases, the substituted amino acid is substituted with a Thr (where the original amino acid is not a Thr). In some cases, the substituted amino acid is substituted with a Cys (where the original amino acid is not a Cys). In some cases, the substituted amino acid is substituted with a Met (where the original amino acid is not a Met). In some cases, the substituted amino acid is substituted with an Asn (where the original amino acid is not an Asn). In some cases, the substituted amino acid is substituted with a Gln (where the original amino acid is not a Gln). In some cases, the substituted amino acid is substituted with a Lys (where the original amino acid is not a Lys). In some cases, the substituted amino acid is substituted with an Arg (where the original amino acid is not an Arg). In some cases, the substituted amino acid is substituted with a His (where the original amino acid is not a His). In some cases, the substituted amino acid is substituted with an Asp (where the original amino acid is not an Asp). In some cases, the substituted amino acid is substituted with a Glu (where the original amino acid is not a Glu).

Nucleic Acids

The present disclosure provides nucleic acids comprising nucleotide sequences encoding a multimeric polypeptide of the present disclosure. In some cases, the individual polypeptide chains of a multimeric polypeptide of the present disclosure are encoded in separate nucleic acids. In some cases, all polypeptide chains of a multimeric polypeptide of the present disclosure are encoded in a single nucleic acid. In some cases, a first nucleic acid comprises a nucleotide sequence encoding a first polypeptide of a multimeric polypeptide of the present disclosure; and a second nucleic acid comprises a nucleotide sequence encoding a second polypeptide of a multimeric polypeptide of the present disclosure. In some cases, single nucleic acid comprises a nucleotide sequence encoding a first polypeptide of a multimeric polypeptide of the present disclosure and a second polypeptide of a multimeric polypeptide of the present disclosure.

Separate Nucleic Acids Encoding Individual Polypeptide Chains of a Multimeric Polypeptide The present disclosure provides nucleic acids comprising nucleotide sequences encoding a multimeric polypeptide of the present disclosure. As noted above, in some cases, the individual polypeptide chains of a multimeric polypeptide of the present disclosure are encoded in separate nucleic acids. In some cases, nucleotide sequences encoding the separate polypeptide chains of a multimeric polypeptide of the present disclosure are operably linked to transcriptional control elements, e.g., promoters, such as promoters that are functional in a eukaryotic cell, where the promoter can be a constitutive promoter or an inducible promoter.

The present disclosure provides a first nucleic acid and a second nucleic acid, where the first nucleic acid comprises a nucleotide sequence encoding a first polypeptide of a multimeric polypeptide of the present disclosure, where the first polypeptide comprises, in order from N-terminus to C-terminus: a) an epitope (e.g., a T-cell epitope); b) a first MHC polypeptide; and c) a first immunomodulatory polypeptide (e.g., a variant CD80 polypeptide or a variant 4-1BBL polypeptide); and where the second nucleic acid comprises a nucleotide sequence encoding a second polypeptide of a multimeric polypeptide of the present disclosure, where the second polypeptide comprises, in order from N-terminus to C-terminus: a) a second immunomodulatory polypeptide (e.g., a variant CD80 polypeptide or a variant 4-1BBL polypeptide); b) a second MHC polypeptide; and c) an Ig Fc polypeptide. Suitable T-cell epitopes, MHC polypeptides, immunomodulatory polypeptides, and Ig Fc polypeptides, are described above. In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

The present disclosure provides a first nucleic acid and a second nucleic acid, where the first nucleic acid comprises a nucleotide sequence encoding a first polypeptide of a multimeric polypeptide of the present disclosure, where the first polypeptide comprises, in order from N-terminus to C-terminus: a) an epitope (e.g., a T-cell epitope); b) a first MHC polypeptide; and c) a first immunomodulatory polypeptide (e.g., a variant CD80 polypeptide or a variant 4-1BBL polypeptide); and where the second nucleic acid comprises a nucleotide sequence encoding a second polypeptide of a multimeric polypeptide of the present disclosure, where the second polypeptide comprises, in order from N-terminus to C-terminus: a) a second immunomodulatory polypeptide (e.g., a variant CD80 polypeptide or a variant 4-1BBL polypeptide); b) a second MHC polypeptide; and c) an Ig Fc polypeptide. Suitable T-cell epitopes, MHC polypeptides, immunomodulatory polypeptides, and Ig Fc polypeptides, are described above. In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

Nucleic Acid Encoding Two or More Polypeptides Present in a Multimeric Polypeptide The present disclosure provides a nucleic acid comprising nucleotide sequences encoding at least the first polypeptide and the second polypeptide of a multimeric polypeptide of the present disclosure. In some cases, where a multimeric polypeptide of the present disclosure includes a first, second, and third polypeptide, the nucleic acid includes a nucleotide sequence encoding the first, second, and third polypeptides. In some cases, the nucleotide sequences encoding the first polypeptide and the second polypeptide of a multimeric polypeptide of the present disclosure include a proteolytically cleavable linker interposed between the nucleotide sequence encoding the first polypeptide and the nucleotide sequence encoding the second polypeptide. In some cases, the nucleotide sequences encoding the first polypeptide and the second polypeptide of a multimeric polypeptide of the present disclosure includes an internal ribosome entry site (IRES) interposed between the nucleotide sequence encoding the first polypeptide and the nucleotide sequence encoding the second polypeptide. In some cases, the nucleotide sequences encoding the first polypeptide and the second polypeptide of a multimeric polypeptide of the present disclosure includes a ribosome skipping signal (or cis-acting hydrolase element, CHYSEL) interposed between the nucleotide sequence encoding the first polypeptide and the nucleotide sequence encoding the second polypeptide. Examples of nucleic acids are described below, where a proteolytically cleavable linker is provided between nucleotide sequences encoding the first polypeptide and the second polypeptide of a multimeric polypeptide of the present disclosure; in any of these embodiments, an IRES or a ribosome skipping signal can be used in place of the nucleotide sequence encoding the proteolytically cleavable linker.

In some cases, a first nucleic acid (e.g., a recombinant expression vector, an mRNA, a viral RNA, etc.) comprises a nucleotide sequence encoding a first polypeptide chain of a multimeric polypeptide of the present disclosure; and a second nucleic acid (e.g., a recombinant expression vector, an mRNA, a viral RNA, etc.) comprises a nucleotide sequence encoding a second polypeptide chain of a multimeric polypeptide of the present disclosure. In some cases, the nucleotide sequence encoding the first polypeptide, and the second nucleotide sequence encoding the second polypeptide, are each operably linked to transcriptional control elements, e.g., promoters, such as promoters that are functional in a eukaryotic cell, where the promoter can be a constitutive promoter or an inducible promoter.

The present disclosure provides a nucleic acid comprising a nucleotide sequence encoding a recombinant polypeptide, where the recombinant polypeptide comprises, in order from N-terminus to C-terminus: a) an epitope (e.g., a T-cell epitope); b) a first MHC polypeptide; c) a first immunomodulatory polypeptide (e.g., a variant CD80 polypeptide or a variant 4-1BBL polypeptide); d) a proteolytically cleavable linker; e) a second immunomodulatory polypeptide (e.g., a variant CD80 polypeptide or a variant 4-1BBL polypeptide); f) a second MHC polypeptide; and g) an immunoglobulin (Ig) Fc polypeptide. The present disclosure provides a nucleic acid comprising a nucleotide sequence encoding a recombinant polypeptide, where the recombinant polypeptide comprises, in order from N-terminus to C-terminus: a) a first leader peptide; b) the epitope; c) the first MHC polypeptide; d) the first immunomodulatory polypeptide (e.g., a variant CD80 polypeptide or a variant 4-1BBL polypeptide); e) the proteolytically cleavable linker; f) a second leader peptide; g) the second immunomodulatory polypeptide (e.g., a variant CD80 polypeptide or a variant 4-1BBL polypeptide); h) the second MHC polypeptide; and i) the Ig Fc polypeptide. The present disclosure provides a nucleic acid comprising a nucleotide sequence encoding a recombinant polypeptide, where the recombinant polypeptide comprises, in order from N-terminus to C-terminus: a) an epitope; b) a first MHC polypeptide; c) a proteolytically cleavable linker; d) a first immunomodulatory polypeptide (e.g., a variant CD80 polypeptide or a variant 4-1BBL polypeptide); e) a second immunomodulatory polypeptide (e.g., a variant CD80 polypeptide or a variant 4-1BBL polypeptide); f) a second MHC polypeptide; and g) an Ig Fc polypeptide. In some cases, the first leader peptide and the second leader peptide is a β2-M leader peptide. In some cases, the nucleotide sequence is operably linked to a transcriptional control element. In some cases, the transcriptional control element is a promoter that is functional in a eukaryotic cell.

Suitable MHC polypeptides are described above. In some cases, the first MHC polypeptide is a β2-microglobulin polypeptide; and wherein the second MHC polypeptide is an MHC class I heavy chain polypeptide. In some cases, the β2-microglobulin polypeptide comprises an amino acid sequence having at least 85%, at least 90%, at least 95%, at least 98%, at least 99%, or 100%, amino acid sequence identity to one of the amino acid sequences depicted in FIG. 8. In some cases, the MHC class I heavy chain polypeptide is an HLA-A, HLA-B, HLA-C, HLA-E, HLA-F, HLA-G, HLA-K, or HLA-L heavy chain. In some cases, the MHC class I heavy chain polypeptide comprises an amino acid sequence having at least 85%, at least 90%, at least 95%, at least 98%, at least 99%, or 100%, amino acid sequence identity to the amino acid sequence depicted in one of FIG. 7A-7C. In some cases, the first MHC polypeptide is an MHC Class II alpha chain polypeptide; and wherein the second MHC polypeptide is an MHC class II beta chain polypeptide.

Suitable Fc polypeptides are described above. In some cases, the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide. In some cases, the Ig Fc polypeptide comprises an amino acid sequence having at least 85%, at least 90%, at least 95%, at least 98%, at least 99%, or 100%, amino acid sequence identity to an amino acid sequence depicted in FIGS. 6A-6C.

Suitable immunomodulatory polypeptides are described above.

Suitable proteolytically cleavable linkers are described above. In some cases, the proteolytically cleavable linker comprises an amino acid sequence selected from:

a)
(SEQ ID NO: 28)
LEVLFQGP;

b)
(SEQ ID NO: 29)
ENLYTQS;

c)
(SEQ ID NO: 30)
DDDDK;

d)
(SEQ ID NO: 31)
LVPR;
and e)
(SEQ ID NO: 32)
GSGATNFSLLKQAGDVEENPGP.

In some cases, a linker between the epitope and the first MHC polypeptide comprises a first Cys residue, and the second MHC polypeptide comprises an amino acid substitution to provide a second Cys residue, such that the first and the second Cys residues provide for a disulfide linkage between the linker and the second MHC polypeptide. In some cases, first MHC polypeptide comprises an amino acid substitution to provide a first Cys residue, and the second MHC polypeptide comprises an amino acid substitution to provide a second Cys residue, such that the first Cys residue and the second Cys residue provide for a disulfide linkage between the first MHC polypeptide and the second MHC polypeptide.

Recombinant Expression Vectors

The present disclosure provides recombinant expression vectors comprising nucleic acids of the present disclosure. In some cases, the recombinant expression vector is a non-viral vector. In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, a non-integrating viral vector, etc.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology,* 153:516-544).

In some embodiments, a nucleotide sequence encoding a DNA-targeting RNA and/or a site-directed modifying polypeptide is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some embodiments, a nucleotide sequence encoding a DNA-targeting RNA and/or a site-directed modifying polypeptide is operably linked to multiple control elements that allow expression of the nucleotide sequence encoding a DNA-targeting RNA and/or a site-directed modifying polypeptide in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

Genetically Modified Host Cells

The present disclosure provides a genetically modified host cell, where the host cell is genetically modified with a nucleic acid of the present disclosure.

Suitable host cells include eukaryotic cells, such as yeast cells, insect cells, and mammalian cells. In some cases, the host cell is a cell of a mammalian cell line. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), Chinese hamster ovary (CHO) cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some cases, the host cell is a mammalian cell that has been genetically modified such that it does not synthesize endogenous MHC β2-M.

Methods of Producing a Multimeric Polypeptide

The present disclosure provides methods of producing a multimeric polypeptide of the present disclosure. The methods generally involve culturing, in a culture medium, a host cell that is genetically modified with a recombinant expression vector comprising a nucleotide sequence encoding the multimeric polypeptide; and isolating the multimeric polypeptide from the genetically modified host cell and/or the culture medium. A host cell that is genetically modified with a recombinant expression vector comprising a nucleotide sequence encoding the multimeric polypeptide is also referred to as an "expression host." As noted above, in some cases, the individual polypeptide chains of a multimeric polypeptide of the present disclosure are encoded in separate recombinant expression vectors. In some cases, all polypeptide chains of a multimeric polypeptide of the present disclosure are encoded in a single recombinant expression vector.

Isolation of the multimeric polypeptide from the expression host cell (e.g., from a lysate of the expression host cell) and/or the culture medium in which the host cell is cultured, can be carried out using standard methods of protein purification.

For example, a lysate may be prepared of the expression host and the lysate purified using high performance liquid chromatography (HPLC), exclusion chromatography, gel electrophoresis, affinity chromatography, or other purification technique. Alternatively, where the multimeric polypeptide is secreted from the expression host cell into the culture medium, the multimeric polypeptide can be purified from the culture medium using HPLC, exclusion chromatography, gel electrophoresis, affinity chromatography, or other purification technique. In some cases, the compositions which are used will comprise at least 80% by weight of the desired product, at least about 85% by weight, at least about 95% by weight, or at least about 99.5% by weight, in relation to contaminants related to the method of preparation of the product and its purification. The percentages can be based upon total protein.

In some cases, e.g., where the multimeric polypeptide comprises an affinity tag, the multimeric polypeptide can be purified using an immobilized binding partner of the affinity tag.

Compositions

The present disclosure provides compositions, including pharmaceutical compositions, comprising a multimeric polypeptide of the present disclosure. The present disclosure provides compositions, including pharmaceutical compositions, comprising a nucleic acid or a recombinant expression vector of the present disclosure.

Compositions Comprising a Multimeric Polypeptide

A composition of the present disclosure can comprise, in addition to a multimeric polypeptide of the present disclosure, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS), N-tris[Hydroxymethyl] methyl-3-aminopropanesulfonic acid (TAPS), etc.; a solubilizing agent; a detergent, e.g., a non-ionic detergent such as Tween-20, etc.; a protease inhibitor; glycerol; and the like.

The composition may comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", $19^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A pharmaceutical composition can comprise a multimeric polypeptide of the present disclosure, and a pharmaceutically acceptable excipient. In some cases, a subject pharmaceutical composition will be suitable for administration to a subject, e.g., will be sterile. For example, in some embodiments, a subject pharmaceutical composition will be suitable for administration to a human subject, e.g., where the composition is sterile and is free of detectable pyrogens and/or other toxins.

The protein compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

For example, compositions may include aqueous solution, powder form, granules, tablets, pills, suppositories, capsules, suspensions, sprays, and the like. The composition may be formulated according to the various routes of administration described below.

Where a multimeric polypeptide of the present disclosure is administered as an injectable (e.g. subcutaneously, intraperitoneally, intramuscularly, and/or intravenously) directly into a tissue, a formulation can be provided as a ready-to-use dosage form, or as non-aqueous form (e.g. a reconstitutable storage-stable powder) or aqueous form, such as liquid composed of pharmaceutically acceptable carriers and excipients. The protein-containing formulations may also be provided so as to enhance serum half-life of the subject protein following administration. For example, the protein may be provided in a liposome formulation, prepared as a colloid, or other conventional techniques for extending serum half-life. A variety of methods are available for preparing liposomes, as described in, e.g., Szoka et al. 1980 Ann. Rev. Biophys. Bioeng. 9:467, U.S. Pat. Nos. 4,235,871, 4,501,728 and 4,837,028. The preparations may also be provided in controlled release or slow-release forms.

Other examples of formulations suitable for parenteral administration include isotonic sterile injection solutions, anti-oxidants, bacteriostats, and solutes that render the formulation isotonic with the blood of the intended recipient, suspending agents, solubilizers, thickening agents, stabilizers, and preservatives. For example, a subject pharmaceutical composition can be present in a container, e.g., a sterile container, such as a syringe. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The concentration of a multimeric polypeptide of the present disclosure in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

The present disclosure provides a container comprising a composition of the present disclosure, e.g., a liquid composition. The container can be, e.g., a syringe, an ampoule, and the like. In some cases, the container is sterile. In some cases, both the container and the composition are sterile.

Compositions Comprising a Nucleic Acid or a Recombinant Expression Vector

The present disclosure provides compositions, e.g., pharmaceutical compositions, comprising a nucleic acid or a recombinant expression vector of the present disclosure. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A composition of the present disclosure can include: a) a subject nucleic acid or recombinant expression vector; and b) one or more of: a buffer, a surfactant, an antioxidant, a hydrophilic polymer, a dextrin, a chelating agent, a suspending agent, a solubilizer, a thickening agent, a stabilizer, a bacteriostatic agent, a wetting agent, and a preservative. Suitable buffers include, but are not limited to, (such as N,N-bis(2-hydroxyethyl)-2-aminoethanesulfonic acid (BES), bis(2-hydroxyethyl)amino-tris(hydroxymethyl) methane (BIS-Tris), N-(2-hydroxyethyl)piperazine-N'3-propanesulfonic acid (EPPS or HEPPS), glycylglycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris (hydroxymethyl)-aminomethane (Tris), etc.). Suitable salts include, e.g., NaCl, $MgCl_2$, KCl, $MgSO_4$, etc.

A pharmaceutical formulation of the present disclosure can include a nucleic acid or recombinant expression vector of the present disclosure in an amount of from about 0.001% to about 90% (w/w). In the description of formulations, below, "subject nucleic acid or recombinant expression vector" will be understood to include a nucleic acid or recombinant expression vector of the present disclosure. For example, in some embodiments, a subject formulation comprises a nucleic acid or recombinant expression vector of the present disclosure.

A subject nucleic acid or recombinant expression vector can be admixed, encapsulated, conjugated or otherwise associated with other compounds or mixtures of compounds; such compounds can include, e.g., liposomes or receptor-targeted molecules. A subject nucleic acid or recombinant expression vector can be combined in a formulation with one or more components that assist in uptake, distribution and/or absorption.

A subject nucleic acid or recombinant expression vector composition can be formulated into any of many possible dosage forms such as, but not limited to, tablets, capsules, gel capsules, liquid syrups, soft gels, suppositories, and enemas. A subject nucleic acid or recombinant expression vector composition can also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

A formulation comprising a subject nucleic acid or recombinant expression vector can be a liposomal formulation. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that can interact with negatively charged DNA molecules to form a stable complex. Liposomes that are pH sensitive or negatively charged are believed to entrap DNA rather than complex with it. Both cationic and non-cationic liposomes can be used to deliver a subject nucleic acid or recombinant expression vector.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein by reference in its entirety.

The formulations and compositions of the present disclosure may also include surfactants. The use of surfactants in drug products, formulations and in emulsions is well known in the art. Surfactants and their uses are further described in U.S. Pat. No. 6,287,860.

In one embodiment, various penetration enhancers are included, to effect the efficient delivery of nucleic acids. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein by reference in its entirety.

Compositions and formulations for oral administration include powders or granules, microparticulates, nanoparticulates, suspensions or solutions in water or non-aqueous media, capsules, gel capsules, sachets, tablets, or minitablets. Thickeners, flavoring agents, diluents, emulsifiers, dispersing aids or binders may be desirable. Suitable oral formulations include those in which a subject antisense nucleic acid is administered in conjunction with one or more penetration enhancers surfactants and chelators. Suitable surfactants include, but are not limited to, fatty acids and/or esters or salts thereof, bile acids and/or salts thereof. Suitable bile acids/salts and fatty acids and their uses are further described in U.S. Pat. No. 6,287,860. Also suitable are combinations of penetration enhancers, for example, fatty acids/salts in combination with bile acids/salts. An exemplary suitable combination is the sodium salt of lauric acid, capric acid, and UDCA. Further penetration enhancers include, but are not limited to, polyoxyethylene-9-lauryl ether, and polyoxyethylene-20-cetyl ether. Suitable penetration enhancers also include propylene glycol, dimethylsulfoxide, triethanoiamine, N,N-dimethylacetamide, N,N-dimethylformamide, 2-pyrrolidone and derivatives thereof, tetrahydrofurfuryl alcohol, and AZONE™.

Methods of Modulating T Cell Activity

The present disclosure provides a method of selectively modulating the activity of an epitope-specific T cell, the method comprising contacting the T cell with a multimeric polypeptide of the present disclosure, where contacting the T cell with a multimeric polypeptide of the present disclosure selectively modulates the activity of the epitope-specific T cell. In some cases, the contacting occurs in vitro. In some cases, the contacting occurs in vivo. In some cases, the contacting occurs ex vivo.

In some cases, e.g., where the target T cell is a $CD8^+$ T cell, the multimeric polypeptide comprises Class I MHC polypeptides (e.g., β2-microglobulin and Class I MHC heavy chain). In some cases, e.g., where the target T cell is a $CD4^+$ T cell, the multimeric polypeptide comprises Class II MHC polypeptides (e.g., Class II MHC α chain; Class II MHC β chain).

Where a multimeric polypeptide of the present disclosure includes an immunomodulatory polypeptide that is an activating polypeptide, contacting the T cell with the multimeric polypeptide activates the epitope-specific T cell. In some instances, the epitope-specific T cell is a T cell that is specific for an epitope present on a cancer cell, and contacting the epitope-specific T cell with the multimeric polypeptide increases cytotoxic activity of the T cell toward the cancer cell. In some instances, the epitope-specific T cell is a T cell that is specific for an epitope present on a cancer cell, and contacting the epitope-specific T cell with the multimeric polypeptide increases the number of the epitope-specific T cells.

In some instances, the epitope-specific T cell is a T cell that is specific for an epitope present on a virus-infected cell, and contacting the epitope-specific T cell with the multimeric polypeptide increases cytotoxic activity of the T cell toward the virus-infected cell. In some instances, the epitope-specific T cell is a T cell that is specific for an epitope present on a virus-infected cell, and contacting the epitope-specific T cell with the multimeric polypeptide increases the number of the epitope-specific T cells.

Treatment Methods

The present invention provides a method of selectively modulating the activity of an epitope-specific T cell in an individual, the method comprising administering to the individual an amount of the multimeric polypeptide of the present disclosure, or one or more nucleic acids encoding the multimeric polypeptide, effective to selectively modulate the activity of an epitope-specific T cell in an individual. In some cases, a treatment method of the present disclosure comprises administering to an individual in need thereof one or more recombinant expression vectors comprising nucleotide sequences encoding a multimeric polypeptide of the present disclosure. In some cases, a treatment method of the present disclosure comprises administering to an individual in need thereof one or more mRNA molecules comprising nucleotide sequences encoding a multimeric polypeptide of the present disclosure. In some cases, a treatment method of the present disclosure comprises administering to an individual in need thereof a multimeric polypeptide of the present disclosure.

The present disclosure provides a method of selectively modulating the activity of an epitope-specific T cell in an individual, the method comprising administering to the individual an effective amount of a multimeric polypeptide of the present disclosure, or one or more nucleic acids (e.g., expression vectors; mRNA; etc.) comprising nucleotide sequences encoding the multimeric polypeptide, where the multimeric polypeptide selectively modulates the activity of the epitope-specific T cell in the individual. Selectively modulating the activity of an epitope-specific T cell can treat a disease or disorder in the individual. Thus, the present disclosure provides a treatment method comprising administering to an individual in need thereof an effective amount of a multimeric polypeptide of the present disclosure.

In some cases, the immunomodulatory polypeptide is an activating polypeptide, and the multimeric polypeptide activates the epitope-specific T cell. In some cases, the epitope is a cancer-associated epitope, and the multimeric polypeptide increases the activity of a T cell specific for the cancer-associate epitope.

The present disclosure provides a method of treating cancer in an individual, the method comprising administering to the individual an effective amount of a multimeric polypeptide of the present disclosure, or one or more nucleic acids (e.g., expression vectors; mRNA; etc.) comprising nucleotide sequences encoding the multimeric polypeptide, where the multimeric polypeptide comprises a T-cell epitope that is a cancer epitope, and where the multimeric polypeptide comprises a stimulatory immunomodulatory polypeptide. In some cases, an "effective amount" of a multimeric polypeptide is an amount that, when administered in one or more doses to an individual in need thereof, reduces the number of cancer cells in the individual. For example, in some cases, an "effective amount" of a multimeric polypeptide of the present disclosure is an amount that, when administered in one or more doses to an individual in need thereof, reduces the number of cancer cells in the individual by at least 10%, at least 15%, at least 20%, at least 25%, at least 30%, at least 40%, at least 50%, at least 60%, at least 70%, at least 80%, at least 90%, or at least 95%, compared to the number of cancer cells in the individual before administration of the multimeric polypeptide, or in the absence of administration with the multimeric polypeptide. In some cases, an "effective amount" of a multimeric polypeptide of the present disclosure is an amount that, when administered in one or more doses to an individual in need thereof, reduces the number of cancer cells in the individual to undetectable levels. In some cases, an "effective amount" of a multimeric polypeptide of the present disclosure is an amount that, when administered in one or more doses to an individual in need thereof, reduces the tumor mass in the individual. For example, in some cases, an "effective amount" of a multimeric polypeptide of the present disclosure is an amount that, when administered in one or more doses to an individual in need thereof, reduces the tumor mass in the individual by at least 10%, at least 15%, at least 20%, at least 25%, at least 30%, at least 40%, at least 50%, at least 60%, at least 70%, at least 80%, at least 90%, or at least 95%, compared to the tumor mass in the individual before administration of the multimeric polypeptide, or in the absence of administration with the multimeric polypeptide. In some cases, an "effective amount" of a multimeric polypeptide of the present disclosure is an amount that, when administered in one or more doses to an individual in need thereof, increases survival time of the individual. For example, in some cases, an "effective amount" of a multimeric polypeptide of the present disclosure is an amount that, when administered in one or more doses to an individual in need thereof, increases survival time of the individual by at least 1 month, at least 2 months, at least 3 months, from 3 months to 6 months, from 6 months to 1 year, from 1 year to 2 years, from 2 years to 5 years, from 5 years to 10 years, or more than 10 years, compared to the expected survival time of the individual in the absence of administration with the multimeric polypeptide.

In some instances, the epitope-specific T cell is a T cell that is specific for an epitope present on a virus-infected cell, and contacting the epitope-specific T cell with the multimeric polypeptide increases cytotoxic activity of the T cell toward the virus-infected cell. In some instances, the epitope-specific T cell is a T cell that is specific for an epitope present on a virus-infected cell, and contacting the epitope-specific T cell with the multimeric polypeptide increases the number of the epitope-specific T cells.

Thus, the present disclosure provides a method of treating a virus infection in an individual, the method comprising administering to the individual an effective amount of a multimeric polypeptide of the present disclosure, or one or more nucleic acids comprising nucleotide sequences encoding the multimeric polypeptide, where the multimeric polypeptide comprises a T-cell epitope that is a viral epitope, and where the multimeric polypeptide comprises a stimulatory immunomodulatory polypeptide. In some cases, an "effective amount" of a multimeric polypeptide is an amount that, when administered in one or more doses to an individual in need thereof, reduces the number of virus-infected cells in the individual. For example, in some cases, an "effective amount" of a multimeric polypeptide of the present disclosure is an amount that, when administered in one or more doses to an individual in need thereof, reduces the number of virus-infected cells in the individual by at least 10%, at least 15%, at least 20%, at least 25%, at least 30%, at least 40%, at least 50%, at least 60%, at least 70%, at least 80%, at least 90%, or at least 95%, compared to the number of virus-infected cells in the individual before administration of the multimeric polypeptide, or in the absence of administration with the multimeric polypeptide. In some cases, an "effective amount" of a multimeric polypeptide of the present disclosure is an amount that, when administered in one or more doses to an individual in need thereof, reduces the number of virus-infected cells in the individual to undetectable levels.

Thus, the present disclosure provides a method of treating an infection in an individual, the method comprising administering to the individual an effective amount of a multimeric polypeptide of the present disclosure, or one or more nucleic acids comprising nucleotide sequences encoding the multimeric polypeptide, where the multimeric polypeptide comprises a T-cell epitope that is a pathogen-associated epitope, and where the multimeric polypeptide comprises a stimulatory immunomodulatory polypeptide. In some cases, an "effective amount" of a multimeric polypeptide is an amount that, when administered in one or more doses to an individual in need thereof, reduces the number of pathogens in the individual. For example, in some cases, an "effective amount" of a multimeric polypeptide of the present disclosure is an amount that, when administered in one or more doses to an individual in need thereof, reduces the number of pathogens in the individual by at least 10%, at least 15%, at least 20%, at least 25%, at least 30%, at least 40%, at least 50%, at least 60%, at least 70%, at least 80%, at least 90%, or at least 95%, compared to the number of pathogens in the individual before administration of the multimeric polypeptide, or in the absence of administration with the multimeric polypeptide. In some cases, an "effective amount" of a multimeric polypeptide of the present disclosure is an amount that, when administered in one or more doses to an individual in need thereof, reduces the number of pathogens in the individual to undetectable levels. Pathogens include viruses, bacteria, protozoans, and the like.

As noted above, in some cases, in carrying out a subject treatment method, a multimeric polypeptide of the present disclosure is administered to an individual in need thereof, as the polypeptide per se. In other instances, in carrying out a subject treatment method, one or more nucleic acids comprising nucleotide sequences encoding a multimeric polypeptide of the present disclosure is/are administering to an individual in need thereof. Thus, in other instances, one or more nucleic acids of the present disclosure, e.g., one or more recombinant expression vectors of the present disclosure, is/are administered to an individual in need thereof.

Formulations

Suitable formulations are described above, where suitable formulations include a pharmaceutically acceptable excipient. In some cases, a suitable formulation comprises: a) a multimeric polypeptide of the present disclosure; and b) a pharmaceutically acceptable excipient. In some cases, a suitable formulation comprises: a) a nucleic acid comprising a nucleotide sequence encoding a multimeric polypeptide of the present disclosure; and b) a pharmaceutically acceptable excipient; in some instances, the nucleic acid is an mRNA. In some cases, a suitable formulation comprises: a) a first nucleic acid comprising a nucleotide sequence encoding the first polypeptide of a multimeric polypeptide of the present disclosure; b) a second nucleic acid comprising a nucleotide sequence encoding the second polypeptide of a multimeric polypeptide of the present disclosure; and c) a pharmaceutically acceptable excipient. In some cases, a suitable formulation comprises: a) a recombinant expression vector comprising a nucleotide sequence encoding a multimeric polypeptide of the present disclosure; and b) a pharmaceutically acceptable excipient. In some cases, a suitable formulation comprises: a) a first recombinant expression vector comprising a nucleotide sequence encoding the first polypeptide of a multimeric polypeptide of the present disclosure; b) a second recombinant expression vector comprising a nucleotide sequence encoding the second polypeptide of a multimeric polypeptide of the present disclosure; and c) a pharmaceutically acceptable excipient.

Suitable pharmaceutically acceptable excipients are described above.

Dosages

A suitable dosage can be determined by an attending physician or other qualified medical personnel, based on various clinical factors. As is well known in the medical arts, dosages for any one patient depend upon many factors, including the patient's size, body surface area, age, the particular polypeptide or nucleic acid to be administered, sex of the patient, time, and route of administration, general health, and other drugs being administered concurrently. A multimeric polypeptide of the present disclosure may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute.

In some cases, a suitable dose of a multimeric polypeptide of the present disclosure is from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight. Persons of ordinary skill in the art can easily estimate repetition rates for dosing based on measured residence times and concentrations of the administered agent in bodily fluids or tissues. Following successful treatment, it may be desirable to have the patient undergo maintenance therapy to prevent the recurrence of the disease state, wherein a multimeric polypeptide of the present disclosure is administered in maintenance doses, ranging from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight.

Those of skill will readily appreciate that dose levels can vary as a function of the specific multimeric polypeptide, the severity of the symptoms and the susceptibility of the subject to side effects. Preferred dosages for a given compound are readily determinable by those of skill in the art by a variety of means.

In some embodiments, multiple doses of a multimeric polypeptide of the present disclosure, a nucleic acid of the present disclosure, or a recombinant expression vector of the present disclosure are administered. The frequency of administration of a multimeric polypeptide of the present disclosure, a nucleic acid of the present disclosure, or a recombinant expression vector of the present disclosure can vary depending on any of a variety of factors, e.g., severity of the symptoms, etc. For example, in some embodiments, a multimeric polypeptide of the present disclosure, a nucleic acid of the present disclosure, or a recombinant expression vector of the present disclosure is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a multimeric polypeptide of the present disclosure, a nucleic acid of the present disclosure, or a recombinant expression vector of the present disclosure, e.g., the period of time over which a multimeric polypeptide of the present disclosure, a nucleic acid of the present disclosure, or a recombinant expression vector of the present disclosure is administered, can vary, depending on any of a variety of factors, e.g., patient response, etc. For example, a multimeric polypeptide of the present disclosure, a nucleic acid of the present disclosure, or a recombinant expression vector of the present disclosure can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Routes of Administration

An active agent (a multimeric polypeptide of the present disclosure, a nucleic acid of the present disclosure, or a recombinant expression vector of the present disclosure) is administered to an individual using any available method and route suitable for drug delivery, including in vivo and ex vivo methods, as well as systemic and localized routes of administration.

Conventional and pharmaceutically acceptable routes of administration include intratumoral, peritumoral, intramuscular, intratracheal, intracranial, subcutaneous, intradermal, topical application, intravenous, intraarterial, rectal, nasal, oral, and other enteral and parenteral routes of administration. Routes of administration may be combined, if desired, or adjusted depending upon the multimeric polypeptide and/or the desired effect. A multimeric polypeptide of the present disclosure, or a nucleic acid or recombinant expression vector of the present disclosure, can be administered in a single dose or in multiple doses.

In some embodiments, a multimeric polypeptide of the present disclosure, a nucleic acid of the present disclosure, or a recombinant expression vector of the present disclosure is administered intravenously. In some embodiments, a multimeric polypeptide of the present disclosure, a nucleic acid of the present disclosure, or a recombinant expression vector of the present disclosure is administered intramuscularly. In some embodiments, a multimeric polypeptide of the present disclosure, a nucleic acid of the present disclosure, or a recombinant expression vector of the present disclosure is administered locally. In some embodiments, a multimeric polypeptide of the present disclosure, a nucleic acid of the present disclosure, or a recombinant expression vector of the present disclosure is administered intratumorally. In some embodiments, a multimeric polypeptide of the present disclosure, a nucleic acid of the present disclosure, or a recombinant expression vector of the present disclosure is administered peritumorally. In some embodiments, a multimeric polypeptide of the present disclosure, a nucleic acid of the present disclosure, or a recombinant expression vector of the present disclosure is administered intracranially. In some embodiments, a multimeric polypeptide of the present disclosure, a nucleic acid of the present disclosure, or a recombinant expression vector of the present disclosure is administered subcutaneously.

In some embodiments, a multimeric polypeptide of the present disclosure is administered intravenously. In some embodiments, a multimeric polypeptide of the present disclosure is administered intramuscularly. In some embodiments, a multimeric polypeptide of the present disclosure is administered locally. In some embodiments, a multimeric polypeptide of the present disclosure is administered intratumorally. In some embodiments, a multimeric polypeptide of the present disclosure is administered peritumorally. In some embodiments, a multimeric polypeptide of the present disclosure is administered intracranially. In some embodiments, a multimeric polypeptide is administered subcutaneously.

A multimeric polypeptide of the present disclosure, a nucleic acid of the present disclosure, or a recombinant expression vector of the present disclosure can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, intratumoral, peritumoral, and intravenous routes, i.e., any route of administration other than through the alimentary canal. Parenteral administration can be carried to effect systemic or local delivery of a multimeric polypeptide of the present disclosure, a nucleic acid of the present disclosure, or a recombinant expression vector of the present disclosure. Where systemic delivery is desired, administration typically involves invasive or systemically absorbed topical or mucosal administration of pharmaceutical preparations.

Subjects Suitable for Treatment

Subjects suitable for treatment with a method of the present disclosure include individuals who have cancer, including individuals who have been diagnosed as having cancer, individuals who have been treated for cancer but who failed to respond to the treatment, and individuals who have been treated for cancer and who initially responded but subsequently became refractory to the treatment.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-68 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A multimeric polypeptide comprising: a) a first polypeptide comprising, in order from N-terminus to C-terminus: i) an epitope; ii) a first major histocompatibility complex (MHC) polypeptide; and b) a second polypeptide comprising, in order from N-terminus to C-terminus: i) a second MHC polypeptide; and ii) optionally an immunoglobulin (Ig) Fc polypeptide or a non-Ig scaffold, wherein the multimeric polypeptide comprises at least a first and a second immunomodulatory domain, wherein the first and the second immunomodulatory domains are each independently: A) at the C-terminus of the first polypeptide; B) at the N-terminus of the second polypeptide; C) at the C-terminus of the second polypeptide; or D) at the C-terminus of the first polypeptide and at the N-terminus of the second polypeptide, wherein one of the first and second immunomodulatory domains is a variant CD80 polypeptide having at least one amino acid substitution relative to SEQ ID NO:1, wherein one of the first and second immunomodulatory domains is a variant 4-1BBL polypeptide having at least one amino acid substitution relative to one of SEQ ID NOs:2-4.

Aspect 2. The multimeric polypeptide of aspect 1, wherein the multimeric polypeptide exhibits reduced binding affinity to a CD28 polypeptide having an amino acid sequence depicted in one of FIG. 4A-4C, compared to the binding affinity of a control multimeric polypeptide comprising an immunomodulatory domain comprising the CD80 amino acid sequence depicted in FIG. 2, or compared to the binding affinity of a control multimeric polypeptide comprising an immunomodulatory domain comprising the CD80 amino acid sequence as set forth in SEQ ID NO:1, for the CD28 polypeptide, and/or wherein: i) the multimeric polypeptide exhibits reduced binding affinity to a 4-1BB polypeptide having an amino acid sequence depicted in FIG. 5, compared to the binding affinity of a control multimeric polypeptide comprising an immunomodulatory domain comprising the 4-1BBL amino acid sequence depicted in FIG. 3 or set forth in one of SEQ ID NOs:2-4 for the 4-1BB polypeptide.

Aspect 3. The multimeric polypeptide of aspect 1 or 2, wherein the multimeric polypeptide comprises: a) a first polypeptide comprising, in order from N-terminus to C-terminus: i) the epitope; ii) the first MHC polypeptide; and iii) a variant 4-1BBL polypeptide; and b) a second polypeptide comprising, in order from N-terminus to C-terminus: i) a variant CD80 polypeptide; ii) the second MHC polypeptide.

Aspect 4. The multimeric polypeptide of aspect 1, wherein the multimeric polypeptide comprises: a) a first polypeptide comprising, in order from N-terminus to C-terminus: i) the epitope; ii) the first MHC polypeptide; and iii) a variant CD80 polypeptide; and b) a second polypeptide comprising, in order from N-terminus to C-terminus: i) a variant 4-1BBL polypeptide; ii) the second MHC polypeptide.

Aspect 5. The multimeric polypeptide of aspect 1, wherein the non-Ig scaffold is an XTEN polypeptide, a transferrin polypeptide, an elastin-like polypeptide, a silk-like polypeptide, or a silk-elastin-like polypeptide.

Aspect 6. The multimeric polypeptide of any one of aspects 1-5, wherein the first MHC polypeptide is a β2-microglobulin polypeptide; and wherein the second MHC polypeptide is an MHC class I heavy chain polypeptide.

Aspect 7. The multimeric polypeptide of aspect 6, wherein the β2-microglobulin polypeptide comprises an amino acid sequence having at least 85% amino acid sequence identity to one of the amino acid sequences set forth in FIG. 8.

Aspect 8. The multimeric polypeptide of aspect 6, wherein the MHC class I heavy chain polypeptide is an HLA-A, an HLA-B, or an HLA-C heavy chain.

Aspect 9. The multimeric polypeptide of aspect 8, wherein the MHC class I heavy chain polypeptide comprises an amino acid sequence having at least 85% amino acid sequence identity to the amino acid sequence set forth in one of FIG. 7A-7C.

Aspect 10. The multimeric polypeptide of any one of aspects 1-5, wherein the first MHC polypeptide is an MHC Class II alpha chain polypeptide; and wherein the second MHC polypeptide is an MHC class II beta chain polypeptide.

Aspect 11. The multimeric polypeptide of any one of aspects 1-10, wherein the epitope is a T-cell epitope.

Aspect 12. The multimeric polypeptide of any one of aspects 1-11, wherein multimeric polypeptide comprises an Fc polypeptide, and wherein the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide; optionally where the IgFc polypeptide comprises an amino acid substitution that provides for reduced effector function.

Aspect 13. The multimeric polypeptide of aspect 12, wherein the Ig Fc polypeptide comprises an amino acid sequence having at least 85% amino acid sequence identity to an amino acid sequence depicted in FIG. 6A-6C.

Aspect 14. The multimeric polypeptide of any one of aspects 1-13, wherein the first polypeptide and the second polypeptide are non-covalently associated.

Aspect 15. The multimeric polypeptide of any one of aspects 1-13, wherein the first polypeptide and the second polypeptide are covalently linked.

Aspect 16. The multimeric polypeptide of aspect 15, wherein the covalent linkage is via a disulfide bond.

Aspect 17. The multimeric polypeptide of aspect 16, wherein the first MHC polypeptide or a linker between the epitope and the first MHC polypeptide comprises an amino acid substitution to provide a first Cys residue, and the second MHC polypeptide comprises an amino acid substitution to provide a second Cys residue, and wherein the disulfide linkage is between the first and the second Cys residues.

Aspect 18. The multimeric polypeptide of any one of aspects 1-17, comprising a first linker interposed between the epitope and the first MHC polypeptide.

Aspect 19. The multimeric polypeptide of any one of aspects 1-18, wherein the first or the second immunomodulatory polypeptide is a variant CD80 immunomodulatory polypeptide that comprises a substitution of amino acid I67, K86, or D158.

Aspect 20. The multimeric polypeptide of any one of aspects 1-18, wherein the first or the second immunomodulatory polypeptide is a variant 4-1BBL immunomodulatory polypeptide that comprises a substitution of K127.

Aspect 21. The multimeric polypeptide of any one of aspects 1-20, wherein the variant 4-1BBL polypeptide comprises an amino acid sequence having at least 90% amino acid sequence identity to the amino acid sequence PAGLLD-LRQG MFAQLVAQNV LLIDGPLSWY SDPGLAGVSL TGGLSYXEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEI-PAGLPS PRSE (SEQ ID NO:11), wherein X is Ala, Gly, Val, Ile, Leu, Arg, His, Glu, or Asp.

Aspect 22. The multimeric polypeptide of aspect 21, wherein the variant CD80 polypeptide comprises an amino acid sequence having at least 90% amino acid sequence identity to the amino acid sequence VIHVTK EVKEV-ATLSC GHNVSVEELA QTRIYWQKEK KMVLTMMSGD MNIWPEYKNR TIFDITNNLS XVILA-LRPSD EGTYECVVLK YEKDAFKREH LAEVTLSVKA DFPTPSISDF EIPTSNIRRI ICSTSGGFPE PHLSW-LENGE ELNAINTTVS QDPETELYAV SSKLDFNMTT NHSFMCLIKY GHLRVNQTFN WNTTKQEHFP DN (SEQ ID NO:5), where X is Ala, Gly, Val, Leu, Arg, His, Lys, Glu, or Asp.

Aspect 23. The multimeric polypeptide of aspect 21, wherein the variant CD80 polypeptide comprises an amino acid sequence having at least 90% amino acid sequence identity to the amino acid sequence VIHVTK EVKEV-ATLSC GHNVSVEELA QTRIYWQKEK KMVLTMMSGD MNIWPEYKNR TIFDITNNLS IVILA-LRPSD EGTYECVVLX YEKDAFKREH LAEVTLSVKA DFPTPSISDF EIPTSNIRRI ICSTSGGFPE PHLSW-LENGE ELNAINTTVS QDPETELYAV SSKLDFNMTT NHSFMCLIKY GHLRVNQTFN WNTTKQEHFP DN (SEQ ID NO:7), where X is Ala, Gly, Val, Leu, Ile, Arg, His, Glu, or Asp.

Aspect 24. The multimeric polypeptide of aspect 21, wherein the variant CD80 polypeptide comprises an amino acid sequence having at least 90% amino acid sequence identity to the amino acid sequence VIHVTK EVKEV-ATLSC GHNVSVEELA QTRIYWQKEK KMVLTMMSGD MNIWPEYKNR TIFDITNNLS IVILA-LRPSD EGTYECVVLK YEKDAFKREH LAEVTLSVKA DFPTPSISDF EIPTSNIRRI ICSTSGGFPE PHLSW-LENGE ELNAINTTVS QXPETELYAV SSKLDFNMTT NHSFMCLIKY GHLRVNQTFN WNTTKQEHFP DN (SEQ ID NO:9), where X is Ala, Gly, Val, Leu, Ile, Arg, His, Lys, or Glu.

Aspect 25. A nucleic acid comprising a nucleotide sequence encoding a recombinant polypeptide, wherein the recombinant polypeptide comprises, in order from N-terminus to C-terminus: i) an epitope; ii) a first major histocompatibility complex (MHC) polypeptide; iii) a first immunomodulatory polypeptide; iv) a proteolytically cleavable linker or a ribosome skipping signal; v) a second immunomodulatory polypeptide; vi) a second MHC polypeptide; and vii) an immunoglobulin (Ig) Fc polypeptide or a non-Ig scaffold, wherein one of the first and second immunomodulatory domains is a variant CD80 polypeptide having at least one amino acid substitution relative to SEQ ID NO:1, and wherein one of the first and second immunomodulatory domains is a variant 4-1BBL polypeptide having at least one amino acid substitution relative to one of SEQ ID NOs:2-4.

Aspect 26. The nucleic acid of aspect 25, wherein the first MHC polypeptide is a β2-microglobulin polypeptide; and wherein the second MHC polypeptide is an MHC class I heavy chain polypeptide.

Aspect 27. The nucleic acid of aspect 25, wherein the β2-microglobulin polypeptide comprises an amino acid sequence having at least 85% amino acid sequence identity to any one of the amino acid sequences depicted in FIG. 8.

Aspect 28. The nucleic acid of aspect 25, wherein the MHC class I heavy chain polypeptide is an HLA-A, HLA-B, or HLA-C heavy chain.

Aspect 29. The nucleic acid of aspect 28, wherein the MHC class I heavy chain polypeptide comprises an amino acid sequence having at least 85% amino acid sequence identity to the amino acid sequence depicted in any one of FIG. 7A-7C.

Aspect 30. The nucleic acid of aspect 25, wherein the first MHC polypeptide is an MHC Class II alpha chain polypeptide; and wherein the second MHC polypeptide is an MHC class II beta chain polypeptide.

Aspect 31. The nucleic acid of aspect 25, wherein the epitope is a T-cell epitope.

Aspect 32: The nucleic acid of aspect 25, wherein the Ig Fc polypeptide is an IgG1 Fc polypeptide, an IgG2 Fc polypeptide, an IgG3 Fc polypeptide, an IgG4 Fc polypeptide, an IgA Fc polypeptide, or an IgM Fc polypeptide.

Aspect 33. The nucleic acid of aspect 27, wherein the Ig Fc polypeptide comprises an amino acid sequence having at least 85% amino acid sequence identity to an amino acid sequence depicted in FIGS. 6A-6C.

Aspect 34. The nucleic acid of any one of aspects 25-33, wherein the first or the second immunomodulatory polypeptide is a variant CD80 immunomodulatory polypeptide that comprises a substitution of amino acid I67, K86, or D158.

Aspect 35. The nucleic acid of any one of aspects 25-33, wherein the first or the second immunomodulatory polypeptide is a variant 4-1BBL immunomodulatory polypeptide that comprises a substitution of K127

Aspect 36. The nucleic acid of any one of aspects 25-35, wherein the proteolytically cleavable linker or ribosome skipping signal comprises an amino acid sequence selected from:

a)
(SEQ ID NO: 28)
LEVLFQGP;

b)
(SEQ ID NO: 29)
ENLYTQS;

c)
a furin cleavage site;

d)
(SEQ ID NO: 31)
LVPR;

e)
(SEQ ID NO: 32)
GSGATNFSLLKQAGDVEENPGP;

f)
(SEQ ID NO: 33)
GSGEGRGSLLTCGDVEENPGP;

g)
(SEQ ID NO: 34)
GSGQCTNYALLKLAGDVESNPGP;

h)
(SEQ ID NO: 35)
GSGVKQTLNFDLLKLAGDVESNPGP;

i)
(SEQ ID NO: 36)
LVPRGS;
and j)
(SEQ ID NO: 30)
DDDDK.

Aspect 37. The nucleic acid of aspect 25, wherein the recombinant polypeptide comprises, in order from N-terminus to C-terminus: i) a first leader peptide; ii) the epitope; iii) the first MHC polypeptide; iv) the first immunomodulatory polypeptide; v) a proteolytically cleavable linker or a ribosome skipping signal; vi) a second leader peptide; vii) the second immunomodulatory polypeptide; viii) the second MHC polypeptide; and vii) an Ig Fc polypeptide.

Aspect 38. The nucleic acid of aspect 37, wherein the first leader peptide and the second leader peptide is a β2-M leader peptide.

Aspect 39. The nucleic acid of any one of aspects 25-38, wherein the nucleotide sequence is operably linked to a transcriptional control element.

Aspect 40. The nucleic acid of aspect 39, wherein the transcriptional control element is a promoter that is functional in a eukaryotic cell.

Aspect 41. A recombinant expression vector comprising the nucleic acid of any one of aspects 25-40.

Aspect 42. The recombinant expression vector of aspect 41, wherein the vector is a viral vector or a non-viral vector.

Aspect 43. A host cell genetically modified with the recombinant expression vector of aspect 41 or aspect 42.

Aspect 44. The host cell of aspect 43, wherein the host cell is in vitro.

Aspect 45. The host cell of aspect 43 or 44, wherein the host cell is genetically modified such that the cell does not produce an endogenous MHC β2-microglobulin polypeptide.

Aspect 46. The host cell of aspect 43 or 44, wherein the host cell is a T lymphocyte.

Aspect 47. The host cell of aspect 46, wherein the T lymphocyte is a primary T lymphocyte.

Aspect 48. A composition comprising: a) a first nucleic acid comprising a nucleotide sequence encoding a first polypeptide comprising, in order from N-terminus to C-terminus: i) an epitope; ii) a first major histocompatibility complex (MHC) polypeptide; and iii) a first immunomodulatory polypeptide; and b) a second nucleic acid comprising a nucleotide sequence encoding a second polypeptide comprising, in order from N-terminus to C-terminus: i) a second immunomodulatory polypeptide; ii) a second MHC polypeptide; and iii) an immunoglobulin (Ig) Fc polypeptide, wherein one of the first and second immunomodulatory domains is a variant CD80 polypeptide having at least one amino acid substitution relative to SEQ ID NO:1, and wherein one of the first and second immunomodulatory domains is a variant 4-1BBL polypeptide having at least one amino acid substitution relative to one of SEQ ID NOs:2-4.

Aspect 49. The composition of aspect 48, wherein the first and/or the second nucleic acid is present in a recombinant expression vector.

Aspect 50. A host cell genetically modified with the composition of aspect 48 or aspect 49.

Aspect 51. A method of producing the multimeric polypeptide of any one of aspects 1-24, the method comprising: a) culturing the host cell of any one of aspects 43-47 or 50 in vitro in a culture medium under conditions such that the host cell synthesizes the multimeric polypeptide; and b) isolating the multimeric polypeptide from the host cell and/or from the culture medium.

Aspect 52. The method of aspect 51, wherein the second polypeptide comprises an affinity tag, and wherein said isolating comprises contacting the multimeric polypeptide produced by the cell with a binding partner for the affinity tag, wherein the binding partner is immobilized, thereby immobilizing the multimeric polypeptide.

Aspect 53. The method of aspect 52, comprising eluting the immobilized multimeric polypeptide.

Aspect 54. A method of selectively modulating the activity of an epitope-specific T cell, the method comprising contacting the T cell with the multimeric polypeptide of any one of aspects 1-24, wherein said contacting selectively modulates the activity of the epitope-specific T cell.

Aspect 55. The method of aspect 54, wherein said contacting is in vitro.

Aspect 56. The method of aspect 54, wherein said contacting is in vivo.

Aspect 57. A method of selectively increasing the activity of an epitope-specific T cell in an individual, the method comprising administering to the individual an effective amount of the multimeric polypeptide of any one of aspects 1-24 effective to selectively increase the activity of an epitope-specific T cell in an individual.

Aspect 58. The method of aspect 57, wherein the epitope is a cancer-associated epitope, and wherein said administering selectively increases the activity of a T cell specific for the cancer-associate epitope.

Aspect 59. The method of aspect 57 or aspect 58, wherein said administering is subcutaneous.

Aspect 60. The method of aspect 57 or aspect 58, wherein said administering is intravenous.

Aspect 61. The method of aspect 57 or aspect 58, wherein said administering is intramuscular.

Aspect 62. The method of aspect 57 or aspect 58, wherein said administering is systemic.

Aspect 63. The method of aspect 57 or aspect 58, wherein said administering is distal to a treatment site.

Aspect 64. The method of aspect 57 or aspect 58, wherein said administering is local.

Aspect 65. The method of aspect 57 or aspect 58, wherein said administering is at or near a treatment site.

Aspect 66. The method of aspect 57 or aspect 58, wherein the individual is a human.

Aspect 67. A composition comprising: a) the multimeric polypeptide of any one of aspects 1-24; and b) a pharmaceutically acceptable excipient.

Aspect 68. A composition comprising: a) the nucleic acid of any one of aspects 25-40 or the recombinant expression vector of aspect 41 or aspect 42; and b) a pharmaceutically acceptable excipient.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Generation of synTacs and Expression in CHO Cells

Expression constructs encoding the following synTac were generated: 1) synTac 290-345; 2) synTac 290-348; 3) synTac 639-349; and 4) synTac 617-632.

synTac 290-345 comprises: a) a first polypeptide chain ("345"; amino acid sequence depicted in FIG. 10D) comprising: a β2M signal peptide; an ovalbumin (OVA) epitope (SIINFEKL; SEQ ID NO:37); a β2M polypeptide; a linker; a first copy of a wild-type 4-1BBL; a linker; a second copy of the wild-type 4-1BBL; a linker; and a third copy of the wild-type 4-1BBL, where the linker has the sequence:

(SEQ ID NO: 38)
GGGGSGGGGSGGGGSGGGGSGGGGS;

and b) a second polypeptide chain ("290"; amino acid sequence depicted in FIG. 10B) comprising: a β2M signal peptide (MSRSVALAVLALLSLSGLEA; SEQ ID NO:39); a wild-type CD80 polypeptide; an MHC Class I heavy chain; and a γ2a Fc polypeptide, where the CD80 polypeptide is separated from the MHC Class I heavy chain by the linker GGGGSGGGGSGGGGSGGGGSG (SEQ ID NO:26). In FIG. 10B, the CD80 polypeptide is denoted by single underlining; the N- and C-terminii of the MHC Class I heavy chain are double underlined; and the γ2a Fc polypeptide is italicized and in bold. In FIG. 10D, the β2M signal sequence is underlined, italicized, and in bold; the OVA epitope is double underlined; the β2M polypeptide is italicized and in bold; the wild-type 4-1BBL polypeptides are denoted by single underlining; and the linker polypeptides are in bold.

synTac 290-348 comprises: a) a first polypeptide chain ("290"), as described above; and b) a second polypeptide chain ("348"; amino acid sequence depicted in FIG. 10F) comprising: a β2M signal peptide; an OVA peptide (SIINFEKL); a β2M polypeptide; a linker; a first wild-type 4-1BBL; a linker; a second wild-type 4-1BBL; a linker; and a third wild-type 4-1BBL, where the linker has the sequence:

GGGGSGGGGSGGGGSGGGGSGGGGS, and where the first wild-type 4-1BBL polypeptide includes 30 additional N-terminal amino acids, compared to the second and the third wild-type 4-1BBL polypeptides. In FIG. 10F, the β2M signal sequence is underlined, italicized, and in bold; the OVA epitope is double underlined; the β2M polypeptide is italicized and in bold; the wild-type 4-1BBL polypeptides are denoted by single underlining; and the linker polypeptides are in bold.

synTac 639-349 comprises: a) a first polypeptide chain ("639"; sequence depicted in FIG. 10H) comprising: a β2M signal peptide; a variant CD80 polypeptide (K86A); a linker; an MHC Class I H chain; and a variant γ2a Fc polypeptide; and b) a second polypeptide ("349"; amino acid sequence depicted in FIG. 10J) comprising: a β2M signal peptide; an OVA epitope; a I32M polypeptide; a linker; a variant 4-1BBL polypeptide (K127A); a linker; a variant 4-1BBL polypeptide (K127A); a linker; and a variant 4-1BBL polypeptide (K127A). The variant γ2a Fc polypeptide comprises LL-to-AA substitutions, which reduce effector functions. In FIG. 10H, the variant CD80 polypeptide is denoted by single underlining (with the K-to-A substitution in bold and double underlined); the N- and C-terminii of the MHC Class I heavy chain are double underlined; and the variant γ2a Fc polypeptide is italicized and in bold (with the LL-to-AA substitutions double underlined). In FIG. 10J, the β2M signal peptide is underlined, italicized, and in bold; the OVA peptide is double underlined; the β2-M polypeptide is italicized and in bold; the variant type 4-1BBL polypeptides are denoted by single underlining (with the K-to-A substitution in bold and double underlined); and the linker polypeptides are in bold.

synTac 617-632 comprises: a) a first polypeptide chain ("617"; amino acid sequence depicted in FIG. 10L) comprising: a β2M signal peptide; a variant CD80 polypeptide (K86A); a linker; an MHC Class I H chain; and a variant γ2a Fc polypeptide; and b) a second polypeptide chain ("632"; amino acid sequence depicted in FIG. 10N) comprising: a β2M signal peptide; a human papillomavirus 16 E7(49-56) epitope (RAHYNIVTF; SEQ ID NO:40); a β2M polypeptide; a linker; a variant 4-1BBL polypeptide (K127A); a linker; a variant 4-1BBL polypeptide (K127A); a linker; and a variant 4-1BBL polypeptide (K127A). The variant γ2a Fc polypeptide comprises LL-to-AA substitutions, which reduce effector functions. In FIG. 10L, the variant CD80 polypeptide is denoted by single underlining (with the K-to-A substitution in bold and double underlined); the N- and C-terminii of the MHC Class I heavy chain are double underlined; and the variant γ2a Fc polypeptide is italicized and in bold (with the LL-to-AA substitutions double underlined). In FIG. 10N, the β2M signal peptide is underlined, italicized, and in bold; the E7 epitope is double underlined; the β2-M polypeptide is italicized and in bold; the variant type 4-1BBL polypeptides are denoted by single underlining (with the K-to-A substitution in bold and double underlined); and the linker polypeptides are in bold.

Figure 9:
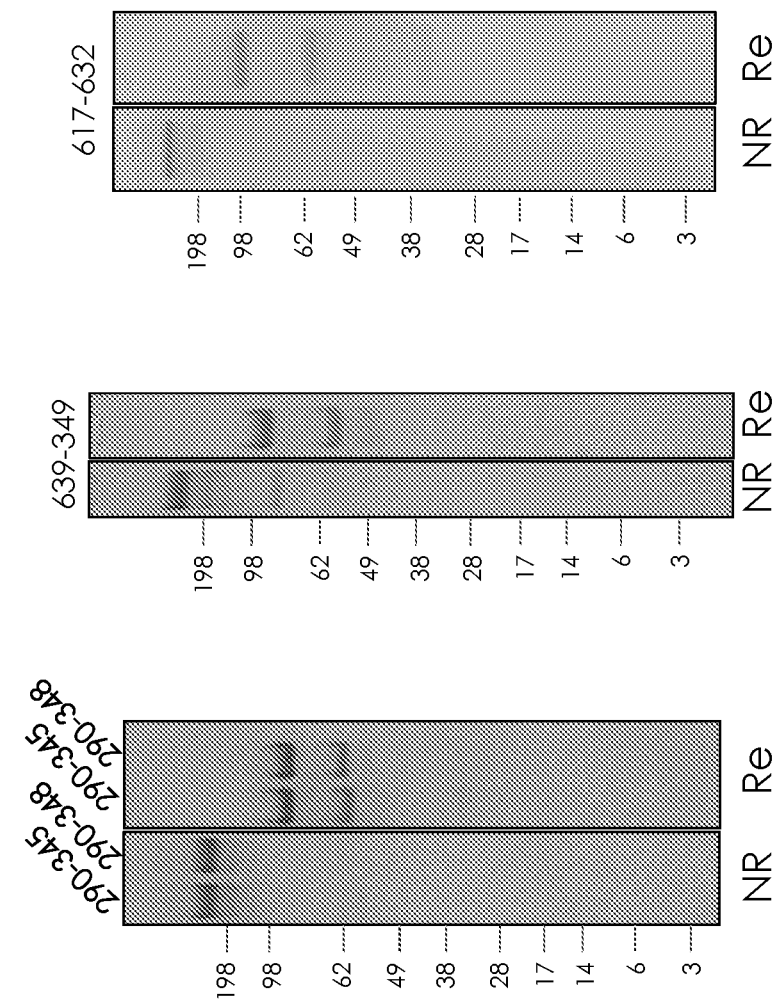
FIG. 9 depicts expression of various synTacs in ExpiCHO-S cells.
Figure 11:
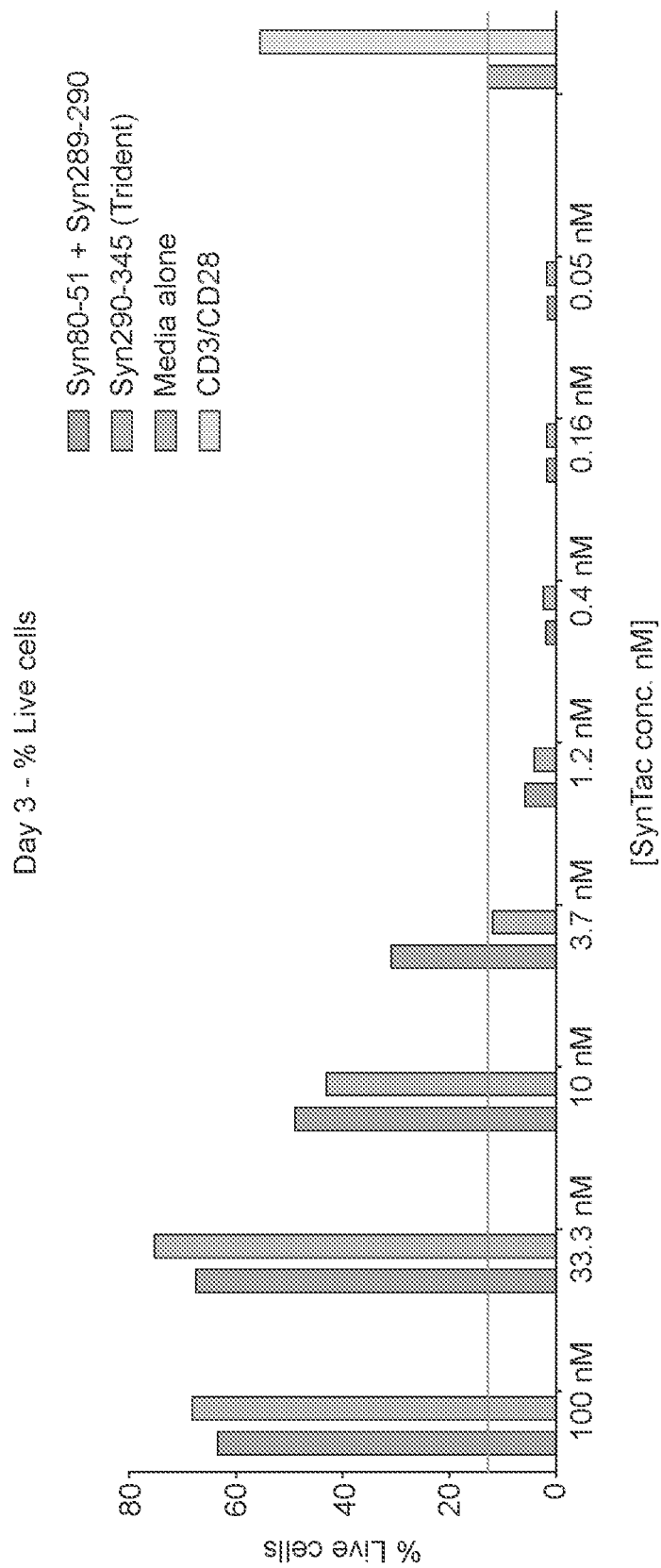
FIG. 11 depicts the effect of synTac 290-345 (comprising wildtype CD80, wildtype 4-1BBL) on T-cell viability.
Figure 12:
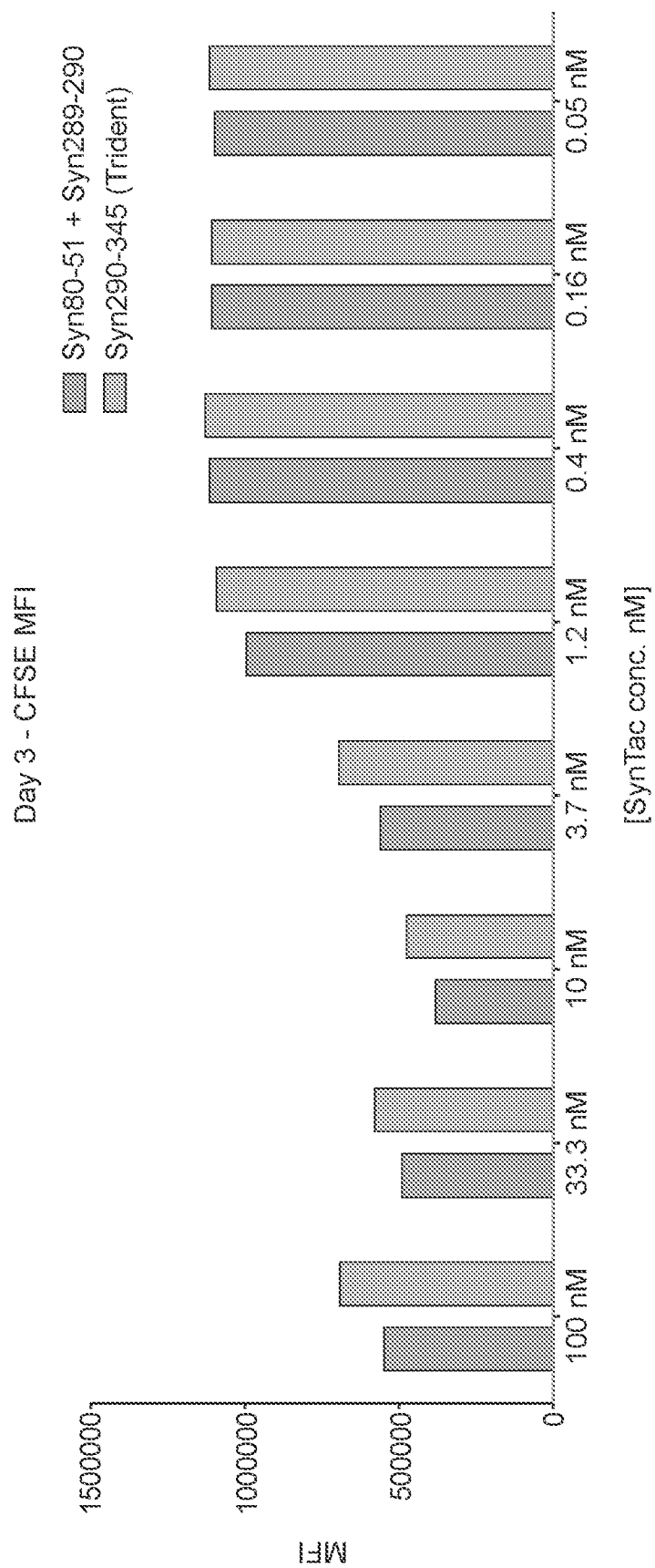
FIG. 12 depicts the effect of synTac 290-345 (comprising wildtype CD80, wildtype 4-1BBL) on T-cell proliferation.
Figure 13:
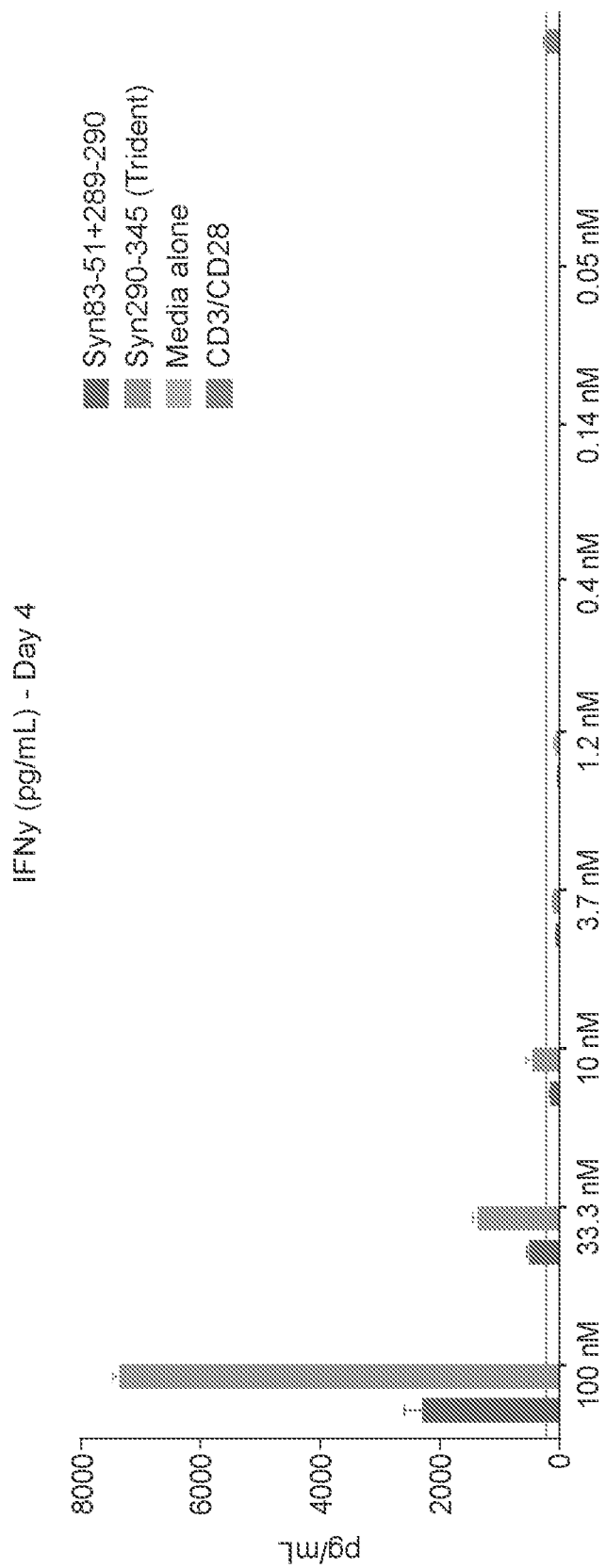
FIG. 13 depicts the effect of synTac 290-345 (comprising wildtype CD80, wildtype 4-1BBL) on IFNγ production by T-cells.

Each construct was introduced into Expi-CHO-S cells (Liu et al. (2015) *Genetic Engineering & Biotechnology News* 35) for transient expression. One to two weeks after transfection, a single-step purification of each expressed synTac was carried out. Clarified conditioned media were subjected to Protein A chromatography. The eluted synTacs (2 μg each) were subjected to reducing (Re) and non-reducing (NR) sodium dodecyl sulfate-polyacrylamide gel electrophoresis (SDS-PAGE). SDS-PAGE images are provided in FIG. 9. As shown in FIG. 9, the expected sizes were obtained.

Example 2: Characterization of synTacs

The synTacs described in Example 1 were characterized for their effects on T cells.

In Vitro T Cell Stimulation Assays.

CD8+ T cells from OT-I T cell receptor (TCR) transgenic C57BL/6 mice were cultured in the presence of the indicated synTac reagents. Control treatments were media alone or anti-CD3+anti-CD28 T cell stimulation beads to benchmark response magnitude. Cells were labeled with carboxyfluorescein succinimidyl ester (CFSE) in order to monitor the extent of T cell activation-induced cellular proliferation. After 3 days, half the cells were harvested and examined using flow cytometry for viability and proliferation. After 4-5 days, supernatants were examined for the expression of the CD8+ T cell effector cytokines interferon-gamma (IFNγ) and tumor necrosis factor-alpha (TNFα) using a multiplexed flow cytometric bead assay.

The data are depicted in FIGS. 11-18.

Figure 14:
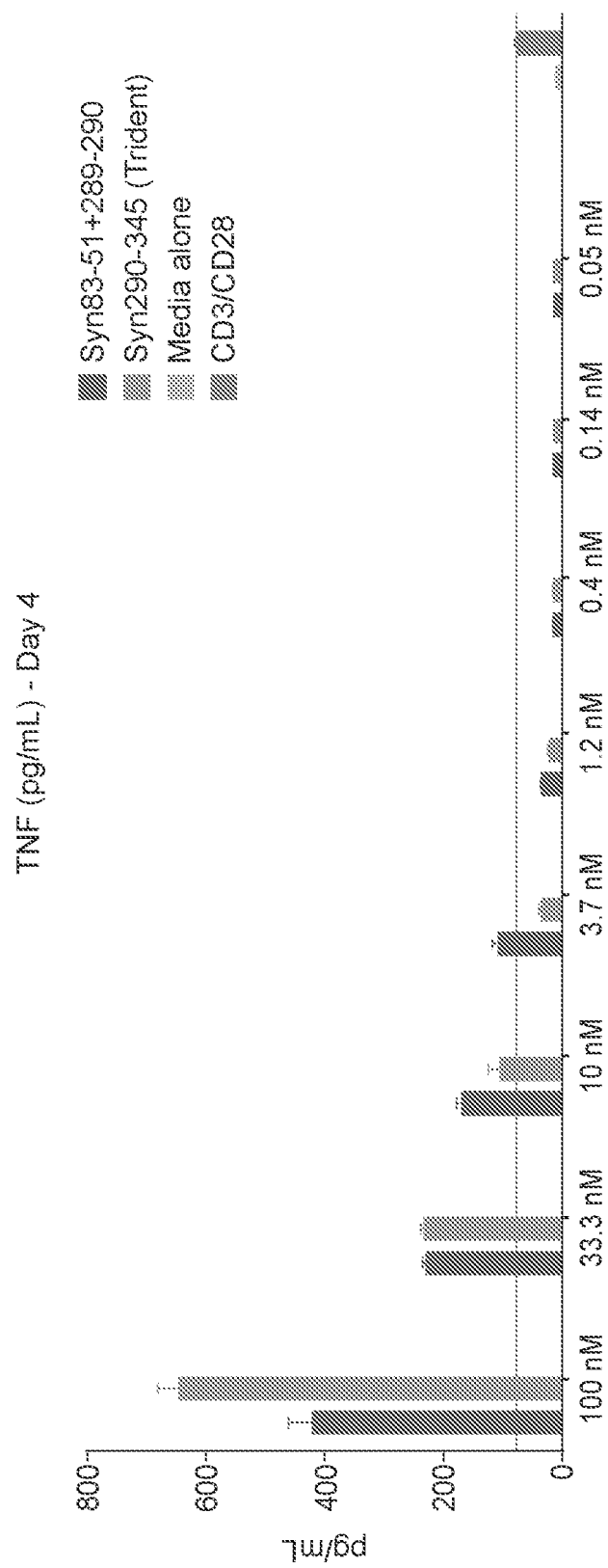
FIG. 14 depicts the effect of synTac 290-345 (comprising wildtype CD80, wildtype 4-1BBL) on TNFα production by T-cells.
Figure 15:
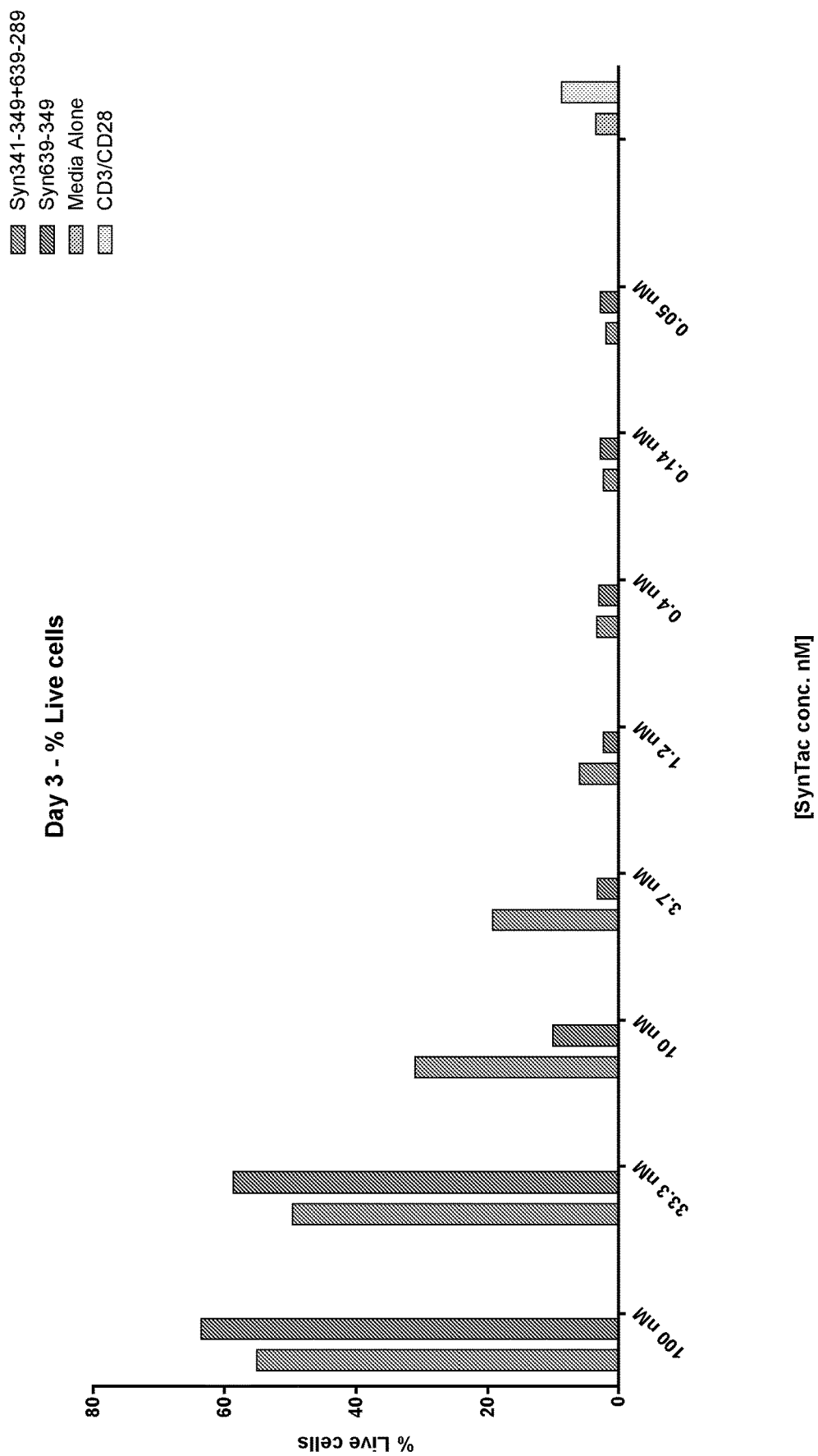
FIG. 15 depicts the effect of syntac 639-349 (comprising affinity attenuated CD80 (CD80-K86A) and affinity attenuated 4-1BBL (4-1BBL-K127A)) on T-cell viability.
Figure 16:
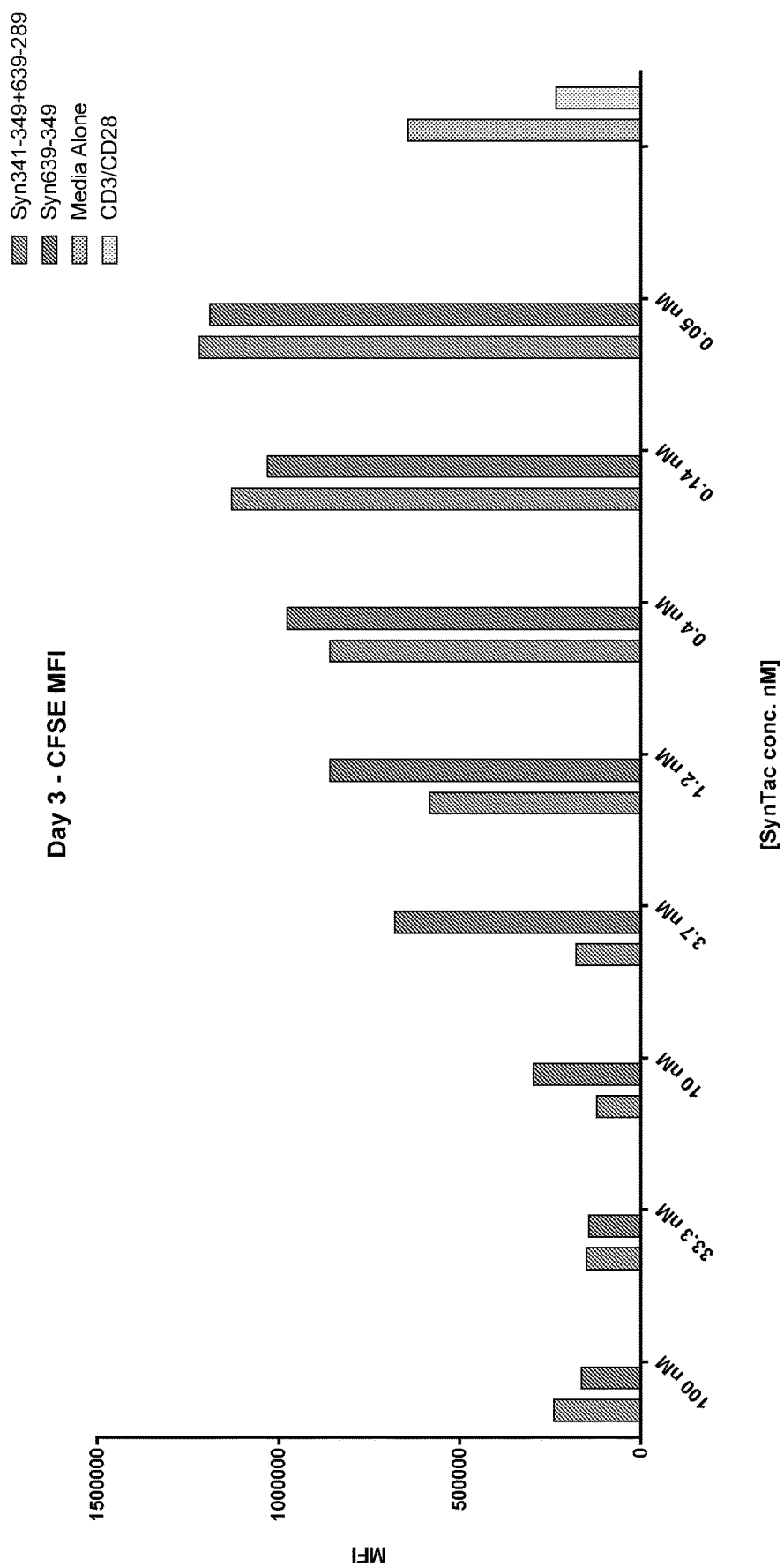
FIG. 16 depicts the effect of syntac 639-349 (comprising affinity attenuated CD80 (CD80-K86A) and affinity attenuated 4-1BBL (4-1BBL-K127A)) on T-cell proliferation.
Figure 17:
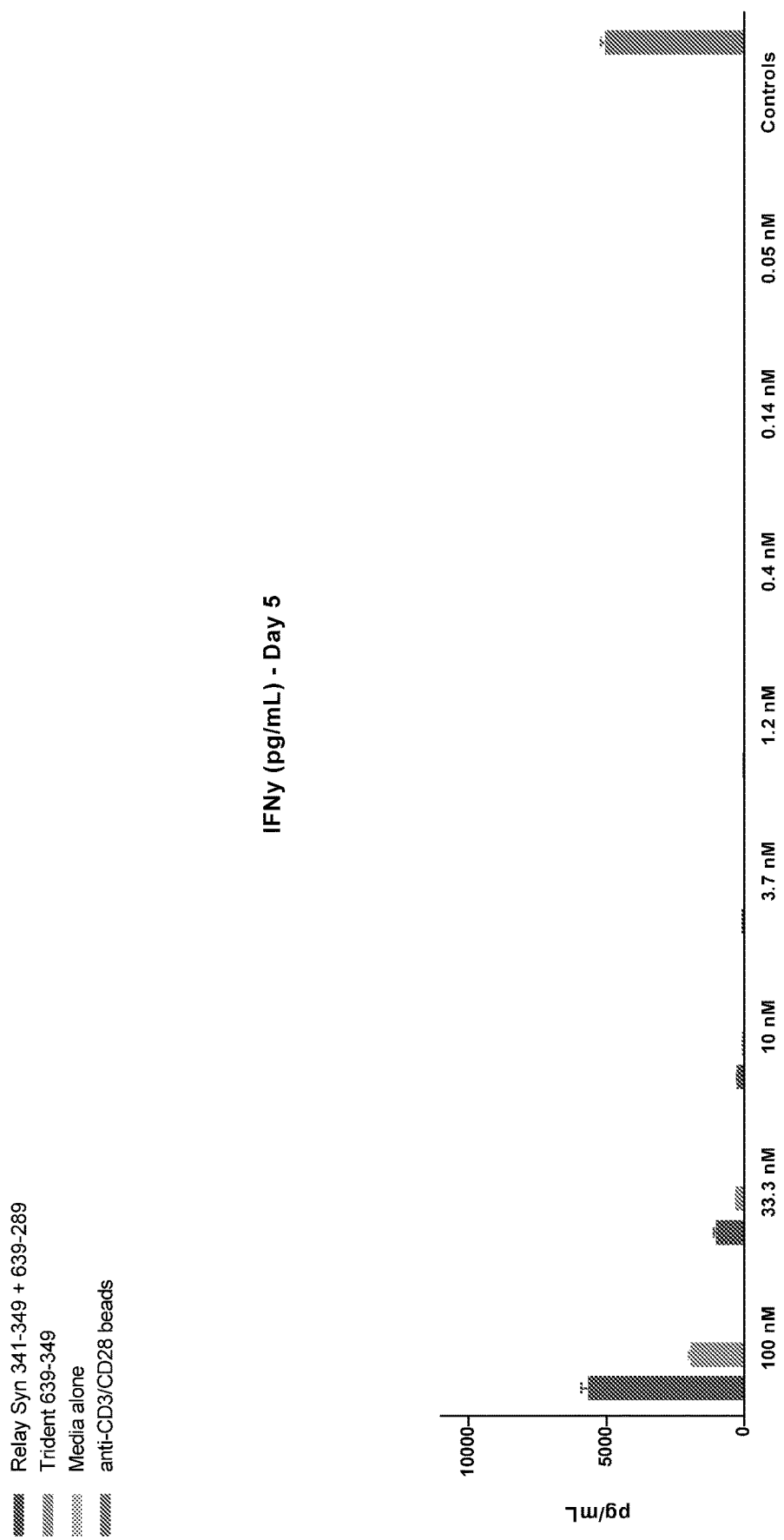
FIG. 17 depicts the effect of syntac 639-349 (comprising affinity attenuated CD80 (CD80-K86A) and affinity attenuated 4-1BBL (4-1BBL-K127A)) on IFNγ production by T-cells.

FIGS. 11-14 relate to syntac 290-345 (mods=wildtype CD80, wildtype 4-1BBL) and contain the following data: viability (FIG. 11), proliferation (FIG. 12), IFNγ production (FIG. 13), and TNFα production (FIG. 14).

Figure 18:
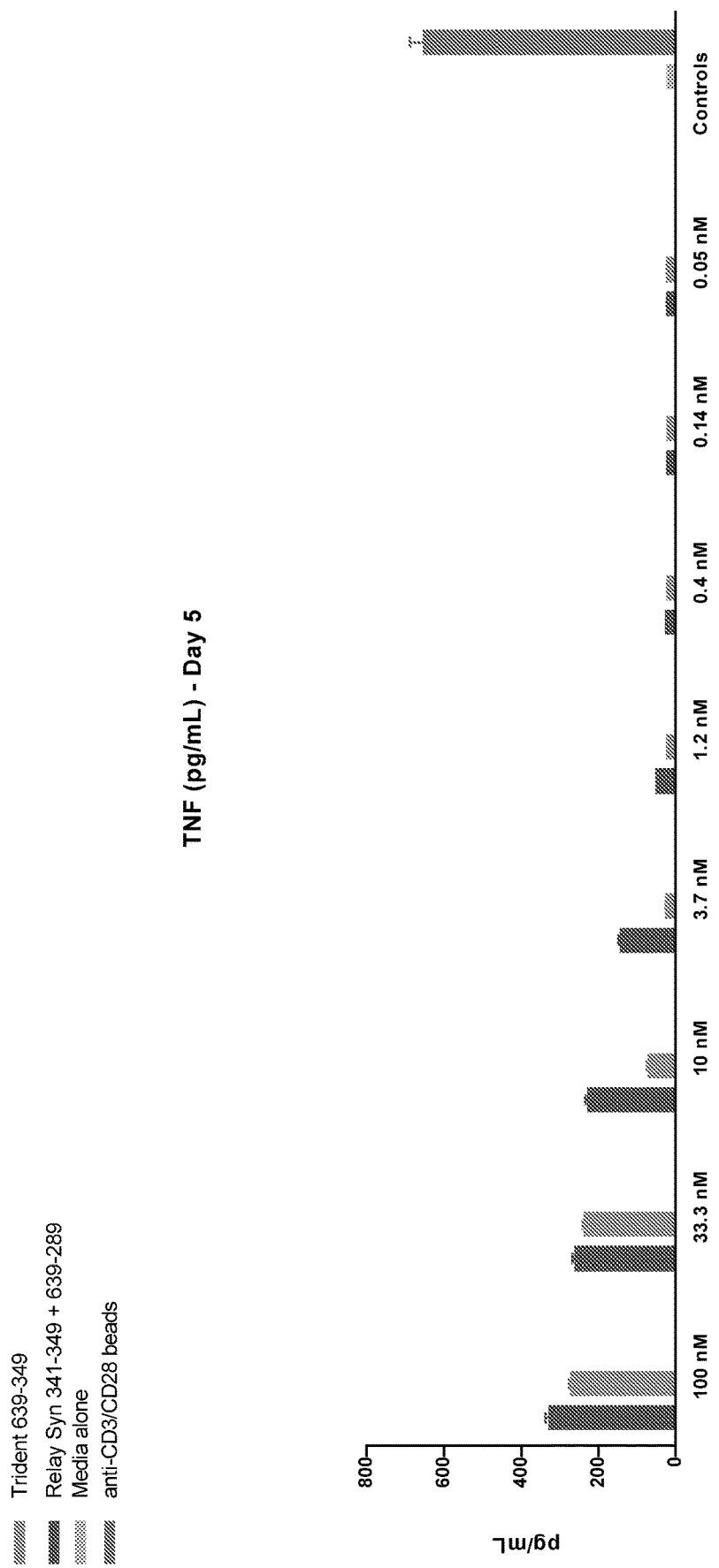
FIG. 18 depicts the effect of syntac 639-349 (comprising affinity attenuated CD80 (CD80-K86A) and affinity attenuated 4-1BBL (4-1BBL-K127A)) on TNFα production by T-cells.

FIGS. 15-18 relate to syntac 639-349 (mods=affinity attenuated CD80 (CD80-K86A), affinity attenuated 4-1BBL (4-1BBL-K127A)) and contain the following data: viability (FIG. 15), proliferation (FIG. 16), IFNγ production (FIG. 17), and TNFα production (FIG. 18).

Example 3: In Vivo Activity

The effect of a trident that includes CD80 and 4-1BBL immunomodulatory polypeptides on tumor volume in vivo was tested. Tumors were engrafted into mice; the tumor-engrafted mice were then treated with: a) phosphate-buffered saline; b) a CD80/4-1BBL synTac comprising wild-type CD80 and a K127A 4-1BBL variant; c) coadministration of: i) CD80/4-1BBL synTac comprising wild-type CD80 and a K127A 4-1BBL variant; and ii) an anti-CTLA4 antibody; or d) a CD80/4-1BBL synTac comprising a K86A CD80 variant and a K127A 4-1BBL variant. At various days post-engraftment, tumor volume was measured. Tumor growth inhibition (TGI) is expressed as (Vc−Vt)/(Vc−Vo)×100. The objective response rate (ORR), the TGI, and the tumor volume are shown in FIG. 19.

Figure 19:
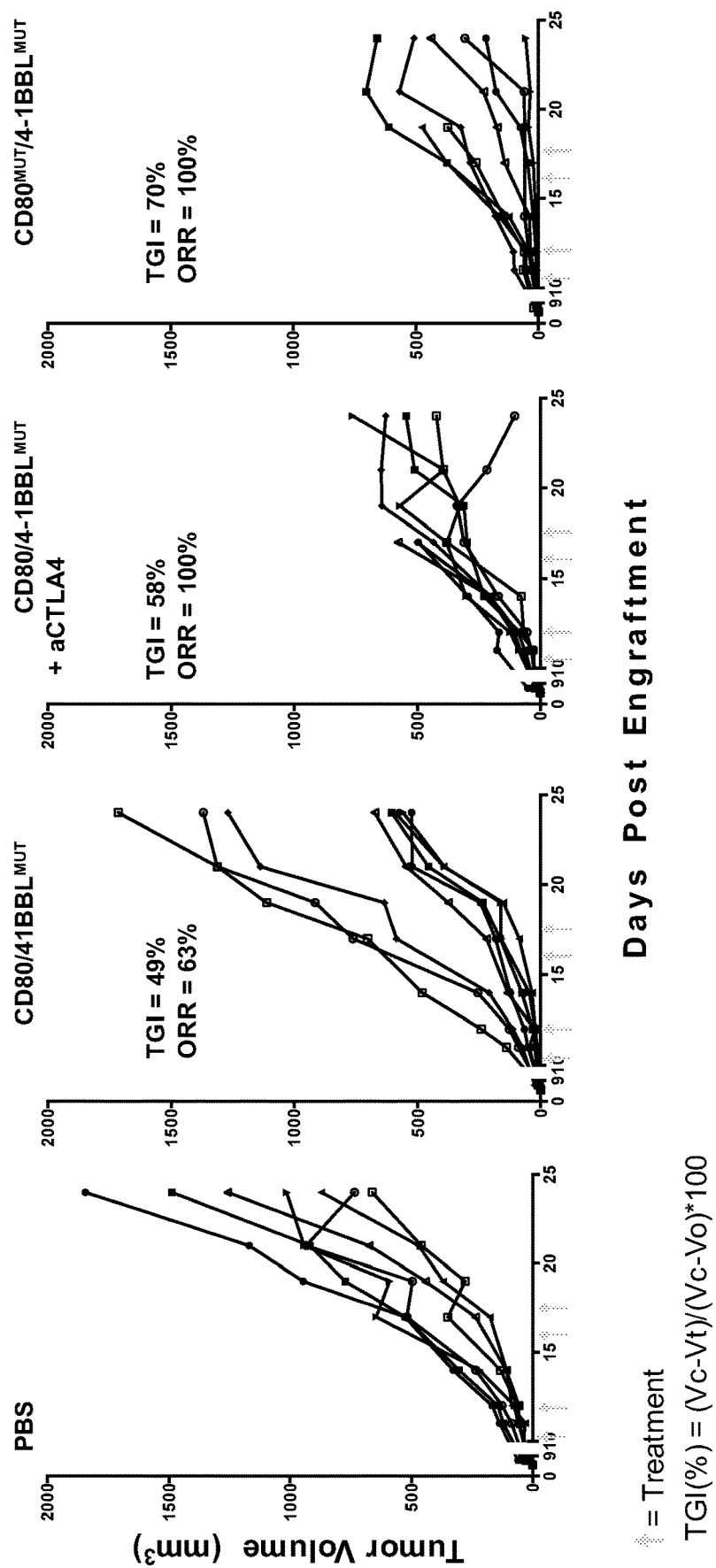
FIG. 19 depicts the effect of 4-1BBL/CD80 synTacs on tumor volume in vivo.

As shown in FIG. 19, administration of a CD80/4-1BBL synTac comprising wild-type CD80 and a K127A 4-1BBL variant (second panel from left) resulted in a TGI of 49% and an ORR of 63%; coadministration of: i) CD80/4-1BBL synTac comprising wild-type CD80 and a K127A 4-1BBL variant (third panel from left) resulted in a TGI of 58% and an ORR of 100%; and administration of a CD80/4-1BBL synTac comprising a K86A CD80 variant and a K127A 4-1BBL variant resulted in a TGI of 70% and an ORR of 100%. The synTac comprising a K86A CD80 variant and a K127A 4-1BBL variant exhibited a biased affinity toward CD28 compared to CTLA4.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A multimeric polypeptide comprising:
a heterodimeric polypeptide comprising:
a) a first polypeptide comprising:
i) an epitope; and
ii) a first major histocompatibility complex (MHC) class I polypeptide, wherein the first MHC polypeptide is a β2-microglobulin polypeptide; and
b) a second polypeptide comprising:
i) a second MHC class I polypeptide, wherein the second MHC polypeptide is an MHC class I heavy chain polypeptide; and
ii) optionally an immunoglobulin (Ig) Fc polypeptide; and
c) at least one first immunomodulatory polypeptide, wherein the at least one first immunomodulatory polypeptide is a CD80 polypeptide, wherein the CD80 polypeptide is a wild-type CD80 polypeptide or variant thereof, wherein the CD80 polypeptide binds a CD28 polypeptide and comprises an amino acid sequence having at least 95% amino acid sequence identity to the CD80 amino acid sequence set forth in SEQ ID NO:1; and
d) at least one second immunomodulatory polypeptide, wherein the at least one second immunomodulatory is a 4-1BBL polypeptide, wherein the 4-1BBL polypeptide comprises an amino acid sequence having at least 95% amino acid sequence identity to the 4-1BBL amino acid sequence set forth in any one of SEQ ID NOs: 2-4, and wherein the 4-1BBL polypeptide is a variant 4-1BBL polypeptide that binds a 4-1BB polypeptide having an amino acid sequence set forth in SEQ ID NO:51 with reduced binding affinity, compared to the binding affinity of a 4-1BBL polypeptide comprising the amino acid sequence set forth in any one of SEQ ID NOs: 2-4 for the 4-1BB polypeptide.

2. The multimeric polypeptide of claim 1, wherein:
a1) the first polypeptide comprising, in order from N-terminus to C-terminus:
i) the epitope;
ii) the first MHC class I polypeptide; and
iii) at least one variant 4-1BBL polypeptide; and
b1) the second polypeptide comprising, in order from N-terminus to C-terminus:
i) at least one variant CD80 polypeptide;
ii) the second MHC class I polypeptide; and
iii) an Ig Fc polypeptide; or a2) the first polypeptide comprising, in order from N-terminus to C-terminus:
i) the epitope;
ii) the first MHC class I polypeptide; and
iii) at least one variant CD80 polypeptide; and
b2) the second polypeptide comprising, in order from N-terminus to C-terminus:
i) at least one variant 4-1BBL polypeptide;
ii) the second MHC class I polypeptide; and
iii) an Ig Fc polypeptide,
optionally wherein one or more peptide linkers are interposed between one or more of the components of the first and/or second polypeptide.

3. A multimeric polypeptide of claim 1, wherein the at least one first immunomodulatory polypeptide is a CD80 polypeptide comprising a wild-type amino acid sequence.

4. A multimeric polypeptide of claim 3, wherein the CD80 polypeptide comprises the amino acid sequence set forth in SEQ ID NO:1.

5. A multimeric polypeptide of claim 1, wherein:
a1) the first polypeptide comprises, in order from N-terminus to C-terminus:
i) the epitope;
ii) the first MHC class I polypeptide; and
iii) at least one 4-1BBL polypeptide; and
b1) the second polypeptide comprises, in order from N-terminus to C-terminus:
i) at least one CD80 polypeptide; and
ii) the second MHC polypeptide; and
iii) an Ig Fc polypeptide; or
a2) the first polypeptide comprises, in order from N-terminus to C-terminus:
i) the epitope;
ii) the first MHC polypeptide; and
iii) at least one CD80 polypeptide; and
b2) the second polypeptide comprises, in order from N-terminus to C-terminus:
i) at least one 4-1BBL polypeptide;
ii) the second MHC polypeptide; and
iii) an Ig Fc polypeptide,
wherein one or more peptide linkers are interposed between one or more of the components of the first and/or second polypeptide.

6. The multimeric polypeptide of claim 5, comprising at least one variant CD80 polypeptide that comprises a substitution of amino acid 167, K86, or D158.

7. The multimeric polypeptide of claim 5, comprising at least one variant 4-1BBL polypeptide that comprises a substitution of K127.

8. The multimeric polypeptide of claim 1, comprising at least one variant CD80 polypeptide that comprises a substitution of amino acid 167, K86, or D158.

9. The multimeric polypeptide of claim 1, comprising at least one variant 4-1BBL polypeptide that comprises a substitution of K127.

10. The multimeric polypeptide of claim 1, wherein the at least one variant 4-1BBL polypeptide comprises an amino acid sequence having at least 95% amino acid sequence identity to the amino acid sequence PAGLLDLRQG MFAQLVAQNV LLIDGPLSWY SDPGLAGVSL TGGL-SYXEDT KELVVAKAGV YYVFFQLELR RVVAGEGSGS VSLALHLQPL RSAAGAAALA LTVDLPPASS EARNSAFGFQ GRLLHLSAGQ RLGVHLHTEA RARHAWQLTQ GATVLGLFRV TPEI-PAGLPS PRSE (SEQ ID NO:11), wherein X is Ala, Gly, Val, Ile, Leu, Arg, His, Glu, or Asp.

11. The multimeric polypeptide of claim 1, wherein the at least one CD80 polypeptide is a variant that comprises:
  a) an amino acid sequence having at least 95% amino acid sequence identity to the amino acid sequence VIHVTK EVKEVATLSC GHNVSVEELA QTRIYWQKEK KMVLTMMSGD MNIWPEYKNR TIFDITNNLS XVILALRPSD EGTYECVVLK YEKDAFKREH LAEVTLSVKA DFPTPSISDF EIPTSNIRRI ICST-SGGFPE PHLSWLENGE ELNAINTTVS QDPETE-LYAV SSKLDFNMTT NHSFMCLIKY GHLRVNQTFN WNTTKQEHFP DN (SEQ ID NO:5), where X is Ala, Gly, Val, Leu, Arg, His, Lys, Glu, or Asp; or
  b) an amino acid sequence having at least 95% amino acid sequence identity to the amino acid sequence VIHVTK EVKEVATLSC GHNVSVEELA QTRIYWQKEK KMVLTMMSGD MNIWPEYKNR TIFDITNNLS IVILALRPSD EGTYECVVLX YEKDAFKREH LAEVTLSVKA DFPTPSISDF EIPTSNIRRI ICST-SGGFPE PHLSWLENGE ELNAINTTVS QDPETE-LYAV SSKLDFNMTT NHSFMCLIKY GHLRVNQTFN WNTTKQEHFP DN (SEQ ID NO:7), where X is Ala, Gly, Val, Leu, Ile, Arg, His, Glu, or Asp; or
  c) an amino acid sequence having at least 95% amino acid sequence identity to the amino acid sequence VIHVTK EVKEVATLSC GHNVSVEELA QTRIYWQKEK KMVLTMMSGD MNIWPEYKNR TIFDITNNLS IVILALRPSD EGTYECVVLK YEKDAFKREH LAEVTLSVKA DFPTPSISDF EIPTSNIRRI ICST-SGGFPE PHLSWLENGE ELNAINTTVS QXPETE-LYAV SSKLDFNMTT NHSFMCLIKY GHLRVNQTFN WNTTKQEHFP DN (SEQ ID NO:9), where X is Ala, Gly, Val, Leu, Ile, Arg, His, Lys, or Glu.

12. One or more nucleic acids, wherein the one or more nucleic acids individually or collectively encode the first and second polypeptides of a multimeric polypeptide according to claim 1.

13. One or more expression vectors comprising the one or more nucleic acids of claim 12.

14. A host cell genetically modified with the one or more expression vectors of claim 13.

15. A composition comprising:
  a) the multimeric polypeptide of claim 1; and
  b) a pharmaceutically acceptable excipient.

16. A method of producing a multimeric polypeptide, the method comprising:
  a) culturing the host cell of claim 14 in vitro in a culture medium under conditions such that the host cell synthesizes the multimeric polypeptide; and
  b) isolating the multimeric polypeptide from the host cell and/or from the culture medium.

17. A method of selectively modulating the activity of an epitope-specific T cell, the method comprising contacting the T cell with the multimeric polypeptide of claim 1, wherein said contacting selectively modulates the activity of the epitope-specific T cell.

\* \* \* \* \*

SEQUENCE LISTING

```
<160> NUMBER OF SEQ ID NOS: 81

<210> SEQ ID NO 1
<211> LENGTH: 208
<212> TYPE: PRT
<213> ORGANISM: Homo sapiens

<400> SEQUENCE: 1

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

<210> SEQ ID NO 2
<211> LENGTH: 174
<212> TYPE: PRT
<213> ORGANISM: Homo sapiens

<400> SEQUENCE: 2

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30
```

-continued

Pro Gly Leu Ala Gly Val Ser Leu Thr Gly Gly Leu Ser Tyr Lys Glu
            35                  40                  45

Asp Thr Lys Glu Leu Val Val Ala Lys Ala Gly Val Tyr Tyr Val Phe
        50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
            115                 120                 125

Gly Gln Arg Leu Gly Val His Leu His Thr Glu Ala Arg Ala Arg His
            130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170

<210> SEQ ID NO 3
<211> LENGTH: 175
<212> TYPE: PRT
<213> ORGANISM: Homo sapiens

<400> SEQUENCE: 3

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
            35                  40                  45

Glu Asp Thr Lys Glu Leu Val Val Ala Lys Ala Gly Val Tyr Tyr Val
        50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
            115                 120                 125

Ala Gly Gln Arg Leu Gly Val His Leu His Thr Glu Ala Arg Ala Arg
            130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu
                165                 170                 175

<210> SEQ ID NO 4
<211> LENGTH: 167
<212> TYPE: PRT
<213> ORGANISM: Homo sapiens

```
<400> SEQUENCE: 4

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45

Glu Asp Thr Lys Glu Leu Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
            115                 120                 125

Ala Gly Gln Arg Leu Gly Val His Leu His Thr Glu Ala Arg Ala Arg
        130                 135                 140

His Ala Trp Gln Leu Thr Gln Gly Ala Thr Val Leu Gly Leu Phe Arg
145                 150                 155                 160

Val Thr Pro Glu Ile Pro Ala
                165

<210> SEQ ID NO 5
<211> LENGTH: 208
<212> TYPE: PRT
<213> ORGANISM: Artificial sequence
<220> FEATURE:
<223> OTHER INFORMATION: Synthetic sequence
<220> FEATURE:
<221> NAME/KEY: Misc_feature
<222> LOCATION: (67)..(67)
<223> OTHER INFORMATION: Xaa is any amino acid other than Isoleucine

<400> SEQUENCE: 5

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Xaa Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
            115                 120                 125

Ser Thr Ser Gly Gly Phe Pro Glu Pro His Leu Ser Trp Leu Glu Asn
        130                 135                 140

Gly Glu Glu Leu Asn Ala Ile Asn Thr Thr Val Ser Gln Asp Pro Glu
145                 150                 155                 160
```

Thr Glu Leu Tyr Ala Val Ser Ser Lys Leu Asp Phe Asn Met Thr Thr
            165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

<210> SEQ ID NO 6
<211> LENGTH: 208
<212> TYPE: PRT
<213> ORGANISM: Artificial sequence
<220> FEATURE:
<223> OTHER INFORMATION: Synthetic sequence

<400> SEQUENCE: 6

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ala Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

<210> SEQ ID NO 7
<211> LENGTH: 208
<212> TYPE: PRT
<213> ORGANISM: Artificial sequence
<220> FEATURE:
<223> OTHER INFORMATION: Synthetic sequence
<220> FEATURE:
<221> NAME/KEY: Misc_feature
<222> LOCATION: (86)..(86)
<223> OTHER INFORMATION: Xaa is any amino acid other than Lysine

<400> SEQUENCE: 7

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

-continued

```
Gln Lys Glu Lys Lys Met Val Leu Thr Met Met Ser Gly Asp Met Asn
             35                  40                  45

Ile Trp Pro Glu Tyr Lys Asn Arg Thr Ile Phe Asp Ile Thr Asn Asn
 50                      55                  60

Leu Ser Ile Val Ile Leu Ala Leu Arg Pro Ser Asp Glu Gly Thr Tyr
 65                  70                  75                  80

Glu Cys Val Val Leu Xaa Tyr Glu Lys Asp Ala Phe Lys Arg Glu His
                 85                  90                  95

Leu Ala Glu Val Thr Leu Ser Val Lys Ala Asp Phe Pro Thr Pro Ser
             100                 105                 110

Ile Ser Asp Phe Glu Ile Pro Thr Ser Asn Ile Arg Arg Ile Ile Cys
         115                 120                 125

Ser Thr Ser Gly Gly Phe Pro Glu Pro His Leu Ser Trp Leu Glu Asn
 130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                 165                 170                 175

Asn His Ser Phe Met Cys Leu Ile Lys Tyr Gly His Leu Arg Val Asn
             180                 185                 190

Gln Thr Phe Asn Trp Asn Thr Lys Gln His Phe Pro Asp Asn
         195                 200                 205

<210> SEQ ID NO 8
<211> LENGTH: 208
<212> TYPE: PRT
<213> ORGANISM: Artificial sequence
<220> FEATURE:
<223> OTHER INFORMATION: Synthetic sequence

<400> SEQUENCE: 8

Val Ile His Val Thr Lys Glu Val Lys Glu Val Ala Thr Leu Ser Cys
 1               5                  10                  15

Gly His Asn Val Ser Val Glu Glu Leu Ala Gln Thr Arg Ile Tyr Trp
             20                  25                  30

Gln Lys Glu Lys Lys Met Val Leu Thr Met Met Ser Gly Asp Met Asn
         35                      40                  45

Ile Trp Pro Glu Tyr Lys Asn Arg Thr Ile Phe Asp Ile Thr Asn Asn
 50                      55                  60

Leu Ser Ile Val Ile Leu Ala Leu Arg Pro Ser Asp Glu Gly Thr Tyr
 65                  70                  75                  80

Glu Cys Val Val Leu Ala Tyr Glu Lys Asp Ala Phe Lys Arg Glu His
                 85                  90                  95

Leu Ala Glu Val Thr Leu Ser Val Lys Ala Asp Phe Pro Thr Pro Ser
             100                 105                 110

Ile Ser Asp Phe Glu Ile Pro Thr Ser Asn Ile Arg Arg Ile Ile Cys
         115                 120                 125

Ser Thr Ser Gly Gly Phe Pro Glu Pro His Leu Ser Trp Leu Glu Asn
 130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                 165                 170                 175
```

Asn His Ser Phe Met Cys Leu Ile Lys Tyr Gly His Leu Arg Val Asn
              180                 185                 190

Gln Thr Phe Asn Trp Asn Thr Thr Lys Gln Glu His Phe Pro Asp Asn
        195                 200                 205

<210> SEQ ID NO 9
<211> LENGTH: 208
<212> TYPE: PRT
<213> ORGANISM: Artificial sequence
<220> FEATURE:
<223> OTHER INFORMATION: Synthetic sequence
<220> FEATURE:
<221> NAME/KEY: Misc_feature
<222> LOCATION: (158)..(158)
<223> OTHER INFORMATION: Xaa is any amino acid other than Aspartic acid

<400> SEQUENCE: 9

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
              20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
              100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Xaa Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
              180                 185                 190

Gln Thr Phe Asn Trp Asn Thr Thr Lys Gln Glu His Phe Pro Asp Asn
        195                 200                 205

<210> SEQ ID NO 10
<211> LENGTH: 208
<212> TYPE: PRT
<213> ORGANISM: Artificial sequence
<220> FEATURE:
<223> OTHER INFORMATION: Synthetic sequence

<400> SEQUENCE: 10

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
              20                  25                  30

Gln Lys Glu Lys Lys Met Val Leu Thr Met Met Ser Gly Asp Met Asn
        35                  40                  45

```
Ile Trp Pro Glu Tyr Lys Asn Arg Thr Ile Phe Asp Ile Thr Asn Asn
 50                  55                  60

Leu Ser Ile Val Ile Leu Ala Leu Arg Pro Ser Asp Glu Gly Thr Tyr
 65                  70                  75                  80

Glu Cys Val Val Leu Lys Tyr Glu Lys Asp Ala Phe Lys Arg Glu His
                 85                  90                  95

Leu Ala Glu Val Thr Leu Ser Val Lys Ala Asp Phe Pro Thr Pro Ser
                100                 105                 110

Ile Ser Asp Phe Glu Ile Pro Thr Ser Asn Ile Arg Ile Ile Cys
            115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Ala Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
                180                 185                 190

Gln Thr Phe Asn Trp Asn Thr Lys Gln His Phe Pro Asp Asn
                195                 200                 205

<210> SEQ ID NO 11
<211> LENGTH: 174
<212> TYPE: PRT
<213> ORGANISM: Artificial sequence
<220> FEATURE:
<223> OTHER INFORMATION: Synthetic sequence
<220> FEATURE:
<221> NAME/KEY: Misc_feature
<222> LOCATION: (47)..(47)
<223> OTHER INFORMATION: Xaa is any amino acid other than Lysine

<400> SEQUENCE: 11

Pro Ala Gly Leu Leu Asp Leu Arg Gln Gly Met Phe Ala Gln Leu Val
 1               5                  10                  15

Ala Gln Asn Val Leu Leu Ile Asp Gly Pro Leu Ser Trp Tyr Ser Asp
                 20                  25                  30

Pro Gly Leu Ala Gly Val Ser Leu Thr Gly Gly Leu Ser Tyr Xaa Glu
             35                  40                  45

Asp Thr Lys Glu Leu Val Val Ala Lys Ala Gly Val Tyr Tyr Val Phe
 50                  55                  60

Phe Gln Leu Glu Leu Arg Arg Val Val Ala Gly Glu Gly Ser Gly Ser
 65                  70                  75                  80

Val Ser Leu Ala Leu His Leu Gln Pro Leu Arg Ser Ala Ala Gly Ala
                 85                  90                  95

Ala Ala Leu Ala Leu Thr Val Asp Leu Pro Pro Ala Ser Ser Glu Ala
                100                 105                 110

Arg Asn Ser Ala Phe Gly Phe Gln Gly Arg Leu Leu His Leu Ser Ala
            115                 120                 125

Gly Gln Arg Leu Gly Val His Leu His Thr Glu Ala Arg Ala Arg His
130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 12
<211> LENGTH: 174
<212> TYPE: PRT
<213> ORGANISM: Artificial sequence
<220> FEATURE:
<223> OTHER INFORMATION: Synthetic sequence

<400> SEQUENCE: 12

```
Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
            20                  25                  30

Pro Gly Leu Ala Gly Val Ser Leu Thr Gly Gly Leu Ser Tyr Ala Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140

Ala Trp Gln Leu Thr Gln Gly Ala Thr Val Leu Gly Leu Phe Arg Val
145                 150                 155                 160

Thr Pro Glu Ile Pro Ala Gly Leu Pro Ser Pro Arg Ser Glu
                165                 170
```

<210> SEQ ID NO 13
<211> LENGTH: 175
<212> TYPE: PRT
<213> ORGANISM: Artificial sequence
<220> FEATURE:
<223> OTHER INFORMATION: Synthetic sequence
<220> FEATURE:
<221> NAME/KEY: Misc_feature
<222> LOCATION: (48)..(48)
<223> OTHER INFORMATION: Xaa is any amino acid other than Lysine

<400> SEQUENCE: 13

```
Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Xaa
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125
```

Ala Gly Gln Arg Leu Gly Val His Leu His Thr Glu Ala Arg Ala Arg
        130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu
                165                 170                 175

<210> SEQ ID NO 14
<211> LENGTH: 175
<212> TYPE: PRT
<213> ORGANISM: Artificial sequence
<220> FEATURE:
<223> OTHER INFORMATION: Synthetic sequence

<400> SEQUENCE: 14

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Ala
        35                  40                  45

Glu Asp Thr Lys Glu Leu Val Val Ala Lys Ala Gly Val Tyr Tyr Val
50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu
                165                 170                 175

<210> SEQ ID NO 15
<211> LENGTH: 167
<212> TYPE: PRT
<213> ORGANISM: Artificial sequence
<220> FEATURE:
<223> OTHER INFORMATION: Synthetic sequence
<220> FEATURE:
<221> NAME/KEY: Misc_feature
<222> LOCATION: (48)..(48)
<223> OTHER INFORMATION: Xaa is any amino acid other than Lysine

<400> SEQUENCE: 15

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Xaa
        35                  40                  45

Glu Asp Thr Lys Glu Leu Val Val Ala Lys Ala Gly Val Tyr Tyr Val
50                  55                  60

```
Phe Phe Gln Leu Glu Leu Arg Arg Val Val Ala Gly Glu Gly Ser Gly
 65                  70                  75                  80

Ser Val Ser Leu Ala Leu His Leu Gln Pro Leu Arg Ser Ala Ala Gly
                 85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
            115                 120                 125

Ala Gly Gln Arg Leu Gly Val His Leu His Thr Glu Ala Arg Ala Arg
        130                 135                 140

His Ala Trp Gln Leu Thr Gln Gly Ala Thr Val Leu Gly Leu Phe Arg
145                 150                 155                 160

Val Thr Pro Glu Ile Pro Ala
                165

<210> SEQ ID NO 16
<211> LENGTH: 167
<212> TYPE: PRT
<213> ORGANISM: Artificial sequence
<220> FEATURE:
<223> OTHER INFORMATION: Synthetic sequence

<400> SEQUENCE: 16

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
                20                  25                  30

Asp Pro Gly Leu Ala Gly Val Ser Leu Thr Gly Leu Ser Tyr Ala
            35                  40                  45

Glu Asp Thr Lys Glu Leu Val Val Ala Lys Ala Gly Val Tyr Tyr Val
        50                  55                  60

Phe Phe Gln Leu Glu Leu Arg Arg Val Val Ala Gly Glu Gly Ser Gly
 65                  70                  75                  80

Ser Val Ser Leu Ala Leu His Leu Gln Pro Leu Arg Ser Ala Ala Gly
                 85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
            115                 120                 125

Ala Gly Gln Arg Leu Gly Val His Leu His Thr Glu Ala Arg Ala Arg
        130                 135                 140

His Ala Trp Gln Leu Thr Gln Gly Ala Thr Val Leu Gly Leu Phe Arg
145                 150                 155                 160

Val Thr Pro Glu Ile Pro Ala
                165

<210> SEQ ID NO 17
<211> LENGTH: 9
<212> TYPE: PRT
<213> ORGANISM: Artificial sequence
<220> FEATURE:
<223> OTHER INFORMATION: Synthetic sequence

<400> SEQUENCE: 17

Tyr Pro Tyr Asp Val Pro Asp Tyr Ala
1               5
```

```
<210> SEQ ID NO 18
<211> LENGTH: 8
<212> TYPE: PRT
<213> ORGANISM: Artificial sequence
<220> FEATURE:
<223> OTHER INFORMATION: Synthetic sequence

<400> SEQUENCE: 18

Asp Tyr Lys Asp Asp Asp Asp Lys
1               5

<210> SEQ ID NO 19
<211> LENGTH: 10
<212> TYPE: PRT
<213> ORGANISM: Artificial sequence
<220> FEATURE:
<223> OTHER INFORMATION: Synthetic sequence

<400> SEQUENCE: 19

Glu Gln Lys Leu Ile Ser Glu Glu Asp Leu
1               5                   10

<210> SEQ ID NO 20
<211> LENGTH: 5
<212> TYPE: PRT
<213> ORGANISM: Artificial sequence
<220> FEATURE:
<223> OTHER INFORMATION: Synthetic sequence

<400> SEQUENCE: 20

His His His His His
1               5

<210> SEQ ID NO 21
<211> LENGTH: 6
<212> TYPE: PRT
<213> ORGANISM: Artificial sequence
<220> FEATURE:
<223> OTHER INFORMATION: Synthetic sequence

<400> SEQUENCE: 21

His His His His His His
1               5

<210> SEQ ID NO 22
<211> LENGTH: 8
<212> TYPE: PRT
<213> ORGANISM: Artificial sequence
<220> FEATURE:
<223> OTHER INFORMATION: Synthetic sequence

<400> SEQUENCE: 22

Trp Ser His Pro Gln Phe Glu Lys
1               5

<210> SEQ ID NO 23
<211> LENGTH: 5
<212> TYPE: PRT
<213> ORGANISM: Artificial sequence
<220> FEATURE:
<223> OTHER INFORMATION: Synthetic sequence

<400> SEQUENCE: 23

Arg Tyr Ile Arg Ser
1               5
```

```
<210> SEQ ID NO 24
<211> LENGTH: 4
<212> TYPE: PRT
<213> ORGANISM: Artificial sequence
<220> FEATURE:
<223> OTHER INFORMATION: Synthetic sequence

<400> SEQUENCE: 24

Phe His His Thr
1

<210> SEQ ID NO 25
<211> LENGTH: 17
<212> TYPE: PRT
<213> ORGANISM: Artificial sequence
<220> FEATURE:
<223> OTHER INFORMATION: Synthetic sequence

<400> SEQUENCE: 25

Trp Glu Ala Ala Ala Arg Glu Ala Cys Cys Arg Glu Cys Cys Ala Arg
1               5                   10                  15

Ala

<210> SEQ ID NO 26
<211> LENGTH: 25
<212> TYPE: PRT
<213> ORGANISM: Artificial sequence
<220> FEATURE:
<223> OTHER INFORMATION: Synthetic sequence

<400> SEQUENCE: 26

Gly Gly Gly Gly Ser Gly Gly Gly Ser Gly Gly Gly Gly Ser Gly
1               5                   10                  15

Gly Gly Ser Gly Gly Gly Gly Ser
            20                  25

<210> SEQ ID NO 27
<211> LENGTH: 166
<212> TYPE: PRT
<213> ORGANISM: Artificial sequence
<220> FEATURE:
<223> OTHER INFORMATION: Synthetic sequence

<400> SEQUENCE: 27

Pro Ala Gly Leu Leu Asp Leu Arg Gln Gly Met Phe Ala Gln Leu Val
1               5                   10                  15

Ala Gln Asn Val Leu Leu Ile Asp Gly Pro Leu Ser Trp Tyr Ser Asp
                20                  25                  30

Pro Gly Leu Ala Gly Val Ser Leu Thr Gly Gly Leu Ser Tyr Ala Glu
        35                  40                  45

Asp Thr Lys Glu Leu Val Val Ala Lys Ala Gly Val Tyr Tyr Val Phe
    50                  55                  60

Phe Gln Leu Glu Leu Arg Arg Val Val Ala Gly Glu Gly Ser Gly Ser
65                  70                  75                  80

Val Ser Leu Ala Leu His Leu Gln Pro Leu Arg Ser Ala Ala Gly Ala
                85                  90                  95

Ala Ala Leu Ala Leu Thr Val Asp Leu Pro Pro Ala Ser Ser Glu Ala
            100                 105                 110

Arg Asn Ser Ala Phe Gly Phe Gln Gly Arg Leu Leu His Leu Ser Ala
        115                 120                 125

Gly Gln Arg Leu Gly Val His Leu His Thr Glu Ala Arg Ala Arg His
    130                 135                 140
```

```
Ala Trp Gln Leu Thr Gln Gly Ala Thr Val Leu Gly Leu Phe Arg Val
145                 150                 155                 160

Thr Pro Glu Ile Pro Ala
                165

<210> SEQ ID NO 28
<211> LENGTH: 8
<212> TYPE: PRT
<213> ORGANISM: Artificial sequence
<220> FEATURE:
<223> OTHER INFORMATION: Synthetic sequence

<400> SEQUENCE: 28

Leu Glu Val Leu Phe Gln Gly Pro
1               5

<210> SEQ ID NO 29
<211> LENGTH: 7
<212> TYPE: PRT
<213> ORGANISM: Artificial sequence
<220> FEATURE:
<223> OTHER INFORMATION: Synthetic sequence

<400> SEQUENCE: 29

Glu Asn Leu Tyr Thr Gln Ser
1               5

<210> SEQ ID NO 30
<211> LENGTH: 5
<212> TYPE: PRT
<213> ORGANISM: Artificial sequence
<220> FEATURE:
<223> OTHER INFORMATION: Synthetic sequence

<400> SEQUENCE: 30

Asp Asp Asp Asp Lys
1               5

<210> SEQ ID NO 31
<211> LENGTH: 4
<212> TYPE: PRT
<213> ORGANISM: Artificial sequence
<220> FEATURE:
<223> OTHER INFORMATION: Synthetic sequence

<400> SEQUENCE: 31

Leu Val Pro Arg
1

<210> SEQ ID NO 32
<211> LENGTH: 22
<212> TYPE: PRT
<213> ORGANISM: Artificial sequence
<220> FEATURE:
<223> OTHER INFORMATION: Synthetic sequence

<400> SEQUENCE: 32

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 33
<211> LENGTH: 21
<212> TYPE: PRT
<213> ORGANISM: Artificial sequence
```

```
<220> FEATURE:
<223> OTHER INFORMATION: Synthetic sequence

<400> SEQUENCE: 33

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 34
<211> LENGTH: 23
<212> TYPE: PRT
<213> ORGANISM: Artificial sequence
<220> FEATURE:
<223> OTHER INFORMATION: Synthetic sequence

<400> SEQUENCE: 34

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 35
<211> LENGTH: 25
<212> TYPE: PRT
<213> ORGANISM: Artificial sequence
<220> FEATURE:
<223> OTHER INFORMATION: Synthetic sequence

<400> SEQUENCE: 35

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 36
<211> LENGTH: 6
<212> TYPE: PRT
<213> ORGANISM: Artificial sequence
<220> FEATURE:
<223> OTHER INFORMATION: Synthetic sequence

<400> SEQUENCE: 36

Leu Val Pro Arg Gly Ser
1               5

<210> SEQ ID NO 37
<211> LENGTH: 8
<212> TYPE: PRT
<213> ORGANISM: Artificial sequence
<220> FEATURE:
<223> OTHER INFORMATION: Synthetic sequence

<400> SEQUENCE: 37

Ser Ile Ile Asn Phe Glu Lys Leu
1               5

<210> SEQ ID NO 38
<211> LENGTH: 25
<212> TYPE: PRT
<213> ORGANISM: Artificial sequence
<220> FEATURE:
<223> OTHER INFORMATION: Synthetic sequence
```

-continued

```
<400> SEQUENCE: 38

Gly Gly Gly Gly Ser Gly Gly Gly Ser Gly Gly Gly Ser Gly
1               5                   10                  15

Gly Gly Gly Ser Gly Gly Gly Gly Ser
            20                  25

<210> SEQ ID NO 39
<211> LENGTH: 20
<212> TYPE: PRT
<213> ORGANISM: Artificial sequence
<220> FEATURE:
<223> OTHER INFORMATION: Synthetic sequence

<400> SEQUENCE: 39

Met Ser Arg Ser Val Ala Leu Ala Val Leu Ala Leu Leu Ser Leu Ser
1               5                   10                  15

Gly Leu Glu Ala
            20

<210> SEQ ID NO 40
<211> LENGTH: 9
<212> TYPE: PRT
<213> ORGANISM: Artificial sequence
<220> FEATURE:
<223> OTHER INFORMATION: Synthetic sequence

<400> SEQUENCE: 40

Arg Ala His Tyr Asn Ile Val Thr Phe
1               5

<210> SEQ ID NO 41
<211> LENGTH: 167
<212> TYPE: PRT
<213> ORGANISM: Artificial sequence
<220> FEATURE:
<223> OTHER INFORMATION: Synthetic sequence
<220> FEATURE:
<221> NAME/KEY: Misc_feature
<222> LOCATION: (48)..(48)
<223> OTHER INFORMATION: Xaa is selected from amino acid A, D, or E
<220> FEATURE:
<221> NAME/KEY: Misc_feature
<222> LOCATION: (148)..(148)
<223> OTHER INFORMATION: Xaa is selected from amino acid A, R, E, or L

<400> SEQUENCE: 41

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
                20                  25                  30

Asp Pro Gly Leu Ala Gly Val Ser Leu Thr Gly Gly Leu Ser Tyr Xaa
            35                  40                  45

Glu Asp Thr Lys Glu Leu Val Val Ala Lys Ala Gly Val Tyr Tyr Val
        50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125
```

```
Ala Gly Gln Arg Leu Gly Val His Leu His Thr Glu Ala Arg Ala Arg
        130                 135                 140

His Ala Trp Xaa Leu Thr Gln Gly Ala Thr Val Leu Gly Leu Phe Arg
145                 150                 155                 160

Val Thr Pro Glu Ile Pro Ala
                165

<210> SEQ ID NO 42
<211> LENGTH: 208
<212> TYPE: PRT
<213> ORGANISM: Artificial sequence
<220> FEATURE:
<223> OTHER INFORMATION: Synthetic sequence

<400> SEQUENCE: 42

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Ala Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

<210> SEQ ID NO 43
<211> LENGTH: 167
<212> TYPE: PRT
<213> ORGANISM: Artificial sequence
<220> FEATURE:
<223> OTHER INFORMATION: Synthetic sequence

<400> SEQUENCE: 43

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Ala
        35                  40                  45

Glu Asp Thr Lys Glu Leu Val Val Ala Lys Ala Gly Val Tyr Tyr Val
    50                  55                  60
```

```
Phe Phe Gln Leu Glu Leu Arg Arg Val Val Ala Gly Glu Gly Ser Gly
 65                  70                  75                  80

Ser Val Ser Leu Ala Leu His Leu Gln Pro Leu Arg Ser Ala Ala Gly
                 85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
            115                 120                 125

Ala Gly Gln Arg Leu Gly Val His Leu His Thr Glu Ala Arg Ala Arg
        130                 135                 140

His Ala Trp Ala Leu Thr Gln Gly Ala Thr Val Leu Gly Leu Phe Arg
145                 150                 155                 160

Val Thr Pro Glu Ile Pro Ala
                165

<210> SEQ ID NO 44
<211> LENGTH: 167
<212> TYPE: PRT
<213> ORGANISM: Artificial sequence
<220> FEATURE:
<223> OTHER INFORMATION: Synthetic sequence

<400> SEQUENCE: 44

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
                20                  25                  30

Asp Pro Gly Leu Ala Gly Val Ser Leu Thr Gly Gly Leu Ser Tyr Ala
            35                  40                  45

Glu Asp Thr Lys Glu Leu Val Val Ala Lys Ala Gly Val Tyr Tyr Val
        50                  55                  60

Phe Phe Gln Leu Glu Leu Arg Arg Val Val Ala Gly Glu Gly Ser Gly
 65                  70                  75                  80

Ser Val Ser Leu Ala Leu His Leu Gln Pro Leu Arg Ser Ala Ala Gly
                 85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
            115                 120                 125

Ala Gly Gln Arg Leu Gly Val His Leu His Thr Glu Ala Arg Ala Arg
        130                 135                 140

His Ala Trp Arg Leu Thr Gln Gly Ala Thr Val Leu Gly Leu Phe Arg
145                 150                 155                 160

Val Thr Pro Glu Ile Pro Ala
                165

<210> SEQ ID NO 45
<211> LENGTH: 167
<212> TYPE: PRT
<213> ORGANISM: Artificial sequence
<220> FEATURE:
<223> OTHER INFORMATION: Synthetic sequence

<400> SEQUENCE: 45

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
                20                  25                  30
```

```
Asp Pro Gly Leu Ala Gly Val Ser Leu Thr Gly Gly Leu Ser Tyr Ala
            35                  40                  45

Glu Asp Thr Lys Glu Leu Val Val Ala Lys Ala Gly Val Tyr Tyr Val
        50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Glu Leu Thr Gln Gly Ala Thr Val Leu Gly Leu Phe Arg
145                 150                 155                 160

Val Thr Pro Glu Ile Pro Ala
                165

<210> SEQ ID NO 46
<211> LENGTH: 167
<212> TYPE: PRT
<213> ORGANISM: Artificial sequence
<220> FEATURE:
<223> OTHER INFORMATION: Synthetic sequence

<400> SEQUENCE: 46

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Ala
            35                  40                  45

Glu Asp Thr Lys Glu Leu Val Val Ala Lys Ala Gly Val Tyr Tyr Val
        50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Leu Leu Thr Gln Gly Ala Thr Val Leu Gly Leu Phe Arg
145                 150                 155                 160

Val Thr Pro Glu Ile Pro Ala
                165

<210> SEQ ID NO 47
<211> LENGTH: 254
<212> TYPE: PRT
<213> ORGANISM: Homo sapiens
```

<400> SEQUENCE: 47

```
Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250
```

<210> SEQ ID NO 48
<211> LENGTH: 220
<212> TYPE: PRT
<213> ORGANISM: Homo sapiens

<400> SEQUENCE: 48

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110
```

```
Lys Ile Glu Val Met Tyr Pro Pro Tyr Leu Asp Asn Glu Lys Ser
            115                 120                 125

Asn Gly Thr Ile Ile His Val Lys Gly Lys His Leu Cys Pro Ser Pro
        130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
                180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
            210                 215                 220

<210> SEQ ID NO 49
<211> LENGTH: 123
<212> TYPE: PRT
<213> ORGANISM: Homo sapiens

<400> SEQUENCE: 49

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Trp Lys His Leu Cys Pro Ser Pro Leu
        35                  40                  45

Phe Pro Gly Pro Ser Lys Pro Phe Trp Val Leu Val Val Val Gly Gly
    50                  55                  60

Val Leu Ala Cys Tyr Ser Leu Leu Val Thr Val Ala Phe Ile Ile Phe
65                  70                  75                  80

Trp Val Arg Ser Lys Arg Ser Arg Leu Leu His Ser Asp Tyr Met Asn
                85                  90                  95

Met Thr Pro Arg Arg Pro Gly Pro Thr Arg Lys His Tyr Gln Pro Tyr
            100                 105                 110

Ala Pro Pro Arg Asp Phe Ala Ala Tyr Arg Ser
        115                 120

<210> SEQ ID NO 50
<211> LENGTH: 101
<212> TYPE: PRT
<213> ORGANISM: Homo sapiens

<400> SEQUENCE: 50

Met Leu Arg Leu Leu Ala Leu Asn Leu Phe Pro Ser Ile Gln Val
1               5                   10                  15

Thr Gly Lys His Leu Cys Pro Ser Pro Leu Phe Pro Gly Pro Ser Lys
            20                  25                  30

Pro Phe Trp Val Leu Val Val Val Gly Gly Val Leu Ala Cys Tyr Ser
            35                  40                  45

Leu Leu Val Thr Val Ala Phe Ile Ile Phe Trp Val Arg Ser Lys Arg
        50                  55                  60

Ser Arg Leu Leu His Ser Asp Tyr Met Asn Met Thr Pro Arg Arg Pro
65                  70                  75                  80
```

Gly Pro Thr Arg Lys His Tyr Gln Pro Tyr Ala Pro Pro Arg Asp Phe
                    85                  90                  95

Ala Ala Tyr Arg Ser
                100

<210> SEQ ID NO 51
<211> LENGTH: 255
<212> TYPE: PRT
<213> ORGANISM: Homo sapiens

<400> SEQUENCE: 51

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 52
<211> LENGTH: 227
<212> TYPE: PRT
<213> ORGANISM: Homo sapiens

<400> SEQUENCE: 52

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                  55                  60

His Asn Ala Lys Thr Lys Pro Arg Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225

<210> SEQ ID NO 53
<211> LENGTH: 325
<212> TYPE: PRT
<213> ORGANISM: Homo sapiens

<400> SEQUENCE: 53

Ser Thr Lys Gly Pro Ser Val Phe Pro Leu Ala Pro Cys Ser Arg Ser
 1               5                  10                  15

Thr Ser Glu Ser Thr Ala Ala Leu Gly Cys Leu Val Lys Asp Tyr Phe
             20                  25                  30

Pro Glu Pro Val Thr Val Ser Trp Asn Ser Gly Ala Leu Thr Ser Gly
         35                  40                  45

Val His Thr Phe Pro Ala Val Leu Gln Ser Ser Gly Leu Tyr Ser Leu
     50                  55                  60

Ser Ser Val Val Thr Val Pro Ser Ser Asn Phe Gly Thr Gln Thr Tyr
 65                  70                  75                  80

Thr Cys Asn Val Asp His Lys Pro Ser Asn Thr Lys Val Asp Lys Thr
                 85                  90                  95

Val Glu Arg Lys Cys Cys Val Glu Cys Pro Pro Cys Pro Ala Pro Pro
            100                 105                 110

Val Ala Gly Pro Ser Val Phe Leu Phe Pro Pro Lys Pro Lys Asp Thr
            115                 120                 125

Leu Met Ile Ser Arg Thr Pro Glu Val Thr Cys Val Val Val Asp Val
130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

```
Asn Gly Lys Glu Tyr Lys Cys Lys Val Ser Asn Lys Gly Leu Pro Ala
            195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
    275                 280                 285

Thr Val Asp Lys Ser Arg Trp Gln Gln Gly Asn Val Phe Ser Cys Ser
290                 295                 300

Val Met His Glu Ala Leu His Asn His Tyr Thr Gln Lys Ser Leu Ser
305                 310                 315                 320

Leu Ser Pro Gly Lys
                325

<210> SEQ ID NO 54
<211> LENGTH: 246
<212> TYPE: PRT
<213> ORGANISM: Homo sapiens

<400> SEQUENCE: 54

His Lys Pro Ser Asn Thr Lys Val Asp Lys Arg Val Glu Leu Lys Thr
1               5                   10                  15

Pro Leu Gly Asp Thr Thr His Thr Cys Pro Pro Cys Pro Ala Pro Glu
                20                  25                  30

Leu Leu Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
            115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
    195                 200                 205

Leu Thr Val Asp Lys Ser Arg Trp Gln Gln Gly Asn Val Phe Ser Cys
210                 215                 220
```

```
Ser Val Met His Glu Ala Leu His Asn His Tyr Thr Gln Lys Ser Leu
225                 230                 235                 240

Ser Leu Ser Pro Gly Lys
                245

<210> SEQ ID NO 55
<211> LENGTH: 383
<212> TYPE: PRT
<213> ORGANISM: Homo sapiens

<400> SEQUENCE: 55

Pro Thr Lys Ala Pro Asp Val Phe Pro Ile Ile Ser Gly Cys Arg His
1               5                   10                  15

Pro Lys Asp Asn Ser Pro Val Val Leu Ala Cys Leu Ile Thr Gly Tyr
                20                  25                  30

His Pro Thr Ser Val Thr Val Thr Trp Tyr Met Gly Thr Gln Ser Gln
            35                  40                  45

Pro Gln Arg Thr Phe Pro Glu Ile Gln Arg Arg Asp Ser Tyr Tyr Met
        50                  55                  60

Thr Ser Ser Gln Leu Ser Thr Pro Leu Gln Gln Trp Arg Gln Gly Glu
65                  70                  75                  80

Tyr Lys Cys Val Val Gln His Thr Ala Ser Lys Ser Lys Lys Glu Ile
                85                  90                  95

Phe Arg Trp Pro Glu Ser Pro Lys Ala Gln Ala Ser Ser Val Pro Thr
            100                 105                 110

Ala Gln Pro Gln Ala Glu Gly Ser Leu Ala Lys Ala Thr Thr Ala Pro
        115                 120                 125

Ala Thr Thr Arg Asn Thr Gly Arg Gly Gly Glu Lys Lys Lys Glu
130                 135                 140

Lys Glu Lys Glu Glu Gln Glu Glu Arg Glu Thr Lys Thr Pro Glu Cys
145                 150                 155                 160

Pro Ser His Thr Gln Pro Leu Gly Val Tyr Leu Leu Thr Pro Ala Val
                165                 170                 175

Gln Asp Leu Trp Leu Arg Asp Lys Ala Thr Phe Thr Cys Phe Val Val
            180                 185                 190

Gly Ser Asp Leu Lys Asp Ala His Leu Thr Trp Glu Val Ala Gly Lys
        195                 200                 205

Val Pro Thr Gly Gly Val Glu Glu Gly Leu Leu Glu Arg His Ser Asn
210                 215                 220

Gly Ser Gln Ser Gln His Ser Arg Leu Thr Leu Pro Arg Ser Leu Trp
225                 230                 235                 240

Asn Ala Gly Thr Ser Val Thr Cys Thr Leu Asn His Pro Ser Leu Pro
                245                 250                 255

Pro Gln Arg Leu Met Ala Leu Arg Glu Pro Ala Ala Gln Ala Pro Val
            260                 265                 270

Lys Leu Ser Leu Asn Leu Leu Ala Ser Ser Asp Pro Pro Glu Ala Ala
        275                 280                 285

Ser Trp Leu Leu Cys Glu Val Ser Gly Phe Ser Pro Pro Asn Ile Leu
290                 295                 300

Leu Met Trp Leu Glu Asp Gln Arg Glu Val Asn Thr Ser Gly Phe Ala
305                 310                 315                 320

Pro Ala Arg Pro Pro Pro Gln Pro Arg Ser Thr Thr Phe Trp Ala Trp
                325                 330                 335

Ser Val Leu Arg Val Pro Ala Pro Pro Ser Pro Gln Pro Ala Thr Tyr
            340                 345                 350
```

```
Thr Cys Val Ser His Glu Asp Ser Arg Thr Leu Leu Asn Ala Ser
        355                 360                 365
Arg Ser Leu Glu Val Ser Tyr Val Thr Asp His Gly Pro Met Lys
    370                 375                 380

<210> SEQ ID NO 56
<211> LENGTH: 276
<212> TYPE: PRT
<213> ORGANISM: Homo sapiens

<400> SEQUENCE: 56

Val Thr Ser Thr Leu Thr Ile Lys Glx Ser Asp Trp Leu Gly Glu Ser
1               5                   10                  15
Met Phe Thr Cys Arg Val Asp His Arg Gly Leu Thr Phe Gln Gln Asn
            20                  25                  30
Ala Ser Ser Met Cys Val Pro Asp Gln Asp Thr Ala Ile Arg Val Phe
        35                  40                  45
Ala Ile Pro Pro Ser Phe Ala Ser Ile Phe Leu Thr Lys Ser Thr Lys
    50                  55                  60
Leu Thr Cys Leu Val Thr Asp Leu Thr Thr Tyr Asx Ser Val Thr Ile
65                  70                  75                  80
Ser Trp Thr Arg Glu Glu Asn Gly Ala Val Lys Thr His Thr Asn Ile
                85                  90                  95
Ser Glu Ser His Pro Asn Ala Thr Phe Ser Ala Val Gly Glu Ala Ser
            100                 105                 110
Ile Cys Glu Asp Asx Asp Trp Ser Gly Glu Arg Phe Thr Cys Thr Val
        115                 120                 125
Thr His Thr Asp Leu Pro Ser Pro Leu Lys Gln Thr Ile Ser Arg Pro
    130                 135                 140
Lys Gly Val Ala Leu His Arg Pro Asx Val Tyr Leu Leu Pro Pro Ala
145                 150                 155                 160
Arg Glx Glx Leu Asn Leu Arg Glu Ser Ala Thr Ile Thr Cys Leu Val
                165                 170                 175
Thr Gly Phe Ser Pro Ala Asp Val Phe Val Glu Trp Met Gln Arg Gly
            180                 185                 190
Glu Pro Leu Ser Pro Gln Lys Tyr Val Thr Ser Ala Pro Met Pro Glu
        195                 200                 205
Pro Gln Ala Pro Gly Arg Tyr Phe Ala His Ser Ile Leu Thr Val Ser
    210                 215                 220
Glu Glu Glu Trp Asn Thr Gly Gly Thr Tyr Thr Cys Val Val Ala His
225                 230                 235                 240
Glu Ala Leu Pro Asn Arg Val Thr Glu Arg Thr Val Asp Lys Ser Thr
                245                 250                 255
Gly Lys Pro Thr Leu Tyr Asn Val Ser Leu Val Met Ser Asp Thr Ala
            260                 265                 270
Gly Thr Cys Tyr
    275

<210> SEQ ID NO 57
<211> LENGTH: 353
<212> TYPE: PRT
<213> ORGANISM: Homo sapiens
```

```
<400> SEQUENCE: 57

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 58
<211> LENGTH: 222
<212> TYPE: PRT
<213> ORGANISM: Homo sapiens
```

<400> SEQUENCE: 58

```
Ala Asp Pro Cys Asp Ser Asn Pro Arg Gly Val Ser Ala Tyr Leu Ser
1               5                   10                  15

Arg Pro Ser Pro Phe Asp Leu Phe Ile Arg Lys Ser Pro Thr Ile Thr
            20                  25                  30

Cys Leu Val Val Asp Leu Ala Pro Ser Lys Gly Thr Val Asn Leu Thr
        35                  40                  45

Trp Ser Arg Ala Ser Gly Lys Pro Val Asn His Ser Thr Arg Lys Glu
    50                  55                  60

Glu Lys Gln Arg Asn Gly Thr Leu Thr Val Thr Ser Thr Leu Pro Val
65                  70                  75                  80

Gly Thr Arg Asp Trp Ile Glu Gly Glu Thr Tyr Gln Cys Arg Val Thr
                85                  90                  95

His Pro His Leu Pro Arg Ala Leu Met Arg Ser Thr Thr Lys Thr Ser
            100                 105                 110

Gly Pro Arg Ala Ala Pro Glu Val Tyr Ala Phe Ala Thr Pro Glu Trp
        115                 120                 125

Pro Gly Ser Arg Asp Lys Arg Thr Leu Ala Cys Leu Ile Gln Asn Phe
    130                 135                 140

Met Pro Glu Asp Ile Ser Val Gln Trp Leu His Asn Glu Val Gln Leu
145                 150                 155                 160

Pro Asp Ala Arg His Ser Thr Thr Gln Pro Arg Lys Thr Lys Gly Ser
                165                 170                 175

Gly Phe Phe Val Phe Ser Arg Leu Glu Val Thr Arg Ala Glu Trp Glu
            180                 185                 190

Gln Lys Asp Glu Phe Ile Cys Arg Ala Val His Glu Ala Ala Ser Pro
        195                 200                 205

Ser Gln Thr Val Gln Arg Ala Val Ser Val Asn Pro Gly Lys
    210                 215                 220
```

<210> SEQ ID NO 59
<211> LENGTH: 327
<212> TYPE: PRT
<213> ORGANISM: Homo sapiens

<400> SEQUENCE: 59

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 60
<211> LENGTH: 365
<212> TYPE: PRT
<213> ORGANISM: Homo sapiens

<400> SEQUENCE: 60

Met Ala Val Met Ala Pro Arg Thr Leu Leu Leu Leu Leu Ser Gly Ala
1               5                   10                  15

Leu Ala Leu Thr Gln Thr Trp Ala Gly Ser His Ser Met Arg Tyr Phe
                20                  25                  30

Phe Thr Ser Val Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
        50                  55                  60

Ala Ser Gln Lys Met Glu Pro Arg Ala Pro Trp Ile Glu Gln Glu Gly
65                  70                  75                  80

Pro Glu Tyr Trp Asp Gln Glu Thr Arg Asn Met Lys Ala His Ser Gln
                85                  90                  95

Thr Asp Arg Ala Asn Leu Gly Thr Leu Arg Gly Tyr Tyr Asn Gln Ser
            100                 105                 110

Glu Asp Gly Ser His Thr Ile Gln Ile Met Tyr Gly Cys Asp Val Gly
        115                 120                 125

Pro Asp Gly Arg Phe Leu Arg Gly Tyr Arg Gln Asp Ala Tyr Asp Gly
    130                 135                 140

Lys Asp Tyr Ile Ala Leu Asn Glu Asp Leu Arg Ser Trp Thr Ala Ala
145                 150                 155                 160

Asp Met Ala Ala Gln Ile Thr Lys Arg Lys Trp Glu Ala Val His Ala
                165                 170                 175

Ala Glu Gln Arg Arg Val Tyr Leu Glu Gly Arg Cys Val Asp Gly Leu
            180                 185                 190
```

Arg Arg Tyr Leu Glu Asn Gly Lys Glu Thr Leu Gln Arg Thr Asp Pro
            195                 200                 205

Pro Lys Thr His Met Thr His His Pro Ile Ser Asp His Glu Ala Thr
        210                 215                 220

Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
            245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Lys Pro Leu Thr Leu Arg Trp Glu Leu Ser Ser Gln Pro
        290                 295                 300

Thr Ile Pro Ile Val Gly Ile Ile Ala Gly Leu Val Leu Leu Gly Ala
305                 310                 315                 320

Val Ile Thr Gly Ala Val Val Ala Val Met Trp Arg Arg Lys Ser
            325                 330                 335

Ser Asp Arg Lys Gly Gly Ser Tyr Thr Gln Ala Ala Ser Ser Asp Ser
            340                 345                 350

Ala Gln Gly Ser Asp Val Ser Leu Thr Ala Cys Lys Val
            355                 360                 365

<210> SEQ ID NO 61
<211> LENGTH: 362
<212> TYPE: PRT
<213> ORGANISM: Homo sapiens

<400> SEQUENCE: 61

Met Leu Val Met Ala Pro Arg Thr Val Leu Leu Leu Leu Ser Ala Ala
1               5                   10                  15

Leu Ala Leu Thr Glu Thr Trp Ala Gly Ser His Ser Met Arg Tyr Phe
            20                  25                  30

Tyr Thr Ser Val Ser Arg Pro Gly Arg Gly Glu Pro Arg Phe Ile Ser
        35                  40                  45

Val Gly Tyr Val Asp Asp Thr Gln Phe Val Arg Phe Asp Ser Asp Ala
    50                  55                  60

Ala Ser Pro Arg Glu Glu Pro Arg Ala Pro Trp Ile Glu Gln Glu Gly
65                  70                  75                  80

Pro Glu Tyr Trp Asp Arg Asn Thr Gln Ile Tyr Lys Ala Gln Ala Gln
                85                  90                  95

Thr Asp Arg Glu Ser Leu Arg Asn Leu Arg Gly Tyr Tyr Asn Gln Ser
            100                 105                 110

Glu Ala Gly Ser His Thr Leu Gln Ser Met Tyr Gly Cys Asp Val Gly
        115                 120                 125

Pro Asp Gly Arg Leu Leu Arg Gly His Asp Gln Tyr Ala Tyr Asp Gly
    130                 135                 140

Lys Asp Tyr Ile Ala Leu Asn Glu Asp Leu Arg Ser Trp Thr Ala Ala
145                 150                 155                 160

Asp Thr Ala Ala Gln Ile Thr Gln Arg Lys Trp Glu Ala Ala Arg Glu
                165                 170                 175

Ala Glu Gln Arg Arg Ala Tyr Leu Glu Gly Glu Cys Val Glu Trp Leu
            180                 185                 190

Arg Arg Tyr Leu Glu Asn Gly Lys Asp Lys Leu Glu Arg Ala Asp Pro
        195                 200                 205

```
Pro Lys Thr His Val Thr His His Pro Ile Ser Asp His Glu Ala Thr
    210                 215                 220
Leu Arg Cys Trp Ala Leu Gly Phe Tyr Pro Ala Glu Ile Thr Leu Thr
225                 230                 235                 240
Trp Gln Arg Asp Gly Glu Asp Gln Thr Gln Asp Thr Glu Leu Val Glu
                    245                 250                 255
Thr Arg Pro Ala Gly Asp Arg Thr Phe Gln Lys Trp Ala Ala Val Val
                260                 265                 270
Val Pro Ser Gly Glu Glu Gln Arg Tyr Thr Cys His Val Gln His Glu
                275                 280                 285
Gly Leu Pro Lys Pro Leu Thr Leu Arg Trp Glu Pro Ser Ser Gln Ser
290                 295                 300
Thr Val Pro Ile Val Gly Ile Val Ala Gly Leu Ala Val Leu Ala Val
305                 310                 315                 320
Val Val Ile Gly Ala Val Val Ala Ala Val Met Cys Arg Arg Lys Ser
                325                 330                 335
Ser Gly Gly Lys Gly Gly Ser Tyr Ser Gln Ala Ala Cys Ser Asp Ser
                340                 345                 350
Ala Gln Gly Ser Asp Val Ser Leu Thr Ala
                355                 360

<210> SEQ ID NO 62
<211> LENGTH: 366
<212> TYPE: PRT
<213> ORGANISM: Homo sapiens

<400> SEQUENCE: 62

Met Arg Val Met Ala Pro Arg Ala Leu Leu Leu Leu Leu Ser Gly Gly
1               5                   10                  15
Leu Ala Leu Thr Glu Thr Trp Ala Cys Ser His Ser Met Arg Tyr Phe
                20                  25                  30
Asp Thr Ala Val Ser Arg Pro Gly Arg Gly Glu Pro Arg Phe Ile Ser
            35                  40                  45
Val Gly Tyr Val Asp Asp Thr Gln Phe Val Arg Phe Asp Ser Asp Ala
    50                  55                  60
Ala Ser Pro Arg Gly Glu Pro Arg Ala Pro Trp Val Glu Gln Glu Gly
65                  70                  75                  80
Pro Glu Tyr Trp Asp Arg Glu Thr Gln Asn Tyr Lys Arg Gln Ala Gln
                85                  90                  95
Ala Asp Arg Val Ser Leu Arg Asn Leu Arg Gly Tyr Tyr Asn Gln Ser
                100                 105                 110
Glu Asp Gly Ser His Thr Leu Gln Arg Met Tyr Gly Cys Asp Leu Gly
            115                 120                 125
Pro Asp Gly Arg Leu Leu Arg Gly Tyr Asp Gln Ser Ala Tyr Asp Gly
        130                 135                 140
Lys Asp Tyr Ile Ala Leu Asn Glu Asp Leu Arg Ser Trp Thr Ala Ala
145                 150                 155                 160
Asp Thr Ala Ala Gln Ile Thr Gln Arg Lys Leu Glu Ala Ala Arg Ala
                165                 170                 175
Ala Glu Gln Leu Arg Ala Tyr Leu Glu Gly Thr Cys Val Glu Trp Leu
                180                 185                 190
Arg Arg Tyr Leu Glu Asn Gly Lys Glu Thr Leu Gln Arg Ala Glu Pro
            195                 200                 205
Pro Lys Thr His Val Thr His His Pro Leu Ser Asp His Glu Ala Thr
        210                 215                 220
```

```
Leu Arg Cys Trp Ala Leu Gly Phe Tyr Pro Ala Glu Ile Thr Leu Thr
225                 230                 235                 240

Trp Gln Arg Asp Gly Glu Asp Gln Thr Gln Asp Thr Glu Leu Val Glu
            245                 250                 255

Thr Arg Pro Ala Gly Asp Gly Thr Phe Gln Lys Trp Ala Ala Val Val
        260                 265                 270

Val Pro Ser Gly Gln Glu Gln Arg Tyr Thr Cys His Met Gln His Glu
    275                 280                 285

Gly Leu Gln Glu Pro Leu Thr Leu Ser Trp Glu Pro Ser Ser Gln Pro
290                 295                 300

Thr Ile Pro Ile Met Gly Ile Val Ala Gly Leu Ala Val Leu Val Val
305                 310                 315                 320

Leu Ala Val Leu Gly Ala Val Val Thr Ala Met Met Cys Arg Arg Lys
                325                 330                 335

Ser Ser Gly Gly Lys Gly Gly Ser Cys Ser Gln Ala Ala Cys Ser Asn
            340                 345                 350

Ser Ala Gln Gly Ser Asp Glu Ser Leu Ile Thr Cys Lys Ala
        355                 360                 365

<210> SEQ ID NO 63
<211> LENGTH: 119
<212> TYPE: PRT
<213> ORGANISM: Homo sapiens

<400> SEQUENCE: 63

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 64
<211> LENGTH: 119
<212> TYPE: PRT
<213> ORGANISM: Pan troglodytes

<400> SEQUENCE: 64

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60
```

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 65
<211> LENGTH: 119
<212> TYPE: PRT
<213> ORGANISM: Macaca mulatta

<400> SEQUENCE: 65

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Pro Glu Asn Gly Lys Pro Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Lys Met Gly Lys Val Glu His Ser Asp Leu Ser Phe Ser Lys Asp Trp
65                  70                  75                  80

Ser Phe Tyr Leu Leu Tyr Tyr Thr Glu Phe Thr Pro Asn Glu Lys Asp
                85                  90                  95

Glu Tyr Ala Cys Arg Val Asn His Val Thr Leu Ser Gly Pro Arg Thr
            100                 105                 110

Val Lys Trp Asp Arg Asp Met
        115

<210> SEQ ID NO 66
<211> LENGTH: 118
<212> TYPE: PRT
<213> ORGANISM: Bos Taurus

<400> SEQUENCE: 66

Met Ala Arg Phe Val Ala Leu Val Leu Leu Gly Leu Ser Leu Ser
1               5                   10                  15

Gly Leu Asp Ala Ile Gln Arg Pro Pro Lys Ile Gln Val Tyr Ser Arg
            20                  25                  30

His Pro Pro Glu Asp Gly Lys Pro Asn Tyr Leu Asn Cys Tyr Val Tyr
        35                  40                  45

Gly Phe His Pro Pro Gln Ile Glu Ile Asp Leu Leu Lys Asn Gly Glu
    50                  55                  60

Lys Ile Lys Ser Glu Gln Ser Asp Leu Ser Phe Ser Lys Asp Trp Ser
65                  70                  75                  80

Phe Tyr Leu Leu Ser His Ala Glu Phe Thr Pro Asn Ser Lys Asp Gln
                85                  90                  95

Tyr Ser Cys Arg Val Lys His Val Thr Leu Glu Gln Pro Arg Ile Val
            100                 105                 110

Lys Trp Asp Arg Asp Leu
        115

<210> SEQ ID NO 67
<211> LENGTH: 119
<212> TYPE: PRT
<213> ORGANISM: Mus musculus

<400> SEQUENCE: 67

Met Ala Arg Ser Val Thr Leu Val Phe Leu Val Leu Val Ser Leu Thr
1               5                   10                  15

Gly Leu Tyr Ala Ile Gln Lys Thr Pro Gln Ile Gln Val Tyr Ser Arg
            20                  25                  30

His Pro Pro Glu Asn Gly Lys Pro Asn Ile Leu Asn Cys Tyr Val Thr
        35                  40                  45

Gln Phe His Pro Pro His Ile Glu Ile Gln Met Leu Lys Asn Gly Lys
    50                  55                  60

Lys Ile Pro Lys Val Glu Met Ser Asp Met Ser Phe Ser Lys Asp Trp
65                  70                  75                  80

Ser Phe Tyr Ile Leu Ala His Thr Glu Phe Thr Pro Thr Glu Thr Asp
                85                  90                  95

Thr Tyr Ala Cys Arg Val Lys His Ala Ser Met Ala Glu Pro Lys Thr
            100                 105                 110

Val Tyr Trp Asp Arg Asp Met
        115

<210> SEQ ID NO 68
<211> LENGTH: 2316
<212> TYPE: DNA
<213> ORGANISM: Artificial sequence
<220> FEATURE:
<223> OTHER INFORMATION: Synthetic sequence

<400> SEQUENCE: 68
atgtctcgct ccgtggcctt agctgtgctc gcgctactct ctctttctgg cctggaggcc      60
gttatccacg tgaccaagga agtgaaagaa gtggcaacgc tgtcctgtgg tcacaatgtt     120
tctgttgaag agctggcaca aactcgcatc tactggcaaa aggagaagaa aatggtgctg     180
actatgatgt ctggggacat gaatatatgg cccgagtaca gaaccggac catctttgat      240 atcactaata acctctccat tgtgatcctg gctctgcgcc atctgacga gggcacatac      300 gagtgtgttg ttctgaagta tgaaaaagac gctttcaagc gggaacacct ggctgaagtg     360
acgttatcag tcaaagctga cttccctaca cctagtatat ctgactttga aattccaact     420
tctaatatta aaggataat ttgctcaacc tctggaggtt ttccagagcc tcacctctcc      480
tggttggaaa atggagaaga attaaatgcc atcaacacaa cagtttccca agatcctgaa     540
actgagctct atgctgttag cagcaaactg gatttcaata tgacaaccaa ccacagcttc     600
atgtgtctca tcaagtatgg acatttaaga gtgaatcaga ccttcaactg gaatacaacc     660
aagcaagagc attttcctga taacggaggc ggaggatctg tggtggagg ttctggtggt      720 gggggatctg gaggcggagg atctggcccg cattccctgc gctactttgt gaccgctgtt     780
agccgcccgg gcctgggtga accgcgttac atggaggtcg gttatgtgga tgacacggag     840
tttgtgcgtt tcgattcaga cgctgagaac ccgcgttacg aaccgcgtgc aagatggatg     900
gaacaggaag gcccggaata ttgggaaga gagacccaaa aggcaaaagg caacgaacaa     960
agcttccgtg tggacctgcg taccctgctg ggcgcctaca accaatcaaa aggtggctcg    1020
cacacgatcc aggtgatcag cggctgcgag gttggtagcg atggccgtct gctgcgcggc    1080
tatcagcaat acgcctacga cggttgcgat tatatcgcac tgaatgaaga cctgaaaacc    1140

```
tggacggcgg ccgatatggc agctctgatt acgaagcaca atgggaaca ggctggcgag    1200 gcggaaagac tgcgcgccta cctggagggt acctgcgtgg aatggctgcg tcgctatctg    1260
aagaacggca atgccacctt gctgcgtacg gatagcccga agcacatgt tacccaccac    1320 agccgccccg aggacaaggt tacgctgcgt tgttgggctc tgggcttta tccggcggat    1380 attaccctga cgtggcagct gaacggtgaa gagctgatcc aagatatgga actggtggaa    1440
acccgtccgt gcggcgatgg cacgttccag aaatgggcaa gcgtggttgt cccgctgggt    1500
aaagaacaat actacacctg tcatgtttac caccagggtc tgccggaacc gctgacgctg    1560
cgttgggcag ctgcgggtgg ccccagaggg cccacaatca gccctgtcc tccatgcaaa    1620 tgcccagcac ctaacctctt gggtggacca tccgtcttca tcttccctcc aaagatcaag    1680
gatgtactca tgatctccct gagccccata gtcacatgtg tggtggtgga tgtgagcgag    1740
gatgacccag atgtccagat cagctggttt gtgaacaacg tggaagtaca cacagctcag    1800
acacaaaccc atagagagga ttacaacagt actctccggg tggtcagtgc cctccccatc    1860
cagcaccagg actggatgag tggcaaggag ttcaaatgca aggtcaacaa caaagacctc    1920
ccagcgccca tcgagagaac catctcaaaa cccaaagggt cagtaagagc tccacaggta    1980
tatgtcttgc ctccaccaga agaagagatg actaagaaac aggtcactct gacctgcatg    2040
gtcacagact tcatgcctga agacatttac gtggagtgga ccaacaacgg gaaaacagag    2100
ctaaactaca gaacactga accagtcctg gactctgatg gttcttactt catgtacagc    2160
aagctgagag tggaaaagaa gaactgggtg gaaagaaata gctactcctg ttcagtggtc    2220
cacgagggtc tgcacaatca ccacacgact aagagcttct cccggactcc gggtaaaggc    2280
ggatcacatc accatcacca tcaccatcac tagtga                            2316
```

<210> SEQ ID NO 69
<211> LENGTH: 770
<212> TYPE: PRT
<213> ORGANISM: Artificial sequence
<220> FEATURE:
<223> OTHER INFORMATION: Synthetic sequence

<400> SEQUENCE: 69

```
Met Ser Arg Ser Val Ala Leu Ala Val Leu Ala Leu Leu Ser Leu Ser
1               5                   10                  15

Gly Leu Glu Ala Val Ile His Val Thr Lys Glu Val Lys Glu Val Ala
            20                  25                  30

Thr Leu Ser Cys Gly His Asn Val Ser Val Glu Glu Leu Ala Gln Thr
        35                  40                  45

Arg Ile Tyr Trp Gln Lys Glu Lys Lys Met Val Leu Thr Met Met Ser
    50                  55                  60

Gly Asp Met Asn Ile Trp Pro Glu Tyr Lys Asn Arg Thr Ile Phe Asp
65                  70                  75                  80

Ile Thr Asn Asn Leu Ser Ile Val Ile Leu Ala Leu Arg Pro Ser Asp
                85                  90                  95

Glu Gly Thr Tyr Glu Cys Val Val Leu Lys Tyr Glu Lys Asp Ala Phe
            100                 105                 110

Lys Arg Glu His Leu Ala Glu Val Thr Leu Ser Val Lys Ala Asp Phe
        115                 120                 125

Pro Thr Pro Ser Ile Ser Asp Phe Glu Ile Pro Thr Ser Asn Ile Arg
    130                 135                 140

Arg Ile Ile Cys Ser Thr Ser Gly Gly Phe Pro Glu Pro His Leu Ser
145                 150                 155                 160
```

```
Trp Leu Glu Asn Gly Glu Leu Asn Ala Ile Asn Thr Thr Val Ser
            165                 170                 175

Gln Asp Pro Glu Thr Glu Leu Tyr Ala Val Ser Ser Lys Leu Asp Phe
        180                 185                 190

Asn Met Thr Thr Asn His Ser Phe Met Cys Leu Ile Lys Tyr Gly His
            195                 200                 205

Leu Arg Val Asn Gln Thr Phe Asn Trp Asn Thr Thr Lys Gln Glu His
        210                 215                 220

Phe Pro Asp Asn Gly Gly Gly Ser Gly Gly Gly Ser Gly Gly
225                 230                 235                 240

Gly Gly Ser Gly Gly Gly Ser Gly Pro His Ser Leu Arg Tyr Phe
                245                 250                 255

Val Thr Ala Val Ser Arg Pro Gly Leu Gly Glu Pro Arg Tyr Met Glu
            260                 265                 270

Val Gly Tyr Val Asp Asp Thr Glu Phe Val Arg Phe Asp Ser Asp Ala
        275                 280                 285

Glu Asn Pro Arg Tyr Glu Pro Arg Ala Arg Trp Met Glu Gln Glu Gly
        290                 295                 300

Pro Glu Tyr Trp Glu Arg Glu Thr Gln Lys Ala Lys Gly Asn Glu Gln
305                 310                 315                 320

Ser Phe Arg Val Asp Leu Arg Thr Leu Leu Gly Ala Tyr Asn Gln Ser
                325                 330                 335

Lys Gly Gly Ser His Thr Ile Gln Val Ile Ser Gly Cys Glu Val Gly
                340                 345                 350

Ser Asp Gly Arg Leu Leu Arg Gly Tyr Gln Gln Tyr Ala Tyr Asp Gly
            355                 360                 365

Cys Asp Tyr Ile Ala Leu Asn Glu Asp Leu Lys Thr Trp Thr Ala Ala
        370                 375                 380

Asp Met Ala Ala Leu Ile Thr Lys His Lys Trp Glu Gln Ala Gly Glu
385                 390                 395                 400

Ala Glu Arg Leu Arg Ala Tyr Leu Glu Gly Thr Cys Val Glu Trp Leu
                405                 410                 415

Arg Arg Tyr Leu Lys Asn Gly Asn Ala Thr Leu Leu Arg Thr Asp Ser
                420                 425                 430

Pro Lys Ala His Val Thr His His Ser Arg Pro Glu Asp Lys Val Thr
        435                 440                 445

Leu Arg Cys Trp Ala Leu Gly Phe Tyr Pro Ala Asp Ile Thr Leu Thr
        450                 455                 460

Trp Gln Leu Asn Gly Glu Glu Leu Ile Gln Asp Met Glu Leu Val Glu
465                 470                 475                 480

Thr Arg Pro Cys Gly Asp Gly Thr Phe Gln Lys Trp Ala Ser Val Val
                485                 490                 495

Val Pro Leu Gly Lys Glu Gln Tyr Tyr Thr Cys His Val Tyr His Gln
                500                 505                 510

Gly Leu Pro Glu Pro Leu Thr Leu Arg Trp Ala Ala Ala Gly Gly Pro
        515                 520                 525

Arg Gly Pro Thr Ile Lys Pro Cys Pro Pro Cys Lys Cys Pro Ala Pro
        530                 535                 540

Asn Leu Leu Gly Gly Pro Ser Val Phe Ile Phe Pro Pro Lys Ile Lys
545                 550                 555                 560

Asp Val Leu Met Ile Ser Leu Ser Pro Ile Val Thr Cys Val Val Val
                565                 570                 575
```

```
Asp Val Ser Glu Asp Asp Pro Asp Val Gln Ile Ser Trp Phe Val Asn
            580                 585                 590

Asn Val Glu Val His Thr Ala Gln Thr Gln Thr His Arg Glu Asp Tyr
        595                 600                 605

Asn Ser Thr Leu Arg Val Val Ser Ala Leu Pro Ile Gln His Gln Asp
    610                 615                 620

Trp Met Ser Gly Lys Glu Phe Lys Cys Lys Val Asn Asn Lys Asp Leu
625                 630                 635                 640

Pro Ala Pro Ile Glu Arg Thr Ile Ser Lys Pro Lys Gly Ser Val Arg
                645                 650                 655

Ala Pro Gln Val Tyr Val Leu Pro Pro Glu Glu Glu Met Thr Lys
            660                 665                 670

Lys Gln Val Thr Leu Thr Cys Met Val Thr Asp Phe Met Pro Glu Asp
        675                 680                 685

Ile Tyr Val Glu Trp Thr Asn Asn Gly Lys Thr Glu Leu Asn Tyr Lys
    690                 695                 700

Asn Thr Glu Pro Val Leu Asp Ser Asp Gly Ser Tyr Phe Met Tyr Ser
705                 710                 715                 720

Lys Leu Arg Val Glu Lys Lys Asn Trp Val Glu Arg Asn Ser Tyr Ser
                725                 730                 735

Cys Ser Val Val His Glu Gly Leu His Asn His His Thr Thr Lys Ser
            740                 745                 750

Phe Ser Arg Thr Pro Gly Lys Gly Gly Ser His His His His His His
        755                 760                 765

His His
    770

<210> SEQ ID NO 70
<211> LENGTH: 2166
<212> TYPE: DNA
<213> ORGANISM: Artificial sequence
<220> FEATURE:
<223> OTHER INFORMATION: Synthetic sequence

<400> SEQUENCE: 70
atgtcccgct ccgtggcgct tgcggtgctg gccctgctgt cgttgtccgg gctggaagcg      60
tccattatca acttcgagaa actggggggga ggagcctcag gaggaggagg atccgggggt     120
ggaggtagca tgattcaaaa gaccectcaa atccaggtct actcgtgcca cccacccgag     180
aacggaaagc ctaatatcct gaactgttac gtgacccaat ccacccgcc gcatatcgag      240 atccagatgc tcaagaacgg caagaagatc cccaaggtgg aaatgtccga catgagcttt     300
tccaaggatt ggtcgttcta tatcctggct cataccgagt caccccccac cgaaaccgat    360
acttacgcct ccgcgtcaa gcacgcctca atggcggagc taagaccgt gtactgggac      420 cgggacatgg gtggcggggg gtccggagga ggtggatccg gcggaggggg atctggcgga    480
ggcggatcag gaggtggcgg ctctgacct gcaggcctgc tggatctgcg gcagggcatg    540
ttcgcacaac tcgtggccca gaacgtgctg ctgatcgatg gaccgctgtc ctggtactcc   600
gacccgggac ttgccggagt gtcactgact ggaggattgt cctacaagga agatacgaag    660
gagctcgtcg tggcgaaggc cggagtgtac tatgtgttct ccagctcga actccggaga    720 gtcgtggccg gggaaggctc cggctccgtg tcacttgccc tgcacctcca gccacttcgg    780
tcggccgctg agccgccgc actggccctg accgtcgacc tcctcctgc gtcctccgag      840 gctcgcaact cggccttcgg attccaaggg cgccttctgc acctgtccgc gggacagagg    900
```

```
ctggggtgc atctgcatac tgaagcgcgg gcacggcatg cttggcagct gactcaggga    960
gcaactgtcc tgggtctgtt ccgcgtgact ccggaaatcc ccgccggtgg aggtggctca   1020
ggaggcggcg gcagcggtgg aggagggagc ggaggaggcg gatccggtgg aggcggaagc   1080
gaccctgccg gactcctgga tctgcggcag ggcatgttcg cccagttggt ggcgcagaac   1140
gtcctgctca ttgacgggcc gctgtcgtgg tacagcgatc cgggcttggc cggagtctcg   1200
ctgaccggag gactcagcta caaggaagat accaaggagc tggtcgtggc caaggccgga   1260
gtgtactacg tgttcttcca actggaactg cgccgggtgg tggctggcga aggatccggg   1320
tcggtgtccc tggccctgca tctgcagcct ctgcgctcag ccgcaggagc agccgccttg   1380
gcgctcaccg tggaccttcc gcccgcctcc tcggaagccc ggaacagcgc cttcggcttc   1440
caaggcagac tcctgcactt gagcgcgggc cagagactgg gagtgcacct ccacaccgaa   1500
gcgcgcgcaa ggcacgcctg gcagctcacc cagggagcca ccgtgctggg cttgtttcga   1560 gtcaccccg agatcccagc cggcggagga ggttccggtg gcggtggatc aggcggtgga   1620
ggctcgggtg aggggggtag cggaggggt ggttccgacc ccgcaggact gctggacctc    1680
cggcagggga tgttcgcgca actggtggct cagaatgtcc tgctgattga cggccccctg   1740
tcgtggtact cggaccctgg ccttgccggc gtgtccttga ctggagggct gtcgtacaag   1800
gaggacacta aggagctggt cgtggccaaa gccggcgtgt actacgtgtt ctttcagctg   1860
gaactgagga gagtggtggc gggagaaggc agcggctcag tgtccctcgc cctgcacctt   1920
caaccactcc gctctgccgc tggtgcagct gcgctcgccc tcactgtgga tcttccaccg   1980
gcaagctccg aggccagaaa ctccgccttc gggttccagg ggaggctgct gcatctctcc   2040
gccggccaga gactgggcgt gcacttgcac actgaggcta gggctcgcca tgcctggcag   2100
ctgacccagg gcgccactgt gctgggactg ttccgggtga ccccagaaat cccggcctcc   2160
tgatag                                                             2166
```

<210> SEQ ID NO 71
<211> LENGTH: 720
<212> TYPE: PRT
<213> ORGANISM: Artificial sequence
<220> FEATURE:
<223> OTHER INFORMATION: Synthetic sequence

<400> SEQUENCE: 71

```
Met Ser Arg Ser Val Ala Leu Ala Val Leu Ala Leu Leu Ser Leu Ser
1               5                   10                  15

Gly Leu Glu Ala Ser Ile Ile Asn Phe Glu Lys Leu Gly Gly Gly Ala
            20                  25                  30

Ser Gly Gly Gly Gly Ser Gly Gly Gly Ser Met Ile Gln Lys Thr
        35                  40                  45

Pro Gln Ile Gln Val Tyr Ser Cys His Pro Glu Asn Gly Lys Pro
    50                  55                  60

Asn Ile Leu Asn Cys Tyr Val Thr Gln Phe His Pro Pro His Ile Glu
65                  70                  75                  80

Ile Gln Met Leu Lys Asn Gly Lys Lys Ile Pro Lys Val Glu Met Ser
                85                  90                  95

Asp Met Ser Phe Ser Lys Asp Trp Ser Phe Tyr Ile Leu Ala His Thr
            100                 105                 110

Glu Phe Thr Pro Thr Glu Thr Asp Thr Tyr Ala Cys Arg Val Lys His
        115                 120                 125
```

```
Ala Ser Met Ala Glu Pro Lys Thr Val Tyr Trp Asp Arg Asp Met Gly
        130                 135                 140

Gly Gly Gly Ser Gly Gly Gly Ser Gly Gly Gly Ser Gly Gly
145                 150                 155                 160

Gly Gly Ser Gly Gly Gly Ser Asp Pro Ala Gly Leu Leu Asp Leu
            165                 170                 175

Arg Gln Gly Met Phe Ala Gln Leu Val Ala Gln Asn Val Leu Leu Ile
                180                 185                 190

Asp Gly Pro Leu Ser Trp Tyr Ser Asp Pro Gly Leu Ala Gly Val Ser
            195                 200                 205

Leu Thr Gly Gly Leu Ser Tyr Lys Glu Asp Thr Lys Glu Leu Val Val
210                 215                 220

Ala Lys Ala Gly Val Tyr Tyr Val Phe Phe Gln Leu Glu Leu Arg Arg
225                 230                 235                 240

Val Val Ala Gly Glu Gly Ser Gly Ser Val Ser Leu Ala Leu His Leu
                245                 250                 255

Gln Pro Leu Arg Ser Ala Ala Gly Ala Ala Leu Ala Leu Thr Val
            260                 265                 270

Asp Leu Pro Pro Ala Ser Ser Glu Ala Arg Asn Ser Ala Phe Gly Phe
            275                 280                 285

Gln Gly Arg Leu Leu His Leu Ser Ala Gly Gln Arg Leu Gly Val His
            290                 295                 300

Leu His Thr Glu Ala Arg Ala Arg His Ala Trp Gln Leu Thr Gln Gly
305                 310                 315                 320

Ala Thr Val Leu Gly Leu Phe Arg Val Thr Pro Glu Ile Pro Ala Gly
                325                 330                 335

Gly Gly Gly Ser Gly Gly Gly Ser Gly Gly Gly Ser Gly Gly
                340                 345                 350

Gly Gly Ser Gly Gly Gly Ser Asp Pro Ala Gly Leu Leu Asp Leu
            355                 360                 365

Arg Gln Gly Met Phe Ala Gln Leu Val Ala Gln Asn Val Leu Leu Ile
                370                 375                 380

Asp Gly Pro Leu Ser Trp Tyr Ser Asp Pro Gly Leu Ala Gly Val Ser
385                 390                 395                 400

Leu Thr Gly Gly Leu Ser Tyr Lys Glu Asp Thr Lys Glu Leu Val Val
                405                 410                 415

Ala Lys Ala Gly Val Tyr Tyr Val Phe Phe Gln Leu Glu Leu Arg Arg
                420                 425                 430

Val Val Ala Gly Glu Gly Ser Gly Ser Val Ser Leu Ala Leu His Leu
            435                 440                 445

Gln Pro Leu Arg Ser Ala Ala Gly Ala Ala Leu Ala Leu Thr Val
            450                 455                 460

Asp Leu Pro Pro Ala Ser Ser Glu Ala Arg Asn Ser Ala Phe Gly Phe
465                 470                 475                 480

Gln Gly Arg Leu Leu His Leu Ser Ala Gly Gln Arg Leu Gly Val His
                485                 490                 495

Leu His Thr Glu Ala Arg Ala Arg His Ala Trp Gln Leu Thr Gln Gly
                500                 505                 510

Ala Thr Val Leu Gly Leu Phe Arg Val Thr Pro Glu Ile Pro Ala Gly
            515                 520                 525

Gly Gly Gly Ser Gly Gly Gly Ser Gly Gly Gly Ser Gly Gly
            530                 535                 540
```

-continued

Gly Gly Ser Gly Gly Gly Ser Asp Pro Ala Gly Leu Leu Asp Leu
545                 550                 555                 560

Arg Gln Gly Met Phe Ala Gln Leu Val Ala Gln Asn Val Leu Ile
            565                 570                 575

Asp Gly Pro Leu Ser Trp Tyr Ser Asp Pro Gly Leu Ala Gly Val Ser
            580                 585                 590

Leu Thr Gly Gly Leu Ser Tyr Lys Glu Asp Thr Lys Glu Leu Val Val
        595                 600                 605

Ala Lys Ala Gly Val Tyr Tyr Val Phe Phe Gln Leu Glu Leu Arg Arg
    610                 615                 620

Val Val Ala Gly Glu Gly Ser Gly Ser Val Ser Leu Ala Leu His Leu
625                 630                 635                 640

Gln Pro Leu Arg Ser Ala Ala Gly Ala Ala Leu Ala Leu Thr Val
            645                 650                 655

Asp Leu Pro Pro Ala Ser Ser Glu Ala Arg Asn Ser Ala Phe Gly Phe
        660                 665                 670

Gln Gly Arg Leu Leu His Leu Ser Ala Gly Gln Arg Leu Gly Val His
            675                 680                 685

Leu His Thr Glu Ala Arg Ala Arg His Ala Trp Gln Leu Thr Gln Gly
690                 695                 700

Ala Thr Val Leu Gly Leu Phe Arg Val Thr Pro Glu Ile Pro Ala Ser
705                 710                 715                 720

<210> SEQ ID NO 72
<211> LENGTH: 2256
<212> TYPE: DNA
<213> ORGANISM: Artificial sequence
<220> FEATURE:
<223> OTHER INFORMATION: Synthetic sequence

<400> SEQUENCE: 72
atgtcccgct ccgtggcgct tgcggtgctg gccctgctgt cgttgtccgg gctggaagcg      60
tccattatca acttcgagaa actgggggga ggagcctcag gaggaggagg atccggggt     120 ggaggtagca tgattcaaaa gaccccctcaa atccaggtct actcgtgcca cccacccgag    180
aacggaaagc ctaatatcct gaactgttac gtgacccaat ccacccgcc gcatatcgag      240 atccagatgc tcaagaacgg caagaagatc cccaaggtgg aaatgtccga catgagcttt    300
tccaaggatt ggtcgttcta tatcctggct cataccgagt tcacccccac cgaaaccgat    360
acttacgcct gccgcgtcaa gcacgcctca atggcggagc taagaccgt gtactgggac     420 cgggacatgg gtggcggggg gtccggagga ggtggatccg gcggaggggg atctggcgga    480
ggcggatcag gaggtggcgg ctctgcctgc ccctgggccg tgtccgggc tcgcgcctcg     540 cccggctccg cggccagccc gagactccgc gagggtcccg agctttcgcc gacgaccct    600 gcaggcctgc tggatctgcg gcagggcatg ttcgcacaac tcgtggccca gaacgtgctg    660
ctgatcgatg accgctgtc ctggtactcc gacccgggac ttgccggagt gtcactgact    720
ggaggattgt cctacaagga agatacgaag gagctcgtcg tggcgaaggc cggagtgtac    780
tatgtgttct tccagctcga actccggaga gtcgtggccg ggaaggctc cggctccgtg    840 tcacttgccc tgcacctcca gccacttcgg tcggccgctg agccgccgc actggccctg    900 accgtcgacc tcctcctgc gtcctccgag gctcgcaact cggccttcgg attccaaggg    960
cgccttctgc acctgtccgc gggacagagg ctggggtgc atctgcatac tgaagcgcg   1020 gcacggcatg cttggcagct gactcaggga gcaactgtcc tgggtctgtt ccgcgtgact   1080

-continued

```
ccggaaatcc cgccggtgg aggtggctca ggaggcggcg gcagcggtgg aggagggagc   1140
ggaggaggcg gatccggtgg aggcggaagc gaccctgccg gactcctgga tctgcggcag   1200
ggcatgttcg cccagttggt ggcgcagaac gtcctgctca ttgacgggcc gctgtcgtgg   1260
tacagcgatc cgggcttggc cggagtctcg ctgaccggag gactcagcta caaggaagat   1320
accaaggagc tggtcgtggc caaggccgga gtgtactacg tgttcttcca actggaactg   1380
cgccgggtgg tggctggcga aggatccggg tcggtgtccc tggccctgca tctgcagcct   1440
ctgcgctcag ccgcaggagc agccgccttg gcgctcaccg tggaccttcc gcccgcctcc   1500
tcggaagccc ggaacagcgc cttcggcttc aaggcagac tcctgcactt gagcgcgggc   1560
cagagactgg gagtgcacct ccacaccgaa gcgcgcgcaa ggcacgcctg gcagctcacc   1620
caggagccca ccgtgctggg cttgtttcga gtcaccccg agatcccagc cggcggagga   1680
ggttccggtg gcggtggatc aggcggtgga ggctcgggtg gaggggtag cggagggggt   1740 ggttccgacc ccgcaggact gctggacctc cggcagggga tgttcgcgca actggtggct   1800
cagaatgtcc tgctgattga cggccccctg tcgtggtact cggaccctgg ccttgccggc   1860
gtgtccttga ctggagggct gtcgtacaag gaggacacta aggagctggt cgtggccaaa   1920
gccggcgtgt actacgtgtt ctttcagctg gaactgagga gagtggtggc gggagaaggc   1980
agcggctcag tgtccctcgc cctgcacctt caaccactcc gctctgccgc tggtgcagct   2040
gcgctcgccc tcactgtgga tcttccaccg gcaagctccg aggccagaaa ctccgccttc   2100
gggttccagg ggaggctgct gcatctctcc gccggccaga gactgggcgt gcacttgcac   2160
actgaggcta gggctcgcca tgcctggcag ctgacccagg gcgccactgt gctgggactg   2220
ttccgggtga ccccagaaat cccggcctcc tgatag                           2256
```

<210> SEQ ID NO 73
<211> LENGTH: 750
<212> TYPE: PRT
<213> ORGANISM: Artificial sequence
<220> FEATURE:
<223> OTHER INFORMATION: Synthetic sequence

<400> SEQUENCE: 73

```
Met Ser Arg Ser Val Ala Leu Ala Val Leu Ala Leu Leu Ser Leu Ser
1               5                   10                  15

Gly Leu Glu Ala Ser Ile Ile Asn Phe Glu Lys Leu Gly Gly Gly Ala
            20                  25                  30

Ser Gly Gly Gly Gly Ser Gly Gly Gly Gly Ser Met Ile Gln Lys Thr
        35                  40                  45

Pro Gln Ile Gln Val Tyr Ser Cys His Pro Pro Glu Asn Gly Lys Pro
    50                  55                  60

Asn Ile Leu Asn Cys Tyr Val Thr Gln Phe His Pro Pro His Ile Glu
65                  70                  75                  80

Ile Gln Met Leu Lys Asn Gly Lys Lys Ile Pro Lys Val Glu Met Ser
                85                  90                  95

Asp Met Ser Phe Ser Lys Asp Trp Ser Phe Tyr Ile Leu Ala His Thr
            100                 105                 110

Glu Phe Thr Pro Thr Glu Thr Asp Thr Tyr Ala Cys Arg Val Lys His
        115                 120                 125

Ala Ser Met Ala Glu Pro Lys Thr Val Tyr Trp Asp Arg Asp Met Gly
    130                 135                 140

Gly Gly Gly Ser Gly Gly Gly Gly Ser Gly Gly Gly Gly Ser Gly Gly
145                 150                 155                 160
```

```
Gly Gly Ser Gly Gly Gly Gly Ser Ala Cys Pro Trp Ala Val Ser Gly
            165                 170                 175
Ala Arg Ala Ser Pro Gly Ser Ala Ala Ser Pro Arg Leu Arg Glu Gly
            180                 185                 190
Pro Glu Leu Ser Pro Asp Asp Pro Ala Gly Leu Leu Asp Leu Arg Gln
            195                 200                 205
Gly Met Phe Ala Gln Leu Val Ala Gln Asn Val Leu Leu Ile Asp Gly
            210                 215                 220
Pro Leu Ser Trp Tyr Ser Asp Pro Gly Leu Ala Gly Val Ser Leu Thr
225                 230                 235                 240
Gly Gly Leu Ser Tyr Lys Glu Asp Thr Lys Glu Leu Val Val Ala Lys
            245                 250                 255
Ala Gly Val Tyr Tyr Val Phe Phe Gln Leu Glu Leu Arg Arg Val Val
            260                 265                 270
Ala Gly Glu Gly Ser Gly Ser Val Ser Leu Ala Leu His Leu Gln Pro
            275                 280                 285
Leu Arg Ser Ala Ala Gly Ala Ala Ala Leu Ala Leu Thr Val Asp Leu
            290                 295                 300
Pro Pro Ala Ser Ser Glu Ala Arg Asn Ser Ala Phe Gly Phe Gln Gly
305                 310                 315                 320
Arg Leu Leu His Leu Ser Ala Gly Gln Arg Leu Gly Val His Leu His
            325                 330                 335
Thr Glu Ala Arg Ala Arg His Ala Trp Gln Leu Thr Gln Gly Ala Thr
            340                 345                 350
Val Leu Gly Leu Phe Arg Val Thr Pro Glu Ile Pro Ala Gly Gly Gly
            355                 360                 365
Gly Ser Gly Gly Gly Gly Ser Gly Gly Gly Ser Gly Gly Gly Gly
            370                 375                 380
Ser Gly Gly Gly Gly Ser Asp Pro Ala Gly Leu Leu Asp Leu Arg Gln
385                 390                 395                 400
Gly Met Phe Ala Gln Leu Val Ala Gln Asn Val Leu Leu Ile Asp Gly
            405                 410                 415
Pro Leu Ser Trp Tyr Ser Asp Pro Gly Leu Ala Gly Val Ser Leu Thr
            420                 425                 430
Gly Gly Leu Ser Tyr Lys Glu Asp Thr Lys Glu Leu Val Val Ala Lys
            435                 440                 445
Ala Gly Val Tyr Tyr Val Phe Phe Gln Leu Glu Leu Arg Arg Val Val
            450                 455                 460
Ala Gly Glu Gly Ser Gly Ser Val Ser Leu Ala Leu His Leu Gln Pro
465                 470                 475                 480
Leu Arg Ser Ala Ala Gly Ala Ala Ala Leu Ala Leu Thr Val Asp Leu
            485                 490                 495
Pro Pro Ala Ser Ser Glu Ala Arg Asn Ser Ala Phe Gly Phe Gln Gly
            500                 505                 510
Arg Leu Leu His Leu Ser Ala Gly Gln Arg Leu Gly Val His Leu His
            515                 520                 525
Thr Glu Ala Arg Ala Arg His Ala Trp Gln Leu Thr Gln Gly Ala Thr
            530                 535                 540
Val Leu Gly Leu Phe Arg Val Thr Pro Glu Ile Pro Ala Gly Gly Gly
545                 550                 555                 560
Gly Ser Gly Gly Gly Gly Ser Gly Gly Gly Ser Gly Gly Gly Gly
            565                 570                 575
```

Ser Gly Gly Gly Gly Ser Asp Pro Ala Gly Leu Leu Asp Leu Arg Gln
            580                 585                 590

Gly Met Phe Ala Gln Leu Val Ala Gln Asn Val Leu Leu Ile Asp Gly
        595                 600                 605

Pro Leu Ser Trp Tyr Ser Asp Pro Gly Leu Ala Gly Val Ser Leu Thr
    610                 615                 620

Gly Gly Leu Ser Tyr Lys Glu Asp Thr Lys Glu Leu Val Val Ala Lys
625                 630                 635                 640

Ala Gly Val Tyr Tyr Val Phe Phe Gln Leu Glu Leu Arg Arg Val Val
                645                 650                 655

Ala Gly Glu Gly Ser Gly Ser Val Ser Leu Ala Leu His Leu Gln Pro
            660                 665                 670

Leu Arg Ser Ala Ala Gly Ala Ala Leu Ala Leu Thr Val Asp Leu
        675                 680                 685

Pro Pro Ala Ser Ser Glu Ala Arg Asn Ser Ala Phe Gly Phe Gln Gly
    690                 695                 700

Arg Leu Leu His Leu Ser Ala Gly Gln Arg Leu Gly Val His Leu His
705                 710                 715                 720

Thr Glu Ala Arg Ala Arg His Ala Trp Gln Leu Thr Gln Gly Ala Thr
                725                 730                 735

Val Leu Gly Leu Phe Arg Val Thr Pro Glu Ile Pro Ala Ser
            740                 745                 750

<210> SEQ ID NO 74
<211> LENGTH: 2316
<212> TYPE: PRT
<213> ORGANISM: Artificial sequence
<220> FEATURE:
<223> OTHER INFORMATION: Synthetic sequence

<400> SEQUENCE: 74

Ala Thr Gly Thr Cys Thr Cys Gly Cys Thr Cys Cys Gly Thr Gly Gly
1               5                   10                  15

Cys Cys Thr Thr Ala Gly Cys Thr Gly Thr Gly Cys Thr Cys Gly Cys
            20                  25                  30

Gly Cys Thr Ala Cys Thr Cys Thr Cys Thr Cys Thr Thr Thr Cys Thr
        35                  40                  45

Gly Gly Cys Cys Thr Gly Gly Ala Gly Gly Cys Cys Gly Thr Thr Ala
    50                  55                  60

Thr Cys Cys Ala Cys Gly Thr Gly Ala Cys Cys Ala Gly Gly Thr Ala
65                  70                  75                  80

Ala Gly Thr Gly Ala Ala Gly Ala Ala Gly Thr Gly Gly Cys Thr Ala
                85                  90                  95

Ala Cys Gly Cys Thr Gly Thr Cys Cys Thr Gly Thr Gly Gly Thr Cys
            100                 105                 110

Ala Cys Ala Ala Thr Gly Thr Thr Thr Cys Thr Gly Thr Thr Gly Ala
        115                 120                 125

Ala Gly Ala Gly Cys Thr Gly Gly Cys Ala Cys Ala Ala Ala Cys Thr
    130                 135                 140

Cys Gly Cys Ala Thr Cys Thr Ala Cys Thr Gly Gly Cys Ala Ala Ala
145                 150                 155                 160

Ala Gly Gly Ala Gly Ala Ala Gly Ala Ala Ala Ala Thr Gly Gly Thr
                165                 170                 175

Gly Cys Thr Gly Ala Cys Thr Ala Thr Gly Ala Thr Gly Thr Cys Thr
            180                 185                 190

-continued

```
Gly Gly Gly Gly Ala Cys Ala Thr Gly Ala Ala Thr Ala Thr Ala Thr
        195                 200                 205

Gly Gly Cys Cys Cys Gly Ala Gly Thr Ala Cys Ala Ala Gly Ala Ala
    210                 215                 220

Cys Cys Gly Gly Ala Cys Cys Ala Thr Cys Thr Thr Thr Gly Ala Thr
225                 230                 235                 240
Ala Thr Cys Ala Cys Thr Ala Ala Thr Ala Ala Cys Cys Thr Cys Thr
                245                 250                 255
Cys Cys Ala Thr Thr Gly Thr Gly Ala Thr Cys Cys Thr Gly Gly Cys
            260                 265                 270

Thr Cys Thr Gly Cys Gly Cys Cys Cys Ala Thr Cys Thr Gly Ala Cys
        275                 280                 285

Gly Ala Gly Gly Gly Cys Ala Cys Ala Thr Ala Cys Gly Ala Gly Thr
    290                 295                 300

Gly Thr Gly Thr Thr Gly Thr Thr Cys Thr Gly Gly Cys Cys Thr Ala
305                 310                 315                 320

Thr Gly Ala Ala Ala Ala Ala Gly Ala Cys Gly Cys Thr Thr Thr Cys
                325                 330                 335
Ala Ala Gly Cys Gly Gly Gly Ala Ala Cys Ala Cys Cys Thr Gly Gly
            340                 345                 350
Cys Thr Gly Ala Ala Gly Thr Gly Ala Cys Gly Thr Thr Ala Thr Cys
        355                 360                 365

Ala Gly Thr Cys Ala Ala Ala Gly Cys Thr Gly Ala Cys Thr Thr Cys
    370                 375                 380

Cys Cys Thr Ala Cys Ala Cys Cys Thr Ala Gly Thr Ala Thr Ala Thr
385                 390                 395                 400

Cys Thr Gly Ala Cys Thr Thr Thr Gly Ala Ala Ala Thr Thr Cys Cys
                405                 410                 415

Ala Ala Cys Thr Thr Cys Thr Ala Ala Thr Ala Thr Thr Ala Gly Ala
            420                 425                 430

Ala Gly Gly Ala Thr Ala Ala Thr Thr Thr Gly Cys Thr Cys Ala Ala
        435                 440                 445

Cys Cys Thr Cys Thr Gly Gly Ala Gly Gly Thr Thr Thr Thr Cys Cys
    450                 455                 460

Ala Gly Ala Gly Cys Cys Thr Cys Ala Cys Cys Thr Cys Thr Cys Cys
465                 470                 475                 480

Thr Gly Gly Thr Thr Gly Gly Ala Ala Ala Ala Thr Gly Gly Ala Gly
                485                 490                 495

Ala Ala Gly Ala Ala Thr Thr Ala Ala Ala Thr Gly Cys Cys Ala Thr
            500                 505                 510

Cys Ala Ala Cys Ala Cys Ala Ala Cys Ala Gly Thr Thr Thr Cys Cys
        515                 520                 525

Cys Ala Ala Gly Ala Thr Cys Cys Thr Gly Ala Ala Ala Cys Thr Gly
    530                 535                 540

Ala Gly Cys Thr Cys Thr Ala Thr Gly Cys Thr Gly Thr Thr Ala Gly
545                 550                 555                 560

Cys Ala Gly Cys Ala Ala Ala Cys Thr Gly Gly Ala Thr Thr Thr Cys
                565                 570                 575

Ala Ala Thr Ala Thr Gly Ala Cys Ala Ala Cys Cys Ala Ala Cys Cys
            580                 585                 590

Ala Cys Ala Gly Cys Thr Thr Cys Ala Thr Gly Thr Gly Thr Cys Thr
        595                 600                 605
```

-continued

```
Cys Ala Thr Cys Ala Ala Gly Thr Ala Thr Gly Ala Cys Ala Thr
    610                 615                 620

Thr Thr Ala Ala Gly Ala Gly Thr Gly Ala Ala Thr Cys Ala Gly Ala
625                 630                 635                 640

Cys Cys Thr Thr Cys Ala Ala Cys Thr Gly Gly Ala Ala Thr Ala Cys
                645                 650                 655

Ala Ala Cys Cys Ala Ala Gly Cys Ala Ala Gly Ala Gly Cys Ala Thr
            660                 665                 670

Thr Thr Thr Cys Cys Thr Gly Ala Thr Ala Ala Cys Gly Gly Ala Gly
        675                 680                 685

Gly Cys Gly Gly Ala Gly Gly Ala Thr Cys Thr Gly Gly Thr Gly Gly
    690                 695                 700

Thr Gly Gly Ala Gly Gly Thr Thr Cys Thr Gly Gly Thr Gly Gly Thr
705                 710                 715                 720

Gly Gly Gly Gly Gly Ala Thr Cys Thr Gly Gly Ala Gly Gly Cys Gly
                725                 730                 735

Gly Ala Gly Gly Ala Thr Cys Thr Gly Gly Cys Cys Cys Gly Cys Ala
            740                 745                 750

Thr Thr Cys Cys Cys Thr Gly Cys Gly Cys Thr Ala Cys Thr Thr Thr
        755                 760                 765

Gly Thr Gly Ala Cys Cys Gly Cys Thr Gly Thr Thr Ala Gly Cys Cys
    770                 775                 780

Gly Cys Cys Cys Gly Gly Gly Cys Cys Thr Gly Gly Gly Thr Gly Ala
785                 790                 795                 800

Ala Cys Cys Gly Cys Gly Thr Thr Ala Cys Ala Thr Gly Gly Ala Gly
                805                 810                 815

Gly Thr Cys Gly Gly Thr Thr Ala Thr Gly Thr Gly Gly Ala Thr Gly
            820                 825                 830

Ala Cys Ala Cys Gly Gly Ala Gly Thr Thr Thr Gly Thr Gly Cys Gly
        835                 840                 845

Thr Thr Thr Cys Gly Ala Thr Thr Cys Ala Gly Ala Cys Gly Cys Thr
    850                 855                 860

Gly Ala Gly Ala Ala Cys Cys Gly Cys Gly Thr Thr Ala Cys Gly Gly
865                 870                 875                 880

Ala Ala Cys Cys Gly Cys Gly Thr Gly Cys Ala Ala Gly Ala Thr Gly
                885                 890                 895

Gly Ala Thr Gly Gly Ala Ala Cys Ala Gly Gly Ala Ala Gly Gly Cys
            900                 905                 910

Cys Cys Gly Gly Ala Ala Thr Ala Thr Thr Gly Gly Gly Ala Ala Ala
        915                 920                 925

Gly Ala Gly Ala Gly Ala Cys Cys Ala Ala Ala Ala Gly Gly Cys
    930                 935                 940

Ala Ala Ala Ala Gly Gly Cys Ala Ala Cys Gly Ala Ala Cys Ala Ala
945                 950                 955                 960

Ala Gly Cys Thr Thr Cys Cys Gly Thr Gly Thr Gly Gly Ala Cys Cys
                965                 970                 975

Thr Gly Cys Gly Thr Ala Cys Cys Cys Thr Gly Cys Thr Gly Gly Gly
            980                 985                 990

Cys Gly Cys Cys Thr Ala Cys Ala  Ala Cys Cys Ala Ala  Thr Cys Ala
        995                 1000                 1005

Ala Ala  Ala Gly Gly Thr Gly  Gly Cys Thr Cys Gly  Cys Ala Cys
    1010                 1015                 1020
```

| | | | | | | | | | | |
|---|---|---|---|---|---|---|---|---|---|---|
|Ala|Cys|Gly|Ala|Thr|Cys|Cys|Ala|Gly|Gly|Thr|Gly|Ala|Thr|Cys|
| |1025| | | |1030| | | |1035| |

Ala Gly Cys Gly Gly Cys Thr Gly Cys Gly Ala Gly Gly Thr Thr
    1040                    1045                    1050

Gly Gly Thr Ala Gly Cys Gly Ala Thr Gly Gly Cys Cys Gly Thr
    1055                    1060                    1065

Cys Thr Gly Cys Thr Gly Cys Gly Cys Gly Gly Cys Thr Ala Thr
    1070                    1075                    1080

Cys Ala Gly Cys Ala Ala Thr Ala Cys Gly Cys Cys Thr Ala Cys
    1085                    1090                    1095

Gly Ala Cys Gly Gly Thr Thr Gly Cys Gly Ala Thr Thr Ala Thr
    1100                    1105                    1110

Ala Thr Cys Gly Cys Ala Cys Thr Gly Ala Ala Thr Gly Ala Ala
    1115                    1120                    1125

Gly Ala Cys Cys Thr Gly Ala Ala Ala Cys Cys Thr Gly Gly
    1130                    1135                    1140

Ala Cys Gly Gly Cys Gly Gly Cys Cys Gly Ala Thr Ala Thr Gly
    1145                    1150                    1155

Gly Cys Ala Gly Cys Thr Cys Thr Gly Ala Thr Thr Ala Cys Gly
    1160                    1165                    1170

Ala Ala Gly Cys Ala Cys Ala Ala Thr Gly Gly Gly Ala Ala
    1175                    1180                    1185

Cys Ala Gly Gly Cys Thr Gly Gly Cys Gly Ala Gly Gly Cys Gly
    1190                    1195                    1200

Gly Ala Ala Ala Gly Ala Cys Thr Gly Cys Gly Cys Gly Cys Cys
    1205                    1210                    1215

Thr Ala Cys Cys Thr Gly Gly Ala Gly Gly Gly Thr Ala Cys Cys
    1220                    1225                    1230

Thr Gly Cys Gly Thr Gly Gly Ala Ala Thr Gly Gly Cys Thr Gly
    1235                    1240                    1245

Cys Gly Thr Cys Gly Cys Thr Ala Thr Cys Thr Gly Ala Ala Gly
    1250                    1255                    1260

Ala Ala Cys Gly Gly Cys Ala Ala Thr Gly Cys Cys Ala Cys Cys
    1265                    1270                    1275

Thr Thr Gly Cys Thr Gly Cys Gly Thr Ala Cys Gly Gly Ala Thr
    1280                    1285                    1290

Ala Gly Cys Cys Cys Gly Ala Ala Gly Cys Ala Cys Ala Thr
    1295                    1300                    1305

Gly Thr Thr Ala Cys Cys Ala Cys Cys Ala Cys Ala Gly Cys
    1310                    1315                    1320

Cys Gly Cys Cys Cys Gly Ala Gly Gly Ala Cys Ala Ala Gly
    1325                    1330                    1335

Gly Thr Thr Ala Cys Gly Cys Thr Gly Cys Gly Thr Thr Gly Thr
    1340                    1345                    1350

Thr Gly Gly Gly Cys Thr Cys Thr Gly Gly Cys Thr Thr Thr
    1355                    1360                    1365

Thr Ala Thr Cys Cys Gly Gly Cys Gly Gly Ala Thr Ala Thr Thr
    1370                    1375                    1380

Ala Cys Cys Cys Thr Gly Ala Cys Gly Thr Gly Cys Ala Gly
    1385                    1390                    1395

Cys Thr Gly Ala Ala Cys Gly Gly Thr Gly Ala Ala Gly Ala Gly
    1400                    1405                    1410

-continued

```
Cys Thr Gly Ala Thr Cys Cys Ala Ala Gly Ala Thr Ala Thr Gly
    1415                1420                1425
Gly Ala Ala Cys Thr Gly Thr Gly Gly Ala Ala Ala Cys Cys
    1430                1435                1440
Cys Gly Thr Cys Cys Gly Thr Gly Cys Gly Gly Cys Gly Ala Thr
    1445                1450                1455
Gly Gly Cys Ala Cys Gly Thr Thr Cys Cys Ala Gly Ala Ala Ala
    1460                1465                1470
Thr Gly Gly Gly Cys Ala Ala Gly Cys Gly Thr Gly Gly Thr Thr
    1475                1480                1485
Gly Thr Cys Cys Cys Gly Cys Thr Gly Gly Gly Thr Ala Ala Ala
    1490                1495                1500
Gly Ala Ala Cys Ala Ala Thr Ala Cys Thr Ala Cys Ala Cys Cys
    1505                1510                1515
Thr Gly Thr Cys Ala Thr Gly Thr Thr Ala Cys Cys Ala Cys
    1520                1525                1530
Cys Ala Gly Gly Gly Thr Cys Thr Gly Cys Cys Gly Gly Ala Ala
    1535                1540                1545
Cys Cys Gly Cys Thr Gly Ala Cys Gly Cys Thr Gly Cys Gly Thr
    1550                1555                1560
Thr Gly Gly Gly Cys Ala Gly Cys Thr Gly Cys Gly Gly Gly Thr
    1565                1570                1575
Gly Gly Cys Cys Cys Cys Ala Gly Ala Gly Gly Cys Cys Cys
    1580                1585                1590
Ala Cys Ala Ala Thr Cys Ala Ala Gly Cys Cys Cys Thr Gly Thr
    1595                1600                1605
Cys Cys Thr Cys Cys Ala Thr Gly Cys Ala Ala Ala Thr Gly Cys
    1610                1615                1620
Cys Cys Ala Gly Cys Ala Cys Cys Thr Ala Ala Cys Gly Cys Cys
    1625                1630                1635
Gly Cys Cys Gly Gly Thr Gly Gly Ala Cys Cys Ala Thr Cys Cys
    1640                1645                1650
Gly Thr Cys Thr Thr Cys Ala Thr Cys Thr Thr Cys Cys Cys Thr
    1655                1660                1665
Cys Cys Ala Ala Ala Gly Ala Thr Cys Ala Ala Gly Gly Ala Thr
    1670                1675                1680
Gly Thr Ala Cys Thr Cys Ala Thr Gly Ala Thr Cys Thr Cys Cys
    1685                1690                1695
Cys Thr Gly Ala Gly Cys Cys Cys Ala Thr Ala Gly Thr Cys
    1700                1705                1710
Ala Cys Ala Thr Gly Thr Gly Thr Gly Gly Thr Gly Gly Thr Gly
    1715                1720                1725
Gly Ala Thr Gly Thr Gly Ala Gly Cys Gly Ala Gly Gly Ala Thr
    1730                1735                1740
Gly Ala Cys Cys Cys Ala Gly Ala Thr Gly Thr Cys Cys Ala Gly
    1745                1750                1755
Ala Thr Cys Ala Gly Cys Thr Gly Gly Thr Thr Thr Gly Thr Gly
    1760                1765                1770
Ala Ala Cys Ala Ala Cys Gly Thr Gly Gly Ala Ala Gly Thr Ala
    1775                1780                1785
Cys Ala Cys Ala Cys Ala Gly Cys Thr Cys Ala Gly Ala Cys Ala
    1790                1795                1800
```

-continued

```
Cys Ala Ala Ala Cys Cys Cys Ala Thr Ala Gly Ala Gly Ala Gly
1805                1810                1815

Gly Ala Thr Thr Ala Cys Ala Ala Cys Ala Gly Thr Ala Cys Thr
1820                1825                1830

Cys Thr Cys Cys Gly Gly Gly Thr Gly Gly Thr Cys Ala Gly Thr
1835                1840                1845

Gly Cys Cys Cys Thr Cys Cys Cys Ala Thr Cys Cys Ala Gly
1850                1855                1860

Cys Ala Cys Cys Ala Gly Gly Ala Cys Thr Gly Gly Ala Thr Gly
1865                1870                1875

Ala Gly Thr Gly Gly Cys Ala Ala Gly Gly Ala Gly Thr Thr Cys
1880                1885                1890

Ala Ala Ala Thr Gly Cys Ala Ala Gly Gly Thr Cys Ala Ala Cys
1895                1900                1905

Ala Ala Cys Ala Ala Ala Gly Ala Cys Cys Thr Cys Cys Cys Ala
1910                1915                1920

Gly Cys Gly Cys Cys Cys Ala Thr Cys Gly Ala Gly Ala Gly Ala
1925                1930                1935

Ala Cys Cys Ala Thr Cys Thr Cys Ala Ala Ala Ala Cys Cys Cys
1940                1945                1950

Ala Ala Ala Gly Gly Gly Thr Cys Ala Gly Thr Ala Ala Gly Ala
1955                1960                1965

Gly Cys Thr Cys Cys Ala Cys Ala Gly Gly Thr Ala Thr Ala Thr
1970                1975                1980

Gly Thr Cys Thr Thr Gly Cys Cys Thr Cys Cys Ala Cys Cys Ala
1985                1990                1995

Gly Ala Ala Gly Ala Ala Gly Ala Gly Ala Thr Gly Ala Cys Thr
2000                2005                2010

Ala Ala Gly Ala Ala Ala Cys Ala Gly Gly Thr Cys Ala Cys Thr
2015                2020                2025

Cys Thr Gly Ala Cys Cys Thr Gly Cys Ala Thr Gly Gly Thr Cys
2030                2035                2040

Ala Cys Ala Gly Ala Cys Thr Thr Cys Ala Thr Gly Cys Cys Thr
2045                2050                2055

Gly Ala Ala Gly Ala Cys Ala Thr Thr Thr Ala Cys Gly Thr Gly
2060                2065                2070

Gly Ala Gly Thr Gly Gly Ala Cys Cys Ala Ala Cys Ala Ala Cys
2075                2080                2085

Gly Gly Gly Ala Ala Ala Ala Cys Ala Gly Ala Gly Cys Thr Ala
2090                2095                2100

Ala Ala Cys Thr Ala Cys Ala Ala Gly Ala Ala Cys Ala Cys Thr
2105                2110                2115

Gly Ala Ala Cys Cys Ala Gly Thr Cys Cys Thr Gly Gly Ala Cys
2120                2125                2130

Thr Cys Thr Gly Ala Thr Gly Gly Thr Thr Cys Thr Thr Ala Cys
2135                2140                2145

Thr Thr Cys Ala Thr Gly Thr Ala Cys Ala Gly Cys Ala Ala Gly
2150                2155                2160

Cys Thr Gly Ala Gly Ala Gly Thr Gly Gly Ala Ala Ala Ala Gly
2165                2170                2175

Ala Ala Gly Ala Ala Cys Thr Gly Gly Gly Thr Gly Gly Ala Ala
2180                2185                2190
```

Ala Gly Ala Ala Ala Thr Ala Gly Cys Thr Ala Cys Thr Cys Cys
            2195                2200                2205

Thr Gly Thr Thr Cys Ala Gly Thr Gly Gly Thr Cys Cys Ala Cys
        2210                2215                2220

Gly Ala Gly Gly Gly Thr Cys Thr Gly Cys Ala Cys Ala Ala Thr
    2225                2230                2235

Cys Ala Cys Cys Ala Cys Ala Cys Gly Ala Cys Thr Ala Ala Gly
2240                2245                2250

Ala Gly Cys Thr Thr Cys Thr Cys Cys Cys Gly Gly Ala Cys Thr
    2255                2260                2265

Cys Cys Gly Gly Gly Thr Ala Ala Ala Gly Gly Cys Gly Gly Ala
2270                2275                2280

Thr Cys Ala Cys Ala Thr Cys Ala Cys Cys Ala Thr Cys Ala Cys
    2285                2290                2295

Cys Ala Thr Cys Ala Cys Cys Ala Thr Cys Ala Cys Thr Ala Gly
2300                2305                2310

Thr Gly Ala
    2315

<210> SEQ ID NO 75
<211> LENGTH: 770
<212> TYPE: PRT
<213> ORGANISM: Artificial sequence
<220> FEATURE:
<223> OTHER INFORMATION: Synthetic sequence

<400> SEQUENCE: 75

Met Ser Arg Ser Val Ala Leu Ala Val Leu Ala Leu Leu Ser Leu Ser
1               5                   10                  15

Gly Leu Glu Ala Val Ile His Val Thr Lys Glu Val Lys Glu Val Ala
            20                  25                  30

Thr Leu Ser Cys Gly His Asn Val Ser Val Glu Glu Leu Ala Gln Thr
        35                  40                  45

Arg Ile Tyr Trp Gln Lys Glu Lys Lys Met Val Leu Thr Met Met Ser
    50                  55                  60

Gly Asp Met Asn Ile Trp Pro Glu Tyr Lys Asn Arg Thr Ile Phe Asp
65                  70                  75                  80

Ile Thr Asn Asn Leu Ser Ile Val Ile Leu Ala Leu Arg Pro Ser Asp
                85                  90                  95

Glu Gly Thr Tyr Glu Cys Val Val Leu Ala Tyr Glu Lys Asp Ala Phe
            100                 105                 110

Lys Arg Glu His Leu Ala Glu Val Thr Leu Ser Val Lys Ala Asp Phe
        115                 120                 125

Pro Thr Pro Ser Ile Ser Asp Phe Glu Ile Pro Thr Ser Asn Ile Arg
    130                 135                 140

Arg Ile Ile Cys Ser Thr Ser Gly Gly Phe Pro Glu Pro His Leu Ser
145                 150                 155                 160

Trp Leu Glu Asn Gly Glu Glu Leu Asn Ala Ile Asn Thr Thr Val Ser
                165                 170                 175

Gln Asp Pro Glu Thr Glu Leu Tyr Ala Val Ser Ser Lys Leu Asp Phe
            180                 185                 190

Asn Met Thr Thr Asn His Ser Phe Met Cys Leu Ile Lys Tyr Gly His
        195                 200                 205

Leu Arg Val Asn Gln Thr Phe Asn Trp Asn Thr Thr Lys Gln Glu His
    210                 215                 220

Phe Pro Asp Asn Gly Gly Gly Ser Gly Gly Gly Ser Gly Gly
225                 230                 235                 240

Gly Gly Ser Gly Gly Gly Ser Gly Pro His Ser Leu Arg Tyr Phe
            245                 250                 255

Val Thr Ala Val Ser Arg Pro Gly Leu Gly Glu Pro Arg Tyr Met Glu
        260                 265                 270

Val Gly Tyr Val Asp Asp Thr Glu Phe Val Arg Phe Asp Ser Asp Ala
    275                 280                 285

Glu Asn Pro Arg Tyr Glu Pro Arg Ala Arg Trp Met Glu Gln Glu Gly
    290                 295                 300

Pro Glu Tyr Trp Glu Arg Glu Thr Gln Lys Ala Lys Gly Asn Glu Gln
305                 310                 315                 320

Ser Phe Arg Val Asp Leu Arg Thr Leu Leu Gly Ala Tyr Asn Gln Ser
            325                 330                 335

Lys Gly Gly Ser His Thr Ile Gln Val Ile Ser Gly Cys Glu Val Gly
            340                 345                 350

Ser Asp Gly Arg Leu Leu Arg Gly Tyr Gln Gln Tyr Ala Tyr Asp Gly
            355                 360                 365

Cys Asp Tyr Ile Ala Leu Asn Glu Asp Leu Lys Thr Trp Thr Ala Ala
    370                 375                 380

Asp Met Ala Ala Leu Ile Thr Lys His Lys Trp Glu Gln Ala Gly Glu
385                 390                 395                 400

Ala Glu Arg Leu Arg Ala Tyr Leu Glu Gly Thr Cys Val Glu Trp Leu
                405                 410                 415

Arg Arg Tyr Leu Lys Asn Gly Asn Ala Thr Leu Leu Arg Thr Asp Ser
            420                 425                 430

Pro Lys Ala His Val Thr His His Ser Arg Pro Glu Asp Lys Val Thr
            435                 440                 445

Leu Arg Cys Trp Ala Leu Gly Phe Tyr Pro Ala Asp Ile Thr Leu Thr
    450                 455                 460

Trp Gln Leu Asn Gly Glu Glu Leu Ile Gln Asp Met Glu Leu Val Glu
465                 470                 475                 480

Thr Arg Pro Cys Gly Asp Gly Thr Phe Gln Lys Trp Ala Ser Val Val
            485                 490                 495

Val Pro Leu Gly Lys Glu Gln Tyr Tyr Thr Cys His Val Tyr His Gln
            500                 505                 510

Gly Leu Pro Glu Pro Leu Thr Leu Arg Trp Ala Ala Ala Gly Gly Pro
            515                 520                 525

Arg Gly Pro Thr Ile Lys Pro Cys Pro Pro Cys Lys Cys Pro Ala Pro
    530                 535                 540

Asn Ala Ala Gly Gly Pro Ser Val Phe Ile Phe Pro Pro Lys Ile Lys
545                 550                 555                 560

Asp Val Leu Met Ile Ser Leu Ser Pro Ile Val Thr Cys Val Val Val
            565                 570                 575

Asp Val Ser Glu Asp Asp Pro Asp Val Gln Ile Ser Trp Phe Val Asn
            580                 585                 590

Asn Val Glu Val His Thr Ala Gln Thr Gln Thr His Arg Glu Asp Tyr
            595                 600                 605

Asn Ser Thr Leu Arg Val Val Ser Ala Leu Pro Ile Gln His Gln Asp
            610                 615                 620

Trp Met Ser Gly Lys Glu Phe Lys Cys Lys Val Asn Asn Lys Asp Leu
625                 630                 635                 640

```
Pro Ala Pro Ile Glu Arg Thr Ile Ser Lys Pro Lys Gly Ser Val Arg
                645                 650                 655

Ala Pro Gln Val Tyr Val Leu Pro Pro Glu Glu Met Thr Lys
        660                 665                 670

Lys Gln Val Thr Leu Thr Cys Met Val Thr Asp Phe Met Pro Glu Asp
        675                 680                 685

Ile Tyr Val Glu Trp Thr Asn Asn Gly Lys Thr Glu Leu Asn Tyr Lys
        690                 695                 700

Asn Thr Glu Pro Val Leu Asp Ser Asp Gly Ser Tyr Phe Met Tyr Ser
705                 710                 715                 720

Lys Leu Arg Val Glu Lys Lys Asn Trp Val Glu Arg Asn Ser Tyr Ser
                725                 730                 735

Cys Ser Val Val His Glu Gly Leu His Asn His His Thr Thr Lys Ser
            740                 745                 750

Phe Ser Arg Thr Pro Gly Lys Gly Gly Ser His His His His His His
        755                 760                 765

His His
    770

<210> SEQ ID NO 76
<211> LENGTH: 2166
<212> TYPE: DNA
<213> ORGANISM: Artificial sequence
<220> FEATURE:
<223> OTHER INFORMATION: Synthetic sequence

<400> SEQUENCE: 76
```

| | | | | | |
|---|---|---|---|---|---|
| atgtcccgct | ccgtggcgct | tgcggtgctg | gccctgctgt | cgttgtccgg | gctggaagcg | 60 |
| tccattatca | acttcgagaa | actgggggga | ggagcctcag | gaggaggagg | atccggggt | 120 |
| ggaggtagca | tgattcaaaa | gacccctcaa | atccaggtct | actcgtgcca | cccacccgag | 180 |
| aacggaaagc | ctaatatcct | gaactgttac | gtgacccaat | ccacccgcc | gcatatcgag | 240 |
| atccagatgc | tcaagaacgg | caagaagatc | cccaaggtgg | aaatgtccga | catgagcttt | 300 |
| tccaaggatt | ggtcgttcta | tatcctggct | cataccgagt | tcaccccac | cgaaaccgat | 360 |
| acttacgcct | gccgcgtcaa | gcacgcctca | atggcggagc | taagaccgt | gtactgggac | 420 |
| cgggacatgg | tggcggggg | gtccggagga | ggtggatccg | gcggaggggg | atctggcgga | 480 |
| ggcggatcag | gaggtggcgg | ctctgaccct | gcaggcctgc | tggatctgcg | gcagggcatg | 540 |
| ttcgcacaac | tcgtggccca | gaacgtgctg | ctgatcgatg | gaccgctgtc | ctggtactcc | 600 |
| gacccgggac | ttgccggagt | gtcactgact | ggaggattgt | cctacgccga | agatacgaag | 660 |
| gagctcgtcg | tggcgaaggc | cggagtgtac | tatgtgttct | ccagctcga | actccggaga | 720 |
| gtcgtggccg | gggaaggctc | cggctccgtg | tcacttgccc | tgcacctcca | gccacttcgg | 780 |
| tcggccgctg | agccgccgc | actggccctg | accgtcgacc | tccctcctgc | gtcctccgag | 840 |
| gctcgcaact | cggccttcgg | attccaaggg | cgccttctgc | acctgtccgc | gggacagagg | 900 |
| ctgggggtgc | atctgcatac | tgaagcgcgg | gcacggcatg | cttggcagct | gactcaggga | 960 |
| gcaactgtcc | tggtctgtt | ccgcgtgact | ccggaaatcc | ccgccggtgg | aggtggctca | 1020 |
| ggaggcggcg | gcagcggtgg | aggagggagc | ggaggaggcg | gatccggtgg | aggcggaagc | 1080 |
| gaccctgccg | gactcctgga | tctgcggcag | ggcatgttcg | cccagttggt | ggcgcagaac | 1140 |
| gtcctgctca | ttgacgggcc | gctgtcgtgg | tacagcgatc | cgggcttggc | cggagtctcg | 1200 |
| ctgaccggag | gactcagcta | cgccgaagat | accaaggagc | tggtcgtggc | caaggccgga | 1260 |

```
gtgtactacg tgttcttcca actggaactg cgccgggtgg tggctggcga aggatccggg    1320
tcggtgtccc tggccctgca tctgcagcct ctgcgctcag ccgcaggagc agccgccttg    1380
gcgctcaccg tggaccttcc gcccgcctcc tcggaagccc ggaacagcgc cttcggcttc    1440
caaggcagac tcctgcactt gagcgcgggc cagagactgg gagtgcacct ccacaccgaa    1500
gcgcgcgcaa ggcacgcctg gcagctcacc cagggagcca ccgtgctggg cttgtttcga    1560 gtcaccccg agatcccagc cggcggagga ggttccggtg cggtggatc aggcggtgga    1620 ggctcgggtg gagggggtag cggaggggt ggttccgacc ccgcaggact gctggacctc    1680
cggcagggga tgttcgcgca actggtggct cagaatgtcc tgctgattga cggccccctg    1740
tcgtggtact cggaccctgg ccttgccggc gtgtccttga ctggagggct gtcgtacgcc    1800
gaggacacta aggagctggt cgtggccaaa gccggcgtgt actacgtgtt ctttcagctg    1860
gaactgagga gagtggtggc gggagaaggc agcggctcag tgtccctcgc cctgcacctt    1920
caaccactcc gctctgccgc tggtgcagct gcgctcgccc tcactgtgga tcttccaccg    1980
gcaagctccg aggccagaaa ctccgccttc gggttccagg ggaggctgct gcatctctcc    2040
gccggccaga gactgggcgt gcacttgcac actgaggcta gggctcgcca tgcctggcag    2100
ctgacccagg gcgccactgt gctgggactg ttccgggtga ccccagaaat cccggcctcc    2160
tgatag                                                              2166
```

<210> SEQ ID NO 77
<211> LENGTH: 720
<212> TYPE: PRT
<213> ORGANISM: Artificial sequence
<220> FEATURE:
<223> OTHER INFORMATION: Synthetic sequence

<400> SEQUENCE: 77

```
Met Ser Arg Ser Val Ala Leu Ala Val Leu Ala Leu Leu Ser Leu Ser
1               5                   10                  15

Gly Leu Glu Ala Ser Ile Ile Asn Phe Glu Lys Leu Gly Gly Gly Ala
                20                  25                  30

Ser Gly Gly Gly Gly Ser Gly Gly Gly Ser Met Ile Gln Lys Thr
            35                  40                  45

Pro Gln Ile Gln Val Tyr Ser Cys His Pro Pro Glu Asn Gly Lys Pro
        50                  55                  60

Asn Ile Leu Asn Cys Tyr Val Thr Gln Phe His Pro Pro His Ile Glu
65                  70                  75                  80

Ile Gln Met Leu Lys Asn Gly Lys Lys Ile Pro Lys Val Glu Met Ser
                85                  90                  95

Asp Met Ser Phe Ser Lys Asp Trp Ser Phe Tyr Ile Leu Ala His Thr
            100                 105                 110

Glu Phe Thr Pro Thr Glu Thr Asp Thr Tyr Ala Cys Arg Val Lys His
        115                 120                 125

Ala Ser Met Ala Glu Pro Lys Thr Val Tyr Trp Asp Arg Asp Met Gly
    130                 135                 140

Gly Gly Gly Ser Gly Gly Gly Ser Gly Gly Gly Ser Gly Gly Gly Gly
145                 150                 155                 160

Gly Gly Ser Gly Gly Gly Gly Ser Asp Pro Ala Gly Leu Leu Asp Leu
                165                 170                 175

Arg Gln Gly Met Phe Ala Gln Leu Val Ala Gln Asn Val Leu Leu Ile
            180                 185                 190
```

```
Asp Gly Pro Leu Ser Trp Tyr Ser Asp Pro Gly Leu Ala Gly Val Ser
            195                 200                 205

Leu Thr Gly Gly Leu Ser Tyr Ala Glu Asp Thr Lys Glu Leu Val Val
            210                 215                 220

Ala Lys Ala Gly Val Tyr Tyr Val Phe Phe Gln Leu Glu Leu Arg Arg
225                 230                 235                 240

Val Val Ala Gly Glu Gly Ser Gly Ser Val Ser Leu Ala Leu His Leu
                245                 250                 255

Gln Pro Leu Arg Ser Ala Ala Gly Ala Ala Leu Ala Leu Thr Val
            260                 265                 270

Asp Leu Pro Pro Ala Ser Ser Glu Ala Arg Asn Ser Ala Phe Gly Phe
            275                 280                 285

Gln Gly Arg Leu Leu His Leu Ser Ala Gly Gln Arg Leu Gly Val His
            290                 295                 300

Leu His Thr Glu Ala Arg Ala Arg His Ala Trp Gln Leu Thr Gln Gly
305                 310                 315                 320

Ala Thr Val Leu Gly Leu Phe Arg Val Thr Pro Glu Ile Pro Ala Gly
                325                 330                 335

Gly Gly Gly Ser Gly Gly Gly Ser Gly Gly Gly Ser Gly Gly
                340                 345                 350

Gly Gly Ser Gly Gly Gly Ser Asp Pro Ala Gly Leu Leu Asp Leu
            355                 360                 365

Arg Gln Gly Met Phe Ala Gln Leu Val Ala Gln Asn Val Leu Leu Ile
            370                 375                 380

Asp Gly Pro Leu Ser Trp Tyr Ser Asp Pro Gly Leu Ala Gly Val Ser
385                 390                 395                 400

Leu Thr Gly Gly Leu Ser Tyr Ala Glu Asp Thr Lys Glu Leu Val Val
                405                 410                 415

Ala Lys Ala Gly Val Tyr Tyr Val Phe Phe Gln Leu Glu Leu Arg Arg
            420                 425                 430

Val Val Ala Gly Glu Gly Ser Gly Ser Val Ser Leu Ala Leu His Leu
            435                 440                 445

Gln Pro Leu Arg Ser Ala Ala Gly Ala Ala Leu Ala Leu Thr Val
450                 455                 460

Asp Leu Pro Pro Ala Ser Ser Glu Ala Arg Asn Ser Ala Phe Gly Phe
465                 470                 475                 480

Gln Gly Arg Leu Leu His Leu Ser Ala Gly Gln Arg Leu Gly Val His
                485                 490                 495

Leu His Thr Glu Ala Arg Ala Arg His Ala Trp Gln Leu Thr Gln Gly
            500                 505                 510

Ala Thr Val Leu Gly Leu Phe Arg Val Thr Pro Glu Ile Pro Ala Gly
            515                 520                 525

Gly Gly Gly Ser Gly Gly Gly Ser Gly Gly Gly Ser Gly Gly
            530                 535                 540

Gly Gly Ser Gly Gly Gly Ser Asp Pro Ala Gly Leu Leu Asp Leu
545                 550                 555                 560

Arg Gln Gly Met Phe Ala Gln Leu Val Ala Gln Asn Val Leu Leu Ile
                565                 570                 575

Asp Gly Pro Leu Ser Trp Tyr Ser Asp Pro Gly Leu Ala Gly Val Ser
            580                 585                 590

Leu Thr Gly Gly Leu Ser Tyr Ala Glu Asp Thr Lys Glu Leu Val Val
            595                 600                 605
```

| | | | | | | | | | | | | | | |
|---|---|---|---|---|---|---|---|---|---|---|---|---|---|---|
|Ala|Lys|Ala|Gly|Val|Tyr|Tyr|Val|Phe|Phe|Gln|Leu|Glu|Leu|Arg|Arg|
| |610| | | |615| | | |620| | | | | |

Val Val Ala Gly Glu Gly Ser Gly Ser Val Ser Leu Ala Leu His Leu
625                 630                 635                 640

Gln Pro Leu Arg Ser Ala Ala Gly Ala Ala Leu Ala Leu Thr Val
            645                 650                 655

Asp Leu Pro Pro Ala Ser Ser Glu Ala Arg Asn Ser Ala Phe Gly Phe
            660                 665                 670

Gln Gly Arg Leu Leu His Leu Ser Ala Gly Gln Arg Leu Gly Val His
            675                 680                 685

Leu His Thr Glu Ala Arg Ala Arg His Ala Trp Gln Leu Thr Gln Gly
            690                 695                 700

Ala Thr Val Leu Gly Leu Phe Arg Val Thr Pro Glu Ile Pro Ala Ser
705                 710                 715                 720

<210> SEQ ID NO 78
<211> LENGTH: 2316
<212> TYPE: DNA
<213> ORGANISM: Artificial sequence
<220> FEATURE:
<223> OTHER INFORMATION: Synthetic sequence

<400> SEQUENCE: 78

```
atgtctcgct ccgtggcctt agctgtgctc gcgctactct ctctttctgg cctggaggcc      60
gttatccacg tgaccaagga agtgaaagaa gtggcaacgc tgtcctgtgg tcacaatgtt     120
tctgttgaag agctggcaca aactcgcatc tactggcaaa aggagaagaa aatggtgctg     180
actatgatgt ctggggacat gaatatatgg cccgagtaca agaaccggac catctttgat     240
atcactaata acctctccat tgtgatcctg gctctgcgcc catctgacga gggcacatac     300
gagtgtgttg ttctggccta tgaaaaagac gctttcaagc gggaacacct ggctgaagtg     360
acgttatcag tcaaagctga cttccctaca cctagtatat ctgactttga aattccaact     420
tctaatatta gaggataat tgctcaacc tctggaggtt ttccagagcc tcacctctcc      480
tggttggaaa atggagaaga attaaatgcc atcaacacaa cagtttccca agatcctgaa     540
actgagctct atgctgttag cagcaaactg gatttcaata tgacaaccaa ccacagcttc     600
atgtgtctca tcaagtatgg acatttaaga gtgaatcaga ccttcaactg gaatacaacc     660
aagcaagagc atttcctga taacggaggc ggaggatctg gtggtggagg ttctggtggt     720
gggggatctg gaggcggagg atctggcccca cactcgatgc ggtatttcga ccgccgtg     780
tcccggcccg gcctcgagga gccccggtac atctctgtcg gctatgtgga caacaaggag     840
ttcgtgcgct ccgacagcga cgcggagaat ccgagatatg agccgcgggc gccgtggatg     900
gagcaggagg ggccggagta ttgggagcgg gaaacacaga agccaagggg ccaagagcag     960
tggttccgag tgagcctgag gaacctgctc ggcgcctaca accagagcgc gggcggctct    1020
cacactctcc agcagatgtc tggctgtgac ttggggtcgg actggcgcct cctccgcggg    1080
tacctgcagt tcgcctatga aggccgcgat tacatcgccc tgaacgaaga cctgaaaacg    1140
tggacggcgg cggacatggc ggcgcagatc acccgacgca gtgggagca gagtggtgct    1200
gcagagcatt acaaggccta cctggagggc gagtgcgtgg agtggctcca cagatacctg    1260
aagaacggga acgcgacgct gctgcgcaca gattccccaa aggcacatgt gacccatcac    1320
cccagatcta aggtgaagt cacctgagg tgctgggccc tgggcttcta ccctgctgac    1380
atcaccctga cctggcagtt gaatggggag gagctgaccc aggacatgga gcttgtggag    1440
```

```
accaggcctt gcggggatgg aaccttccag aagtgggcat ctgtggtggt gcctcttggg    1500
aaggagcaga attacacatg ccgtgtgtac catgaggggc tgcctgagcc cctcaccctg    1560
agatgggcag ctgcgggtgg ccccagaggg cccacaatca agccctgtcc tccatgcaaa    1620
tgcccagcac ctaacgccgc cggtggacca tccgtcttca tcttccctcc aaagatcaag    1680
gatgtactca tgatctccct gagccccata gtcacatgtg tggtggtgga tgtgagcgag    1740
gatgacccag atgtccagat cagctggttt gtgaacaacg tggaagtaca cacagctcag    1800
acacaaaccc atagagagga ttacaacagt actctccggg tggtcagtgc cctccccatc    1860
cagcaccagg actggatgag tggcaaggag ttcaaatgca aggtcaacaa caaagacctc    1920
ccagcgccca tcgagagaac catctcaaaa cccaaggggt cagtaagagc tccacaggta    1980
tatgtcttgc ctccaccaga agaagagatg actaagaaac aggtcactct gacctgcatg    2040
gtcacagact tcatgcctga agacatttac gtggagtgga ccaacaacgg gaaaacagag    2100
ctaaactaca gaacactga accagtcctg gactctgatg gttcttactt catgtacagc    2160
aagctgagag tggaaaagaa gaactgggtg aaaagaaata gctactcctg ttcagtggtc    2220
cacgagggtc tgcacaatca ccacacgact aagagcttct cccggactcc gggtaaaggc    2280
ggatcacatc accatcacca tcaccatcac tagtga                              2316
```

<210> SEQ ID NO 79
<211> LENGTH: 770
<212> TYPE: PRT
<213> ORGANISM: Artificial sequence
<220> FEATURE:
<223> OTHER INFORMATION: Synthetic sequence

<400> SEQUENCE: 79

Met Ser Arg Ser Val Ala Leu Ala Val Leu Ala Leu Leu Ser Leu Ser
1               5                   10                  15

Gly Leu Glu Ala Val Ile His Val Thr Lys Glu Val Lys Glu Val Ala
            20                  25                  30

Thr Leu Ser Cys Gly His Asn Val Ser Val Glu Glu Leu Ala Gln Thr
        35                  40                  45

Arg Ile Tyr Trp Gln Lys Glu Lys Lys Met Val Leu Thr Met Met Ser
    50                  55                  60

Gly Asp Met Asn Ile Trp Pro Glu Tyr Lys Asn Arg Thr Ile Phe Asp
65                  70                  75                  80

Ile Thr Asn Asn Leu Ser Ile Val Ile Leu Ala Leu Arg Pro Ser Asp
                85                  90                  95

Glu Gly Thr Tyr Glu Cys Val Val Leu Ala Tyr Glu Lys Asp Ala Phe
            100                 105                 110

Lys Arg Glu His Leu Ala Glu Val Thr Leu Ser Val Lys Ala Asp Phe
        115                 120                 125

Pro Thr Pro Ser Ile Ser Asp Phe Glu Ile Pro Thr Ser Asn Ile Arg
    130                 135                 140

Arg Ile Ile Cys Ser Thr Ser Gly Gly Phe Pro Glu Pro His Leu Ser
145                 150                 155                 160

Trp Leu Glu Asn Gly Glu Glu Leu Asn Ala Ile Asn Thr Thr Val Ser
                165                 170                 175

Gln Asp Pro Glu Thr Glu Leu Tyr Ala Val Ser Ser Lys Leu Asp Phe
            180                 185                 190

Asn Met Thr Thr Asn His Ser Phe Met Cys Leu Ile Lys Tyr Gly His
        195                 200                 205

-continued

Leu Arg Val Asn Gln Thr Phe Asn Trp Asn Thr Thr Lys Gln Glu His
210                 215                 220

Phe Pro Asp Asn Gly Gly Gly Ser Gly Gly Gly Ser Gly Gly
225                 230                 235                 240

Gly Gly Ser Gly Gly Gly Ser Gly Pro His Ser Met Arg Tyr Phe
        245                 250                 255

Glu Thr Ala Val Ser Arg Pro Gly Leu Glu Glu Pro Arg Tyr Ile Ser
            260                 265                 270

Val Gly Tyr Val Asp Asn Lys Glu Phe Val Arg Phe Asp Ser Asp Ala
        275                 280                 285

Glu Asn Pro Arg Tyr Glu Pro Arg Ala Pro Trp Met Glu Gln Glu Gly
290                 295                 300

Pro Glu Tyr Trp Glu Arg Glu Thr Gln Lys Ala Lys Gly Gln Glu Gln
305                 310                 315                 320

Trp Phe Arg Val Ser Leu Arg Asn Leu Leu Gly Ala Tyr Asn Gln Ser
                325                 330                 335

Ala Gly Gly Ser His Thr Leu Gln Gln Met Ser Gly Cys Asp Leu Gly
            340                 345                 350

Ser Asp Trp Arg Leu Leu Arg Gly Tyr Leu Gln Phe Ala Tyr Glu Gly
        355                 360                 365

Arg Asp Tyr Ile Ala Leu Asn Glu Asp Leu Lys Thr Trp Thr Ala Ala
370                 375                 380

Asp Met Ala Ala Gln Ile Thr Arg Arg Lys Trp Glu Gln Ser Gly Ala
385                 390                 395                 400

Ala Glu His Tyr Lys Ala Tyr Leu Glu Gly Glu Cys Val Glu Trp Leu
                405                 410                 415

His Arg Tyr Leu Lys Asn Gly Asn Ala Thr Leu Leu Arg Thr Asp Ser
            420                 425                 430

Pro Lys Ala His Val Thr His His Pro Arg Ser Lys Gly Glu Val Thr
        435                 440                 445

Leu Arg Cys Trp Ala Leu Gly Phe Tyr Pro Ala Asp Ile Thr Leu Thr
450                 455                 460

Trp Gln Leu Asn Gly Glu Glu Leu Thr Gln Asp Met Glu Leu Val Glu
465                 470                 475                 480

Thr Arg Pro Cys Gly Asp Gly Thr Phe Gln Lys Trp Ala Ser Val Val
                485                 490                 495

Val Pro Leu Gly Lys Glu Gln Asn Tyr Thr Cys Arg Val Tyr His Glu
            500                 505                 510

Gly Leu Pro Glu Pro Leu Thr Leu Arg Trp Ala Ala Ala Gly Gly Pro
        515                 520                 525

Arg Gly Pro Thr Ile Lys Pro Cys Pro Pro Cys Lys Cys Pro Ala Pro
530                 535                 540

Asn Ala Ala Gly Gly Pro Ser Val Phe Ile Phe Pro Pro Lys Ile Lys
545                 550                 555                 560

Asp Val Leu Met Ile Ser Leu Ser Pro Ile Val Thr Cys Val Val Val
                565                 570                 575

Asp Val Ser Glu Asp Asp Pro Asp Val Gln Ile Ser Trp Phe Val Asn
            580                 585                 590

Asn Val Glu Val His Thr Ala Gln Thr Gln Thr His Arg Glu Asp Tyr
        595                 600                 605

Asn Ser Thr Leu Arg Val Val Ser Ala Leu Pro Ile Gln His Gln Asp
610                 615                 620

| | | | | | | | | | | | | | | |
|---|---|---|---|---|---|---|---|---|---|---|---|---|---|---|
Trp | Met | Ser | Gly | Lys | Glu | Phe | Lys | Cys | Lys | Val | Asn | Asn | Lys | Asp | Leu
625 | | | | 630 | | | | | 635 | | | | | 640

Pro Ala Pro Ile Glu Arg Thr Ile Ser Lys Pro Lys Gly Ser Val Arg
                                  645                            650                            655

Ala Pro Gln Val Tyr Val Leu Pro Pro Pro Glu Glu Glu Met Thr Lys
                      660                            665                            670

Lys Gln Val Thr Leu Thr Cys Met Val Thr Asp Phe Met Pro Glu Asp
            675                        680                            685

Ile Tyr Val Glu Trp Thr Asn Asn Gly Lys Thr Glu Leu Asn Tyr Lys
          690                        695                          700

Asn Thr Glu Pro Val Leu Asp Ser Asp Gly Ser Tyr Phe Met Tyr Ser
705                        710                        715                      720

Lys Leu Arg Val Glu Lys Lys Asn Trp Val Glu Arg Asn Ser Tyr Ser
            725                        730                            735

Cys Ser Val Val His Glu Gly Leu His Asn His His Thr Thr Lys Ser
                740                        745                        750

Phe Ser Arg Thr Pro Gly Lys Gly Gly Ser His His His His His
            755                        760                          765

His His
    770

<210> SEQ ID NO 80
<211> LENGTH: 2169
<212> TYPE: DNA
<213> ORGANISM: Artificial sequence
<220> FEATURE:
<223> OTHER INFORMATION: Synthetic sequence

<400> SEQUENCE: 80

```
atgtcccgct ccgtggcgct tgcggtgctg gccctgctgt cgttgtccgg gctggaagcg      60
cgagcccact acaacattgt gacatttggg ggaggagcct caggaggagg aggatccggg     120
ggtggaggta gcatgattca aaagaccct caaatccagg tctactcgtg ccacccaccc     180
gagaacggaa agcctaatat cctgaactgt tacgtgaccc aattccaccc gccgcatatc     240
gagatccaga tgctcaagaa cggcaagaag atccccaagg tggaaatgtc cgacatgagc     300
ttttccaagg attggtcgtt ctatatcctg gctcataccg agttcacccc caccgaaacc     360
gatacttacg cctgccgcgt caagcacgcc tcaatggcgg agcctaagac cgtgtactgg     420
gaccgggaca tgggtggcgg ggggtccgga ggaggtggat ccggcggagg gggatctggc     480
ggaggcggat caggaggtgg cggctctgac cctgcaggcc tgctggatct gcggcagggc     540
atgttcgcac aactcgtggc ccagaacgtg ctgctgatcg atggaccgct gtcctggtac     600
tccgacccgg gacttgccgg agtgtcactg actggaggat tgtcctacgc cgaagatacg     660
aaggagctcg tcgtggcgaa ggccggagtg tactatgtgt tcttccagct cgaactccgg     720
agagtcgtgg ccggggaagg ctccggctcc gtgtcacttg ccctgcacct ccagccactt     780
cggtcggccg ctggagccgc cgcactggcc ctgaccgtcg acctccctcc tgcgtcctcc     840
gaggctcgca actcggcctt cggattccaa gggcgccttc tgcacctgtc cgcgggacag     900
aggctggggg tgcatctgca tactgaagcg cgggcacggc atgcttggca gctgactcag     960
ggagcaactg tcctgggtct gttccgcgtg actccggaaa tccccgccgg tggaggtggc    1020
tcaggaggcg gcggcagcgg tggaggaggg agcggaggag gcggatccgg tggaggcgga    1080
agcgaccctg ccggactcct ggatctgcgc agggcatgt tcgcccagtt ggtggcgcag    1140
aacgtcctgc tcattgacgg gccgctgtcg tggtacagcg atccgggctt ggccggagtc    1200
```

```
tcgctgaccg gaggactcag ctacgccgaa gataccaagg agctggtcgt ggccaaggcc    1260
ggagtgtact acgtgttctt ccaactggaa ctgcgccggg tggtggctgg cgaaggatcc    1320
gggtcggtgt ccctggccct gcatctgcag cctctgcgct cagccgcagg agcagccgcc    1380
ttggcgctca ccgtggacct tccgcccgcc tcctcggaag cccggaacag cgccttcggc    1440
ttccaaggca gactcctgca cttgagcgcg ggccagagac tgggagtgca cctccacacc    1500
gaagcgcgcg caaggcacgc ctggcagctc acccagggag ccaccgtgct gggcttgttt    1560
cgagtcaccc ccgagatccc agccggcgga ggaggttccg gtggcggtgg atcaggcggt    1620
ggaggctcgg gtggagggggg tagcggaggg ggtggttccg accccgcagg actgctggac    1680
ctccggcagg ggatgttcgc gcaactggtg gctcagaatg tcctgctgat tgacggcccc    1740
ctgtcgtggt actcggaccc tggccttgcc ggcgtgtcct tgactggagg gctgtcgtac    1800
aaggaggaca ctaaggagct ggtcgtggcc aaagccggcg tgtactacgt gttctttcag    1860
ctggaactga ggagagtggt ggcgggagaa ggcagcggct cagtgtccct cgccctgcac    1920
cttcaaccac tccgctctgc cgctggtgca gctgcgctcg ccctcactgt ggatcttcca    1980
ccggcaagct ccgaggccag aaactccgcc ttcgggttcc aggggaggct gctgcatctc    2040
tccgccggcc agagactggg cgtgcacttg cacactgagg ctagggctcg ccatgcctgg    2100
cagctgaccc agggcgccac tgtgctggga ctgttccggg tgaccccaga aatcccggcc    2160
tcctgatag                                                            2169
```

<210> SEQ ID NO 81
<211> LENGTH: 720
<212> TYPE: PRT
<213> ORGANISM: Artificial sequence
<220> FEATURE:
<223> OTHER INFORMATION: Synthetic sequence

<400> SEQUENCE: 81

```
Ser Arg Ser Val Ala Leu Ala Val Leu Ala Leu Leu Ser Leu Ser Gly
1               5                   10                  15

Leu Glu Ala Arg Ala His Tyr Asn Ile Val Thr Phe Gly Gly Gly Ala
                20                  25                  30

Ser Gly Gly Gly Gly Ser Gly Gly Gly Ser Met Ile Gln Lys Thr
        35                  40                  45

Pro Gln Ile Gln Val Tyr Ser Cys His Pro Glu Asn Gly Lys Pro
    50                  55                  60

Asn Ile Leu Asn Cys Tyr Val Thr Gln Phe His Pro Pro His Ile Glu
65                  70                  75                  80

Ile Gln Met Leu Lys Asn Gly Lys Lys Ile Pro Lys Val Glu Met Ser
                85                  90                  95

Asp Met Ser Phe Ser Lys Asp Trp Ser Phe Tyr Ile Leu Ala His Thr
            100                 105                 110

Glu Phe Thr Pro Thr Glu Thr Asp Thr Tyr Ala Cys Arg Val Lys His
        115                 120                 125

Ala Ser Met Ala Glu Pro Lys Thr Val Tyr Trp Asp Arg Asp Met Gly
    130                 135                 140

Gly Gly Gly Ser Gly Gly Gly Gly Ser Gly Gly Gly Gly Ser Gly Gly
145                 150                 155                 160

Gly Gly Ser Gly Gly Gly Gly Ser Asp Pro Ala Gly Leu Leu Asp Leu
                165                 170                 175

Arg Gln Gly Met Phe Ala Gln Leu Val Ala Gln Asn Val Leu Leu Ile
            180                 185                 190
```

```
Asp Gly Pro Leu Ser Trp Tyr Ser Asp Pro Gly Leu Ala Gly Val Ser
            195                 200                 205

Leu Thr Gly Gly Leu Ser Tyr Ala Glu Asp Thr Lys Glu Leu Val Val
        210                 215                 220

Ala Lys Ala Gly Val Tyr Tyr Val Phe Phe Gln Leu Glu Leu Arg Arg
225                 230                 235                 240

Val Val Ala Gly Glu Gly Ser Gly Ser Val Ser Leu Ala Leu His Leu
                245                 250                 255

Gln Pro Leu Arg Ser Ala Ala Gly Ala Ala Leu Ala Leu Thr Val
            260                 265                 270

Asp Leu Pro Pro Ala Ser Ser Glu Ala Arg Asn Ser Ala Phe Gly Phe
            275                 280                 285

Gln Gly Arg Leu Leu His Leu Ser Ala Gly Gln Arg Leu Gly Val His
        290                 295                 300

Leu His Thr Glu Ala Arg Ala Arg His Ala Trp Gln Leu Thr Gln Gly
305                 310                 315                 320

Ala Thr Val Leu Gly Leu Phe Arg Val Thr Pro Glu Ile Pro Ala Gly
                325                 330                 335

Gly Gly Gly Ser Gly Gly Gly Ser Gly Gly Gly Ser Gly Gly
            340                 345                 350

Gly Gly Ser Gly Gly Gly Ser Asp Pro Ala Gly Leu Leu Asp Leu
        355                 360                 365

Arg Gln Gly Met Phe Ala Gln Leu Val Ala Gln Asn Val Leu Leu Ile
        370                 375                 380

Asp Gly Pro Leu Ser Trp Tyr Ser Asp Pro Gly Leu Ala Gly Val Ser
385                 390                 395                 400

Leu Thr Gly Gly Leu Ser Tyr Ala Glu Asp Thr Lys Glu Leu Val Val
                405                 410                 415

Ala Lys Ala Gly Val Tyr Tyr Val Phe Phe Gln Leu Glu Leu Arg Arg
            420                 425                 430

Val Val Ala Gly Glu Gly Ser Gly Ser Val Ser Leu Ala Leu His Leu
            435                 440                 445

Gln Pro Leu Arg Ser Ala Ala Gly Ala Ala Leu Ala Leu Thr Val
450                 455                 460

Asp Leu Pro Pro Ala Ser Ser Glu Ala Arg Asn Ser Ala Phe Gly Phe
465                 470                 475                 480

Gln Gly Arg Leu Leu His Leu Ser Ala Gly Gln Arg Leu Gly Val His
            485                 490                 495

Leu His Thr Glu Ala Arg Ala Arg His Ala Trp Gln Leu Thr Gln Gly
            500                 505                 510

Ala Thr Val Leu Gly Leu Phe Arg Val Thr Pro Glu Ile Pro Ala Gly
        515                 520                 525

Gly Gly Gly Ser Gly Gly Gly Ser Gly Gly Gly Ser Gly Gly
        530                 535                 540

Gly Gly Ser Gly Gly Gly Ser Asp Pro Ala Gly Leu Leu Asp Leu
545                 550                 555                 560

Arg Gln Gly Met Phe Ala Gln Leu Val Ala Gln Asn Val Leu Leu Ile
                565                 570                 575

Asp Gly Pro Leu Ser Trp Tyr Ser Asp Pro Gly Leu Ala Gly Val Ser
            580                 585                 590

Leu Thr Gly Gly Leu Ser Tyr Lys Glu Asp Thr Lys Glu Leu Val Val
        595                 600                 605
```

```
Ala Lys Ala Gly Val Tyr Tyr Val Phe Phe Gln Leu Glu Leu Arg Arg
    610                 615                 620
Val Val Ala Gly Glu Gly Ser Gly Ser Val Ser Leu Ala Leu His Leu
625                 630                 635                 640
Gln Pro Leu Arg Ser Ala Ala Gly Ala Ala Ala Leu Ala Leu Thr Val
                645                 650                 655
Asp Leu Pro Pro Ala Ser Ser Glu Ala Arg Asn Ser Ala Phe Gly Phe
            660                 665                 670
Gln Gly Arg Leu Leu His Leu Ser Ala Gly Gln Arg Leu Gly Val His
        675                 680                 685
Leu His Thr Glu Ala Arg Ala Arg His Ala Trp Gln Leu Thr Gln Gly
    690                 695                 700
Ala Thr Val Leu Gly Leu Phe Arg Val Thr Pro Glu Ile Pro Ala Ser
705                 710                 715                 720
```